(12) United States Patent
Echeverri et al.

(10) Patent No.: US 7,479,369 B2
(45) Date of Patent: Jan. 20, 2009

(54) USE OF EUKARYOTIC GENES AFFECTING SPINDLE FORMATION OR MICROTUBULE FUNCTION DURING CELL DIVISION FOR DIAGNOSIS AND TREATMENT OF PROLIFERATIVE DISEASES

(75) Inventors: Christophe Echeverri, Dresden (DE); Anthony Hyman, Dresden (DE); Pierre Gönczy, Lausanne (CH); Birte Sönnichsen, Dresden (DE); Steven Jones, Vancouver (CA); Andrew Walsh, Dresden (DE); Liisa Koski, Dresden (DE)

(73) Assignee: Cenix BioScience GmbH, Dresden (DE)

( * ) Notice: Subject to any disclaimer, the term of this patent is extended or adjusted under 35 U.S.C. 154(b) by 0 days.

(21) Appl. No.: 10/572,004

(22) PCT Filed: Sep. 15, 2004

(86) PCT No.: PCT/EP2004/010307

§ 371 (c)(1),
(2), (4) Date: Sep. 15, 2006

(87) PCT Pub. No.: WO2005/026359

PCT Pub. Date: Mar. 24, 2005

(65) Prior Publication Data
US 2007/0093438 A1    Apr. 26, 2007

Related U.S. Application Data

(60) Provisional application No. 60/502,633, filed on Sep. 15, 2003.

(51) Int. Cl.
C12Q 1/68     (2006.01)
C12P 19/34    (2006.01)
C07H 21/02    (2006.01)
C07H 21/04    (2006.01)

(52) U.S. Cl. ............. 435/6; 435/91.1; 435/91.31; 536/23.1; 536/23.5; 536/24.5

(58) Field of Classification Search ............. 435/6, 435/91.1, 91.31, 69.1, 455, 375; 536/23.1, 536/23.5, 24.5
See application file for complete search history.

(56) References Cited

FOREIGN PATENT DOCUMENTS

EP    1 041 147    10/2000

(Continued)

OTHER PUBLICATIONS

The C. elegans Sequencing Consortium, "Genome Sequence of the Nematode C. elegans: A Platform for Investigating Biology", Science, 1998, vol. 282, pp. 2012-2018.

(Continued)

Primary Examiner—Jane Zara
(74) Attorney, Agent, or Firm—Connolly Bove Lodge & Hutz LLP

(57) ABSTRACT

The present invention relates to the significant functional role of several C. elegans genes and of their corresponding gene products in spindle formation or microtubule function during cell division that could be identified by means of RNA-mediated interference (RNAi) and to the identification and isolation of functional orthologs of said genes including all biologically functional derivatives thereof. The invention further relates to the use of said genes and gene products (including said orthologs) in the development or isolation of anti-proliferative agents, particularly their use in appropriate screening assays, and their use for diagnosis and treatment of proliferative and other diseases. In particular, the invention relates to the use of small interfering RNAs derived from said genes for the treatment of proliferative diseases.

3 Claims, 25 Drawing Sheets

C13F10.2

FOREIGN PATENT DOCUMENTS

WO    WO-2004/074441    9/2004

OTHER PUBLICATIONS

Feinberg, A. P., et al., "A Technique for Radiolabeling DNA Restriction Endonuclease Fragments to High Specific Activity", Analytical Biochemistry, 1983, vol. 132, pp. 6-13.

Fire, A., et al., "Potent and Specific Genetic Interference by Double-Stranded RNA in *Caenorhabditis elegans*", Nature, 1998, Vo. 391, pp. 806-811.

Gönczy, P. et al., "Dissection of Cell Division Processes in the One Cell Stage *Caenorhabditis elegans* Embryo by Mutational Analysis", The Journal of Cell Biology, 1999, vol. 144, No. 5, pp. 927-946.

Kirby, C., et al., "Mutations in the *par* Genes of *Caenorhabditis elegans* Affect Cytoplasmic Reorganization During the First Cell Cycle", Developmental Biology, 1990, vol. 142, pp. 203-215.

Kufer, T. A., et al., "Human TPX2 is Required for Targeting Aurora-A Kinase to the Spindle", The Journal of Cell Biology, 2002, vol. 158, No. 4, pp. 617-623.

Mollinari, C., et al., "PRC1 is a Microtubule Binding and Bundling Protein Essential to Maintain the Mitotic Spindle Midzone", The Journal of Cell Biology, 2002, vol. 157, No. 7, pp. 1175-1186.

Sulston, J. E., et al., "The Embryonic Cell Lineage of the Nematode *Caenorhabditis elegans*", Developmental Biology, 1983, vol. 100, pp. 64-119.

Tuschl, T., "Expanding Small RNA Interference", Nature Biotechnology, 2002, vol. 20, pp. 446-448.

"OSTR158G4_1 AD-wrmcDNA *Caenorhabditis elegans* cDNA, mRNA Sequence", EMBL GenBank Assession No. CB395559, May 16, 2003.

"Hypothetical Protein C13F10.2", UniProt Database Accession No. O01488, Jul. 1, 1997.

Surka, M. C., "The Mammalian Septin MSF Localizes with Microtubules and is Required for Completion of Cytokinesis", Molecular Biology of the Cell, 2002, vol. 13, pp. 3532-3545.

Kalikin L. M., et al., "*Homo sapiens* MLL Septin Like Fusion Protein MSF-A mRNA, Complete cds., Alternatively Spliced", EMBL GenBank Accession No. AF189713, Jan. 11, 2000.

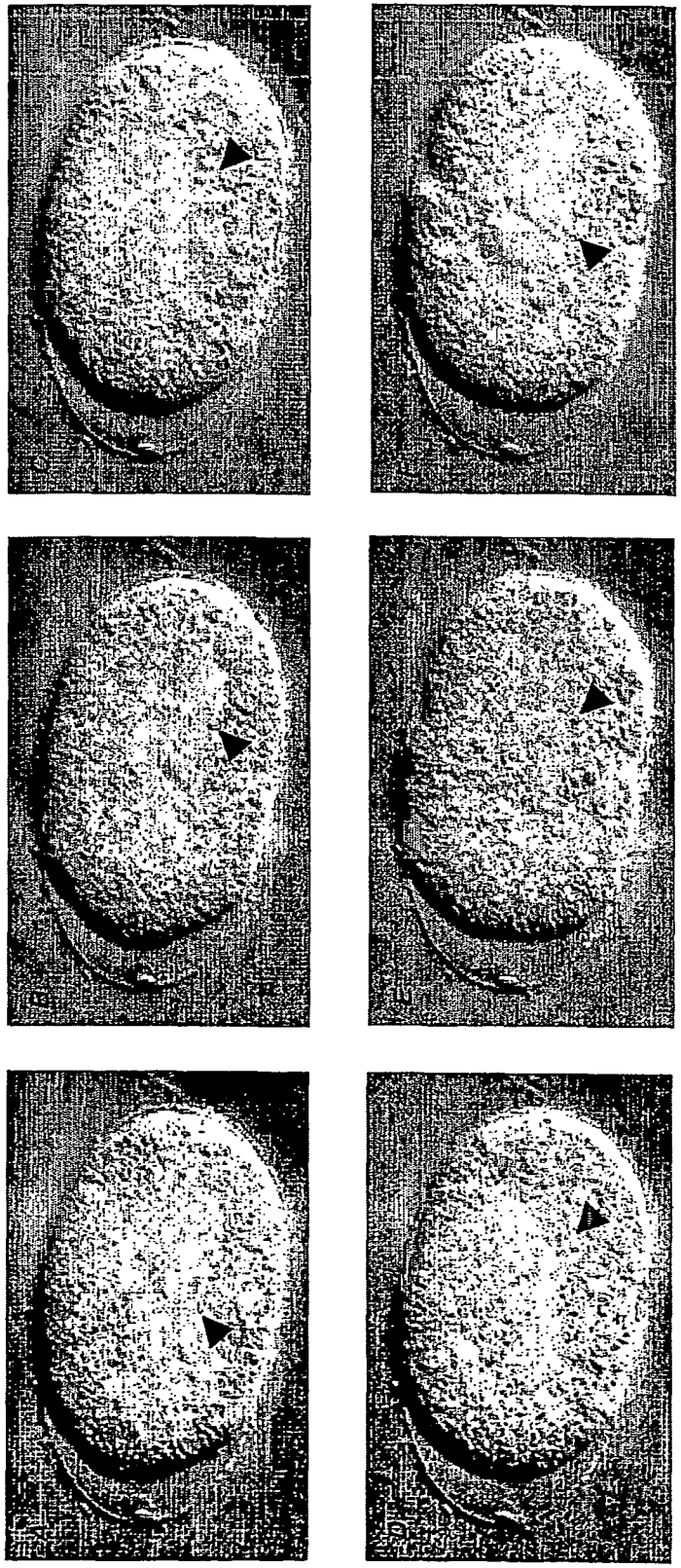
Fig.1 C13F10.2

Fig. 2

CLUSTAL W (1.8) multiple sequence alignment

```
NP_076974    ------------------------MDLPDSASRVFCGRILSMVNTDDVNAIILAQKNML
AAF49911     ---MSHLGLADVHQSEDATPDLESFTGFGNSAAEAFIQSLAGMVNQGDVETMIRAQKQML
C13F10.2     MAEKNHQQQERLPGNPFFPSRSNAGSSFDMPETPHLIDSLTSQIDEFTIQSIIDTQRQSL
                                     .    ..   ..  ::.*  .    : :* *.

NP_076974    DRFEKTNEMLLNFNNLSSARLQQMSERFLHHTRTLVEMKRDLDSIFRRIRTLKGKLARQH
AAF49911     QRFEKTNEMLLNCNALSQSRLKSASEDFKRHVKCLSEMKKDLDYIFRKIRIIKQKLQSQF
C13F10.2     KRFEKTNEMLMNCAQLGDRRIEKAKRDSVGHKETILQMKTDLEFIFKKIRMFKTVLSSKY
              ********: *  .*:::  .    *   . :  ::** **::*** :*  .  : .*

NP_076974    PEAFSHI-PEASFLEEEDEDPIPPSTTTTIATSEQSTG-----SCDTSPDTVSPSLSPGFE
AAF49911     PAIYAEVQPQRSSLAEEAEDDTEAQAKKTAETPAPAAAKPVLSTKKKSAATIEYVQMEEAV
C13F10.2     PEVYAEVSAELTPKRSEEDE-----------------------------------------
              :  :   .:   : ::*  .  *  ::

NP_076974    DLSHVQAGSPAIN-------GRSQTDDEEMTGE---
AAF49911     DNGTVEIENELIKRVCSVETANPNDSSDCTSEDTG
C13F10.2     ------------------------------------
                                           *
```

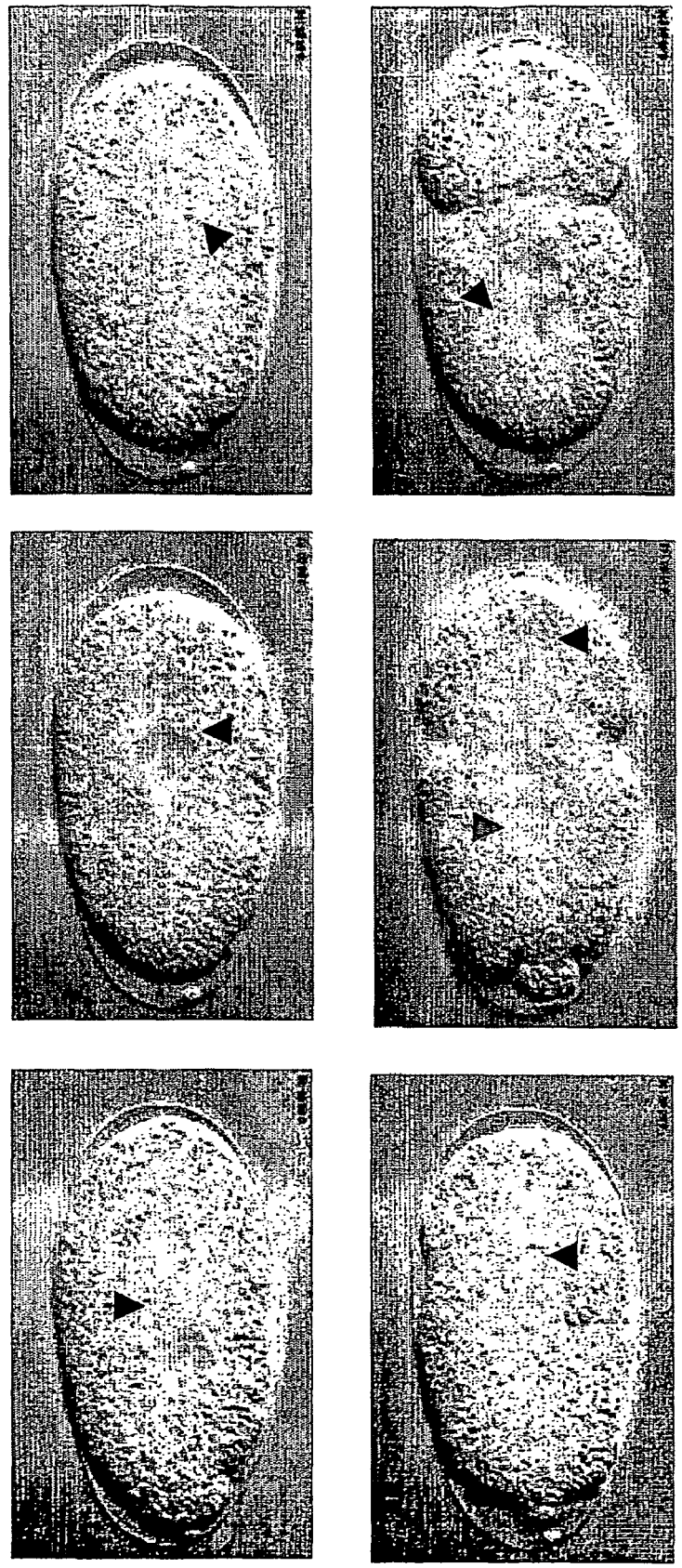
Fig.3 C25A1.9

Fig. 4

CLUSTAL W (1.8) multiple sequence alignment

```
C25A1.9        MPTDEPSKRKSILPTIPTSLMLKKSNEALSDFERTFNDRVMDIFAENRRIDVEEFKKNAE
NP_060387      MDWKEVLRRR--LATPNTCPNKKKSEQELKDEEMDLFTKYYSEWKGGRKNTNEFYKTIPR
                 *  :*: *.* *.  ****:: *.* *  :   .*: * :*. ..

C25A1.9        CFLNIIRSNKIDLNWGEG------------------------------------GESRYV
NP_060387      FYYRLPAEDVLLQKLREESRAVFLQRKSRELLDNEELQNLWFLLDKRQTPPMIGEEAMI
                 :  :  :: . *::: ::      .     **.  ::

C25A1.9        TITRLMKILKTSPQSIKDLLPHNTVSNFVKITNYNLTIDITLLEELVRTVIHAEESYIKL
NP_060387      NYENFLKVGEKAGAKCKQFFTAKVFAKLLHTDSYGRISIMQFFNYVMRKVWLHQTRIGLS
                :**: ::: .   *::::  .::::::   *.   .: :::  *:*.*.  .      *

C25A1.9        LPFSENSTEISSYSLQDFVATHFIPIMIEEPENP---VYYTAYAVGTIFFLLGARRRDCV
NP_060387      LYDVAGQGYLRESDLENYILELIPTLPQLDGLEKSFYSFYVCTAVRKFFFFLDPLRTGKI
                *  ::   :: :* :   :: :: * :::     . :*.. ** .:**:**... * .:

C25A1.9        YLKDLLASTLLLQLEECIHAENHCLSPPKIDVFTVAQFRTTLSEFRFLDSQRKGLLAPAD
NP_060387      KIQDILACSFIDDLLELRDEE--LSKESQETNWFSAPSALRVYGQYLNLDKDHNGMLSKEE
                 ::*:* *: :. :** :*: *    * : :. **    :.  ::  **.:::**:.  :*

C25A1.9        LKFFRDGIFNEVFTKRIFEISITYEDGRIDFKAFVDFVTALKFRHTTASAKYHFEILDLK
NP_060387      LSRHGTAIMTNVFLDRVFQECLTY-DGEMDYKTYLDFVLALENRKEPAALQYIFKLLDIE
                *.:: ..*:.::*::*:*:* :** :**  *::::***:**.  .*:  **::*:::

C25A1.9        DDGLLDEEEIRSISSFQLQNLPDYVPEDNSVNPEVATAELRDMR-LNQNGITLEEFLAN
NP_060387      NKGYLNVFSLN--YFFRAIQELMKIHGQDPVSFQDVKDEIFDMVKPKDPLKISLQDLLINS
                :  *  ::.    * .: :*: .*  :   :  *: ** *:::  :.  :*:::::

C25A1.9        RMNSTFAGFLSNSDDYMKYERREQ--------------
NP_060387      NQGDTVTTILIDLNGFWTYENREALVANDSENSADLDDT
                .*.::  *.: ::: .:** **
```

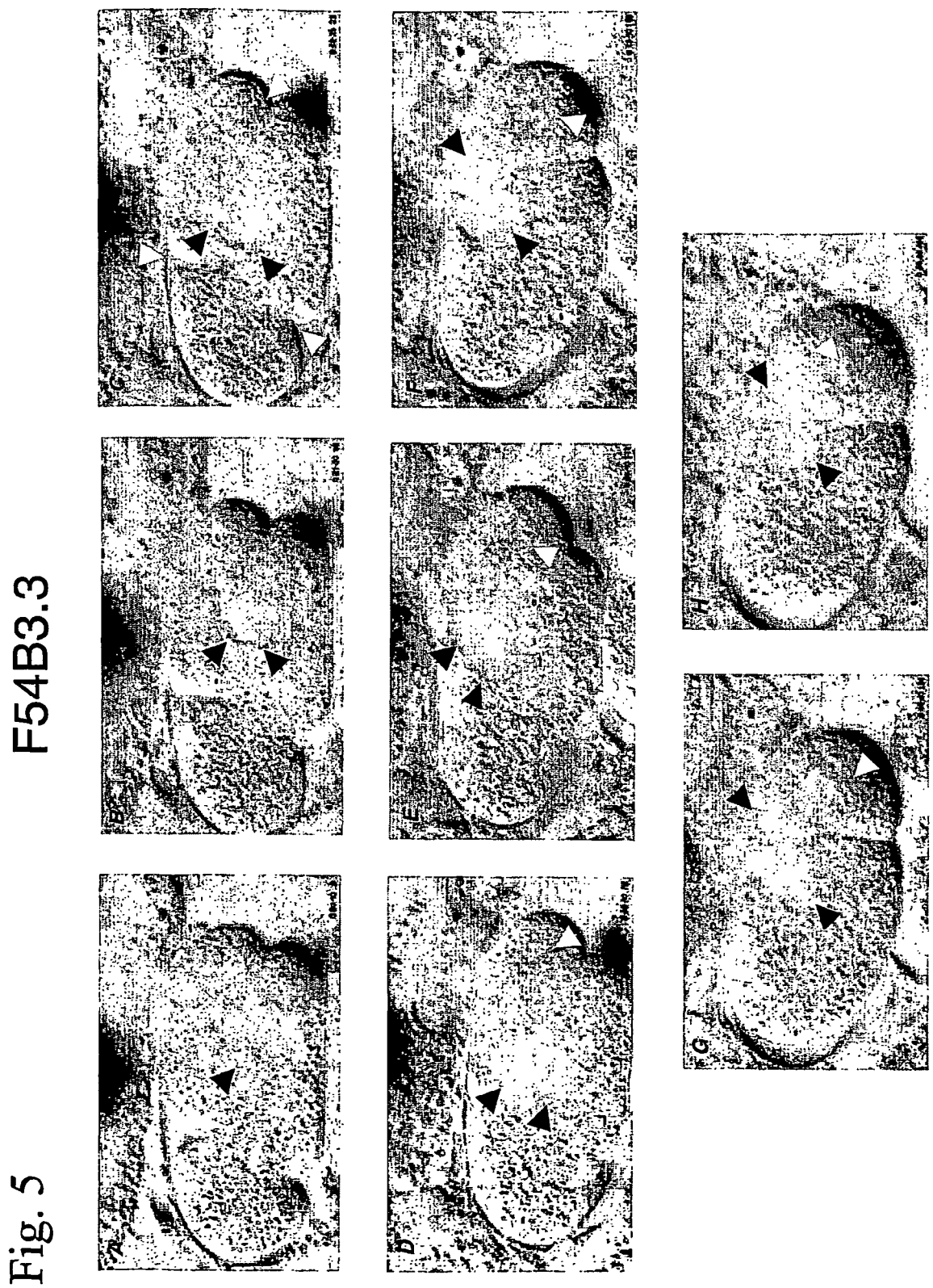
Fig. 5 F54B3.3

Fig. 6

CLUSTAL W (1.8) multiple sequence alignment

```
NP_060658    ------------------MS--WLFGINKG--PK------GEGAGPPPLPPA-QPGAEGGGDRGLGDR
AAF55289     ------------------MS--WLLGRNRQPQPDQTAGFSEGGAADPEG-RTAGEKSGDSQLSRA
F54B3.3      ------------------MSRKICFASSNFTERMSWLFGVQKNATPQIPDDFQAGAAPGGPQQPGQG
XP_109399    MASGADSKGDDLSTAILKQKNRPNRLIVDEAINEDNSVVSLSQPKMDELQLFRGDTVLLK
P46462       MASGADSKGDDLSTAILKQKNRPNRLIVDEAINEDNSVVSLSQPKMDELQLFRGDTVLLK
NP_015349    ------------------------MNVSKLLVSPTVTTNVLRIFAPRLPQIGASLLVQKKWALR
                                    .

NP_060658    PAPKDK---WSNFDPTGLERAAKAARELEHSRYAKDALNLAQMQEQTLQLEQQSKLKEYE
AAF55289     ERKAME---AYRFDSSALERAADAAKTLERSKHAREALELSKMQEATRQTEYNTKVKEYE
F54B3.3      QRQEGNSKMAYSFDSTALERAAKAAARDLEKFPNAKEALELSRMQEVTRQKEVENETKKIE
XP_109399    GKKRREAVCIVLSDDTCSDEKIRMNRVVRNNLRVRLGDVISIQPCPDVKYGKRIEVLPID
P46462       GKKRREAVCIVLSDDTCSDEKIRMNRVVRNNLRVRLGDVISIQPCPDVKYGKRIEVLPID
NP_015349    SKK------FYRFYSEKNSGEMPPKKEADSSGKASNKSTISSIDNSQPPPPSNTNDKTKQ
                                    ::              .

NP_060658    AAVEQLK-----------------------------
AAF55289     AHIEQAK-----------------------------
F54B3.3      AQLANMK-----------------------------
XP_109399    DTVEGITGNLFEVLLKPYFLEAYRPIRKGDIFLVRGGMRAVEFKVVETDPSPYCIVAPDT
P46462       DTVEGITGNLFEVLLKPYFLEAYRPIRKGDIFLVRGGMRAVEFKVVETDPSPYCIVAPDT
NP_015349    ANVAVSH-----------------------------
              .:

NP_060658    ---SEQIRAQAEERRKTLSEETRQHQARAQYQDKLARQRYEDQLKQQQLLN--------
AAF55289     ---VEQKRIDHEEERKTLIEETKQQQQRAQYQDQLSRKRYEDQLLQQQRVQ--------
F54B3.3      ---SEHIRVAEEERRTLGEETKHAHSRAEYQDQLARKRAEEELAMKARMQ---------
XP_109399    VIHCEGEPIKREDEEESLNEVGYDDIGGCRKQLAQIKEMVELPLRHPALFKAIGVKPPRG
P46462       VIHCEGEPIKREDEEESLNEVGYDDIGGCRKQLAQIKEMVELPLRHPALFKAIGVKPPRG
NP_015349    ---AMLATREQEANKDLTSPDAQAAFYKLLQSNYPQYVVSRFETPGIAS----------
                ::   *.    .                 :

NP_060658    ----------------------------EENLRKQBESVQKQE---
AAF55289     ----------------------------EENLRKQBESVQRQE---
F54B3.3      ----------------------------EESLRKQBESVKKQE---
XP_109399    ILLYGPPGTGKTLIARAVANETGAFFFLINGPEIMSKLAGESESNLRKAFEEAEKNAPAI
P46462       ILLYGPPGTGKTLIARAVANETGAFFFLINGPEIMSKLAGESESNLRKAFEEAEKNAPAI
NP_015349    ----------------------------SPECMELYMEALQRIG--
                                         . :: * .:
```

Fig. 6

CLUSTAL W (1.8) multiple sequence alignment (Con't)

```
NP_060658   ------------AMRRATVEREMELRHKNEMLRVEAEARARAK----AERENADIIREQIRLK
AAF55289    ------------AMRRQTIEHEIEMKEKNRLKLLEHELRAKAR----VDRENRDINLEKIRLK
F54B3.3     ------------QLRKQTIEHELALKHKYELEKIDAETRARAK----AARDNRDVNLEQMKLH
XP_109399   IFIDELDAIAPKREKTHGEVERRIVSQLLTLMDGLKQRAHVIVMAATNRPNSIDPALRRF
P46462      IFIDELDAIAPKREKTHGEVERRIVSQLLTLMDGLKQRAHVIVMAATNRPNSIDPALRRF
NP_015349   ------------RHSEADAVRQNLLTASSAGAVNPSLASSSS----NQSGYHGNFPSMYSP
                         :    :         .              .  :

NP_060658   AAEHRQTVLESIRTAG---TLFGEGFRAFVTDWDKVTATVAGLTLLAVGVYSAKNATLVAG
AAF55289    AQEHRTTVLEGIKTAG---TVIGAGAEAMLTDWDKVITAAGGLSLLALGVYTAKGATGVVS
F54B3.3     EEENRKTVIEKIKTSG---ELIGSGLNQFLNDKTKIAAAVGGLTALAVGWTAKRGTGVTA
XP_109399   GRFDREVDIGIPDATGRLEILQIHTKNMKLADDVDLEQVANETHGHVGADLAALCSEEAL
P46462      GRFDREVDIGIPDATGRLEILQIHTKNMKLADDVDLEQVANETHGHVGADLAALCSEEAL
NP_015349   LYGSRKEPLHVVVSESTFTVVSRWVKWLLVFGLITYSFSEGFKYIITENTTLLK-SSEVAD
                     *                    :    :                 :   ::.

NP_060658   RFIEARLGKPSLVRETSRITVLEALRHPIQVSRRLLSRPQ-DALEGVVLSP---------
AAF55289    RYVEARIGKPTLVGETSRFAFLDALKNPLHYLKRLRAKPT-DALQGVTLNP---------
F54B3.3     RYIESRLGKPSLVRETSRITPLEVLKHPIKSVQMMTRQKK-DPLNGVVLPP---------
XP_109399   QAIRKKMDLIDLEDETIDAEVMNSLAVTMDDFRWALSQSNPSALRETVVEVPQVTWEDIG
P46462      QAIRKKMDLIDLEDETIDAEVMNSLAVTMDDFRWALSQSNPSALRETVVEVPQVTWEDIG
NP_015349   KSVDVAKTNVKFDDVCGCDEARAELEEIVDFLKDPTKYES--------------------
                       .                     *

NP_060658   SLEARVRDIAIATRN-------TKKNRSLYRNILMYGPPGTGKILFAKKLALHSGMDYA
AAF55289    KLEERLRDIAIATKN-------TRINKGMYRNVLMHGPPGTGKTMFAKKLAEHSGMDFA
F54B3.3     ALERRLRLRDIAITTSN-----TKRNNGLFRNVMFYGPPGTGKILFAKSLAQHSGLDYA
XP_109399   GLEDVKRELQELVQYPVEHPDKFLKFGMTPSKGVLFYGPPGCGKTLLAKAIANECQANFI
P46462      GLEDVKRELQELVQYPVEHPDKFLKFGMTPSKGVLFYGPPGCGKTLLAKAIANECQANFI
NP_015349   -----------LGGKLPKGVLLTGPPGTGKLLARATAGEAGVDFF
                           :    ****  ****:::*.:     ::

NP_060658   IMTGGDVAPMGR-EGVTAMHKLFDWANTSRRGLLLFVDEADAFLRKRAT--EKISEDLRA
AAF55289    IMTGGDVAPMGK-EGVTAIHKVFDWSHTSRRGLLLFVDEADAFLRKRSS--EKISEDLRA
F54B3.3     VLTGGDIAPLGR-DGVSAIHKVFDWASKSRKGLIVFIDEADAFLQKRSK--NGMSEDTRA
XP_109399   SIKGPELLTMWFGESEANVREIFDKARQAAP-CVLFFDELDSIAKARGGNIGDGGAADR
P46462      SIKGPELLTMWFGESEANVREIFDKARQAAP-CVLFFDELDSIAKARGGNIGDGGAADR
NP_015349   FMSGSEFDEVYVGVGAKIRDLFAQARSRAP-AIIFIDELDAIGGKRNP---KDQAYAKQ
             :*  :  :    ::..*  :  :.:**: .**.** *::
```

Fig. 6

CLUSTAL W (1.8) multiple sequence alignment (Con't)

```
NP_060658      TLNAFLYRTG---QHSNKFMLVLASNQPEQFDWAIN--DRINEMVHFDLPGQEERERLVRM
AAF55289       ALNAFLYRTS---EQNPKFMLVLASNTPEQFDYAIN--DRLDEMVEFTLPGLEERERLLRL
F54B3.3        ALNAFLFRTG---EQSRKFMLVVASNQPEQFDWAVN--DRFDQLVEFTLPGMEERERILLQ
XP_109399      VINQILTEMDGMSTKKNVFIIGATNRPDIIDPAILRPGRLDQLIYIPLPDEKSRVAILKA
P46462         VINQILTEMDGMSTKKNVFIIGATNRPDIIDPAILRPGRLDQLIYIPLPDEKSRVAILKA
NP_015349      TLNQLLVELDGFSQTSGIIIIGATNFPEALDKALTRPGRFDKVVNVDLPDVRGRADILKH
               :*.:*.     .  ::: *:*  *:.** *:     .**::::.  **.. *  ::

NP_060658      YFDKYIVLKPATEGK--QRLK--LAQFDYGRKCSEVARLTEGMSGREIAQLAVSWQA--TA
AAF55289       YFDKYVLQPAAAGA--KRFK--LDTFDYGKTCSKMAALCEGMSGREISKLGVSWQA--AV
F54B3.3        YFNEHIVTPATSGSRSQRLK--LDNFDWVAKCNEVAKKTSGMSGRELSKLVIGWQA--SA
XP_109399      NLRKSPVAKDVDLEFLAKMTNGFSGADLTEICQRACKLAIRESIESEIRRERERQTNPSA
P46462         NLRKSPVAKDVDLEFLAKMTNGFSGADLTEICQRACKLAIRESIESEIRRERERQTNPSA
NP_015349      HMKKITLADNVDPTIIARGTPGLSGAELANLVNQAAVYACQKNAVSVDMSHFEWAKDKIL
               ::  :    .      .:   : :**  :*  :   *  .

NP_060658      YASEDG-----------VLTEAMMDTRVQDAVQQHQQK-
AAF55289       YASEDG-----------LLTEKMVLDRCYSAAQQHKQKRWPG-----------FR
F54B3.3        YASETG-----------VLTEAIVDRNTADAMVQHEHK-MEW-----------LE
XP_109399      MEVEED-----------DPVPEIRRDHFEEAMRFARRSVSDND-----------IR
P46462         MEVEED-----------DPVPEIRRDHFEEAMRFARRSVSDND-----------IR
NP_015349      MGAERKTMVLTDAARKATAFHEAGHAIMAKYTNGATPLYKATILPRGRALGITFQLPEMD
                 *

NP_060658      MCWLKAEGP-----------GRGDEPSPS-------------
AAF55289       IRSVLITNP-----------SQAQLPHPSP-------------
F54B3.3        KEQLKARNQEV---------KFGTTLKRETAV-----------
XP_109399      KYEMFAQTLQQ---------SRGFGSFRFPSGNQGGAGPSQGSQGSGGGTG
P46462         KYEMFAQTLQQ---------SRGFGSFRFPSGNQGGAGPSQGSQGSGGGTG
NP_015349      KVDITKRECQARLDVCMGGKIAEELIYGKDNTTSGCGSDLQSATGTARAMVTQYGMSDDV
                ::
```

CLUSTAL W (1.8) multiple sequence alignment

```
NP_057625      ------MEEWDVPQMKKEVESLKYQLAFQREMASKTIPELLKWIEDGIPKDPFLNPDLMKN
AAF52761       MDPSALQNMDRDALKKQIENMKYQASMERWPLSKSIAEMRSFIEENEKNDPLINAPDKKN
F08B6.2        -------MDKSDMQRTVDSLRSQLNIERTPITVSAAELRRFTES--QEDPLVNPIDKKV
AAA73553       ---MSNNMAKIAEARKTVEQLKLEVNIDRMKVSQAAAELLAFCETHAKDDPLVTPVPAAE
                        ::  :::::.  ::*   .*    .**::.    *

NP_057625      NPWVEKGK-C-------------TIL--------
AAF52761       NPWAEKGK-CPQHQQLDTPSQCSSQVLGQDLGESPDLVPVEMQHYNNNYYYYNYNLSY
F08B6.2        NPWAEKSK-C-------------SML--------
AAA73553       NPFRDKRLFC-------------TLI--------
               *:  :*   *              :*

NP_057625      ----------------------------------
AAF52761       EPPVDRSLGGGGKRSIQRLQQLVRRTRYELQQWPLIMQLLLFVLWLNAKFWQLVNEQVTY
F08B6.2        ----------------------------------
AAA73553       ----------------------------------

NP_057625      --------
AAF52761       RRRRWH
F08B6.2        --------
AAA73553       --------
                  *
```

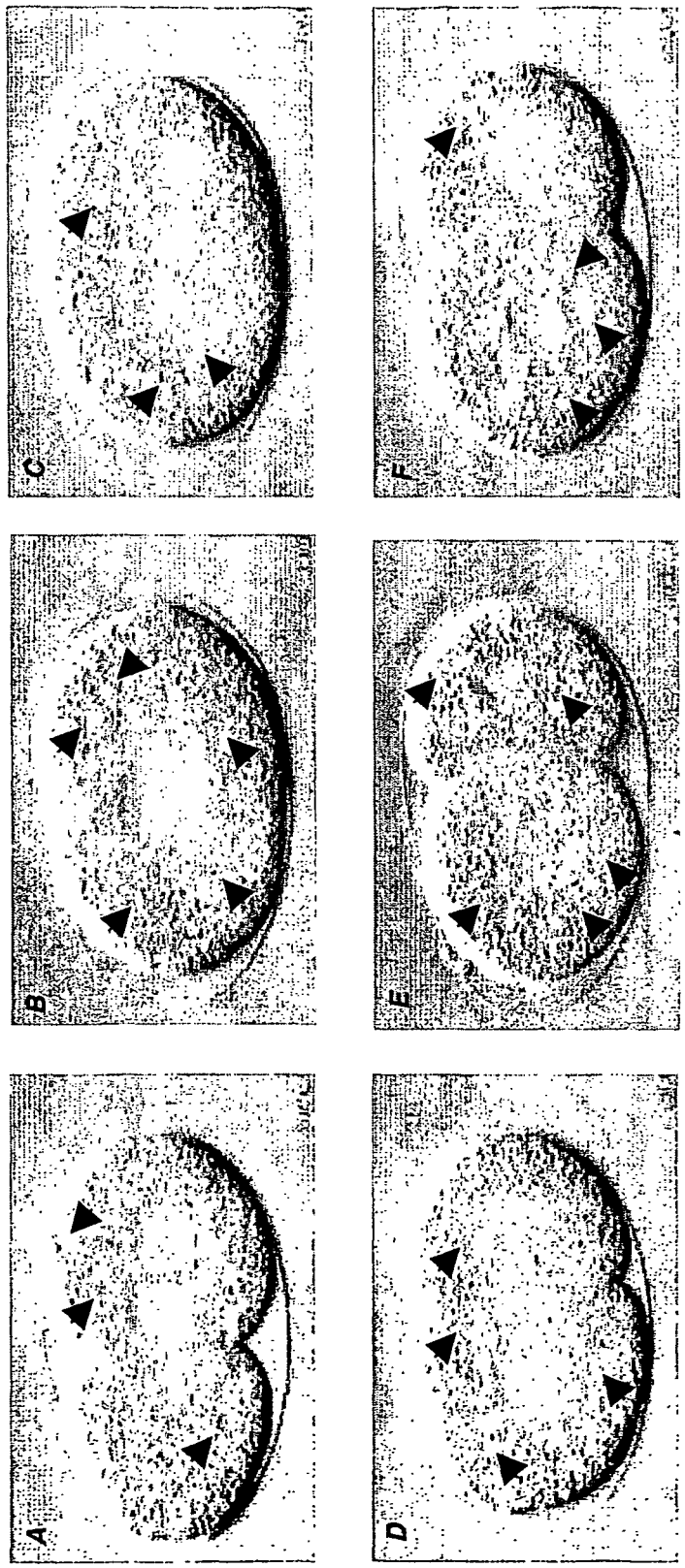
Fig. 9 CD4.4

Fig. 10

```
CLUSTAL W (1.8) multiple sequence alignment

NP_078943     ---------------MAGAGSEARFAGLSLVQLNELLEDEGQLTEMVQKMEETQNVQLN
CAD38936      DAWARLRFNPRWRRRRPWQGRMETLKDKTLQELEELQNDSEAIDQLALESPEVQDLQLE
AAF52060      ---------------MYQEYLYQLRATITPMCHEELKELLNDDKLDEKVD--EVLQVLRTQ
CD4.4         ----MFSQNPYESHVDVAVSAASANLRNMTNEQLISLLDDALLESIIVNLPQVRSMPTD
                               :  :*   *.*:         :  ::    :   ::

NP_078943     KEMTLASNRSLAEGNLLYQPQLDTLKARLTQKYQELQVLFEAYQIKKTKLDRQSSSASLE
CAD38936      REMALATNRSLAERNLEFQGPLEISRSNLSDRYQELRKLVERCQEQKAKLEKFSSALQPG
AAF52060      KTSVFEDNRSRAERNIEREPQIIELRGQLAELSEDGRTRCSSVQEKLSQLKEKSGGVGLE
CD4.4         KESALAANKSLAEWNLAQKPRIDAAKTQTVDLYDQVKKLQGEVAVLKSQLDSVSSKSLD
                : *:*   ** *:    :     :    :     ::**   .  ::**.    *

NP_078943     TLLALLQAEGAKIEEDTENMAEKFLDGELPLDSFIDVYQSKRKLAHMRRVKIEKLQEMVL
CAD38936      TLLDLLQVEGMKIEEESEAMAEKFLEGEVPLETFLENFSSMRMLSHLRRVVEKLQEVVR
AAF52060      TALALLQTAASESEEQTEEMVKKENDSDIGVEDFLDAFLPIRRTMHLRRLKAEKMQELMR
CD4.4         TTSSLMQVAAQEADDDAEALFTQFENGEISVEIFLKQFKDKKTIAHLRKIKSDRLAALLR
              * :* .   : :::::*  :*  :::::   * :. . :* :: ::   ::

NP_078943     KGQRLPQALA---------PLPPR--------PL-P--ELAPTAPL---PYPAPEASGP----P-A
CAD38936      K-PRASQELAGDAPPPRPPPVRPDPQGTPVVEEQPQPPLAMPPYPLPYSPSPSLPVGP
AAF52060      K----QRQG----------------------------------------------PGPNTSLP------
CD4.4         E------QTYS--------------------------------------SYAQPTVPPP------
                  *                                            *      .  *

NP_078943     VAPRRIPPPPPPVP--------AGRLATPFTAMSSGQ-AVPYPGLQCPFLPPRVGLP-TQQ
CAD38936      TAHGALPPAPFPVVSQPSFYSCPLGPTYPAAQIGPRGAAGYSWSPQRSMPPRPGYPGTPM
AAF52060      ----------------------------------AYGNVPSSGFYPASGGS------
CD4.4         ---------MP---HAQPGYPTGNHMPGIGNIQFG----
                                                *

NP_078943     GFS-S-----------QFVSPYP-----PPLPQR------P---P---PRLPPHQPG
CAD38936      GASGPGYPLRGGRAPSPGYPQQSPYPATGGKPPYPIQPQLPSFPGQPQPSVPLQPPYPPG
AAF52060      ---APYPIMG--PLMPMP------------------------PPSRPY
CD4.4         ---SGYSG----YPNISQP-------------------------SAGRHPF
                : *                                            *

NP_078943     ------FILQ---------
CAD38936      PAPPYGFPPPGPAWPGY
AAF52060      -------------
CD4.4         F-------------
                      :
```

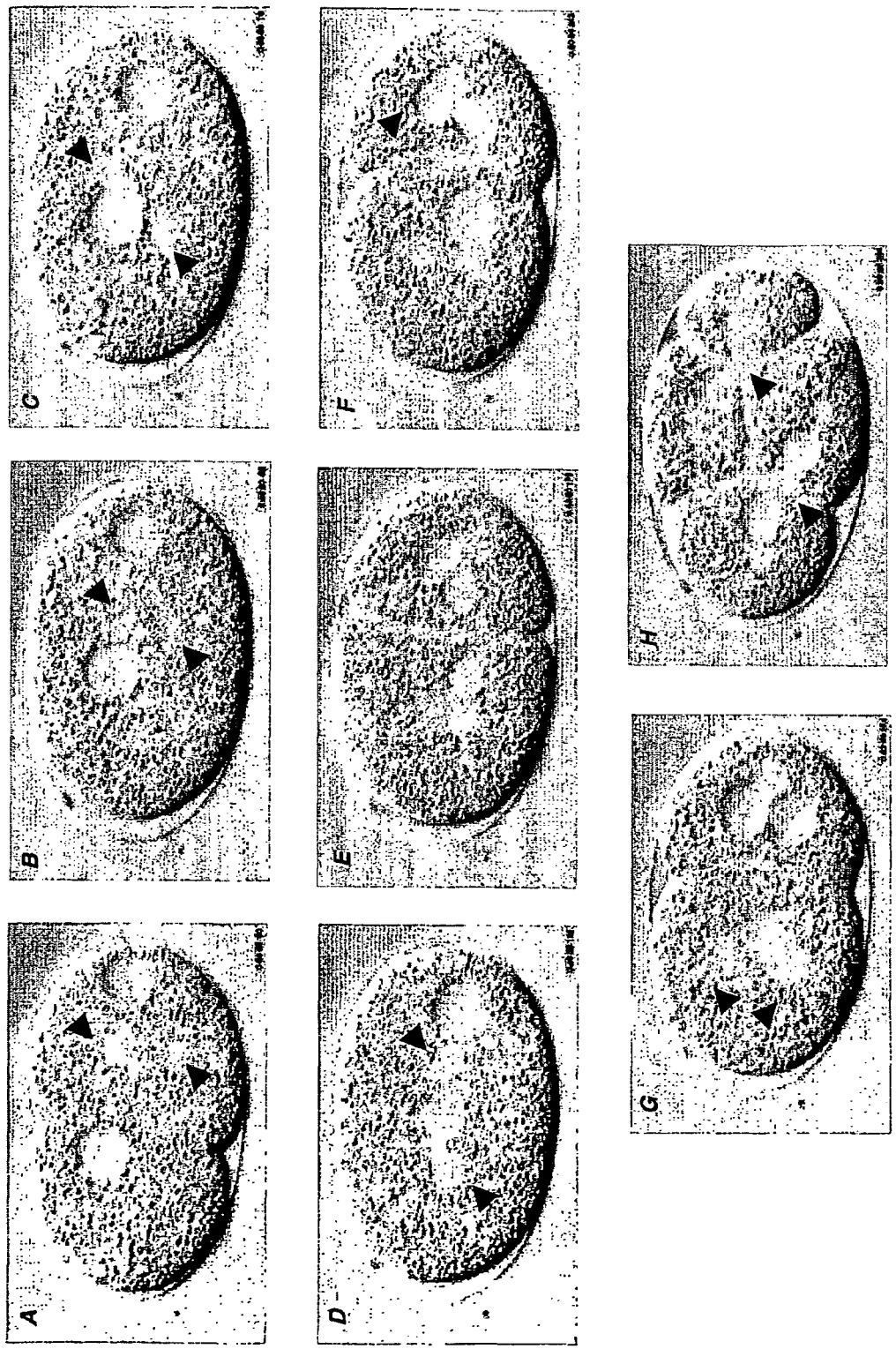
Fig. 11 ZK546.1

Fig. 12 1/7

CLUSTAL W (1.8) multiple sequence alignment

```
NP_056972    ------------------------------------------------------------
AAA74950     ---MAQQAADKYLYVDKNFINNPLAQADCGAKK-LVWVPSTKNGFEPASLKEEVGEEAIV
ZK546.1      ------------------------------------------------------------
NP_010225    -----------MDIIQGLIQQPKIQSVDETIP-TLCDRVENSTLISDRRSAVLGLKAFS
AAF53605     MSDDTSASGGTSAPFPSPVTADPEPGATASKLPGPIRSNIPTPATSGTGIPQPSKMKAPS
XP_109474    ------------------------------------------------------------

NP_056972    ------------------------------------------------------------
AAA74950     ELVENGKKVKVNKDDIQKMNPPKFSKVEDMAELTCLNEASVLHNLKERYYSGLIYTYSGL
ZK546.1      ------------------------------------------------------------
NP_010225    RQYRESVIASGLKPLLNTLKRDYMDEDSVKAILETILILFIRGDGHDDLTRGWISQQS-R
AAF53605     SFGSTGSVSKIGRPCCNHTTPKSGPPPREATSMSRESDDNLSSINSAYTDNSSAVLTANT
XP_109474    ----------------------------MAQSRRHMSSRTPSGSRMSTEASAR

NP_056972    ------------------------------------------------------------
AAA74950     FCVVINPYKNLPIYSEEIVDMYKGKKRHEMPPHIYAITDTAYRSMMQDREDQSILCTGES
ZK546.1      ------------------------------------------------------------
NP_010225    LQNGKYPSPLVMKQEKEQVDQFSLWIADALTQSEDLIHLLVEFWEIDNFHIRLYTIQLLE
AAF53605     EQFIIGQRVWLGGTRPGQIAFIGDTHFAAGEWAGVVLDEPNGKNDGCVSGKRYFQCEPKR
XP_109474    PLRVGSRVEVIGKGHRGTVAYVGATLFATGKWVGVILDEAKGKNDGTVQGRKYFTCDEGH

NP_056972    ------------------------------------------------------------
AAA74950     GAGKTENTKKVIQYLAHVASSHKSKKDQGELERQLLQANPILEAFGNAKTVKNDNSSRFG
ZK546.1      ------------------------------------------------------------
NP_010225    AVMATRPLKARSALISLPTSISTMVSLLDDMHEPIRDEAILLLMAVVNDSPHVQKLVAFE
AAF53605     GIFSRLTRLTTYPLAGAQTPTSPLAKSSPDRSRTVSPTASIRSSMLRSPGIGGKNGMAVG
XP_109474    GIFVRQSQIQVFEDGADTTSPETPDSSASKVLK---------------------------

NP_056972    ------------------------------------------------------------
AAA74950     KFIRINFDVNGYIVGANIETYLLEKSRAIRQAKEERTFHIFYYLLSGAGEHLKTDLLLEP
ZK546.1      ------------------------------------------------------------
NP_010225    NIFERLFSIIEEEGGLRGSLVVNDCLSLINNILKYNTSNQTLFLETGNLPKLAHLLSEPI
AAF53605     ----DRVIVSSGFGSRPGILRYLGETQFAPGNWCGVELDEPSGKNDGTVDDIRYFECKPK
XP_109474    ------------------------------REGADAAAKTSKLRGL
```

Fig. 12 2/7

```
NP_056972   ----------------------------------------------------------
AAA74950    YNKYRFLSNGHVTIPGQQDKDMFQETMEAMRIMGIPEDEQMGLLRVISGVLQLGNIVFKK
ZK546.1     ----------------------------------------------------------
NP_010225   SQDEVFFWNDQRIVNINTALDIVSLTVEPGNTVTTKHQNALLDSSVLMVVLRLAFFHNIP
AAF53605    YGVFVPIAKVSLSPSSKKTRLSRTGSRESLTSIGTMNSIATTATSRMRMNAQQRKSSTPV
XP_109474   KPKKAPTARKTTTRRPKPTRPASTGVAGPSSSLGPSGSASAGELSSSEPSTPAQTPLAAP

NP_056972   ----------------------------------------------------------
AAA74950    ERNTDQASMPDN----TAAQKVSHLLGINVTDFTRGILTPRIKVGRDYVQKAQTKEQADF
ZK546.1     ----------------------------------------------------------
NP_010225   KKVRPVALLTAANMVRSNEHAQLEFSKIDVPYFDPSLPVNSTANGGPIKLIPVVSILINW
AAF53605    KPILATPKSQFS-MQDLLREKQQHVEKLMVERDLDREDAQNQALQLQKNINELKARIVEL
XP_109474   IIPTPALTSPGAAPPLPSPSKEEEGLRAQVRDLEEKLETLRLKRSEDK---AKLKELEKH

NP_056972   ----------------------------------------------------------
AAA74950    AIEALAKATYERMFRWLVLRINKALDKTKRQGASFIGILDIAGFEIFDLNSFEQLCINYT
ZK546.1     ------------------------------------------MLDLTNKESESSSDNG
NP_010225   MLYANSVHTFDTRVACSRLLKAYFMDNFDLQRDFLLKQVQLCNNSTNNVGDNAKENGGSN
AAF53605    ESALDNERKKTEELQCSIDEAQFCGDELNAQSQVYKEKIHDLESKITKLVSATPSLQSIL
XP_109474   KIQLEQVQEWKSKMQEQQADLQRRLKEARKEAKEALEAKERYMEEMADTADAIEMATLDK

NP_056972   ------------------------------------MEETQPPP----------
AAA74950    NEKLQQLFNHTMFILEQEEYQREGIEWNFIDFGLDLQPCIDLIEKPAGPPGILAL---LD
ZK546.1     NSKYEDSID---------------------GREVGTSKPFKEERSLED----------
NP_010225   KSDKESDSD-------KDTDGKDGTEYEGSFKANLFEVLLNYDAELNLNPFKLFFTTDIF
AAF53605    PPDLPSDDG-----ALQEEIAKLQEKMTIQQKEVESRIAEQLEEEQRLREN---------
XP_109474   EMAEERAES--------------------LQQEVEALKERVDELTTDL----------

NP_056972   ----QPKLPLCDSLMIWLQTFNTASPCQD----------VKQLTSGVAMAQVLHQIDAAW
AAA74950    EECWFPKATDKSFVEKVVQEQGTHPKFQK----------PKQLKDKADFCIIHYAGKVDY
ZK546.1     -----LQADLADMAVWMEGLDATKLPLND---------PQLLCNGRAFSEVLHNVDKNF
NP_010225   MFFFQQDHKYSEELREITRNVTTGNDLEDEEPLKAIQTISELLTTSLTAADIRIPISYLT
AAF53605    --VKYLNEQIATLQSELVSKDEALEKFSLSECG------IENLRRELELLKEENEKQAQE
XP_109474   ---EILKAEIEEKGSDGAASSYQLKQLEE----------QNARLKDALVRMRDLSSSEK
```

Fig. 12 3/7

```
NP_056972    FNESWLSRIKEDVGDNWR---------------------------------------
AAA74950     KADEWLMKNMDPLNDNIATLLHQSSDKFVSELWKDVDRIIGLDQVAGMSETALPGAFKTR
ZK546.1      FTDGWLETMPENRTTNIMVFR------------------------------------
NP_010225    FLIYWLFGDFKATNDFLSDKS------------------------------------
AAF53605     AQAEFTRKLAEKSVEVLRLSS------------------------------------
XP_109474    QEHVKLQKLMEKKNQELEVVR------------------------------------

NP_056972    ------------------IKASN--------------------------VKKVLQ
AAA74950     KGMFRTVGQLYKEQLAKLMATLRNTNPNFVCCIIPNHEKKAGKLDPHLVLDQLRCNGVLE
ZK546.1      -------------------------------------------------SCTRKLW
NP_010225    ---------VIKSLLSFSYQIQDEDVTIKCLVTMLLGVAYEFSSKESPFPRKEYFEFIT
AAF53605     ---------ELQNLKATSDSLESERVN---------------------KTDECEILQT
XP_109474    -------------------------------------------------QQRERLQE

NP_056972    GIM--SYYHEFLGQQISEALIPDLNQITECSDPVELG---------------------
AAA74950     GIR--ICRQGFPNRVVFQEFRQRYEILTPNSIPKGFMDGKQACVLMIKALELDSNLYRIG
ZK546.1      RKM--FDYVNHINRTVVSSRWTDIHERIDGIYESDLP---------------------
NP_010225    KTLGKDNYASRIKQFKKDSYFSKVDMNEDSILTPELDETG------------------
AAF53605     EVRMRDEQIRELNQQLDEVTTQLNVQKADSSALDDMLRLQ-----------------
XP_109474    ELSQAESTIDELKEQVDAALGAEEMVEMLTDRNLNLEEKVR-----------------

NP_056972    --------------------RLLQLILGCAINCE---------KKQEHIQNIMTLEES--
AAA74950     QSKVFFRSGVLAHLEEERDLKITDVIIGFQACCRGYLARKAFAKRQQQLTAMKVLQRNCA
ZK546.1      --------------------AMVNLGMAVVTLAHIG-------KNAKRFVDYSKALTS--
NP_010225    ----LPKVYFSTYFIQLFNENIYRIRTALSHDPDEEPINKISFEEVEKLQRQCTKLKG--
AAF53605     ----KEGTEEKSTLLEKTEKELVQSKEQAAKTLNDKEQLEKQISDLKQLAEQEKLVREMT
XP_109474    --------------------ELRETVGDLEAMNEMN-------DELQENARETELELR--

NP_056972    ------------------------------VQHVVMTAIQELMSKEILSSP
AAA74950     AYLRLRNWQWWRLFTKVKPLLNSIRHEDELLAKEAELTKVREKHLAAENRLTEMETMQSQ
ZK546.1      ------------------------------THKSMMSNVAKMVTTVIDEMP
NP_010225    ---------------EITSLQTETESTHENLTEKLIALTNEHKELDEKYQILNSSHSS
AAF53605     EN-------------AINQIQLEKESIEQQLALKQNELEDFQKKQSESEVHLQEIKAQ
XP_109474    ------------------------EQLDMAGARVREAQKRVEAAQETVAD
```

Fig. 12 4/7

```
NP_056972   PNDAVGELEQQLKR------ALEELQEALAEK-EELRQRCEELDMQVTTLQDEKNSLVSE
AAA74950    LMAEKLQLQEQLQAKTELCAEAEELRARLTAKKQELEEICHDLEARVEEEEERCQYLQAE
ZK546.1     ENPCFHEISELHGSQSELN-SLSESSGKLNGN--GSSERRSNADQILVDAELEIERLRTE
NP_010225   LKENFSILETELKNVRDSLDEMTQLRDVLETKDKENQTALLEYKSTIHKQEDSIKTLEKG
AAF53605    NTQKDFELVESGESLKKLQQQLEQKTLGHEKLQAALEELKKEKETIIKEKEQELQQLQSK
XP_109474   YQQTIKKYRQLTAHLQDVNRELTNQQEASVERQQQPPPETFDFKIKFAETKAHAKAIEME
                                  :              :  .      :     : :

NP_056972   NEMMNEKLDQLDGSFDD---PNTVVAKKYFHAQLQLEQLQEE--------NFRLEAAKDD
AAA74950    KKKMQQNIQELEEQLEEEESARQKLQLEKVTTEAKLKKLEEDQI-IMEDQNCKLAKEKKL
ZK546.1     TENQRKEIERLTKSFET---AQHDMSSNSESGDISILEKQNEE---LRQKRRELEEKNLE
NP_010225   LETILSQKKKAEDGINKMGKDLFALSREMQAVEENCKNLQKEKDKSNVNHQKETKSLKED
AAF53605    SAESESALKVVQVQLEQLQQQAAASGEEGSKTVAKLHDEISQLKSQAEETQSELKSTQSN
XP_109474   LRQMEVAQANRHMSLLTAFMPDSFLRPGGDHDCVLVLLLMPR-LICKAELIRKQAQEKFD
                  :                                         .      :

NP_056972   YRVHCEELEKQLIEFQHRNDELTSLAEETRALKDEIDV----LRATS----DKANKLEST
AAA74950    LEDRVAEFTTDLMEEEEKSKSLAKLKNKHEAMITDLEER---LRREE----KQRQELEKT
ZK546.1     LDAAVDQFKGIVFELTNENDVLRRSDKERQRLQTVLDAAQSDLDEWK----TVANQYQKE
NP_010225   IAAKITEIKAINENLEEMKIQCNNLSKEKEHISKELVEYKSRFQSHDNLVAKLTEKLKSL
AAF53605    LEAKSKQLEAANGSLEEEAKKSGHLLEQITKLKSEVGETQAALSSCHTDVESKTKQLEAA
XP_109474   LSENCSERPGLRGAAGEQLSFAAGLVYSLSLLQATLHRYEHALSQCSVDVYKKVGSLYPE
                  :      .         :      :                      .

NP_056972   VEIYRQKLQDLNDLRKQVKTLQETNMMYMHN--------TVSLEEELKKANAARTQLETY
AAA74950    RRKLEGDSTDLSDQIAELQAQIAELKMQLAKKEEELQAALARVEEEAAQKNMALKKIREL
ZK546.1     AELSKQQDKEIKELLSQNKALKSRLDHHVKS--------ATLEDANKNGIAQLRTQVGGL
NP_010225   ANNYKDMQAENESLIKAVEESKNESSIQLSNLQNKIDSMSQEKENFQIERGSIEKNIEQL
AAF53605    NAALEKVNKEYAESRAEASDLQDKVKEITDT-------LHAELQAERSSSSALHTKLSKF
XP_109474   MSAHERSLDFLIELLHKDQLDETVNVEPLTK---------AIKYYQHLYSIHLAEQPEDS
             .    .   .          .                                    :

NP_056972   KRQVQDLHVKLSSE---------------------------------SKR----
AAA74950    ETQISELQEDLESERACRNKAEKQKRDLGEELEALKTELEDTLDSTAAQQELRSKREQEV
ZK546.1     TALNTELKASLDSK----------------------------------KR----
NP_010225   KKTISDLEQTKEEIISKSDSSKDEYESQISLLKEKLETATTANDENVNKISELTKTREEL
AAF53605    SDEIATGHKELTSKADAWS-----------------------------QEMLQKEKEL
XP_109474   TMQLADHIKFTQSALD--------------------------------CM
```

Fig. 12  5/7

```
NP_056972    ---------ADTLAFEMKRLEEKHEALLKEKERLIEQRDTLKETNEELRCSQVQQD---
AAA74950     SILKKTLEDEAKTHEAQIQEMRQKHSQAVEELAEQLEQTKRVKATLEKAKQTLENERGEL
ZK546.1      ---------CVEQLEIQLIQHKEKVKELEDRKDELIEERNRLENQLIFKEAVTPRS----
NP_010225    EAELAAYKNLKNELETKLETSEKALKEVKENEEHLKEEKIQLEKEATETKQQLNSLRAN-
AAF53605     QELRQQLQDSQDSQTKLKAEGERKEKSFEESIKNLQEEVTKAKTENLELSTGTQTTIKD-
XP_109474    G--------VEVGRLRAFLQGGQEATDIALLLRDLETSCSDTRQFCKKIRRRMPGTDAPG
                                       .             .  .

NP_056972    ----------------------------------------------------------HL
AAA74950     ANEVKALLQGKGDSEHKRKKVEAQLQELQVKFSEGERVRTELADKVSKLQVELDSVTGLL
ZK546.1      ----------------------------------------------------------LH
NP_010225    ----------------LESLEKEHEDLAAQLKKYEEQIANKERQYNEEISQLNDEITST
AAF53605     ------------------------LQERLEITNAELQHKEKMASEDAQKIADLKTLVEAI
XP_109474    ----------------------------------------------------IPAALAFG
                                                                      .

NP_056972    NQTDASATKSYENLAAEIMPVEYREVFIR---------------LQHENKM------LR
AAA74950     NQSDSKSSKLTKDFSALESQLQDTQELLQEENRQKLSLS-TKLKQMEDEKNS------FR
ZK546.1      ESMFEAGNLSFEPFS------EKNTLP------------------LEIENK-------R
NP_010225    QQENESIKKKNDELEGEVKAMKSTSEEQSNLKKSEIDALNLQIKELKKKNETNEASLLES
AAF53605     QVANANISATNAELSTVLEVLQAEKSETNHIFELFEMEADMNSERLIEKVTGIKEELKET
XP_109474    SQVSDTLLDCRKHLTWVVAVLQEVAAAAAQLIAPLAENEGLPVAALEELAFKAS-----E
                         :                :                   :

NP_056972    LQQEGSENERIEELQEQLEQKHRKMNELETEQR-------LSKERIRELQQQIEDLQKSL
AAA74950     EQLEEEEEEAKRNLEKQIATLHAQVTDMKKKMEDGVGCLETAEEEAKRRLQKDLEGLSQRL
ZK546.1      LTERIQELESLEPLKGELITLKSKNGVLEEEKL-------FATKQIEELQQQIEDLQENL
NP_010225    IKSVESETVKIKELQDECNFKEKEVSELEDKLKAS----EDKNSKYLELQKESEKIKEEL
AAF53605     HLQLDERQKKFEELEEKLKQAQQSEQKLQQESQ-------TSKEKLTEIQQSLQELQDSV
XP_109474    QIYGSPSSSPYECLRQSCTILISTMNKLATAMQEGEYDAERPPSKPPPVELRAAALRAEI
                .*..               :                .  ::      :    :

NP_056972    QE----------------------------------------------------------
AAA74950     EEKVAAYDKLEKTKTRLQQELDDLLVDLDHQRQSVSNLEKKQKKFDQLLAEEKTISAKYA
ZK546.1      LK----------------------------------------------------------
NP_010225    DAKTTELKIQLEKITN----------------------------------------LS
AAF53605     KQKEELVQNLEEKVRE------------------------------------S---SSIIE
XP_109474    TDAEG-------------------------------------------------------
```

Fig. 12 6/7

```
NP_056972      -QGSKSEGESSSK---------------------------------------
AAA74950       EERDRAEAEAREKETKALSLARALEEAMEQKA-----ELERLNKQFRTEMEDLMSSKDDV
ZK546.1        -NQEHASGDVVG-------------------------------------------
NP_010225      KAKEKSESELSRLKKTSSEERKNAEEQLEKLKNEIQIKNQAFEKERKLLNEGSSTITQEY
AAF53605       AQNTKLNESNVQLENKTSCLKETQDQLLES-------QKK--EKQLQEEAAKLSGELQQV
XP_109474      -LGLKLEDRETVIK-----------------------------------------
                   : .

NP_056972      -------------LKQKLEAHMEKLTEVHEELQK---------------KQELIEDLQPD
AAA74950       GKSVHELEKSNRALEQQVEEMKTQLEELEDELQATEDAKLRLEVNLQAMKAQFERDLQGR
ZK546.1        -------------LKIQLEKAEVEAQQMREAKMRAETN----------QAQVDEILKKR
NP_010225      SEKINTLEDELIRLQNENELKAKEIDNTRSELEKVSLSNDELLEEKQNTIKSLQDEILSY
AAF53605       QEANGDIKDSLVKVEELVKVLEEKLQAATSQLDAQQATN-KELQELLVKSQENEGNLQGE
XP_109474      -----------ELKKSLKIKGEELSEANVRLSLLEKKLDS-------AAKDADERIEKV
                    ::     :      :                       .    :

NP_056972      INQN-------VQKINELEAALQ--------------KKDEDMKAMEERYKMYLEKARNV
AAA74950       DEQSEEKKKQLVRQVREMEAELEDERKQRSIAMAARKKLEMDLKDLEAHIDTANKNREEA
ZK546.1        TAELEVN----ATALQKAKAVID-------------ELEYNSRPVSEDSMTSVQAFKEM
NP_010225      KDKITRNDEKLLSIERDNKRDLESLKEQLRAAQESKAKVEEGLKKLEEESSKEKAELEKS
AAF53605       SLAVTEKLQQLEQANGELKEALCQKENGLKELQG---KLDESNTVLESQKKSHNEIQDKL
XP_109474      QTRLDETQTLLRKKEKDFEETMD--------------ALQADIDQLEAEKAELKQRLNSQ
                   . :  :                        :  .  :.              .

NP_056972      IKTL---------------------------DPKLNPASAEIMLLRKQLAEKE---
AAA74950       IKQLRKLQAQMKDCMRDVDDTRASREEILAQAKENEKKLKSMEAEMIQLQEELAAAERAK
ZK546.1        KEENEK---------------------------LRQKVEKLEIELNTVTQGFEQEN---
NP_010225      KEMMKK---------------------------LESTIESNETELKSSMETIRKSD---
AAF53605       EQAQQK---------------------------ERTLQEETSKLAEQLSQLKQAN---
XP_109474      SKRT-----------------------------IEGLRGPPPSGIATLVSGIAGEE---
                :                                      :   .: :

NP_056972      ----------------------------RRIEILESECKVAKFRDYEEKLIVSAWYNKS-
AAA74950       RQAQQERDELADEIANSSGKGALALEEKRRLEALIALLEEELEEEQGNTELINDRLKKAN
ZK546.1        ----------------------------RLLTSASHQQVLNRSIDEVMSMRAHAGSEEPQ
NP_010225      ----------------------------EKLEQSKKSAEEDIKNLQHEKSDLISRINESE
AAF53605       ----------------------------EELQKSLQQKQLLLEKGNEFDTQLAEYQKVID
XP_109474      ----------------------------PQRGGAPGQAPGALPGPGLVKDSPLLLQQISAMR
```

Fig. 12 7/7

```
NP_056972     LAFQKLGMESRLVSGGGACSDTGACTPA----------RSFLAQQRHITNTRRNLSVKVP
AAA74950      LQIDQINTDLNLERSHAQKNENARQQLE----------RQNKELKAKLQEMESAVKSKYK
ZK546.1       TLLDTQKMSGALPWRSLASETRRELPTA----------MASILVLGFLVFIAWMFININS
NP_010225     KDIEELKSKLRIEAKSGSELETVKQELNNAQEKIRINAEENTVLKSKLEDIERELKDKQA
AAF53605      EMDDAASVKSALLEQLQNRVAELETALRQANDAQKTAYLETKELRRQLESLELEKSREVL
XP_109474     LHISQLQHENSILRGAQMKASLAALPPLH---------VAKLSLPPHEGPGGNLVAGALY
                     .    .    :

NP_056972     ATTSD-------------------------------------------------------
AAA74950      ASIAALEAK-------------IAQLEEQLDNETKERQAASKQVRRAEKKLKDVLLQVED
ZK546.1       ALNAPPNA----------------------------------------------------
NP_010225     EIKSNQEEKELLTSRLKELEQELDSTQQKAQKSEEERRAEVRKFQVEKSQLDEKAMLLET
AAF53605      SLKAQMNGAS-----------------SRSGKGDEVESLDIETSLAKINFLNSIIADMQQ
XP_109474     RKTSQLLEKLN---------------------QLSTHTHVVDITRSSPAAKSPSAQLME
                     :

NP_056972     ------------------------------------------------------------
AAA74950      ERRNAEQFKDQADKASTRLKQLKRQLEEAEEEAQRANASRRKLQRELEDATETADAMNRE
ZK546.1       ------------------------------------------------------------
NP_010225     KYNDLVNKEQAWKRDEDTVKKTTDSQRQEIEKLAKELDNLKAENSKLKEANEDRSEIDDL
AAF53605      KNDALKAKVQTLETLPMDFTKPHAFDALTKRKPAPRLFCDICDEFDQHDTEDCPIQGSED
XP_109474     QVAQLKSLSDTIEKLKDEVLKETVTQRPGATVPTDFATFPSSAFLRAKEEQQDDTVYMGK

NP_056972     ---------------------------------------------
AAA74950      VSSLKNKLRRGDMPFVVTRRIVRKGTGDCSDEEVDGKADGADAKATE
ZK546.1       ---------------------------------------------
NP_010225     MLLVTDLDEKNAKYRSKLKDLGVEISSDEEDDEEDDEEDEEEGQVA-
AAF53605      QDYSTPSSESNNNEKERKLPAPRKYCDSCEVFGHDTSECADDETY--
XP_109474     VTFSCAAGLGQRHRLVLTQEQLHQLHSRLIS----------------
```

C56C10.3
Fig. 13
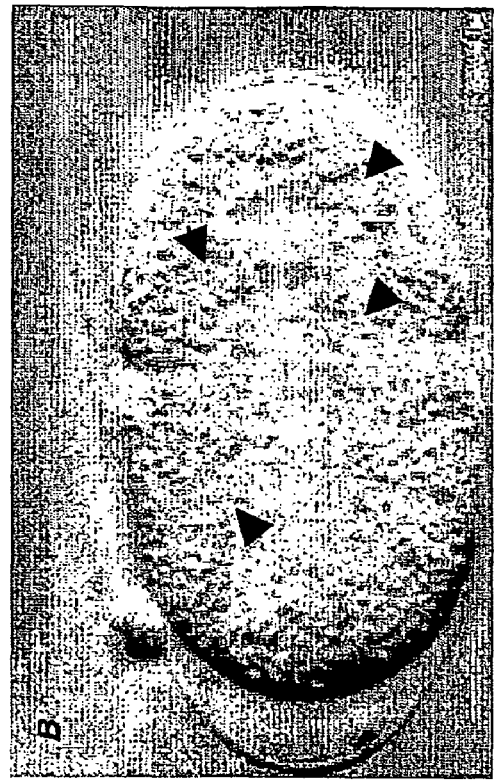
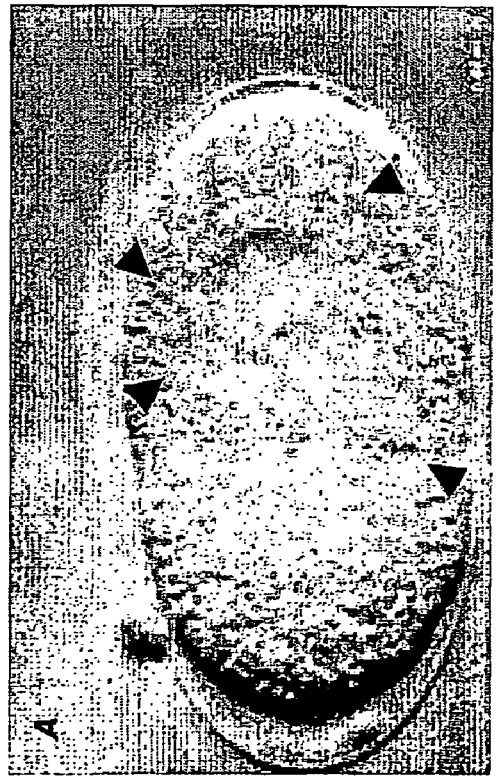

Fig. 14

CLUSTAL W (1.8) multiple sequence alignment for C56C10.3

```
XP_059282    MSVFGKLFGAGGGKAGKGGPTPQEAIQRLRDTEEMLSKKQEFLEKKIEQELTAAKKHGTK
NP_083638    MSVEGKLFGAGGGKAGKGGPTPQEAIQRLRDTEEMLSKKQEFLEKKIEQELTAAKKHGTK
C56C10.3     MSLFGKIF---GGRKQEAPSTPQESIQKLRETEEMLEKKQEFLEKKVIDEKQNAVKYGTK
AAF58977     MSFFGKMF---GGKK-EVAPTTGEAIQKLRETENMLIKKQEFLEAKIEDELNIARKNASK
             *.***:*    **:  : .*. *:***:**:**** ******** *: .*  .:**

XP_059282    NKRAALQALKRKKRYEKQLAQIDGTLSTIEFQREALENANTNTEVLKNMGYAAKAMKAAH
NP_083638    NKRAALQALKRKKRYEKQLAQIDGTLSTIEFQREALENANTNTEVLKNMGYAAKAMKAAH
C56C10.3     NKRMALQCLNRKRNFEKQLAHIDGVLSTIGYQREALENASTNAEVLNVMGTASKALKAAH
AAF58977     NKRVALQALKKKKRLEKQLQQIDGTLSTIEMQREALESANTNTAVLTTMKNAADALKRAH
             *** *** *:.:*:.:*** ****:***    *****::**.  **    .* *:* **:

XP_059282    DNMDIDKVDELMQDIADQQELAEEISTAISKPVGFGEEFDEDELMAELEELEQEELDKNL
NP_083638    DNMDIDKVDELMQDIADQQELAEEISTAISKPVGFGEEFDEDELMAELEELEQEELDKNL
C56C10.3     NNMDIDQVHDLMEDIAEQQEVANEIAEAISNPVGFSTAVDDDDLMRELEALEQEELDKEL
AAF58977     QNMDVDKVHDMDDIAEQQDVAREISDAISNPVAFGADLDDEDIERELDELEQENFDKEI
             :***:**:.::::.::****:. .*   :** **.*    . .:::** *  ****.::*::

XP_059282    LEISGPETVPLPNVPSIALPSKPAKK-------KEEEDDDMKELENWAGSM
NP_083638    LEISGPETVPLPNVPSVALPSKPAKK-------KEEEDDDMKELENWAGSM
C56C10.3     LDARAP-PVTLPDTPNIALPAVPASRP------RAKEADKDLEDLESWANA-
AAF58977     IGIPEP-TPTLPEAPTEDLPEKAKEKKKATTTAVEDDDDPDMKQLLSWSN--
             :  . *   * ::*.  :.*    .:         :.*   :::* .*::
```

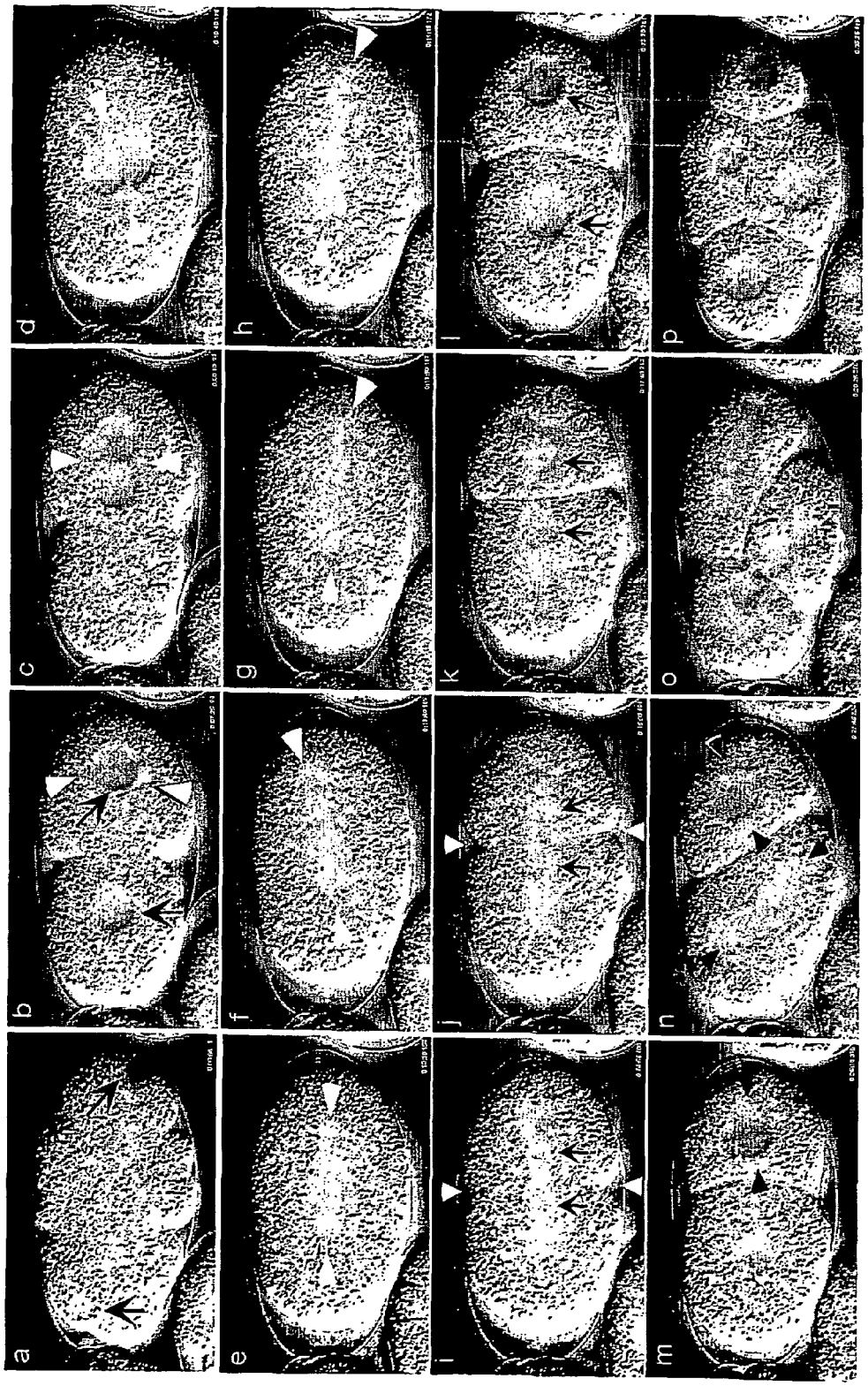

SEQUENCE LISTING

```
<160> NUMBER OF SEQ ID NOS: 91

<210> SEQ ID NO 1
<211> LENGTH: 423
<212> TYPE: DNA
<213> ORGANISM: Caenorhabditis elegans

<400> SEQUENCE: 1
atggctgaga aaaatcacca acaacaagaa cgactacctg gcaacccgtt tttcccatca      60
agaagcaacg ctggctcttc atttgacatg cccgaaacac cacatctcat cgattcgctc     120
acttctcaaa tcgacgaatt cacaattcaa agcataattg atactcagag acagagcttg     180
aaacgcttcg aaaagacaaa tgaaatgctc atgaattgcg ctcaactcgg cgatcgaaga     240
attgaaaaag caaaaaggga ttctgtggga cacaaagaga caattctgca gatgaaaact     300
gatttggaat ttattttcaa aaaaattcgc atgttcaaaa cagtttttgtc gtcaaagtat     360 ccagaagttt atgctgaagt gtcagccgag ctaacgccaa aacgaagcga ggaagacgaa     420
tga                                                                    423

<210> SEQ ID NO 2
<211> LENGTH: 140
<212> TYPE: PRT
<213> ORGANISM: Caenorhabditis elegans

<400> SEQUENCE: 2

Met Ala Glu Lys Asn His Gln Gln Gln Glu Arg Leu Pro Gly Asn Pro
1               5                   10                  15
```

```
Phe Phe Pro Ser Arg Ser Asn Ala Gly Ser Ser Phe Asp Met Pro Glu
            20                  25                  30

Thr Pro His Leu Ile Asp Ser Leu Thr Ser Gln Ile Asp Glu Phe Thr
        35                  40                  45

Ile Gln Ser Ile Ile Asp Thr Gln Arg Gln Ser Leu Lys Arg Phe Glu
    50                  55                  60

Lys Thr Asn Glu Met Leu Met Asn Cys Ala Gln Leu Gly Asp Arg Arg
65                  70                  75                  80

Ile Glu Lys Ala Lys Arg Asp Ser Val Gly His Lys Glu Thr Ile Leu
                85                  90                  95

Gln Met Lys Thr Asp Leu Glu Phe Ile Phe Lys Lys Ile Arg Met Phe
            100                 105                 110

Lys Thr Val Leu Ser Ser Lys Tyr Pro Glu Val Tyr Ala Glu Val Ser
        115                 120                 125

Ala Glu Leu Thr Pro Lys Arg Ser Glu Glu Asp Glu
    130                 135                 140

<210> SEQ ID NO 3
<211> LENGTH: 531
<212> TYPE: DNA
<213> ORGANISM: Homo sapiens

<400> SEQUENCE: 3
atggacctcc cggactcggc ctcgagggtc ttctgcggcc gcatcctgag catggtgaac      60
acagatgatg tcaacgccat catcctggcc cagaagaaca tgctggaccg ctttgagaag     120
accaatgaga tgctgctcaa cttcaacaac ctgtccagtg cccgcctgca gcagatgagc     180
gaacgcttcc tgcaccacac gaggacccta gtagagatga acgggacct  ggacagcatc     240 ttccgccgta tcaggacgct gaaagggaaa ctggccaggc agcacccaga ggccttcagc     300
catatcccag aggcatcctt cctggaggaa gaggatgaag accccatccc acccagcacc     360
acgaccacca ttgccacctc agaacagagc acgggctcat gtgacaccag ccccgacacc     420
gtctcgccct ccctgagccc cggcttcgag gacctgtccc atgtccaggc tggctcccca     480
gccatcaacg ccgcagcca  gacagatgac gaggagatga cgggcgaata g              531

<210> SEQ ID NO 4
<211> LENGTH: 176
<212> TYPE: PRT
<213> ORGANISM: Homo sapiens

<400> SEQUENCE: 4

Met Asp Leu Pro Asp Ser Ala Ser Arg Val Phe Cys Gly Arg Ile Leu
1               5                   10                  15

Ser Met Val Asn Thr Asp Asp Val Asn Ala Ile Ile Leu Ala Gln Lys
            20                  25                  30

Asn Met Leu Asp Arg Phe Glu Lys Thr Asn Glu Met Leu Leu Asn Phe
        35                  40                  45

Asn Asn Leu Ser Ser Ala Arg Leu Gln Gln Met Ser Glu Arg Phe Leu
    50                  55                  60

His His Thr Arg Thr Leu Val Glu Met Lys Arg Asp Leu Asp Ser Ile
65                  70                  75                  80

Phe Arg Arg Ile Arg Thr Leu Lys Gly Lys Leu Ala Arg Gln His Pro
                85                  90                  95

Glu Ala Phe Ser His Ile Pro Glu Ala Ser Phe Leu Glu Glu Glu Asp
            100                 105                 110
```

```
Glu Asp Pro Ile Pro Pro Ser Thr Thr Thr Ile Ala Thr Ser Glu
        115                 120                 125

Gln Ser Thr Gly Ser Cys Asp Thr Ser Pro Asp Thr Val Ser Pro Ser
130                 135                 140

Leu Ser Pro Gly Phe Glu Asp Leu Ser His Val Gln Ala Gly Ser Pro
145                 150                 155                 160

Ala Ile Asn Gly Arg Ser Gln Thr Asp Asp Glu Glu Met Thr Gly Glu
            165                 170                 175

<210> SEQ ID NO 5
<211> LENGTH: 639
<212> TYPE: DNA
<213> ORGANISM: Drosophila melanogaster

<400> SEQUENCE: 5
atgagccact tgggccttgc ggatgtgcac cagtccgagg atgccactcc tgacctggaa      60
tccttcactg gcttcggcaa ctccgccgcc gaggccttca ttcaaagtct cgcaggaatg     120
gtgaatcagg gcgatgtgga gaccatgata cgggctcaaa agcaaatgct gcaacgcttt     180
gagaaaacca acgagatgct gctcaactgc aatgccttat cgcagagtcg tttgaaaagt     240
gccagcgagg atttcaaaag acacgtgaaa tgcctgagcg aaatgaagaa ggatctggat     300
tacatattcc gcaagatacg gatcatcaag cagaagctac agtcgcagtt ccccgccatt     360
tacgccgaag ttcagccgca gcgtagcagt ttggctgagg aagccgagga tgatacggaa     420
gcccaggcta aaagactgc agaaacacct gctcctgctg ccgcaaaacc tgtcctatcc      480
accaagaaaa gtgccgccac catagagtac gtgcagatgg aggaggcagt ggacaatggc     540
actgtggaga tcgaaaacga gctgatcaag cgagtttgtt ccgtggaaac tgccaatccc     600
aatgattcct ccgactgcac atccgaggat acaggttaa                            639

<210> SEQ ID NO 6
<211> LENGTH: 212
<212> TYPE: PRT
<213> ORGANISM: Drosophila melanogaster

<400> SEQUENCE: 6

Met Ser His Leu Gly Leu Ala Asp Val His Gln Ser Glu Asp Ala Thr
1               5                   10                  15

Pro Asp Leu Glu Ser Phe Thr Gly Phe Gly Asn Ser Ala Ala Glu Ala
            20                  25                  30

Phe Ile Gln Ser Leu Ala Gly Met Val Asn Gln Gly Asp Val Glu Thr
        35                  40                  45

Met Ile Arg Ala Gln Lys Gln Met Leu Gln Arg Phe Glu Lys Thr Asn
    50                  55                  60

Glu Met Leu Leu Asn Cys Asn Ala Leu Ser Gln Ser Arg Leu Lys Ser
65                  70                  75                  80

Ala Ser Glu Asp Phe Lys Arg His Val Lys Cys Leu Ser Glu Met Lys
                85                  90                  95

Lys Asp Leu Asp Tyr Ile Phe Arg Lys Ile Arg Ile Ile Lys Gln Lys
            100                 105                 110

Leu Gln Ser Gln Phe Pro Ala Ile Tyr Ala Glu Val Gln Pro Gln Arg
        115                 120                 125

Ser Ser Leu Ala Glu Glu Ala Glu Asp Asp Thr Glu Ala Gln Ala Lys
    130                 135                 140

Lys Thr Ala Glu Thr Pro Ala Pro Ala Ala Lys Pro Val Leu Ser
145                 150                 155                 160
```

Thr Lys Lys Ser Ala Ala Thr Ile Glu Tyr Val Gln Met Glu Glu Ala
            165                 170                 175

Val Asp Asn Gly Thr Val Glu Ile Glu Asn Glu Leu Ile Lys Arg Val
        180                 185                 190

Cys Ser Val Glu Thr Ala Asn Pro Asn Asp Ser Ser Asp Cys Thr Ser
    195                 200                 205

Glu Asp Thr Gly
    210

<210> SEQ ID NO 7
<211> LENGTH: 1215
<212> TYPE: DNA
<213> ORGANISM: Caenorhabditis elegans

<400> SEQUENCE: 7

| | | | | | |
|---|---|---|---|---|---|
| atgccaaccg | acgaaccttc | gaagcgaaaa | tccattttac | caacgattcc | aacatccctg | 60 |
| atgttgaaga | aaagtaacga | agcattgagt | gacttcgaac | gaacatttaa | tgatcgagtt | 120 |
| atggatatat | ttgccgaaaa | tcgaagaata | atgtgtagagg | agtttaaaaa | aaatgccgaa | 180 |
| tgcttttaa | acatcattcg | atcgaacaaa | atcgatttaa | attggggtga | aggggagaa | 240 |
| agtagatatg | tgacgataac | tcgattaatg | aaaatactca | aaacttcacc | acaatcaatc | 300 |
| aaagatctac | ttccacataa | cacagtgtcg | aatttcgtta | aaataaccaa | ttataattta | 360 |
| acaattgata | tcactctttt | agaggagctt | gtacgaacag | tcattcacgc | tgaggagtcc | 420 |
| tacatcaaac | ttcttccatt | tcagaaaat | agcacagaga | tttccagtta | tagtctccaa | 480 |
| gactttgtgg | ccacacattt | tattccaatt | atgattgaag | aaccggaaaa | tcctgtctat | 540 |
| tatacagctt | acgcagttgg | aacaatattt | ttcctattgg | gtgctcgacg | gcgagactgt | 600 |
| gtatatttga | aggatttact | tgcttcaaca | cttctactac | aactcgaaga | gtgtattcat | 660 |
| gcagagaatc | attgcttatc | acctccgaaa | attgatgtat | tcaccgtcgc | tcaatttcga | 720 |
| accactttat | cagaattccg | attccttgac | tcccaacgaa | agggattgtt | ggcgccagcg | 780 |
| gacttgaaat | ttttcagaga | cggaatcttc | aatgaggttt | tcaccaagcg | aatcttcgaa | 840 |
| atttcaataa | cctatgaaga | tggacgtatt | gatttcaaag | cgttcgttga | ttttgtcacc | 900 |
| gctctaaagt | tccgtcatac | cactgcctcc | gccaaatacc | atttcgaaat | tctggatcta | 960 |
| aaggatgatg | gactgttgga | tgaggaagaa | attcgatcaa | tatcatcatt | tcagcttcaa | 1020 |
| aacctgccag | attacgtccc | ggaagataat | agtgtgaacc | cggaagtagc | aactgccgaa | 1080 |
| ctgagagata | tgatgcgtct | gaatcagaat | ggaattacat | tggaagagtt | tcttgctaat | 1140 |
| cggatgaact | cgacgtttgc | tggattcctc | tccaattccg | atgattacat | gaagtacgaa | 1200 |
| cgacgcgagc | aatag | | | | | 1215 |

<210> SEQ ID NO 8
<211> LENGTH: 404
<212> TYPE: PRT
<213> ORGANISM: Caenorhabditis elegans

<400> SEQUENCE: 8

Met Pro Thr Asp Glu Pro Ser Lys Arg Lys Ser Ile Leu Pro Thr Ile
1               5                   10                  15

Pro Thr Ser Leu Met Leu Lys Lys Ser Asn Glu Ala Leu Ser Asp Phe
            20                  25                  30

Glu Arg Thr Phe Asn Asp Arg Val Met Asp Ile Phe Ala Glu Asn Arg
        35                  40                  45

```
Arg Ile Asp Val Glu Glu Phe Lys Lys Asn Ala Glu Cys Phe Leu Asn
         50                  55                  60

Ile Ile Arg Ser Asn Lys Ile Asp Leu Asn Trp Gly Glu Gly Gly Glu
 65                  70                  75                  80

Ser Arg Tyr Val Thr Ile Thr Arg Leu Met Lys Ile Leu Lys Thr Ser
                 85                  90                  95

Pro Gln Ser Ile Lys Asp Leu Leu Pro His Asn Thr Val Ser Asn Phe
            100                 105                 110

Val Lys Ile Thr Asn Tyr Asn Leu Thr Ile Asp Ile Thr Leu Leu Glu
            115                 120                 125

Glu Leu Val Arg Thr Val Ile His Ala Glu Ser Tyr Ile Lys Leu
        130                 135                 140

Leu Pro Phe Ser Glu Asn Ser Thr Glu Ile Ser Ser Tyr Ser Leu Gln
145                 150                 155                 160

Asp Phe Val Ala Thr His Phe Ile Pro Ile Met Ile Glu Glu Pro Glu
                165                 170                 175

Asn Pro Val Tyr Tyr Thr Ala Tyr Ala Val Gly Thr Ile Phe Phe Leu
            180                 185                 190

Leu Gly Ala Arg Arg Arg Asp Cys Val Tyr Leu Lys Asp Leu Leu Ala
        195                 200                 205

Ser Thr Leu Leu Leu Gln Leu Glu Glu Cys Ile His Ala Glu Asn His
    210                 215                 220

Cys Leu Ser Pro Pro Lys Ile Asp Val Phe Thr Val Ala Gln Phe Arg
225                 230                 235                 240

Thr Thr Leu Ser Glu Phe Arg Phe Leu Asp Ser Gln Arg Lys Gly Leu
                245                 250                 255

Leu Ala Pro Ala Asp Leu Lys Phe Phe Arg Asp Gly Ile Phe Asn Glu
            260                 265                 270

Val Phe Thr Lys Arg Ile Phe Glu Ile Ser Ile Thr Tyr Glu Asp Gly
        275                 280                 285

Arg Ile Asp Phe Lys Ala Phe Val Asp Phe Val Thr Ala Leu Lys Phe
290                 295                 300

Arg His Thr Thr Ala Ser Ala Lys Tyr His Phe Glu Ile Leu Asp Leu
305                 310                 315                 320

Lys Asp Asp Gly Leu Leu Asp Glu Glu Glu Ile Arg Ser Ile Ser Ser
                325                 330                 335

Phe Gln Leu Gln Asn Leu Pro Asp Tyr Val Pro Glu Asp Asn Ser Val
            340                 345                 350

Asn Pro Glu Val Ala Thr Ala Glu Leu Arg Asp Met Met Arg Leu Asn
        355                 360                 365

Gln Asn Gly Ile Thr Leu Glu Glu Phe Leu Ala Asn Arg Met Asn Ser
    370                 375                 380

Thr Phe Ala Gly Phe Leu Ser Asn Ser Asp Asp Tyr Met Lys Tyr Glu
385                 390                 395                 400

Arg Arg Glu Gln

<210> SEQ ID NO 9
<211> LENGTH: 1362
<212> TYPE: DNA
<213> ORGANISM: Homo sapiens

<400> SEQUENCE: 9
atggactgga aagaagttct tcgtcggcgc ctagcgacgc ccaacacctg tccaaacaaa    60
```

-continued

```
aaaaaaagtg aacaagaatt aaaagatgaa gaaatggatt tatttacaaa atattactcc    120
gaatggaaag gaggtagaaa aaacacaaat gaattctata agaccattcc ccggtttat     180
tataggctgc ctgctgaaga tgaagtctta ctacagaaat taagagagga atcaagagct    240
gtctttctac aaagaaaaag cagagaactg ttagataatg aagaattaca gaacttatgg    300
ttttttgctgg acaaacgcca gacaccacct atgattggag aggaagcgat gatcaattac    360
gaaaactttt tgaaggttgg tgaaaaggct ggagcaaagt gcaagcaatt tttcacagca    420
aaagtctttg ctaaactcct tcatacagat tcatatggaa gaatttccat catgcagttc    480
tttaattatg tcatgagaaa agtttggctt catcaaacaa gaataggact cagtttatat    540
gatgtcgctg gcaggggta ccttcgggaa tctgatttag aaaactacat attggaactt    600
atccctacgt tgccacaatt agatggtctg aaaaatctt tctactcctt ttatgtttgt    660
acagcagtta ggaagttctt cttctttta gatcctttaa gaacaggaaa gataaaaatt    720
caagatattt tagcatgcag cttcctagat gatttattgg agctaaggga tgaggaactg    780
tccaaggaga gtcaagaaac aaattggttt tctgctcctt ctgccctaag agtttatggc    840
cagtacttga atcttgataa agatcacaat ggcatgctca gtaaagaaga actctcacgc    900
catggaacag ctaccatgac caatgtcttc ttagaccgtg ttttccagga gtgtctcact    960
tatgatggag aaatggacta aagacctac ttggactttg tccttgcatt agaaaacaga   1020
aaggaacctg cagctctaca atatattttc aaactgcttg atattgagaa caaaggatac   1080
ctgaatgtct tttcacttaa ttatttcttt agggccatac aggaactaat gaaaatccat   1140
ggacaagatc ctgtttcatt tcaagatgtc aaggatgaaa tctttgacat ggtaaaacca   1200
aaggatcctt tgaaaatctc tcttcaggat ttaatcaaca gtaatcaagg agacacagta   1260
accaccattc taatcgattt gaatggcttc tggacttacg agaacagaga ggctcttgtt   1320
gcaaatgaca gtgaaaactc tgcagacctt gatgatacat ga                     1362
```

<210> SEQ ID NO 10
<211> LENGTH: 453
<212> TYPE: PRT
<213> ORGANISM: Homo sapiens

<400> SEQUENCE: 10

```
Met Asp Trp Lys Glu Val Leu Arg Arg Arg Leu Ala Thr Pro Asn Thr
1               5                   10                  15

Cys Pro Asn Lys Lys Ser Glu Gln Glu Leu Lys Asp Glu Glu Met
            20                  25                  30

Asp Leu Phe Thr Lys Tyr Tyr Ser Glu Trp Lys Gly Gly Arg Lys Asn
        35                  40                  45

Thr Asn Glu Phe Tyr Lys Thr Ile Pro Arg Phe Tyr Tyr Arg Leu Pro
    50                  55                  60

Ala Glu Asp Glu Val Leu Leu Gln Lys Leu Arg Glu Glu Ser Arg Ala
65                  70                  75                  80

Val Phe Leu Gln Arg Lys Ser Arg Glu Leu Leu Asp Asn Glu Glu Leu
                85                  90                  95

Gln Asn Leu Trp Phe Leu Leu Asp Lys Arg Gln Thr Pro Pro Met Ile
            100                 105                 110

Gly Glu Glu Ala Met Ile Asn Tyr Glu Asn Phe Leu Lys Val Gly Glu
        115                 120                 125

Lys Ala Gly Ala Lys Cys Lys Gln Phe Phe Thr Ala Lys Val Phe Ala
    130                 135                 140
```

```
Lys Leu Leu His Thr Asp Ser Tyr Gly Arg Ile Ser Ile Met Gln Phe
145                 150                 155                 160

Phe Asn Tyr Val Met Arg Lys Val Trp Leu His Gln Thr Arg Ile Gly
                165                 170                 175

Leu Ser Leu Tyr Asp Val Ala Gly Gln Gly Tyr Leu Arg Glu Ser Asp
            180                 185                 190

Leu Glu Asn Tyr Ile Leu Glu Leu Ile Pro Thr Leu Pro Gln Leu Asp
        195                 200                 205

Gly Leu Glu Lys Ser Phe Tyr Ser Phe Tyr Val Cys Thr Ala Val Arg
    210                 215                 220

Lys Phe Phe Phe Phe Leu Asp Pro Leu Arg Thr Gly Lys Ile Lys Ile
225                 230                 235                 240

Gln Asp Ile Leu Ala Cys Ser Phe Leu Asp Asp Leu Leu Glu Leu Arg
                245                 250                 255

Asp Glu Glu Leu Ser Lys Glu Ser Gln Glu Thr Asn Trp Phe Ser Ala
            260                 265                 270

Pro Ser Ala Leu Arg Val Tyr Gly Gln Tyr Leu Asn Leu Asp Lys Asp
        275                 280                 285

His Asn Gly Met Leu Ser Lys Glu Glu Leu Ser Arg His Gly Thr Ala
    290                 295                 300

Thr Met Thr Asn Val Phe Leu Asp Arg Val Phe Gln Glu Cys Leu Thr
305                 310                 315                 320

Tyr Asp Gly Glu Met Asp Tyr Lys Thr Tyr Leu Asp Phe Val Leu Ala
                325                 330                 335

Leu Glu Asn Arg Lys Glu Pro Ala Ala Leu Gln Tyr Ile Phe Lys Leu
            340                 345                 350

Leu Asp Ile Glu Asn Lys Gly Tyr Leu Asn Val Phe Ser Leu Asn Tyr
        355                 360                 365

Phe Phe Arg Ala Ile Gln Glu Leu Met Lys Ile His Gly Gln Asp Pro
    370                 375                 380

Val Ser Phe Gln Asp Val Lys Asp Glu Ile Phe Asp Met Val Lys Pro
385                 390                 395                 400

Lys Asp Pro Leu Lys Ile Ser Leu Gln Asp Leu Ile Asn Ser Asn Gln
                405                 410                 415

Gly Asp Thr Val Thr Thr Ile Leu Ile Asp Leu Asn Gly Phe Trp Thr
            420                 425                 430

Tyr Glu Asn Arg Glu Ala Leu Val Ala Asn Asp Ser Glu Asn Ser Ala
        435                 440                 445

Asp Leu Asp Asp Thr
    450

<210> SEQ ID NO 11
<211> LENGTH: 1833
<212> TYPE: DNA
<213> ORGANISM: Caenorhabditis elegans

<400> SEQUENCE: 11
atgagccgga aaatctgttt tgcatcatct aattttactg aaaagatgtc ttggttattt      60
ggtgttcaaa aaacgctac tccgcagatt ccggatgatt ttcaagcagg tgctgctcct      120
ggcggtccac aacaaccagg tcaaggccaa cggcaagagg gaaacagcaa atggcatat     180 tccttcgact caacagcttt ggagcgtgcc gccaaggctg ctcgtgatct agagaaattt     240
ccaaatgcca agaagctctc tgaattgtcg agaatgcaag aagttacacg ccaaaaagag     300
gtcgagaacg agaccaagaa gatcgaagct caattggcca atatgaaatc agagcacatt     360
```

```
cgtgttgctg aagaagaacg gaggaagact ttgggagaag agactaaaca tgcgcattcg    420
cgtgctgaat atcaagatca attggccaga aagagagccg aagaggagct tgccatgaaa    480
gctagaatgc aggaagaaag cctccgaaaa caagaagagt ctgtcaagaa gcaggaacaa    540
cttcgcaagc aaactattga gcatgagtta gcattaaaac acaaatacga gctcgagaaa    600
attgacgcag agaccagagc cagggcaaag gctgctcgag ataacagaga tgtaaactta    660
gagcaaatga agcttcacga agaagagaac cgaaaaactg tcattgaaaa aattaaaacc    720
agtggagaac ttatcggttc tggactcaat caattttttga atgataaaac gaaaatcgct    780
gctgcagtag gaggattgac tgctttggct gtcggctggt ataccgctaa acgaggaact    840
ggagtcaccg caagatacat cgaatctcgt ctcggaaaac caagtcttgt aagaaaaca     900 tccagaatca ctccacttga agtactcaaa cacccaatta aaagtgttca atgatgact     960 cgtcagaaga aggatccact gaatggagtt gtattaccac tgctttggga acgtcgtctt   1020
cgtgatattg ccattaccac ctcaaacaca aagagaaata atggactttt ccgtaatgta   1080
atgttctacg gaccaccagg aaccggaaag acacttttcg caaagagttt ggctcaacat   1140
tccggactcg attacgcagt tctcactgga ggagatattg ctccacttgg acgtgatgga   1200
gtatctgcaa ttcataaagt attcgactgg gcttcaaaaa gtcgcaaagg gttgattgtt   1260
tttattgacg aagctgacgc tttttttgcaa aagagatcaa agaatggaat gtctgaagac   1320
acacgtgcag ctctcaacgc tttcctcttc agaactggag agcagtcgag aaagttcatg   1380
cttgtcgtgg cttctaatca gccagagcag ttcgattggg cagttaacga tcgtttcgat   1440
cagcttgtcg aattcacact gccaggaatg gaagaacgtg aacgaattct tctgcaatac   1500
ttcaacgagc acatcgtcac tccagcaact agtggatctc gttctcaacg actgaaactc   1560
gataactttg attgggttgc taagtgtaat gaagttgcca aaaagacatc tggaatgagt   1620
ggaagagaat tgagtaaact tgtcatcgga tggcaagctt ctgcatatgc atctgaaacc   1680
ggagtgctca ccgaggctat cgttgatcgt aatactgctg acgcaatggt tcaacatgaa   1740
cataagatgg aatggcttga aaggagcaa ttgaaagctc gtaaccaaga agtcaagttc    1800
ggaactacgt tgaagagaga aactgctgtt taa                                 1833
```

<210> SEQ ID NO 12
<211> LENGTH: 610
<212> TYPE: PRT
<213> ORGANISM: Caenorhabditis elegans

<400> SEQUENCE: 12

```
Met Ser Arg Lys Ile Cys Phe Ala Ser Ser Asn Phe Thr Glu Lys Met
1               5                   10                  15

Ser Trp Leu Phe Gly Val Gln Lys Asn Ala Thr Pro Gln Ile Pro Asp
            20                  25                  30

Asp Phe Gln Ala Gly Ala Ala Pro Gly Gly Pro Gln Pro Gly Gln
        35                  40                  45

Gly Gln Arg Gln Glu Gly Asn Ser Lys Met Ala Tyr Ser Phe Asp Ser
    50                  55                  60

Thr Ala Leu Glu Arg Ala Ala Lys Ala Ala Arg Asp Leu Glu Lys Phe
65                  70                  75                  80

Pro Asn Ala Lys Glu Ala Leu Glu Leu Ser Arg Met Gln Glu Val Thr
                85                  90                  95

Arg Gln Lys Glu Val Glu Asn Glu Thr Lys Lys Ile Glu Ala Gln Leu
            100                 105                 110
```

```
Ala Asn Met Lys Ser Glu His Ile Arg Val Ala Glu Glu Arg Arg
            115                 120                 125

Lys Thr Leu Gly Glu Glu Thr Lys His Ala His Ser Arg Ala Glu Tyr
        130                 135                 140

Gln Asp Gln Leu Ala Arg Lys Arg Ala Glu Glu Leu Ala Met Lys
145                 150                 155                 160

Ala Arg Met Gln Glu Glu Ser Leu Arg Lys Gln Glu Glu Ser Val Lys
                165                 170                 175

Lys Gln Glu Gln Leu Arg Lys Gln Thr Ile Glu His Glu Leu Ala Leu
            180                 185                 190

Lys His Lys Tyr Glu Leu Glu Lys Ile Asp Ala Glu Thr Arg Ala Arg
        195                 200                 205

Ala Lys Ala Ala Arg Asp Asn Arg Asp Val Asn Leu Glu Gln Met Lys
            210                 215                 220

Leu His Glu Glu Asn Arg Lys Thr Val Ile Glu Lys Ile Lys Thr
225                 230                 235                 240

Ser Gly Glu Leu Ile Gly Ser Gly Leu Asn Gln Phe Leu Asn Asp Lys
                245                 250                 255

Thr Lys Ile Ala Ala Ala Val Gly Gly Leu Thr Ala Leu Ala Val Gly
            260                 265                 270

Trp Tyr Thr Ala Lys Arg Gly Thr Gly Val Thr Ala Arg Tyr Ile Glu
        275                 280                 285

Ser Arg Leu Gly Lys Pro Ser Leu Val Arg Glu Thr Ser Arg Ile Thr
            290                 295                 300

Pro Leu Glu Val Leu Lys His Pro Ile Lys Ser Val Gln Met Met Thr
305                 310                 315                 320

Arg Gln Lys Lys Asp Pro Leu Asn Gly Val Leu Pro Pro Ala Leu
                325                 330                 335

Glu Arg Arg Leu Arg Asp Ile Ala Ile Thr Thr Ser Asn Thr Lys Arg
            340                 345                 350

Asn Asn Gly Leu Phe Arg Asn Val Met Phe Tyr Gly Pro Pro Gly Thr
        355                 360                 365

Gly Lys Thr Leu Phe Ala Lys Ser Leu Ala Gln His Ser Gly Leu Asp
        370                 375                 380

Tyr Ala Val Leu Thr Gly Gly Asp Ile Ala Pro Leu Gly Arg Asp Gly
385                 390                 395                 400

Val Ser Ala Ile His Lys Val Phe Asp Trp Ala Ser Lys Ser Arg Lys
                405                 410                 415

Gly Leu Ile Val Phe Ile Asp Glu Ala Asp Ala Phe Leu Gln Lys Arg
            420                 425                 430

Ser Lys Asn Gly Met Ser Glu Asp Thr Arg Ala Ala Leu Asn Ala Phe
        435                 440                 445

Leu Phe Arg Thr Gly Glu Gln Ser Arg Lys Phe Met Leu Val Val Ala
        450                 455                 460

Ser Asn Gln Pro Glu Gln Phe Asp Trp Ala Val Asn Asp Arg Phe Asp
465                 470                 475                 480

Gln Leu Val Glu Phe Thr Leu Pro Gly Met Glu Glu Arg Glu Arg Ile
                485                 490                 495

Leu Leu Gln Tyr Phe Asn Glu His Ile Val Thr Pro Ala Thr Ser Gly
            500                 505                 510

Ser Arg Ser Gln Arg Leu Lys Leu Asp Asn Phe Asp Trp Val Ala Lys
        515                 520                 525
```

```
Cys Asn Glu Val Ala Lys Lys Thr Ser Gly Met Ser Gly Arg Glu Leu
            530                 535                 540

Ser Lys Leu Val Ile Gly Trp Gln Ala Ser Ala Tyr Ala Ser Glu Thr
545                 550                 555                 560

Gly Val Leu Thr Glu Ala Ile Val Asp Arg Asn Thr Ala Asp Ala Met
                565                 570                 575

Val Gln His Glu His Lys Met Glu Trp Leu Glu Lys Glu Gln Leu Lys
            580                 585                 590

Ala Arg Asn Gln Glu Val Lys Phe Gly Thr Thr Leu Lys Arg Glu Thr
        595                 600                 605

Ala Val
    610

<210> SEQ ID NO 13
<211> LENGTH: 1761
<212> TYPE: DNA
<213> ORGANISM: Homo sapiens

<400> SEQUENCE: 13
atgtcgtggc tcttcggcat taacaagggc cccaagggtg aaggcgcggg gccgccgccg      60
cctttgccgc ccgcgcagcc cggggccgag ggcggcgggg accgcggctt gggagaccgg     120
ccggcgccca aggacaaatg gagcaacttc gaccccaccg gcctggagcg cgccgccaag     180
gcggcgcgcg agctggagca ctcgcgttat gccaaggacg ccctgaatct ggcacagatg     240
caggagcaga cgctgcagtt ggagcaacag tccaagctca agagtatgag gccgccgtg     300 gagcagctca gagcgagca gatccgggcg caggctgagg agaggaggaa gaccctgagc     360
gaggagaccc ggcagcacca ggccagggcc cagtatcaag acaagctggc ccggcagcgc     420
tacgaggacc aactgaagca gcagcaactt ctcaatgagg agaatttacg gaagcaggag     480
gagtccgtgc agaagcagga agccatgcgg cgagccaccg tggagcggga gatggagctg     540
cggcacaaga atgagatgct gcgagtggag gccgaggccc gggcgcgcgc caaggccgag     600
cgggagaatg cagacatcat ccgcgagcag atccgcctga aggcggccga gcaccgtcag     660
accgtcttgg agtccatcag gacggctggc accttgtttg gggaaggatt ccgtgccttt     720
gtgacagact gggacaaagt gacagccacg gtggctgggc tgacgctgct ggctgttggg     780
gtctactcag ccaagaatgc cacgcttgtc gccggccgct tcatcgaggc tcggctgggg     840
aagccgtccc tagtgaggga gacgtcccgc atcacggtgc ttgaggcgct gcggcacccc     900
atccaggtca gccggcggct cctcagtcga ccccaggacg cgctggaggg tgttgtgctc     960
agtcccagcc tggaagcacg ggtgcgcgac atcgccatag caacaaggaa caccaagaag    1020
aaccgcagcc tgtacaggaa catcctgatg tacgggccac caggcaccgg gaagacgctg    1080
tttgccaaga aactcgccct gcactcaggc atggactacg ccatcatgac aggcggggac    1140
gtggccccca tggggcggga aggcgtgacc gccatgcaca agctctttga ctgggccaat    1200
accagccggc gcggcctcct gctctttgtg gatgaagcgg acgccttcct tcggaagcga    1260
gccaccgaga agataagcga ggacctcagg gccacactga acgccttcct gtaccgcacg    1320
ggccagcaca gcaacaagtt catgctggtc ctggccagca accaaccaga gcagttcgac    1380
tgggccatca tgaccgcat caatgagatg gtccacttcg acctgccagg caggaggaa    1440 cgggagcgcc tggtgagaat gtattttgac aagtatgttc ttaagccggc cacagaagga    1500
aagcagcgcc tgaagctggc ccagtttgac tacggagga agtgctcgga ggtcgctcgg    1560
ctgacggagg gcatgtcggg ccgggagatc gctcagctgg ccgtgtcctg gcaggccacg    1620
```

-continued

```
gcgtatgcct ccgaggacgg ggtcctgacc gaggccatga tggacacccg cgtgcaagat    1680
gctgtccagc agcaccagca aagatgtgc tggctgaagg cggaagggcc tgggcgtggg     1740
gacgagcctt ccccatcctg a                                              1761
```

<210> SEQ ID NO 14
<211> LENGTH: 586
<212> TYPE: PRT
<213> ORGANISM: Homo sapiens

<400> SEQUENCE: 14

```
Met Ser Trp Leu Phe Gly Ile Asn Lys Gly Pro Lys Gly Glu Gly Ala
1               5                   10                  15

Gly Pro Pro Pro Leu Pro Pro Ala Gln Pro Gly Ala Glu Gly Gly
            20                  25                  30

Gly Asp Arg Gly Leu Gly Asp Arg Pro Ala Pro Lys Asp Lys Trp Ser
        35                  40                  45

Asn Phe Asp Pro Thr Gly Leu Glu Arg Ala Ala Lys Ala Ala Arg Glu
    50                  55                  60

Leu Glu His Ser Arg Tyr Ala Lys Asp Ala Leu Asn Leu Ala Gln Met
65                  70                  75                  80

Gln Glu Gln Thr Leu Gln Leu Glu Gln Gln Ser Lys Leu Lys Glu Tyr
                85                  90                  95

Glu Ala Ala Val Glu Gln Leu Lys Ser Glu Gln Ile Arg Ala Gln Ala
            100                 105                 110

Glu Glu Arg Arg Lys Thr Leu Ser Glu Glu Thr Arg Gln His Gln Ala
        115                 120                 125

Arg Ala Gln Tyr Gln Asp Lys Leu Ala Arg Gln Arg Tyr Glu Asp Gln
    130                 135                 140

Leu Lys Gln Gln Gln Leu Leu Asn Glu Glu Asn Leu Arg Lys Gln Glu
145                 150                 155                 160

Glu Ser Val Gln Lys Gln Glu Ala Met Arg Arg Ala Thr Val Glu Arg
                165                 170                 175

Glu Met Glu Leu Arg His Lys Asn Glu Met Leu Arg Val Glu Ala Glu
            180                 185                 190

Ala Arg Ala Arg Ala Lys Ala Glu Arg Glu Asn Ala Asp Ile Ile Arg
        195                 200                 205

Glu Gln Ile Arg Leu Lys Ala Ala Glu His Arg Gln Thr Val Leu Glu
    210                 215                 220

Ser Ile Arg Thr Ala Gly Thr Leu Phe Gly Glu Gly Phe Arg Ala Phe
225                 230                 235                 240

Val Thr Asp Trp Asp Lys Val Thr Ala Thr Val Ala Gly Leu Thr Leu
                245                 250                 255

Leu Ala Val Gly Val Tyr Ser Ala Lys Asn Ala Thr Leu Val Ala Gly
            260                 265                 270

Arg Phe Ile Glu Ala Arg Leu Gly Lys Pro Ser Leu Val Arg Glu Thr
        275                 280                 285

Ser Arg Ile Thr Val Leu Glu Ala Leu Arg His Pro Ile Gln Val Ser
    290                 295                 300

Arg Arg Leu Leu Ser Arg Pro Gln Asp Ala Leu Glu Gly Val Val Leu
305                 310                 315                 320

Ser Pro Ser Leu Glu Ala Arg Val Arg Asp Ile Ala Ile Ala Thr Arg
                325                 330                 335

Asn Thr Lys Lys Asn Arg Ser Leu Tyr Arg Asn Ile Leu Met Tyr Gly
```

-continued

```
                340             345             350
Pro Pro Gly Thr Gly Lys Thr Leu Phe Ala Lys Lys Leu Ala Leu His
                355                 360                 365
Ser Gly Met Asp Tyr Ala Ile Met Thr Gly Gly Asp Val Ala Pro Met
            370                 375                 380
Gly Arg Glu Gly Val Thr Ala Met His Lys Leu Phe Asp Trp Ala Asn
385                 390                 395                 400
Thr Ser Arg Arg Gly Leu Leu Leu Phe Val Asp Glu Ala Asp Ala Phe
                405                 410                 415
Leu Arg Lys Arg Ala Thr Glu Lys Ile Ser Glu Asp Leu Arg Ala Thr
            420                 425                 430
Leu Asn Ala Phe Leu Tyr Arg Thr Gly Gln His Ser Asn Lys Phe Met
        435                 440                 445
Leu Val Leu Ala Ser Asn Gln Pro Glu Gln Phe Asp Trp Ala Ile Asn
    450                 455                 460
Asp Arg Ile Asn Glu Met Val His Phe Asp Leu Pro Gly Gln Glu Glu
465                 470                 475                 480
Arg Glu Arg Leu Val Arg Met Tyr Phe Asp Lys Tyr Val Leu Lys Pro
                485                 490                 495
Ala Thr Glu Gly Lys Gln Arg Leu Lys Leu Ala Gln Phe Asp Tyr Gly
            500                 505                 510
Arg Lys Cys Ser Glu Val Ala Arg Leu Thr Glu Gly Met Ser Gly Arg
        515                 520                 525
Glu Ile Ala Gln Leu Ala Val Ser Trp Gln Ala Thr Ala Tyr Ala Ser
    530                 535                 540
Glu Asp Gly Val Leu Thr Glu Ala Met Met Asp Thr Arg Val Gln Asp
545                 550                 555                 560
Ala Val Gln Gln His Gln Gln Lys Met Cys Trp Leu Lys Ala Glu Gly
                565                 570                 575
Pro Gly Arg Gly Asp Glu Pro Ser Pro Ser
            580                 585
```

<210> SEQ ID NO 15
<211> LENGTH: 2421
<212> TYPE: DNA
<213> ORGANISM: Mus musculus

<400> SEQUENCE: 15

```
atggcctctg agccgattc aaaaggtgat gatttatcaa cagccattct caaacagaag    60
aaccgaccca atcggttaat tgttgatgaa gccatcaatg aagataacag cgtggtgtcc   120
ttgtcccagc ccaagatgga tgaactgcag ttgttccgag tgacacggt gttgctaaaa    180
ggaaagaaaa gacgggaagc tgtatgcatt gttctttctg atgacacgtg ttctgatgag   240
aagattcgaa tgaatagagt tgttcggaat aacctccgag ttcgcctagg agatgtcatc   300
agcatccagc catgccctga tgtaaagtat ggcaaacgta tccacgttct acccatcgat   360
gacacagtgg aaggcatcac tggcaatctc tttgaggtat accttaagcc gtacttcctg   420
gaagcttatc ggcccatccg taaggagat atttttcttg tccggggtgg gatgcgtgct   480
gtggagttca agttgtaga cagatccc agcccttact gtattgttgc tccagacaca    540
gtgatccact gtgagggga gccaatcaag cgagaggatg aggaggaatc cttgaatgaa   600
gtaggctatg atgacatcgg tggttgcagg aagcagctag ctcagataaa ggagatggtg   660
gagctgccac tgagacatcc tgcgctcttt aaggcgattg gtgtaaagcc tcctcgggga   720
```

-continued

```
atcttgttgt atgggcctcc tgggacaggg aagaccctga ttgctcgagc tgtggcaaat      780
gaaactggag ccttcttctt tctgatcaat ggtcctgaaa tcatgagcaa attggctggt      840
gagtctgaga gcaaccttcg taaagccttt gaggaagctg aaaagaatgc tcctgctatc      900
atcttcatcg atgagcttga tgccattgca cccaaaagag agaaaactca tggggaagtg      960
gagcgtcgca tcgtgtctca gttgttgacc ctcatggatg cctaaagca gagagcacat     1020 gtgatagtta tggcagcaac caatagaccc aacagcattg acccagccct acggcgattt     1080
ggtcgctttg acagagaggt agatattgga atacctgatg ctacaggacg tttggagatt     1140
cttcagatcc ataccaagaa catgaaactg cagatgatg tggacttgga acaggtagcc      1200
aatgagactc atggtcatgt tggtgctgat ttggcagccc tatgttcaga ggctgctctg     1260
caggccatcc ggaaaaaaat ggacctcatt gacctagaag atgagaccat tgatgctgag     1320
gtcatgaatt ccctggcagt tactatggat gacttccggt gggctttgag tcaaagcaac     1380
ccatcagcac ttcgggaaac tgtggtagag gtgccacaag taacctggga agatattgga     1440
ggcctggagg atgtcaaacg tgagcttcag gagttggttc agtatcctgt ggaacatcca     1500
gacaaattcc tcaaatttgg catgactccc tccaaaggcg ttcttttcta tggacctcct     1560
ggctgtggga aaaccttact ggctaaagcc attgctaatg aatgccaggc aacttcatc      1620 tccatcaagg gtcctgagct gcttaccatg tggtttgggg aatctgaggc caatgtccgg     1680 gaaattttg acaaggcacg gcaagctgcc ccctgtgtac tcttctttga tgagttagat      1740
tcaattgcca aggctcgagg tggtaatatt ggagatggtg gtggagctgc tgaccgagtc     1800
atcaatcaga tcctgacaga aatggatggc atgtctacaa aaagaatgt gtttatcatt     1860 ggagctacca acaggcctga catcattgat cctgctatcc taagacctgg ccgtctagat     1920
cagctcattt atatcccact tcctgatgag aagtcccgtg ttgccatcct aaaagccaat     1980
ctgcgaaagt ccccagttgc caaggatgtg gatttggagt tcctggctaa gatgactaat     2040
ggcttttctg gagctgattt gacagaaatt tgccaacggg cttgtaaact ggccattcgt     2100
gaatctattg agagtgagat taggcgagaa cgagagaggc agacaaatcc atcggctatg     2160
gaggtagaag aggacgatcc agtgcctgag atccgcagag atcactttga ggaagccatg     2220
cgttttgccc gacgttctgt cagcgataat gacattcgga gtatgaaat gttcgcccag     2280 acactgcagc agagtcgagg ttttggcagc ttcagattcc cttcagggaa ccagggtgga     2340
gctggtccca gccagggcag tggaggtggc acaggtggca gtgtgtacac agaagacaat     2400
gacgatgacc tgtatggcta a                                               2421
```

<210> SEQ ID NO 16
<211> LENGTH: 806
<212> TYPE: PRT
<213> ORGANISM: Mus musculus

<400> SEQUENCE: 16

Met Ala Ser Gly Ala Asp Ser Lys Gly Asp Asp Leu Ser Thr Ala Ile
1               5                   10                  15

Leu Lys Gln Lys Asn Arg Pro Asn Arg Leu Ile Val Asp Glu Ala Ile
            20                  25                  30

Asn Glu Asp Asn Ser Val Val Ser Leu Ser Gln Pro Lys Met Asp Glu
        35                  40                  45

Leu Gln Leu Phe Arg Gly Asp Thr Val Leu Leu Lys Gly Lys Lys Arg
    50                  55                  60

Arg Glu Ala Val Cys Ile Val Leu Ser Asp Asp Thr Cys Ser Asp Glu

-continued

```
                65                  70                  75                  80
Lys Ile Arg Met Asn Arg Val Val Arg Asn Asn Leu Arg Val Arg Leu
                    85                  90                  95
Gly Asp Val Ile Ser Ile Gln Pro Cys Pro Asp Val Lys Tyr Gly Lys
                100                 105                 110
Arg Ile His Val Leu Pro Ile Asp Asp Thr Val Glu Gly Ile Thr Gly
                115                 120                 125
Asn Leu Phe Glu Val Tyr Leu Lys Pro Tyr Phe Leu Glu Ala Tyr Arg
            130                 135                 140
Pro Ile Arg Lys Gly Asp Ile Phe Leu Val Arg Gly Gly Met Arg Ala
145                 150                 155                 160
Val Glu Phe Lys Val Glu Thr Asp Pro Ser Pro Tyr Cys Ile Val
                165                 170                 175
Ala Pro Asp Thr Val Ile His Cys Glu Gly Glu Pro Ile Lys Arg Glu
                180                 185                 190
Asp Glu Glu Ser Leu Asn Glu Val Gly Tyr Asp Asp Ile Gly Gly
                195                 200                 205
Cys Arg Lys Gln Leu Ala Gln Ile Lys Glu Met Val Glu Leu Pro Leu
            210                 215                 220
Arg His Pro Ala Leu Phe Lys Ala Ile Gly Val Lys Pro Pro Arg Gly
225                 230                 235                 240
Ile Leu Leu Tyr Gly Pro Pro Gly Thr Gly Lys Thr Leu Ile Ala Arg
                245                 250                 255
Ala Val Ala Asn Glu Thr Gly Ala Phe Phe Phe Leu Ile Asn Gly Pro
                260                 265                 270
Glu Ile Met Ser Lys Leu Ala Gly Glu Ser Glu Ser Asn Leu Arg Lys
                275                 280                 285
Ala Phe Glu Glu Ala Glu Lys Asn Ala Pro Ala Ile Ile Phe Ile Asp
            290                 295                 300
Glu Leu Asp Ala Ile Ala Pro Lys Arg Glu Lys Thr His Gly Glu Val
305                 310                 315                 320
Glu Arg Arg Ile Val Ser Gln Leu Leu Thr Leu Met Asp Gly Leu Lys
                325                 330                 335
Gln Arg Ala His Val Ile Val Met Ala Ala Thr Asn Arg Pro Asn Ser
                340                 345                 350
Ile Asp Pro Ala Leu Arg Arg Phe Gly Arg Phe Asp Arg Glu Val Asp
            355                 360                 365
Ile Gly Ile Pro Asp Ala Thr Gly Arg Leu Glu Ile Leu Gln Ile His
        370                 375                 380
Thr Lys Asn Met Lys Leu Ala Asp Asp Val Asp Leu Glu Gln Val Ala
385                 390                 395                 400
Asn Glu Thr His Gly His Val Gly Ala Asp Leu Ala Ala Leu Cys Ser
                405                 410                 415
Glu Ala Ala Leu Gln Ala Ile Arg Lys Lys Met Asp Leu Ile Asp Leu
            420                 425                 430
Glu Asp Glu Thr Ile Asp Ala Glu Val Met Asn Ser Leu Ala Val Thr
        435                 440                 445
Met Asp Asp Phe Arg Trp Ala Leu Ser Gln Ser Asn Pro Ser Ala Leu
    450                 455                 460
Arg Glu Thr Val Val Glu Val Pro Gln Val Thr Trp Glu Asp Ile Gly
465                 470                 475                 480
Gly Leu Glu Asp Val Lys Arg Glu Leu Gln Glu Leu Val Gln Tyr Pro
                485                 490                 495
```

```
Val Glu His Pro Asp Lys Phe Leu Lys Phe Gly Met Thr Pro Ser Lys
            500                 505                 510
Gly Val Leu Phe Tyr Gly Pro Pro Gly Cys Gly Lys Thr Leu Leu Ala
        515                 520                 525
Lys Ala Ile Ala Asn Glu Cys Gln Ala Asn Phe Ile Ser Ile Lys Gly
    530                 535                 540
Pro Glu Leu Leu Thr Met Trp Phe Gly Glu Ser Glu Ala Asn Val Arg
545                 550                 555                 560
Glu Ile Phe Asp Lys Ala Arg Gln Ala Ala Pro Cys Val Leu Phe Phe
                565                 570                 575
Asp Glu Leu Asp Ser Ile Ala Lys Ala Arg Gly Gly Asn Ile Gly Asp
            580                 585                 590
Gly Gly Gly Ala Ala Asp Arg Val Ile Asn Gln Ile Leu Thr Glu Met
        595                 600                 605
Asp Gly Met Ser Thr Lys Lys Asn Val Phe Ile Ile Gly Ala Thr Asn
    610                 615                 620
Arg Pro Asp Ile Ile Asp Pro Ala Ile Leu Arg Pro Gly Arg Leu Asp
625                 630                 635                 640
Gln Leu Ile Tyr Ile Pro Leu Pro Asp Glu Lys Ser Arg Val Ala Ile
                645                 650                 655
Leu Lys Ala Asn Leu Arg Lys Ser Pro Val Ala Lys Asp Val Asp Leu
            660                 665                 670
Glu Phe Leu Ala Lys Met Thr Asn Gly Phe Ser Gly Ala Asp Leu Thr
        675                 680                 685
Glu Ile Cys Gln Arg Ala Cys Lys Leu Ala Ile Arg Glu Ser Ile Glu
    690                 695                 700
Ser Glu Ile Arg Arg Glu Arg Glu Arg Gln Thr Asn Pro Ser Ala Met
705                 710                 715                 720
Glu Val Glu Glu Asp Pro Val Pro Glu Ile Arg Arg Asp His Phe
                725                 730                 735
Glu Glu Ala Met Arg Phe Ala Arg Arg Ser Val Ser Asp Asn Asp Ile
            740                 745                 750
Arg Lys Tyr Glu Met Phe Ala Gln Thr Leu Gln Gln Ser Arg Gly Phe
        755                 760                 765
Gly Ser Phe Arg Phe Pro Ser Gly Asn Gln Gly Ala Gly Pro Ser
    770                 775                 780
Gln Gly Ser Gly Gly Gly Thr Gly Gly Ser Val Tyr Thr Glu Asp Asn
785                 790                 795                 800
Asp Asp Asp Leu Tyr Gly
            805
```

<210> SEQ ID NO 17
<211> LENGTH: 2870
<212> TYPE: DNA
<213> ORGANISM: Rattus norvegicus

<400> SEQUENCE: 17

| gaattccggc | gtttgcagcc | gtcgtttgat | tagtcgcctc | tcgcggatta | ggagctagcg | 60 |
| tctcccgccc | gcctgccgcc | ccggtgccgc | tgggaggaag | cgagagggag | gctgcctgtg | 120 |
| ggtttgtcac | tgctgttgct | cctccacctg | agtgagtcaa | gcccgggcct | agtcggtcgc | 180 |
| ctaccattct | cgtagccgtt | accctcaggc | cgccacagcc | gccgaccggg | agaggcgcgc | 240 |
| gccatggcct | ctggagccga | ttcaaaaggt | gatgatttat | caacagccat | tctcaaacag | 300 |

```
aagaaccgtc ccaatcggtt aattgttgat gaagccatca atgaagataa cagtgtggtg    360
tccttgtccc agcccaagat ggatgaacta cagttgttca gaggtgacac ggtgttgcta    420
aaaggaaaga agagaaggga agctgtatgc attgttcttt ctgatgacac gtgttctgat    480
gagaagattc gaatgaatag agttgttcgg aataacctcc gagttcgcct aggagatgtc    540
atcagcatcc agccatgccc tgatgtaaag tatggcaaac gtatccatgt gctacccatt    600
gatgacacag tggaaggcat cactggcaat cttttgagg tataccttaa gccgtacttc    660
ctggaagcat atcggcccat ccgtaaagga gatattttcc ttgtccgggg tgggatgcgt    720
gctgtggagt tcaaagtagt agagacagat cccagccctt actgtattgt tgctccagac    780
acagtgatcc actgtgaggg ggagccaatc aagcgagagg atgaggagga gtccttgaat    840
gaagtaggct atgatgacat cggtggttgc aggaagcagc tagctcagat aaaggagatg    900
gtggagctgc cactgagaca tcctgcactc tttaaggcaa ttggtgtgaa gcctcctcgg    960
ggaatcttgc tatatggacc tcctgggaca gggaaaacct tgattgcccg agctgtggca   1020
aatgaaactg gagccttctt ctttctgatc aatggtcctg aaatcatgag caaattggct   1080
ggtgagtctg agagcaacct tcgtaaagcc tttgaggaag ctgaaaagaa tgctcctgcc   1140
atcatcttca tcgacgagct tgatgccatt gcacccaaaa gagagaaaac tcacggggaa   1200
gtggagcgtc gcatcgtgtc tcagttgttg acccttatgg atggcctaaa gcagagagca   1260
catgtgatag ttatggcagc aaccaataga cccaacagca ttgacccagc cctacggcga   1320
tttggtcgct ttgacagaga ggtagatatt ggaatccctg atgctacagg acgtttggaa   1380
attcttcaga tccataccaa gaacatgaaa ctggcagatg atgtggactt ggaacaggta   1440
gccaatgaga ctcatggtca tgtgggtgct gacttggcag ccctgtgttc agaggctgct   1500
ctacaggcca tccggaaaaa aatggacctc attgacctag aagatgagac cattgacgct   1560
gaggtcatga attccctggc agttactatg gatgacttcc ggtgggcctt aagtcaaagc   1620
aacccatcag cacttcggga aactgtggta gaagtgccac aagtaacctg ggaagacatt   1680
ggaggcctgg aggatgtcaa acgggagctt caggagttgg ttcagtatcc tgtggagcat   1740
ccagacaaat tcctcaaatt tggcatgact ccttccaaag gtgttctttt ctatggaccg   1800
cctggctgtg ggaaaacctt actggccaaa gccattgcta atgaatgcca ggctaacttc   1860
atctccatca agggtcctga gctgcttacc atgtggtttg gggaatctga ggccaatgtc   1920
agggaaatat tgacaaggc acgacaagct gcccctgtg tactcttctt tgatgagtta   1980
gattcaattg ccaaggctcg tggtggtaat attggagatg tggtggagc tgcagaccga   2040
gtcatcaatc agatcctgac agaaatggat ggcatgtcca caaaaagaa tgtgtttatc   2100
attggagcta ccaaccggcc tgacatcatt gatcctgcta tcctaagacc tggccgtctt   2160
gatcagctca tttatatccc acttcctgat gagaagtccc gtgttgccat cctaaaagcc   2220
aatctgcgaa aatccccagt tgccaaggat gtggatttgg agttcttggc taagatgact   2280
aatggctttt ctggagctga cctgacagaa atttgccaac gtgcttgtaa actagccatt   2340
cgtgaatcta tcgagagtga gattaggcga gaacgagaga ggcagacaaa tccatcagct   2400
atggaagtag aagaggatga tccagtgcct gagatccgca gagatcactt tgaggaagcc   2460
atgcgttttg cccgacgttc tgtcagtgat aatgacattc ggaagtatga atgtttgcc   2520
cagacactgc agcaaagtcg aggttttggc agcttcagat tcccttcagg gaaccagggt   2580
ggagctggcc caagtcaggg cagtggaggt ggcacaggtg gcaatgtgta cacagaagac   2640
aatgacgatg acctctatgg ctaagtgatg tgccagcatg cagcgagctg gcctggctgg   2700
```

```
accttgttcc ctgggggtgg gggcgctcgc ccaatgggaa ccagggggtgt gcccatggcc    2760 tgttccattc ctcagtccga acagttcagc cccagtcaga ctctggacgg gggttttctg    2820
ttgcaaaaaa attacaaaag cgataaaata aaagtgattt tcatttggga              2870
```

<210> SEQ ID NO 18
<211> LENGTH: 806
<212> TYPE: PRT
<213> ORGANISM: Rattus norvegicus

<400> SEQUENCE: 18

```
Met Ala Ser Gly Ala Asp Ser Lys Gly Asp Asp Leu Ser Thr Ala Ile
1               5                   10                  15

Leu Lys Gln Lys Asn Arg Pro Asn Arg Leu Ile Val Asp Glu Ala Ile
            20                  25                  30

Asn Glu Asp Asn Ser Val Val Ser Leu Ser Gln Pro Lys Met Asp Glu
        35                  40                  45

Leu Gln Leu Phe Arg Gly Asp Thr Val Leu Leu Lys Gly Lys Lys Arg
    50                  55                  60

Arg Glu Ala Val Cys Ile Val Leu Ser Asp Asp Thr Cys Ser Asp Glu
65                  70                  75                  80

Lys Ile Arg Met Asn Arg Val Val Arg Asn Asn Leu Arg Val Arg Leu
                85                  90                  95

Gly Asp Val Ile Ser Ile Gln Pro Cys Pro Asp Val Lys Tyr Gly Lys
            100                 105                 110

Arg Ile His Val Leu Pro Ile Asp Asp Thr Val Glu Gly Ile Thr Gly
        115                 120                 125

Asn Leu Phe Glu Val Tyr Leu Lys Pro Tyr Phe Leu Glu Ala Tyr Arg
    130                 135                 140

Pro Ile Arg Lys Gly Asp Ile Phe Leu Val Arg Gly Gly Met Arg Ala
145                 150                 155                 160

Val Glu Phe Lys Val Val Glu Thr Asp Pro Ser Pro Tyr Cys Ile Val
                165                 170                 175

Ala Pro Asp Thr Val Ile His Cys Glu Gly Glu Pro Ile Lys Arg Glu
            180                 185                 190

Asp Glu Glu Glu Ser Leu Asn Glu Val Gly Tyr Asp Asp Ile Gly Gly
        195                 200                 205

Cys Arg Lys Gln Leu Ala Gln Ile Lys Glu Met Val Glu Leu Pro Leu
    210                 215                 220

Arg His Pro Ala Leu Phe Lys Ala Ile Gly Val Lys Pro Pro Arg Gly
225                 230                 235                 240

Ile Leu Leu Tyr Gly Pro Pro Gly Thr Gly Lys Thr Leu Ile Ala Arg
                245                 250                 255

Ala Val Ala Asn Glu Thr Gly Ala Phe Phe Phe Leu Ile Asn Gly Pro
            260                 265                 270

Glu Ile Met Ser Lys Leu Ala Gly Glu Ser Glu Ser Asn Leu Arg Lys
        275                 280                 285

Ala Phe Glu Glu Ala Glu Lys Asn Ala Pro Ala Ile Ile Phe Ile Asp
    290                 295                 300

Glu Leu Asp Ala Ile Ala Pro Lys Arg Glu Lys Thr His Gly Glu Val
305                 310                 315                 320

Glu Arg Arg Ile Val Ser Gln Leu Leu Thr Leu Met Asp Gly Leu Lys
                325                 330                 335

Gln Arg Ala His Val Ile Val Met Ala Ala Thr Asn Arg Pro Asn Ser
```

-continued

```
               340                 345                 350
Ile Asp Pro Ala Leu Arg Arg Phe Gly Arg Phe Asp Arg Glu Val Asp
            355                 360                 365
Ile Gly Ile Pro Asp Ala Thr Gly Arg Leu Glu Ile Leu Gln Ile His
        370                 375                 380
Thr Lys Asn Met Lys Leu Ala Asp Asp Val Asp Leu Glu Gln Val Ala
385                 390                 395                 400
Asn Glu Thr His Gly His Val Gly Ala Asp Leu Ala Ala Leu Cys Ser
                405                 410                 415
Glu Ala Ala Leu Gln Ala Ile Arg Lys Lys Met Asp Leu Ile Asp Leu
            420                 425                 430
Glu Asp Glu Thr Ile Asp Ala Glu Val Met Asn Ser Leu Ala Val Thr
        435                 440                 445
Met Asp Asp Phe Arg Trp Ala Leu Ser Gln Ser Asn Pro Ser Ala Leu
    450                 455                 460
Arg Glu Thr Val Val Glu Val Pro Gln Val Thr Trp Glu Asp Ile Gly
465                 470                 475                 480
Gly Leu Glu Asp Val Lys Arg Glu Leu Gln Glu Leu Val Gln Tyr Pro
                485                 490                 495
Val Glu His Pro Asp Lys Phe Leu Lys Phe Gly Met Thr Pro Ser Lys
            500                 505                 510
Gly Val Leu Phe Tyr Gly Pro Pro Gly Cys Gly Lys Thr Leu Leu Ala
        515                 520                 525
Lys Ala Ile Ala Asn Glu Cys Gln Ala Asn Phe Ile Ser Ile Lys Gly
    530                 535                 540
Pro Glu Leu Leu Thr Met Trp Phe Gly Glu Ser Glu Ala Asn Val Arg
545                 550                 555                 560
Glu Ile Phe Asp Lys Ala Arg Gln Ala Ala Pro Cys Val Leu Phe Phe
                565                 570                 575
Asp Glu Leu Asp Ser Ile Ala Lys Ala Arg Gly Gly Asn Ile Gly Asp
            580                 585                 590
Gly Gly Gly Ala Ala Asp Arg Val Ile Asn Gln Ile Leu Thr Glu Met
        595                 600                 605
Asp Gly Met Ser Thr Lys Lys Asn Val Phe Ile Ile Gly Ala Thr Asn
    610                 615                 620
Arg Pro Asp Ile Ile Asp Pro Ala Ile Leu Arg Pro Gly Arg Leu Asp
625                 630                 635                 640
Gln Leu Ile Tyr Ile Pro Leu Pro Asp Glu Lys Ser Arg Val Ala Ile
                645                 650                 655
Leu Lys Ala Asn Leu Arg Lys Ser Pro Val Ala Lys Asp Val Asp Leu
            660                 665                 670
Glu Phe Leu Ala Lys Met Thr Asn Gly Phe Ser Gly Ala Asp Leu Thr
        675                 680                 685
Glu Ile Cys Gln Arg Ala Cys Lys Leu Ala Ile Arg Glu Ser Ile Glu
    690                 695                 700
Ser Glu Ile Arg Arg Glu Arg Glu Arg Gln Thr Asn Pro Ser Ala Met
705                 710                 715                 720
Glu Val Glu Glu Asp Asp Pro Val Pro Glu Ile Arg Arg Asp His Phe
                725                 730                 735
Glu Glu Ala Met Arg Phe Ala Arg Arg Ser Val Ser Asp Asn Asp Ile
            740                 745                 750
Arg Lys Tyr Glu Met Phe Ala Gln Thr Leu Gln Gln Ser Arg Gly Phe
        755                 760                 765
```

```
Gly Ser Phe Arg Phe Pro Ser Gly Asn Gln Gly Gly Ala Gly Pro Ser
    770                 775                 780
Gln Gly Ser Gly Gly Gly Thr Gly Gly Asn Val Tyr Thr Glu Asp Asn
785                 790                 795                 800
Asp Asp Asp Leu Tyr Gly
            805

<210> SEQ ID NO 19
<211> LENGTH: 2751
<212> TYPE: DNA
<213> ORGANISM: Drosophila melanogaster

<400> SEQUENCE: 19
atgaaaatgt ggacggaatc caatgtgaat tccgcgatgg gtcttcaagc aacagccgcc      60
accaagcgga agcatgagct gaccttcgac agcaaggatg ccaacaccac ctacacgggc     120
aactgtgccc cgccccccgt caaggccaac aagtgggcca tcagcaacaa caactacctg     180
gagtcgctcg aggagcagca gcagcaacag caatcgccat cggagccagc tgttgagtcc     240
aacaacaacc acattgtttt agaagcatca atggatgcgt tgaagccaac ggagccaagt     300
attagcaatg gtcatgaagt tactaccgcc gtcgcagcaa tgaaaagtca gcggaggtg      360 ccactcccgc aacagcgag tgcggcgata ccggaggaca gtatcgccag gttagaggtg      420
gtcacctcag ccgttccttg tgagccctgg acgagcaatg ggcccactac tccttccgcg     480
gtggcaggac ccgcagcatc cgcggaacct gtggattgca tctccaagct gcaggccgtc     540
gcggtgccca gtgatccttg ggtagcatt gccacccgct ccactctggc aacgactttg      600
ctcagtgccg atgagctgga cgacgatgat gatgattttg aggacgacta cgaggaggag     660
gagagcatca tacccaccta ctgtcccatg cgctatcatc cctttgtacc gcatccgcac     720
cctcattcgc accagctgcc gtcccatccc caccagcagc agccgcagca gctctcccaa     780
caacaaccac atccccagca gcagcaactc gcccagcagc agcaacaaca tccgcagcag     840
cagcgaagct atgccccgg atatgggagc aggcaaccca actactattc ggagcctttc      900
ccgcagcaga attgctcgcg gacaggagga ccgcagcaca tgacgcaatc accgccaaca     960
ccgcagcagg cgcgtggttt cgctccaccc cagtgggcga cagcgggtag cagtccggcc    1020
aatccctcat cgggagccca acagttctac gagccgacca cggtggagc ttatgccccg     1080 ccagcggcgc cccagcagac aattcgttgt gcagagaacg gcaaatccta tctggacctg    1140
ggctgcagca gtggcgcatc cggaaatgct ggaggatcgc ccatcagtcc gccgccctca    1200
tcagcgcctg ttgttccatt cgccggcttg cctctccatg gcctgcctct taaaaggtgc    1260
tgcgatggac gacccggtgg ctggtgcagt gccaacagga gttgctacaa ggacacgcgc    1320
ctgaagatac gcaatctgtc catgttcaaa ctctcccgtt ccggcaggt ttctgagcag     1380 tcgctgtacc gctcggtgct catttgcaat acgctgaagc gcattgatcg ggagatcgaa    1440
gcagaggcca aggagctgca ccaggcggcg caacagcacc accaacaggc ggcagcagca    1500
gcagccgcag cagcagcagc ggcggcacaa gcggctcagt accacccagc ctaccagcag    1560
cagcagcagc agcagcaatc cccgccagca cctctgcatc cacatacgca gcagcagatg    1620
gactatcgcg ccgtgttgaa ctgtgctcgt ttggccaaca tggatcacta ccagcaactc    1680 agttttccagc cccaacacca gcagcaacag cagccttcgc agccgcatag ctaccacgag    1740
cgtctggaca gccaacccgc ctacaggggc gcggcagcgg gtgcgggcag cttcgccacg    1800
cagccgagca actgtgatac atcagcgggt gcaagtagca gcaataccag cggcaacagc    1860
```

-continued

| | |
|---|---|
| aacaactcct cagcgacggc ggcgagcagc aacagtagtt tgcaccccta cgatcactat | 1920 |
| cccttcgggg agtcgcaatc tggtcgagca acgcccttc cggcctgccc caccacaaca | 1980 |
| gcagcagcgg cagcagcttc ggcagcagcc gcagcttcca gtggaggagc agcaacaaca | 2040 |
| ctaagtagca acatcagcag ctcccccgca tcaagcagca ctagcagcaa caccacttcc | 2100 |
| tcaacggtga tcagcagcag tagtgggaat accgtgagca gcaacggcac cacgccagtt | 2160 |
| gcacctaccg caagcagcag caactgcgat actagcgatt cgggttatgc ggacgacgac | 2220 |
| tccacgcgat ccatcaactg gagttcggtg ctgagcctca gttcgcaatc ggcgttggat | 2280 |
| ccgctcaaca acaacgattt gtttagcata cttccgtcgg cggccacacc tacagcggtg | 2340 |
| ccagtttcag tgccagccag tagttccagt tcctcctcgg ggtccacgct ggcattcagt | 2400 |
| ggaagcttca ccaccgtaca agccagcggc ggcagtagca gttcctgcgg aagcagctcc | 2460 |
| accaccgcca cattcaccac cctgtcgacc atctcctcgg ccacccactc gctgacctcg | 2520 |
| tcgtatgtaa gcagcattag ctccaatgtg tcggcgggcg ccaatacctg ggagtacgga | 2580 |
| ttcctggaca tggaattcgg actcggttcg gagttcacgg agctggtacc cagctgtaag | 2640 |
| ctcagctccg aggatctgtt caagagcgga ttgggcggtc aggttgtgac cgcctcccgc | 2700 |
| ctgcacgaca acgaactgga gcaccggcc cacatcatgg tcggtagtta g | 2751 |

<210> SEQ ID NO 20
<211> LENGTH: 599
<212> TYPE: PRT
<213> ORGANISM: Drosophila melanogaster

<400> SEQUENCE: 20

Met Ser Trp Leu Leu Gly Arg Asn Arg Gln Gln Pro Gln Pro Asp Gln
1               5                   10                  15

Thr Ala Gly Phe Ser Glu Gly Gly Ala Ala Asp Pro Glu Gly Arg
            20                  25                  30

Thr Ala Gly Glu Lys Ser Gly Asp Ser Gln Leu Ser Arg Ala Glu Arg
        35                  40                  45

Lys Ala Met Glu Ala Tyr Arg Phe Asp Ser Ser Ala Leu Glu Arg Ala
    50                  55                  60

Ala Asp Ala Ala Lys Thr Leu Glu Arg Ser Lys His Ala Arg Glu Ala
65                  70                  75                  80

Leu Glu Leu Ser Lys Met Gln Glu Ala Thr Arg Gln Thr Glu Tyr Asn
                85                  90                  95

Thr Lys Val Lys Glu Tyr Glu Ala His Ile Glu Gln Ala Lys Val Glu
            100                 105                 110

Gln Lys Arg Ile Asp His Glu Glu Arg Lys Thr Leu Ile Glu Glu
        115                 120                 125

Thr Lys Gln Gln Gln Arg Ala Gln Tyr Gln Asp Gln Leu Ser Arg
    130                 135                 140

Lys Arg Tyr Glu Asp Gln Leu Leu Gln Gln Arg Val Gln Glu Glu
145                 150                 155                 160

Asn Leu Arg Lys Gln Glu Glu Ser Val Gln Arg Gln Glu Ala Met Arg
                165                 170                 175

Arg Gln Thr Ile Glu His Glu Ile Glu Met Lys Glu Lys Asn Arg Leu
            180                 185                 190

Lys Leu Leu Glu His Glu Leu Arg Ala Lys Ala Arg Val Asp Arg Glu
        195                 200                 205

Asn Arg Asp Ile Asn Leu Glu Lys Ile Arg Leu Lys Ala Gln Glu His

```
                210                 215                 220
Arg Thr Thr Val Leu Glu Gly Ile Lys Thr Ala Gly Thr Val Ile Gly
225                 230                 235                 240

Ala Gly Ala Glu Ala Met Leu Thr Asp Trp Asp Lys Val Leu Thr Ala
                245                 250                 255

Ala Gly Gly Leu Ser Leu Ala Leu Gly Val Tyr Thr Ala Lys Gly
            260                 265                 270

Ala Thr Gly Val Val Ser Arg Tyr Val Glu Ala Arg Ile Gly Lys Pro
            275                 280                 285

Thr Leu Val Gly Glu Thr Ser Arg Phe Ala Phe Leu Asp Ala Leu Lys
290                 295                 300

Asn Pro Leu His Tyr Leu Lys Arg Leu Arg Ala Lys Pro Thr Asp Ala
305                 310                 315                 320

Leu Gln Gly Val Val Leu Asn Pro Lys Leu Glu Arg Leu Arg Asp
                325                 330                 335

Ile Ala Ile Ala Thr Lys Asn Thr Arg Ile Asn Lys Gly Met Tyr Arg
                340                 345                 350

Asn Val Leu Met His Gly Pro Pro Gly Thr Gly Lys Thr Met Phe Ala
            355                 360                 365

Lys Lys Leu Ala Glu His Ser Gly Met Asp Phe Ala Ile Met Thr Gly
            370                 375                 380

Gly Asp Val Ala Pro Met Gly Lys Glu Gly Val Thr Ala Ile His Lys
385                 390                 395                 400

Val Phe Asp Trp Ser His Thr Ser Arg Arg Gly Leu Leu Leu Phe Val
                405                 410                 415

Asp Glu Ala Asp Ala Phe Leu Arg Lys Arg Ser Ser Glu Lys Ile Ser
                420                 425                 430

Glu Asp Leu Arg Ala Ala Leu Asn Ala Phe Leu Tyr Arg Thr Ser Glu
            435                 440                 445

Gln Asn Pro Lys Phe Met Leu Val Leu Ala Ser Asn Thr Pro Glu Gln
            450                 455                 460

Phe Asp Tyr Ala Ile Asn Asp Arg Leu Asp Glu Met Val Glu Phe Thr
465                 470                 475                 480

Leu Pro Gly Leu Glu Glu Arg Glu Arg Leu Leu Arg Leu Tyr Phe Asp
                485                 490                 495

Lys Tyr Val Leu Gln Pro Ala Ala Gly Ala Lys Arg Phe Lys Leu
            500                 505                 510

Asp Thr Phe Asp Tyr Gly Lys Thr Cys Ser Lys Met Ala Ala Leu Cys
            515                 520                 525

Glu Gly Met Ser Gly Arg Glu Ile Ser Lys Leu Gly Val Ser Trp Gln
530                 535                 540

Ala Ala Val Tyr Ala Ser Glu Asp Gly Leu Leu Thr Glu Lys Met Val
545                 550                 555                 560

Leu Asp Arg Cys Tyr Ser Ala Ala Gln Gln His Lys Gln Lys Arg Trp
                565                 570                 575

Pro Gly Phe Arg Ile Arg Ser Val Leu Ile Thr Asn Pro Ser Gln Ala
            580                 585                 590

Gln Leu Pro His Pro Ser Pro
            595

<210> SEQ ID NO 21
<211> LENGTH: 2244
<212> TYPE: DNA
<213> ORGANISM: Saccharomyces cerevisiae
```

<400> SEQUENCE: 21

```
atgaacgttt caaaaatact tgtgtcgccc acggtcacga caaatgtttt acgcatattt      60
gctcccaggc tacctcaaat cggtgcttct ttgttagttc aaaaaaaatg ggccttaaga     120
tcaaagaagt tctaccgttt ttattctgaa agaatagcg gtgaaatgcc tcctaagaag      180
gaagctgata gctctggaaa ggcatccaat aaatccacga tatcttcaat cgacaattcg     240
caaccaccac ctccatcgaa cactaatgat aaaaccaaac aagcgaacgt agctgtgtca     300
catgctatgc tagcaactag agaacaagag gccaataaag acttaacgag tcctgatgca     360
caagcagcct tttacaaact tctcttacaa tcaaactacc cgcaatacgt ggtctctagg     420
tttgagaccc ccggtattgc gtcatcgcct gaatgcatgg aactgtacat ggaggccctg     480
cagaggatag gcagacactc ggaggctgat gccgttagac aaaacctact gacagccagc     540
tctgctggcg cagttaaccc atcattggcg tcatcttcat caaccagtc aggttatcat      600
ggtaactttc catcgatgta ttctccgctt tatggatctc gcaaagagcc actacatgtt     660
gtcgtatctg aatcaacttt tactgttgta tcgagatggg taaagtggct gcttgttttc     720
ggtatcttaa cctactcttt ttctgaaggt tttaaataca tcacagaaaa tacaacgcta     780
ctaaagtcgt cagaagtagc cgacaaatca gttgatgtag ctaagacaaa tgttaaattt     840
gatgatgtct gcggttgtga tgaggcccgt gcggaattgg aagaaattgt tgatttcctg     900
aaagatccaa ctaagtacga gtccttgggt ggtaaactac caaagggtgt actgttgact     960
ggacctcctg gtacaggtaa aactttgttg gctagggcca ctgccggaga ggctggtgta    1020
gattttttct ttatgtcagg ttctgaattt gatgaagttt acgtcggtgt tggtgctaaa    1080
cgtatccgtg atttgtttgc tcaagcgcgt tctcgtgcac cagctattat ttttattgat    1140
gaattagatg ccatcggtgg taagcgtaat ccaaaggacc aagcttacgc caaacaaacg    1200
ttgaatcagt tattggtcga attagatggt ttctcacaaa caagtggaat tattattatt    1260
ggtgccacaa atttccctga ggctttagat aaggcgttaa ctagaccagg tagatttgat    1320
aaggttgtga atgtggattt gccagatgtt cgtggtcgtg ctgatatttt aaagcatcac    1380
atgaagaaga ttacattggc agacaatgtg atccaacta ttattgcgcg tggtacccc     1440
ggtttatcag cgctgagct ggcaaatta gtcaaccaag cagcagttta cgcgtgtcaa      1500
aaaaatgctg tttccgttga tatgtcccac ttcgagtggg ctaaggataa gatattgatg    1560
ggtgctgaga gaaagactat ggtcttaaca gatgcagcca gaaaggccac tgcttcccac    1620
gaggctggac atgccattat ggccaaatac accaatggtg ctaccccgct atacaaggcc    1680
acgatattgc ctagaggtag ggcattgggt attactttc aattgccaga atggataag      1740
gtcgacatca ccaaaaggga gtgtcaagcc agactggacg tgtgcatggg gggcaaaatt    1800
gcagaagaat taatttatgg taaagataac accacaagtg ttgtgggtc tgacttgcaa     1860
agcgccaccg gcacagcaag ggctatggtt actcaatatg gtatgagtga tgatgtaggt    1920
cccgttaact tgtcagaaaa ttgggaatct tggtctaata agattcgcga tattgctgat    1980
aatgaagtga ttgaacttt gaaggactcc gaggaaagag caagaagact attaactaag    2040
aaaaatgttg agctacatag acttgcgcaa ggtcttattg aatatgaaac tctagatgcc    2100
cacgaaatcg aacaagtttg taaggtgaa aaactgaca aactgaaaac ttccaccaat     2160
acagtcgtag aaggaccaga cagtgatgaa cgtaaagata taggcgatga taaacccaaa    2220
attcctacaa tgttaaatgc atga                                            2244
```

<210> SEQ ID NO 22
<211> LENGTH: 747
<212> TYPE: PRT
<213> ORGANISM: Saccharomyces cerevisiae

<400> SEQUENCE: 22

```
Met Asn Val Ser Lys Ile Leu Val Ser Pro Thr Val Thr Asn Val
1               5                   10                  15

Leu Arg Ile Phe Ala Pro Arg Leu Pro Gln Ile Gly Ala Ser Leu Leu
                20                  25                  30

Val Gln Lys Lys Trp Ala Leu Arg Ser Lys Phe Tyr Arg Phe Tyr
        35                  40                  45

Ser Glu Lys Asn Ser Gly Glu Met Pro Pro Lys Lys Glu Ala Asp Ser
        50                  55                  60

Ser Gly Lys Ala Ser Asn Lys Ser Thr Ile Ser Ser Ile Asp Asn Ser
65                  70                  75                  80

Gln Pro Pro Pro Ser Asn Thr Asn Asp Lys Thr Lys Gln Ala Asn
                85                  90                  95

Val Ala Val Ser His Ala Met Leu Ala Thr Arg Glu Gln Glu Ala Asn
            100                 105                 110

Lys Asp Leu Thr Ser Pro Asp Ala Gln Ala Ala Phe Tyr Lys Leu Leu
        115                 120                 125

Leu Gln Ser Asn Tyr Pro Gln Tyr Val Val Ser Arg Phe Glu Thr Pro
        130                 135                 140

Gly Ile Ala Ser Ser Pro Glu Cys Met Glu Leu Tyr Met Glu Ala Leu
145                 150                 155                 160

Gln Arg Ile Gly Arg His Ser Glu Ala Asp Ala Val Arg Gln Asn Leu
                165                 170                 175

Leu Thr Ala Ser Ser Ala Gly Ala Val Asn Pro Ser Leu Ala Ser Ser
            180                 185                 190

Ser Ser Asn Gln Ser Gly Tyr His Gly Asn Phe Pro Ser Met Tyr Ser
        195                 200                 205

Pro Leu Tyr Gly Ser Arg Lys Glu Pro Leu His Val Val Ser Glu
        210                 215                 220

Ser Thr Phe Thr Val Val Ser Arg Trp Val Lys Trp Leu Leu Val Phe
225                 230                 235                 240

Gly Ile Leu Thr Tyr Ser Phe Ser Glu Gly Phe Lys Tyr Ile Thr Glu
                245                 250                 255

Asn Thr Thr Leu Leu Lys Ser Ser Glu Val Ala Asp Lys Ser Val Asp
            260                 265                 270

Val Ala Lys Thr Asn Val Lys Phe Asp Asp Val Cys Gly Cys Asp Glu
        275                 280                 285

Ala Arg Ala Glu Leu Glu Glu Ile Val Asp Phe Leu Lys Asp Pro Thr
        290                 295                 300

Lys Tyr Glu Ser Leu Gly Gly Lys Leu Pro Lys Gly Val Leu Leu Thr
305                 310                 315                 320

Gly Pro Pro Gly Thr Gly Lys Thr Leu Leu Ala Arg Ala Thr Ala Gly
                325                 330                 335

Glu Ala Gly Val Asp Phe Phe Phe Met Ser Gly Ser Glu Phe Asp Glu
            340                 345                 350

Val Tyr Val Gly Val Gly Ala Lys Arg Ile Arg Asp Leu Phe Ala Gln
        355                 360                 365

Ala Arg Ser Arg Ala Pro Ala Ile Ile Phe Ile Asp Glu Leu Asp Ala
        370                 375                 380
```

```
Ile Gly Gly Lys Arg Asn Pro Lys Asp Gln Ala Tyr Ala Lys Gln Thr
385                 390                 395                 400

Leu Asn Gln Leu Leu Val Glu Leu Asp Gly Phe Ser Gln Thr Ser Gly
            405                 410                 415

Ile Ile Ile Ile Gly Ala Thr Asn Phe Pro Glu Ala Leu Asp Lys Ala
            420                 425                 430

Leu Thr Arg Pro Gly Arg Phe Asp Lys Val Val Asn Val Asp Leu Pro
            435                 440                 445

Asp Val Arg Gly Arg Ala Asp Ile Leu Lys His His Met Lys Lys Ile
        450                 455                 460

Thr Leu Ala Asp Asn Val Asp Pro Thr Ile Ile Ala Arg Gly Thr Pro
465                 470                 475                 480

Gly Leu Ser Gly Ala Glu Leu Ala Asn Leu Val Asn Gln Ala Ala Val
            485                 490                 495

Tyr Ala Cys Gln Lys Asn Ala Val Ser Val Asp Met Ser His Phe Glu
            500                 505                 510

Trp Ala Lys Asp Lys Ile Leu Met Gly Ala Glu Arg Lys Thr Met Val
            515                 520                 525

Leu Thr Asp Ala Ala Arg Lys Ala Thr Ala Phe His Glu Ala Gly His
530                 535                 540

Ala Ile Met Ala Lys Tyr Thr Asn Gly Ala Thr Pro Leu Tyr Lys Ala
545                 550                 555                 560

Thr Ile Leu Pro Arg Gly Arg Ala Leu Gly Ile Thr Phe Gln Leu Pro
            565                 570                 575

Glu Met Asp Lys Val Asp Ile Thr Lys Arg Glu Cys Gln Ala Arg Leu
            580                 585                 590

Asp Val Cys Met Gly Gly Lys Ile Ala Glu Glu Leu Ile Tyr Gly Lys
        595                 600                 605

Asp Asn Thr Thr Ser Gly Cys Gly Ser Asp Leu Gln Ser Ala Thr Gly
610                 615                 620

Thr Ala Arg Ala Met Val Thr Gln Tyr Gly Met Ser Asp Asp Val Gly
625                 630                 635                 640

Pro Val Asn Leu Ser Glu Asn Trp Glu Ser Trp Ser Asn Lys Ile Arg
            645                 650                 655

Asp Ile Ala Asp Asn Glu Val Ile Glu Leu Leu Lys Asp Ser Glu Glu
            660                 665                 670

Arg Ala Arg Arg Leu Leu Thr Lys Lys Asn Val Glu Leu His Arg Leu
        675                 680                 685

Ala Gln Gly Leu Ile Glu Tyr Glu Thr Leu Asp Ala His Glu Ile Glu
        690                 695                 700

Gln Val Cys Lys Gly Glu Lys Leu Asp Lys Leu Lys Thr Ser Thr Asn
705                 710                 715                 720

Thr Val Val Glu Gly Pro Asp Ser Asp Glu Arg Lys Asp Ile Gly Asp
            725                 730                 735

Asp Lys Pro Lys Ile Pro Thr Met Leu Asn Ala
        740                 745

<210> SEQ ID NO 23
<211> LENGTH: 189
<212> TYPE: DNA
<213> ORGANISM: Caenorhabditis elegans

<400> SEQUENCE: 23
atggataaat ctgacatgca acgaaccgtc gactcgcttc gcagccagct caatattgag    60
```

```
cgtactccga tcactgtttc ggcagccgaa cttcgtcgct tcaccgaaag ccaagaagat      120
ccacttgtga acccaatcga caagaaggtt aacccatggg ctgagaagag caagtgcagc      180
atgctctaa                                                              189

<210> SEQ ID NO 24
<211> LENGTH: 62
<212> TYPE: PRT
<213> ORGANISM: Caenorhabditis elegans

<400> SEQUENCE: 24

Met Asp Lys Ser Asp Met Gln Arg Thr Val Asp Ser Leu Arg Ser Gln
1               5                   10                  15

Leu Asn Ile Glu Arg Thr Pro Ile Thr Val Ser Ala Ala Glu Leu Arg
            20                  25                  30

Arg Phe Thr Glu Ser Gln Glu Asp Pro Leu Val Asn Pro Ile Asp Lys
        35                  40                  45

Lys Val Asn Pro Trp Ala Glu Lys Ser Lys Cys Ser Met Leu
    50                  55                  60

<210> SEQ ID NO 25
<211> LENGTH: 204
<212> TYPE: DNA
<213> ORGANISM: Homo sapiens

<400> SEQUENCE: 25
atggaggagt gggacgtgcc acagatgaag aaagaggtgg agagccttaa gtaccagctg       60
gccttccagc gggagatggc gtccaagacc atccccgagc tgctgaagtg gatcgaggac      120
gggatcccca ggaccccctt cctgaacccc gacctgatga gaacaacccc atgggtggaa      180
aagggcaaat gcaccatcct gtga                                             204

<210> SEQ ID NO 26
<211> LENGTH: 67
<212> TYPE: PRT
<213> ORGANISM: Homo sapiens

<400> SEQUENCE: 26

Met Glu Glu Trp Asp Val Pro Gln Met Lys Lys Glu Val Glu Ser Leu
1               5                   10                  15

Lys Tyr Gln Leu Ala Phe Gln Arg Glu Met Ala Ser Lys Thr Ile Pro
            20                  25                  30

Glu Leu Leu Lys Trp Ile Glu Asp Gly Ile Pro Lys Asp Pro Phe Leu
        35                  40                  45

Asn Pro Asp Leu Met Lys Asn Asn Pro Trp Val Glu Lys Gly Lys Cys
    50                  55                  60

Thr Ile Leu
65

<210> SEQ ID NO 27
<211> LENGTH: 560
<212> TYPE: DNA
<213> ORGANISM: Rattus norvegicus

<400> SEQUENCE: 27
ggaggtggag gaggaggagg ggggggggggg gaagaggggg aggagaagga ggattcatta      60
ttgcagggat tggactcaga gaaacagacc caggcatgg agacaggtgg tgcctaggag       120
gaggaggcgg tcctgagggg ctgcacccca ggggaggggg cggggctggg aatgggatct     180
```

```
gcagaaccgc cagccatccc agccctgagc tgcaacagcc atgtccaaca acatggccaa      240
gatcgctgag gcccgcaaga cggtggagca actgaagctg aggtgaaca tcgatcgcat       300 gaaggtgtcg caggcggcag cggagctatt ggctttctgc gaaacgcacg ctaaggatga      360
cccactggtg actcctgtcc ctgccgccga gaatcccttc cgcgacaaac gactcttttg      420
caccctgctc tgagccccca agatagtttt atcctcccgc gcagaaatat gaatccaata      480
aacttggtga cttggtggtg cctgccattt aggggaaaat gaggcacggg gcaaaaacgt      540
gggggccacc tttgtgggga                                                  560
```

<210> SEQ ID NO 28
<211> LENGTH: 70
<212> TYPE: PRT
<213> ORGANISM: Rattus norvegicus

<400> SEQUENCE: 28

```
Met Ser Asn Asn Met Ala Lys Ile Ala Glu Ala Arg Lys Thr Val Glu
1               5                   10                  15

Gln Leu Lys Leu Glu Val Asn Ile Asp Arg Met Lys Val Ser Gln Ala
            20                  25                  30

Ala Ala Glu Leu Leu Ala Phe Cys Glu Thr His Ala Lys Asp Asp Pro
        35                  40                  45

Leu Val Thr Pro Val Pro Ala Ala Glu Asn Pro Phe Arg Asp Lys Arg
    50                  55                  60

Leu Phe Cys Thr Leu Leu
65                  70
```

<210> SEQ ID NO 29
<211> LENGTH: 558
<212> TYPE: DNA
<213> ORGANISM: Drosophila melanogaster

<400> SEQUENCE: 29

```
atggatccca gtgctctaca aaacatggat cgggacgcat taaagaagca atcgagaat      60 atgaaatatc aggcctccat ggagcgctgg ccgttatcta atccatagc agaaatgcgc      120 tcgttcatcg aggagaacga gaaaaatgat ccgttgatca atgcgccgga taagaagaac      180
aatccatggg ccgaaaaggg caatgccct caacatcatc agcaattaga taccctagc       240 caatgtagca gccaagtttt ggggcaggat ttgggtgaat ccccggatct ggtgccggta      300
gagatgcagc actacaacaa caactactac tactattaca actacaactt gagctatgag      360
ccgccggtcg atcggtcgct gggcggcggg gcaagcgga gcattcaacg tctgcagcaa       420
ctggtgcgaa ggacgcggta cgagctgcag caatggccgc tactgatgca gctgctcctg      480
ttcgtccttt ggctaaatgc caagttctgg cagctggtca acgaacaggt gacctaccgc      540
cgcaggaggt ggcactga                                                   558
```

<210> SEQ ID NO 30
<211> LENGTH: 185
<212> TYPE: PRT
<213> ORGANISM: Drosophila melanogaster

<400> SEQUENCE: 30

```
Met Asp Pro Ser Ala Leu Gln Asn Met Asp Arg Asp Ala Leu Lys Lys
1               5                   10                  15

Gln Ile Glu Asn Met Lys Tyr Gln Ala Ser Met Glu Arg Trp Pro Leu
            20                  25                  30
```

Ser Lys Ser Ile Ala Glu Met Arg Ser Phe Ile Glu Glu Asn Glu Lys
                 35                  40                  45

Asn Asp Pro Leu Ile Asn Ala Pro Asp Lys Lys Asn Asn Pro Trp Ala
 50                  55                  60

Glu Lys Gly Lys Cys Pro Gln His His Gln Gln Leu Asp Thr Pro Ser
 65                  70                  75                  80

Gln Cys Ser Ser Gln Val Leu Gly Gln Asp Leu Gly Ser Pro Asp
                 85                  90                  95

Leu Val Pro Val Glu Met Gln His Tyr Asn Asn Tyr Tyr Tyr Tyr
                100                 105                 110

Tyr Asn Tyr Asn Leu Ser Tyr Glu Pro Pro Val Asp Arg Ser Leu Gly
                115                 120                 125

Gly Gly Gly Lys Arg Ser Ile Gln Arg Leu Gln Gln Leu Val Arg Arg
                130                 135                 140

Thr Arg Tyr Glu Leu Gln Gln Trp Pro Leu Leu Met Gln Leu Leu Leu
145                 150                 155                 160

Phe Val Leu Trp Leu Asn Ala Lys Phe Trp Gln Leu Val Asn Glu Gln
                165                 170                 175

Val Thr Tyr Arg Arg Arg Arg Trp His
                180                 185

<210> SEQ ID NO 31
<211> LENGTH: 705
<212> TYPE: DNA
<213> ORGANISM: Caenorhabditis elegans

<400> SEQUENCE: 31
atgtttagtc aaaacccgta cgagtcacac gtcgacgtcg ccgtatctgc agcttcagct      60
aatctccgga atatgacaaa cgaacaatta atttcgttgc tagacgatga tgcccttta    120 gaatcgatta ttgtcaatct cccgcaggtc cgctcaatgc cgactgataa ggaatcagct    180
cttgccgcaa ataaatcatt agcagaatgg aatttagctc aaaagccgag aatcgatgct    240
gccaaaacgc aaacggttga tctctacgac caagtaaaaa agctccaagg agaagttgcc    300
gtgctgaaaa gtcaattgga ctctgtttcc tcatcaaaat cacttgatac aacatcgagc    360
ttgatgcaag tcgccgcaca agaagctgat gatgatgcag aagccctatt cacacaattt    420
gaaaatggag aaatatccgt ggaaattttc ctgaagcaat tcaagataa gaagacaatt    480 gctcatctac gaaaaatcaa gtctgaccgt ctcgcagcac ttcttcgtga caaacgtat    540 tcttcatatg ctcaaccaac tgtacctcct ccaatgccac acgctcagcc tggatacccaa    600 acaggaaatc acatgcctgg aataggaaat attcaattcg gatctggcta ttcaggatat    660
ccaaatattt ctcaaccttc tgctggtcgt catccatttt tctga               705

<210> SEQ ID NO 32
<211> LENGTH: 234
<212> TYPE: PRT
<213> ORGANISM: Caenorhabditis elegans

<400> SEQUENCE: 32

Met Phe Ser Gln Asn Pro Tyr Glu Ser His Val Asp Val Ala Val Ser
 1               5                  10                  15

Ala Ala Ser Ala Asn Leu Arg Asn Met Thr Asn Glu Gln Leu Ile Ser
                 20                  25                  30

Leu Leu Asp Asp Asp Ala Leu Leu Glu Ser Ile Ile Val Asn Leu Pro
                 35                  40                  45

Gln Val Arg Ser Met Pro Thr Asp Lys Glu Ser Ala Leu Ala Ala Asn
    50                  55                  60

Lys Ser Leu Ala Glu Trp Asn Leu Ala Gln Lys Pro Arg Ile Asp Ala
65                  70                  75                  80

Ala Lys Thr Gln Thr Val Asp Leu Tyr Asp Gln Val Lys Lys Leu Gln
                85                  90                  95

Gly Glu Val Ala Val Leu Lys Ser Gln Leu Asp Ser Val Ser Ser Ser
                100                 105                 110

Lys Ser Leu Asp Thr Thr Ser Ser Leu Met Gln Val Ala Ala Gln Glu
            115                 120                 125

Ala Asp Asp Ala Glu Ala Leu Phe Thr Gln Phe Glu Asn Gly Glu
            130                 135                 140

Ile Ser Val Glu Ile Phe Leu Lys Gln Phe Lys Asp Lys Lys Thr Ile
145                 150                 155                 160

Ala His Leu Arg Lys Ile Lys Ser Asp Arg Leu Ala Ala Leu Leu Arg
                165                 170                 175

Glu Gln Thr Tyr Ser Ser Tyr Ala Gln Pro Thr Val Pro Pro Pro Met
                180                 185                 190

Pro His Ala Gln Pro Gly Tyr Pro Thr Gly Asn His Met Pro Gly Ile
            195                 200                 205

Gly Asn Ile Gln Phe Gly Ser Gly Tyr Ser Gly Tyr Pro Asn Ile Ser
    210                 215                 220

Gln Pro Ser Ala Gly Arg His Pro Phe Phe
225                 230

<210> SEQ ID NO 33
<211> LENGTH: 858
<212> TYPE: DNA
<213> ORGANISM: Homo sapiens

<400> SEQUENCE: 33
atggcgggcg ccgggagcga agcccggttc gccgggctgt cgctggtgca gctcaacgag      60
ctgctggagg acgagggcca gctgacggag atggtgcaga agatggagga gacacagaat     120
gttcagctta caaagaaat gacacttgcc agcaaccgga gcctggcaga aggaaacctt     180
ttgtaccagc cccagctgga cacgttgaaa gcacgcttga cccagaaata ccaggaactc     240
caggttctct ttgaagccta tcagataaag aagaccaaat tagacagaca gtctagcagt     300
gcttccttgg agaccctgtt agcacttctt caggcagaag gggccaagat tgaggaagac     360
actgagaaca tggcagagaa gtttctggat ggagaacttc ctctggattc cttcattgat     420
gtctatcaga gcaaacggaa actggcccac atgcgacggg tgaaaatcga aagctccag     480 gagatggtcc taaaggggca gagactccca caggccctgg ccccgctgcc cccaggctg     540 cccgaactgg cacctaccgc cccccttccc taccctgccc cagaggccag tgggcctcct     600
gccgttgcac ctcggcgcat cccccccca ccaccccgg tgcctgcggg acgcttagcc     660
accccgttta ctgcggccat gagttcggga caggccgtgc cgtacccagg attacagtgc     720
ccgcccctgc ccccccgcgt gggcctcccc actcagcaag gattctcttc gcagttcgtg     780
tccccatatc cgccacctct ccctcagaga ccccgcccc ggctccctcc acaccagccg     840
ggtttcatcc tccagtga                                                     858

<210> SEQ ID NO 34
<211> LENGTH: 285
<212> TYPE: PRT

<213> ORGANISM: Homo sapiens

<400> SEQUENCE: 34

```
Met Ala Gly Ala Gly Ser Glu Ala Arg Phe Ala Gly Leu Ser Leu Val
1               5                   10                  15

Gln Leu Asn Glu Leu Glu Asp Glu Gly Gln Leu Thr Glu Met Val
            20                  25                  30

Gln Lys Met Glu Glu Thr Gln Asn Val Gln Leu Asn Lys Glu Met Thr
            35                  40                  45

Leu Ala Ser Asn Arg Ser Leu Ala Glu Gly Asn Leu Leu Tyr Gln Pro
        50                  55                  60

Gln Leu Asp Thr Leu Lys Ala Arg Leu Thr Gln Lys Tyr Gln Glu Leu
65                  70                  75                  80

Gln Val Leu Phe Glu Ala Tyr Gln Ile Lys Lys Thr Lys Leu Asp Arg
                85                  90                  95

Gln Ser Ser Ser Ala Ser Leu Glu Thr Leu Leu Ala Leu Leu Gln Ala
            100                 105                 110

Glu Gly Ala Lys Ile Glu Glu Asp Thr Glu Asn Met Ala Glu Lys Phe
        115                 120                 125

Leu Asp Gly Glu Leu Pro Leu Asp Ser Phe Ile Asp Val Tyr Gln Ser
130                 135                 140

Lys Arg Lys Leu Ala His Met Arg Arg Val Lys Ile Glu Lys Leu Gln
145                 150                 155                 160

Glu Met Val Leu Lys Gly Gln Arg Leu Pro Gln Ala Leu Ala Pro Leu
                165                 170                 175

Pro Pro Arg Leu Pro Glu Leu Ala Pro Thr Ala Pro Leu Pro Tyr Pro
            180                 185                 190

Ala Pro Glu Ala Ser Gly Pro Pro Ala Val Ala Pro Arg Arg Ile Pro
        195                 200                 205

Pro Pro Pro Pro Pro Val Pro Ala Gly Arg Leu Ala Thr Pro Phe Thr
210                 215                 220

Ala Ala Met Ser Ser Gly Gln Ala Val Pro Tyr Pro Gly Leu Gln Cys
225                 230                 235                 240

Pro Pro Leu Pro Pro Arg Val Gly Leu Pro Thr Gln Gly Phe Ser
                245                 250                 255

Ser Gln Phe Val Ser Pro Tyr Pro Pro Leu Pro Gln Arg Pro Pro
            260                 265                 270

Pro Arg Leu Pro Pro His Gln Pro Gly Phe Ile Leu Gln
        275                 280                 285
```

<210> SEQ ID NO 35
<211> LENGTH: 1136
<212> TYPE: DNA
<213> ORGANISM: Homo sapiens

<400> SEQUENCE: 35

```
cggacgcgtg ggcgcggctg cggtttaacc cgcggtggcg gcggcgacgg cggccctggc      60
agggaaggat ggagacgctg aaggataaga ccctgcagga gctggaggag ttgcagaatg     120
actcggaggc gattgaccag ctggccctgg agtccctga ggtccaggac ctacagctgg     180
aacgggagat ggcactggcc accaaccgga gcctggcaga gcggaacttg gagttccagg     240
gtcccctgga gatcagccgc tcaaacctct cggatagata ccaggagctc cggaagctcg     300
tggagcggtg ccaggagcag aaggcaaagc tggagaaatt ttcttcagca ctgcagccag     360
ggaccttgtt agaccttctg caggtggaag gcatgaagat cgaagaagag tccgaggcca     420
```

```
tggctgagaa gttcctggag ggcgaggtgc ccctggaaac gttcctggag aattttttcct   480
ccatgaggat gctgtcccac ctgcgccggg ttcgcgtgga aaagctccag gaagtggtga   540
ggaagcccag ggcttcccag gagctggccg gcgatgcccc tccacccgt ccaccacccc    600
cggtgcgccc agaccccag ggaacacccc ctgtggttga agagcagccg cagccaccat    660
tagccatgcc tccctaccct ttgccctaca gccatcccc cagcctgcct gtgggcccca    720
ctgcccatgg agccctgcca ccggcccctt tcccagtagt gtcccagccc tccttctaca   780
gcgggcctct gggccccact tacccggcag cccagcttgg acccagggg gctgcgggtt    840
actcctggtc ccacagagg agcatgccac cccggccggg ctatcctggg accccaatgg    900
gtgcctctgg gctgggtac cccttgcggg gaggcaggc ccccagtcct ggttatcctc     960
aacagtcccc atacccgca acaggaggaa aacctcccta cccaatacag cctcagctcc   1020
ccagctttcc aggccagccc cagccctcag tgccctgca gccccttat ccccccgggc    1080
ccgcccctcc ctatgggttc ccaccaccgc cggggcctgc ctggcctggg tattag      1136
```

<210> SEQ ID NO 36
<211> LENGTH: 377
<212> TYPE: PRT
<213> ORGANISM: Homo sapiens

<400> SEQUENCE: 36

```
Asp Ala Trp Ala Arg Leu Arg Phe Asn Pro Arg Trp Arg Arg Arg
1               5                   10                  15

Arg Pro Trp Gln Gly Arg Met Glu Thr Leu Lys Asp Lys Thr Leu Gln
            20                  25                  30

Glu Leu Glu Glu Leu Gln Asn Asp Ser Glu Ala Ile Asp Gln Leu Ala
        35                  40                  45

Leu Glu Ser Pro Glu Val Gln Asp Leu Gln Leu Glu Arg Glu Met Ala
    50                  55                  60

Leu Ala Thr Asn Arg Ser Leu Ala Glu Arg Asn Leu Glu Phe Gln Gly
65                  70                  75                  80

Pro Leu Glu Ile Ser Arg Ser Asn Leu Ser Asp Arg Tyr Gln Glu Leu
                85                  90                  95

Arg Lys Leu Val Glu Arg Cys Gln Glu Gln Lys Ala Lys Leu Glu Lys
            100                 105                 110

Phe Ser Ser Ala Leu Gln Pro Gly Thr Leu Leu Asp Leu Leu Gln Val
        115                 120                 125

Glu Gly Met Lys Ile Glu Glu Glu Ser Glu Ala Met Ala Glu Lys Phe
    130                 135                 140

Leu Glu Gly Glu Val Pro Leu Glu Thr Phe Leu Glu Asn Phe Ser Ser
145                 150                 155                 160

Met Arg Met Leu Ser His Leu Arg Arg Val Arg Val Glu Lys Leu Gln
                165                 170                 175

Glu Val Val Arg Lys Pro Arg Ala Ser Gln Glu Leu Ala Gly Asp Ala
            180                 185                 190

Pro Pro Pro Arg Pro Pro Pro Val Arg Pro Asp Pro Gln Gly Thr
        195                 200                 205

Pro Pro Val Val Glu Glu Gln Pro Gln Pro Leu Ala Met Pro Pro
    210                 215                 220

Tyr Pro Leu Pro Tyr Ser Pro Ser Pro Leu Pro Val Gly Pro Thr
225                 230                 235                 240

Ala His Gly Ala Leu Pro Pro Ala Pro Phe Pro Val Val Ser Gln Pro
```

```
                245             250             255
Ser Phe Tyr Ser Gly Pro Leu Gly Pro Thr Tyr Pro Ala Ala Gln Leu
            260             265             270

Gly Pro Arg Gly Ala Ala Gly Tyr Ser Trp Ser Pro Gln Arg Ser Met
        275             280             285

Pro Pro Arg Pro Gly Tyr Pro Gly Thr Pro Met Gly Ala Ser Gly Pro
    290             295             300

Gly Tyr Pro Leu Arg Gly Gly Arg Ala Pro Ser Pro Gly Tyr Pro Gln
305             310             315             320

Gln Ser Pro Tyr Pro Ala Thr Gly Gly Lys Pro Pro Tyr Pro Ile Gln
            325             330             335

Pro Gln Leu Pro Ser Phe Pro Gly Gln Pro Gln Pro Ser Val Pro Leu
        340             345             350

Gln Pro Pro Tyr Pro Pro Gly Pro Ala Pro Pro Tyr Gly Phe Pro Pro
    355             360             365

Pro Pro Gly Pro Ala Trp Pro Gly Tyr
370             375
```

<210> SEQ ID NO 37
<211> LENGTH: 645
<212> TYPE: DNA
<213> ORGANISM: Drosophila melanogaster

<400> SEQUENCE: 37

```
atgtaccagg aatacctata ccaactgcgg gccaccatca ccccgatgtg ccacgaggag    60
ctgaaggaac tgctgaacga tgacgacaag ctggacgaga aggttgacga agttctccag   120
gtgctccgaa cacaaaagac cagtgttttc gaggacaaca ggagtcgggc ggagcgcaat   180
atcgagcggg agccgcagat catcgagctg cgggggcagc tggcagaact ctcggaggat   240
gggcgcacca ggtgctcctc tgtccaggag aaactctcac agctcaagga gaagtcgggc   300
ggagtgggcc ttgaaacggc gctggccctg ctgcagacag ctgcctccga gagcgaggag   360
cagaccgagg agatggtcaa gaagttcaac gacagcgata tcggcgtgga ggactttctg   420
gacgcgttcc tccctatccg gaggaccatg cacctgcgtc gcctcaaggc cgaaaaaatg   480
caggagctga tgcgcaaaca cgcgccaggg ccgggcccaa atacttctct gccagcctac   540
ggaaacgtgc cctccagcgg attctatccc gcgtctgggg gctccgcccc ttacccaatc   600
atgggtcccc tgatgcccat gccaccgcca tccagaccgt actga                  645
```

<210> SEQ ID NO 38
<211> LENGTH: 214
<212> TYPE: PRT
<213> ORGANISM: Drosophila melanogaster

<400> SEQUENCE: 38

```
Met Tyr Gln Glu Tyr Leu Tyr Gln Leu Arg Ala Thr Ile Thr Pro Met
1               5                   10                  15

Cys His Glu Glu Leu Lys Glu Leu Leu Asn Asp Asp Asp Lys Leu Asp
            20                  25                  30

Glu Lys Val Asp Glu Val Leu Gln Val Leu Arg Thr Gln Lys Thr Ser
        35                  40                  45

Val Phe Glu Asp Asn Arg Ser Arg Ala Glu Arg Asn Ile Glu Arg Glu
    50                  55                  60

Pro Gln Ile Ile Glu Leu Arg Gly Gln Leu Ala Glu Leu Ser Glu Asp
65                  70                  75                  80
```

```
Gly Arg Thr Arg Cys Ser Ser Val Gln Glu Lys Leu Ser Gln Leu Lys
                 85                  90                  95
Glu Lys Ser Gly Gly Val Gly Leu Glu Thr Ala Leu Ala Leu Leu Gln
            100                 105                 110
Thr Ala Ala Ser Glu Ser Glu Gln Thr Glu Met Val Lys Lys
        115                 120                 125
Phe Asn Asp Ser Asp Ile Gly Val Glu Asp Phe Leu Asp Ala Phe Leu
    130                 135                 140
Pro Ile Arg Arg Thr Met His Leu Arg Arg Leu Lys Ala Glu Lys Met
145                 150                 155                 160
Gln Glu Leu Met Arg Lys Gln Arg Gln Gly Pro Gly Pro Asn Thr Ser
                165                 170                 175
Leu Pro Ala Tyr Gly Asn Val Pro Ser Ser Gly Phe Tyr Pro Ala Ser
            180                 185                 190
Gly Gly Ser Ala Pro Tyr Pro Ile Met Gly Pro Leu Met Pro Met Pro
        195                 200                 205
Pro Pro Ser Arg Pro Tyr
    210
```

<210> SEQ ID NO 39
<211> LENGTH: 2319
<212> TYPE: DNA
<213> ORGANISM: Caenorhabditis elegans

<400> SEQUENCE: 39

```
atgttagacc tgacaaacaa agaatctgag tcgtcagaca acggaaatag caagtacgaa      60
gattccatag acggacgaga agttggcaca agcaaaccat ttaaagaaga cgatcgttg     120
gaagacttgc aggcggactt ggctgatatg gcagtttgga tggaaggact agatgccact    180
aaactacctc tgaacgatcc acaacttctc tgcaatggtc gtgcattttc agaagtactc    240
cataacgtag acaaaaattt cttcaccgac ggctggcttg aaacaatgcc cgagaacagg    300
accacaaata ttatggtgtt ccgaagttgt actagaaaac tctggcgaaa atgtttgat    360
tacgtgaatc acatcaatcg gacggtcgtc agttcccgtt ggacggatat tcatgaacgt    420
atcgatggaa tctacgaatc agatttaccc gctatggtta atctgggaat ggcagttgtt    480
acgcttgctc acataggaaa gatgcaaag agatttgtgg attattctaa agctcttact    540
tcgacacaca aatcaatgat gtcaaatgtg gctaagatgg tcaccactgt gatagatgaa    600
atgccagaaa atccgtgctt tcatgaaata tcggagcttc acggatcgca gagcgaactc    660
aattcactgt cagaatcgtc tggaaaattg aatggaaatg ttctagtga gcggaggagt    720
aatgctgatc aaattctcgt tgacgcagag ctggaaattg aacgtttacg gactgaaaca    780
gagaatcaga ggaaagaaat tgaacggctg actaaatcct ttgaaactgc acaacacgat    840
atgtcatcaa attctgaatc aggtgatatc agcatcttgg agaagcaaaa tgaggaactc    900
cggcagaaac gtcgagagtt ggaagaaaag aatctcgagt tggatgctgc tgtggatcag    960
tttaaaggga tcgttttga acttaccaac gagaatgatg tgcttcgtag atcggacaaa   1020
gagagacaga gactacaaac agtgctggat gctgctcaat ccgatttaga tgaatggaaa   1080
actgtagcca atcaatatca aaagaagcg gaactctcca gcaacaaga taaggaaatc    1140
aaggagttgc tttcccaaaa caaagcattg aaatcgcgc tcgatcatca tgtcaaaagt   1200
gcaacgttgg aagatgctaa caaaaatggg attgctcagt tgcggacaca agttggcggt   1260
ttgactgctc ttaacactga gttaaaaagct tctctggatt caaagaaacg atgtgttgag   1320
```

```
cagttagaga tccaattgat tcagcataag gagaaagtca aagagttgga agatcgaaaa    1380
gacgaattga ttgaagagcg gaaccggctg gaaaaccaac ttatttcaa agaagctgtc     1440 actccacgat cgcttcatga gtctatgttt gaagcaggaa atctgtctga agaacacg      1500 ttgccattgg aaattgagaa caaacgacta acggagcgta ttcaagagct ggaatcgttg    1560
gagccgctga aggggagct tatcacgctg aaaagtaaaa atggcgtttt ggaagaggag     1620
aaactattcg ccaccaagca aattgaagag ctccagcagc agattgaaga tcttcaagag    1680
aatcttctca agaaccagga acacgctagc ggcgacgttg ttggtttaaa aattcagctg    1740
gagaaagcag aagttgaagc tcaacagatg agagaagcta aaatgcgtgc ggagactaac    1800
caggctcaag ttgatgagat actcaaaaaa cgaactgctg aattggaggt caacgcgact    1860
gctctgcaaa aagctaaagc agtgattgat gaactggaat acaattctcg tccagtgagt    1920
gaagacagta tgacttctgt tcaagctttc aaagaaatga agaagaaaa tgagaagctt     1980 cgccagaaag ttgaaaaatt ggagattgag ctcaatacag taacccaagg attcgaacaa    2040
gagaatcggc ttttaacgag tgcctcgcat caacaggttt tgaatcgatc tatcgacgaa    2100
gtgatgagca tgagagcaca cgctggatcc gaagagccgc agactctgtt ggatacacag    2160
aaaatgagtg gagcacttcc atggagatca cttgcttccg agaccgtcg agaattgccg     2220 acggcgatgg ctagcattct cgtccttgga ttcctcgtct tcatcgcctg gatgttcata    2280
aacataaaca gcgcactgaa tgctcctcca aatgcctaa                           2319
```

<210> SEQ ID NO 40
<211> LENGTH: 777
<212> TYPE: PRT
<213> ORGANISM: Caenorhabditis elegans

<400> SEQUENCE: 40

```
Met Leu Asp Leu Thr Asn Lys Glu Ser Glu Ser Ser Asp Asn Gly Asn
1               5                   10                  15

Ser Lys Tyr Glu Asp Ser Ile Asp Gly Arg Glu Val Gly Thr Ser Lys
            20                  25                  30

Pro Phe Lys Glu Glu Arg Ser Leu Glu Asp Leu Gln Ala Asp Leu Ala
        35                  40                  45

Asp Met Ala Val Trp Met Glu Gly Leu Asp Ala Thr Lys Leu Pro Leu
    50                  55                  60

Asn Asp Pro Gln Leu Leu Cys Asn Gly Arg Ala Phe Ser Glu Val Leu
65                  70                  75                  80

His Asn Val Asp Lys Asn Phe Phe Thr Asp Gly Trp Leu Glu Thr Met
                85                  90                  95

Pro Glu Asn Arg Thr Thr Asn Ile Met Val Phe Arg Ser Cys Thr Arg
            100                 105                 110

Lys Leu Trp Arg Lys Met Phe Asp Tyr Val Asn His Ile Asn Arg Thr
        115                 120                 125

Val Val Ser Ser Arg Trp Thr Asp Ile His Glu Arg Ile Asp Gly Ile
    130                 135                 140

Tyr Glu Ser Asp Leu Pro Ala Met Val Asn Leu Gly Met Ala Val Val
145                 150                 155                 160

Thr Leu Ala His Ile Gly Lys Asn Ala Lys Arg Phe Val Asp Tyr Ser
                165                 170                 175

Lys Ala Leu Thr Ser Thr His Lys Ser Met Met Ser Asn Val Ala Lys
            180                 185                 190

Met Val Thr Thr Val Ile Asp Glu Met Pro Glu Asn Pro Cys Phe His
```

-continued

```
                195                 200                 205
Glu Ile Ser Glu Leu His Gly Ser Gln Ser Glu Leu Asn Ser Leu Ser
    210                 215                 220
Glu Ser Ser Gly Lys Leu Asn Gly Asn Gly Ser Ser Glu Arg Arg Ser
225                 230                 235                 240
Asn Ala Asp Gln Ile Leu Val Asp Ala Glu Leu Glu Ile Glu Arg Leu
                245                 250                 255
Arg Thr Glu Thr Glu Asn Gln Arg Lys Glu Ile Glu Arg Leu Thr Lys
            260                 265                 270
Ser Phe Glu Thr Ala Gln His Asp Met Ser Ser Asn Ser Glu Ser Gly
            275                 280                 285
Asp Ile Ser Ile Leu Glu Lys Gln Asn Glu Glu Leu Arg Gln Lys Arg
        290                 295                 300
Arg Glu Leu Glu Glu Lys Asn Leu Glu Leu Asp Ala Ala Val Asp Gln
305                 310                 315                 320
Phe Lys Gly Ile Val Phe Glu Leu Thr Asn Glu Asn Asp Val Leu Arg
                325                 330                 335
Arg Ser Asp Lys Glu Arg Gln Arg Leu Gln Thr Val Leu Asp Ala Ala
            340                 345                 350
Gln Ser Asp Leu Asp Glu Trp Lys Thr Val Ala Asn Gln Tyr Gln Lys
            355                 360                 365
Glu Ala Glu Leu Ser Lys Gln Gln Asp Lys Glu Ile Lys Glu Leu Leu
        370                 375                 380
Ser Gln Asn Lys Ala Leu Lys Ser Arg Leu Asp His His Val Lys Ser
385                 390                 395                 400
Ala Thr Leu Glu Asp Ala Asn Lys Asn Gly Ile Ala Gln Leu Arg Thr
                405                 410                 415
Gln Val Gly Gly Leu Thr Ala Leu Asn Thr Glu Leu Lys Ala Ser Leu
            420                 425                 430
Asp Ser Lys Lys Arg Cys Val Glu Gln Leu Glu Ile Gln Leu Ile Gln
            435                 440                 445
His Lys Glu Lys Val Lys Glu Leu Glu Asp Arg Lys Asp Glu Leu Ile
        450                 455                 460
Glu Glu Arg Asn Arg Leu Glu Asn Gln Leu Ile Phe Lys Glu Ala Val
465                 470                 475                 480
Thr Pro Arg Ser Leu His Glu Ser Met Phe Glu Ala Gly Asn Leu Ser
                485                 490                 495
Phe Glu Pro Phe Ser Glu Lys Asn Thr Leu Pro Leu Glu Ile Glu Asn
            500                 505                 510
Lys Arg Leu Thr Glu Arg Ile Gln Glu Leu Glu Ser Leu Glu Pro Leu
            515                 520                 525
Lys Gly Glu Leu Ile Thr Leu Lys Ser Lys Asn Gly Val Leu Glu Glu
        530                 535                 540
Glu Lys Leu Phe Ala Thr Lys Gln Ile Glu Glu Leu Gln Gln Gln Ile
545                 550                 555                 560
Glu Asp Leu Gln Glu Asn Leu Leu Lys Asn Gln Glu His Ala Ser Gly
                565                 570                 575
Asp Val Val Gly Leu Lys Ile Gln Leu Glu Lys Ala Glu Val Glu Ala
            580                 585                 590
Gln Gln Met Arg Glu Ala Lys Met Arg Ala Glu Thr Asn Gln Ala Gln
            595                 600                 605
Val Asp Glu Ile Leu Lys Lys Arg Thr Ala Glu Leu Glu Val Asn Ala
        610                 615                 620
```

Thr Ala Leu Gln Lys Ala Lys Ala Val Ile Asp Glu Leu Glu Tyr Asn
625                 630                 635                 640

Ser Arg Pro Val Ser Glu Asp Ser Met Thr Ser Val Gln Ala Phe Lys
            645                 650                 655

Glu Met Lys Glu Glu Asn Glu Lys Leu Arg Gln Lys Val Glu Lys Leu
        660                 665                 670

Glu Ile Glu Leu Asn Thr Val Thr Gln Gly Phe Glu Gln Glu Asn Arg
        675                 680                 685

Leu Leu Thr Ser Ala Ser His Gln Gln Val Leu Asn Arg Ser Ile Asp
        690                 695                 700

Glu Val Met Ser Met Arg Ala His Ala Gly Ser Glu Glu Pro Gln Thr
705                 710                 715                 720

Leu Leu Asp Thr Gln Lys Met Ser Gly Ala Leu Pro Trp Arg Ser Leu
            725                 730                 735

Ala Ser Glu Thr Arg Arg Glu Leu Pro Thr Ala Met Ala Ser Ile Leu
            740                 745                 750

Val Leu Gly Phe Leu Val Phe Ile Ala Trp Met Phe Ile Asn Ile Asn
            755                 760                 765

Ser Ala Leu Asn Ala Pro Pro Asn Ala
770                 775

<210> SEQ ID NO 41
<211> LENGTH: 2187
<212> TYPE: DNA
<213> ORGANISM: Homo sapiens

<400> SEQUENCE: 41

```
atggaggaga cgcagccgcc gccgcagcct aagctgcccc tgtgcgacag cctcatgatc      60
tggctgcaga cattcaatac tgcctcacct tgtcaagatg tcaaacagct gactagtgga     120
gttgccatgg cacaagttct tcatcaaatt gatgcagctt ggtttaacga atcttggtta     180
agccgaatta agaggatgt tggggacaac tggagaataa aggccagtaa tgtaaagaag     240
gtccttcaag gaattatgag ttattatcat gagtttttgg ggcagcagat tcagaagca     300 cttatccctg atttaaacca ataaccgaa tgttcagatc cagtggagct gggaggttg      360 ctccagctta ttttaggttg tgcgatcaac tgtgaaaaga agcaagaaca tattcaaat     420 ataatgacac tggaagagtc tgttcaacat gtggtcatga ctgctattca agagttgatg    480
agtaaagaaa tattgagctc tcctccaaat gatgctgttg agaattgga gcaacagctt     540 aaaagagcct tggaagaact tcaggaagca ctagcagaaa agaagagct gaggcaaaga     600 tgtgaagaat tggatatgca ggtgactaca cttcaagatg aaagaattc actggtttct    660 gaaaatgaga tgatgaatga aaaacttgac cagttggatg gctcttttga tgatccaaac    720
acagtggttg caaaaaagta ttttcatgca caattacaac tagaacaatt acaggaagaa    780
aacttcaggc ttgaagctgc aaaagatgat taccgtgttc actgtgaaga acttgaaaag    840
cagctaatcg aattccagca taggaatgat gaattgacta gtcttgcaga agaaacaaga    900
gccctgaaag atgaaataga tgttcttagg gctacctctg ataaagcaaa taaactggag    960
tcaacagttg agatatatcg tcagaagcta caagatctga tgaccttcg caagcaggtg   1020 aaaactttac aggaaaccaa catgatgtat atgcataata cagtcagctt agaagaagaa   1080
ttaaaaaaag caaatgcagc acgtacacaa ttagaaacat acaaaaggca ggttcaagat   1140
cttcatgtta actttcctc cgaatccaag agggcagaca cactagcgtt tgaaatgaag   1200
```

```
cggcttgaag aaaaacatga agctttactt aaggaaaaag agagactaat tgagcagcgt    1260
gatactttga agaaacaaa tgaagagctt cgatgttcac aagtacaaca ggaccaccta    1320
aaccaaacag atgcatctgc tacaaaaagt tatgagaatc ttgctgctga gattatgcca    1380
gtggaatata gggaggtgtt tattcgactg caacatgaaa ataagatgct tcgcttacag    1440
caagaaggct ctgagaatga acgtattgag gaacttcagg agcagctaga acagaaacac    1500
cgtaaaatga atgaactgga aactgagcag aggctgagca aagagcgtat tagagaattg    1560
cagcagcaga ttgaggaccct ccagaaatct ttacaggaac aaggttccaa gtctgaaggc    1620
gaaagttcca gcaaattaaa gcagaagttg aagctcata tggaaaaact cacagaggtc    1680
catgaagaat tacagaagaa acaagaactc attgaagatc ttcagccaga tataaatcaa    1740
aatgtacaaa agatcaatga acttgaagct gctcttcaga agaaagatga agatatgaaa    1800
gcaatggagg aaagatataa aatgtacttg gagaaagcca gaaatgtaat aaaaactttg    1860
gatcccaagt taaatccagc atcagctgaa ataatgctac taagaaagca gttggcagag    1920
aaagagagaa gaattgagat tctggagagt gaatgcaaag tagcaaaatt ccgtgattat    1980
gaagaaaaac tcattgtttc tgcgtggtat aataagagtc tagcattcca gaaactgggg    2040
atggaatcta gacttgtgag cggcggtggt gcctgcagtg acactggtgc gtgcactcct    2100
gcgcggtctt tcttagcgca gcaacggcac atcaccaaca ccagaagaaa tctctctgtt    2160
aaagtccctg ctacaacatc tgattaa                                       2187
```

<210> SEQ ID NO 42
<211> LENGTH: 728
<212> TYPE: PRT
<213> ORGANISM: Homo sapiens

<400> SEQUENCE: 42

```
Met Glu Glu Thr Gln Pro Pro Gln Pro Lys Leu Pro Leu Cys Asp
1               5                   10                  15

Ser Leu Met Ile Trp Leu Gln Thr Phe Asn Thr Ala Ser Pro Cys Gln
            20                  25                  30

Asp Val Lys Gln Leu Thr Ser Gly Val Ala Met Ala Gln Val Leu His
        35                  40                  45

Gln Ile Asp Ala Ala Trp Phe Asn Glu Ser Trp Leu Ser Arg Ile Lys
    50                  55                  60

Glu Asp Val Gly Asp Asn Trp Arg Ile Lys Ala Ser Asn Val Lys Lys
65                  70                  75                  80

Val Leu Gln Gly Ile Met Ser Tyr Tyr His Glu Phe Leu Gly Gln Gln
                85                  90                  95

Ile Ser Glu Ala Leu Ile Pro Asp Leu Asn Gln Ile Thr Glu Cys Ser
            100                 105                 110

Asp Pro Val Glu Leu Gly Arg Leu Leu Gln Leu Ile Leu Gly Cys Ala
        115                 120                 125

Ile Asn Cys Glu Lys Lys Gln Glu His Ile Gln Asn Ile Met Thr Leu
    130                 135                 140

Glu Glu Ser Val Gln His Val Val Met Thr Ala Ile Gln Glu Leu Met
145                 150                 155                 160

Ser Lys Glu Ile Leu Ser Ser Pro Asn Asp Ala Val Gly Glu Leu
                165                 170                 175

Glu Gln Gln Leu Lys Arg Ala Leu Glu Glu Leu Gln Glu Ala Leu Ala
            180                 185                 190

Glu Lys Glu Glu Leu Arg Gln Arg Cys Glu Glu Leu Asp Met Gln Val
```

-continued

```
                195                 200                 205
Thr Thr Leu Gln Asp Glu Lys Asn Ser Leu Val Ser Glu Asn Glu Met
    210                 215                 220

Met Asn Glu Lys Leu Asp Gln Leu Asp Gly Ser Phe Asp Asp Pro Asn
225                 230                 235                 240

Thr Val Val Ala Lys Lys Tyr Phe His Ala Gln Leu Gln Leu Glu Gln
                245                 250                 255

Leu Gln Glu Glu Asn Phe Arg Leu Glu Ala Ala Lys Asp Asp Tyr Arg
            260                 265                 270

Val His Cys Glu Glu Leu Glu Lys Gln Leu Ile Glu Phe Gln His Arg
        275                 280                 285

Asn Asp Glu Leu Thr Ser Leu Ala Glu Thr Arg Ala Leu Lys Asp
    290                 295                 300

Glu Ile Asp Val Leu Arg Ala Thr Ser Asp Lys Ala Asn Lys Leu Glu
305                 310                 315                 320

Ser Thr Val Glu Ile Tyr Arg Gln Lys Leu Gln Asp Leu Asn Asp Leu
                325                 330                 335

Arg Lys Gln Val Lys Thr Leu Gln Glu Thr Asn Met Met Tyr Met His
            340                 345                 350

Asn Thr Val Ser Leu Glu Glu Leu Lys Lys Ala Asn Ala Ala Arg
        355                 360                 365

Thr Gln Leu Glu Thr Tyr Lys Arg Gln Val Gln Asp Leu His Val Lys
    370                 375                 380

Leu Ser Ser Glu Ser Lys Arg Ala Asp Thr Leu Ala Phe Glu Met Lys
385                 390                 395                 400

Arg Leu Glu Glu Lys His Glu Ala Leu Leu Lys Glu Lys Glu Arg Leu
                405                 410                 415

Ile Glu Gln Arg Asp Thr Leu Lys Glu Thr Asn Glu Glu Leu Arg Cys
            420                 425                 430

Ser Gln Val Gln Gln Asp His Leu Asn Gln Thr Asp Ala Ser Ala Thr
        435                 440                 445

Lys Ser Tyr Glu Asn Leu Ala Ala Glu Ile Met Pro Val Glu Tyr Arg
    450                 455                 460

Glu Val Phe Ile Arg Leu Gln His Glu Asn Lys Met Leu Arg Leu Gln
465                 470                 475                 480

Gln Glu Gly Ser Glu Asn Glu Arg Ile Glu Glu Leu Gln Glu Gln Leu
                485                 490                 495

Glu Gln Lys His Arg Lys Met Asn Glu Leu Glu Thr Glu Gln Arg Leu
            500                 505                 510

Ser Lys Glu Arg Ile Arg Glu Leu Gln Gln Gln Ile Glu Asp Leu Gln
        515                 520                 525

Lys Ser Leu Gln Glu Gln Gly Ser Lys Ser Glu Gly Glu Ser Ser Ser
    530                 535                 540

Lys Leu Lys Gln Lys Leu Glu Ala His Met Glu Lys Leu Thr Glu Val
545                 550                 555                 560

His Glu Glu Leu Gln Lys Gln Glu Leu Ile Glu Asp Leu Gln Pro
                565                 570                 575

Asp Ile Asn Gln Asn Val Gln Lys Ile Asn Glu Leu Glu Ala Ala Leu
            580                 585                 590

Gln Lys Lys Asp Glu Asp Met Lys Ala Met Glu Glu Arg Tyr Lys Met
        595                 600                 605

Tyr Leu Glu Lys Ala Arg Asn Val Ile Lys Thr Leu Asp Pro Lys Leu
    610                 615                 620
```

Asn Pro Ala Ser Ala Glu Ile Met Leu Leu Arg Lys Gln Leu Ala Glu
625                 630                 635                 640

Lys Glu Arg Arg Ile Glu Ile Leu Glu Ser Glu Cys Lys Val Ala Lys
            645                 650                 655

Phe Arg Asp Tyr Glu Glu Lys Leu Ile Val Ser Ala Trp Tyr Asn Lys
        660                 665                 670

Ser Leu Ala Phe Gln Lys Leu Gly Met Glu Ser Arg Leu Val Ser Gly
    675                 680                 685

Gly Gly Ala Cys Ser Asp Thr Gly Ala Cys Thr Pro Ala Arg Ser Phe
690                 695                 700

Leu Ala Gln Gln Arg His Ile Thr Asn Thr Arg Arg Asn Leu Ser Val
705                 710                 715                 720

Lys Val Pro Ala Thr Thr Ser Asp
            725

<210> SEQ ID NO 43
<211> LENGTH: 4597
<212> TYPE: DNA
<213> ORGANISM: Rattus norvegicus

<400> SEQUENCE: 43

| | | |
|---|---|---|
| ggcggccgcg gcggctgctg ctgctgctgc tgctactggg aggcaggtga cggcgaccga | 60 |
| cggcgtctca ggcgacttaa ccaagagact aagttctcta tagaaacacc cacatttgta | 120 |
| tggatgattg gggaaagata gtggcagcag acaagggaaa agcatcctga ccttccgaga | 180 |
| aaatgagtat gctgaaaccc agcgggctga aggccccgac caagatccta aagcctggga | 240 |
| gcacagcctt gaagacccct gctgctgctg cagctccatt ggagaagaca gtacccagtg | 300 |
| aaaaagcctc aggccctcca tcctctgaga cccaagagga gtttgtggac gacttccgag | 360 |
| ttggagaacg tgtttgggtg aacgggaata aacctggatt tatccagttt cttggggaaa | 420 |
| ctcagtttgc accaggccag tgggctggta ttgttttgga tgaacccata ggaaagaacg | 480 |
| acggctcagt ggcaggagtg cggtatttcc agtgtgagcc tttaaagggc atcttcaccc | 540 |
| gaccgtcaaa gctaacgagg aaggtacaag cagaggatga agccaacggc ctgcagacag | 600 |
| ctcacgcgag agctgcttca cctctgtcca ctgctgcagc caccatggtg tcctcttctc | 660 |
| cagccactcc ctcaaatatt ccccagaaac cgtcccagcc agtggcaaaa gaaacttcag | 720 |
| cgacacctca aattagcaac cttacgaaaa ccgccagcga gtcaatctcc aacctttcag | 780 |
| aggctggctc tgtcaagaag ggagagcgag agctcaagat cggagacagg gtgctggtcg | 840 |
| gtggcacgaa ggctggcgtg gtccggtttc ttggagagac tgacttcgcc aagggggagt | 900 |
| ggtgtggtgt ggaattggac gaaccttttgg ggaagaacga cggtgctgtt gctggaacaa | 960 |
| ggtattttca atgtcaaccc aagtacggat tgttcgctcc cgtccacaaa gtgacaaaga | 1020 |
| ttggcttccc ttctaccacc ccagccaaag ccaaagccgc tgctgtgagg cgagtgatgg | 1080 |
| ccaccacgcc cgccagcctg aagcgaagcc ttctgcctc ctccctcagc tccatgagct | 1140 |
| ctgtggcctc ctctgtgagc agcaagccca gccggacagg actattgact gaaacctctt | 1200 |
| cccgctacgc ccgcaagatc tcgggcacca ctgccctcca ggaggcgctg aaggagaagc | 1260 |
| agcagcacat tgagcagctg ctggctgagc gggacctgga gcgggccgag gtggccaagg | 1320 |
| ctaccagcca cgtgggggaa atagagcagg agctagccct ggcccgagat gggcatgacc | 1380 |
| agcatgtcct ggaactggag gccaagatgg accagctgcg taccatggta gaagctgctg | 1440 |
| acagggagaa agtggagctc ctcaaccagc tggaagagga gaaaaggaag gttgaggacc | 1500 |

```
ttcagttccg agttgaagaa gaatcaatta ccaaaggtga tcttgagacg cagaccaaac   1560
tggagcatgc ccgcattaag gagcttgaac agagcctgct ctttgaaaag accaaagctg   1620
acaaactcca gagggagtta gaagacacta gggtggctac agtatcagaa aagtcccgaa   1680
taatggaact agaaaaggac ctagcgttga gagtacagga agtagctgag ctccgaagaa   1740
ggctagagtc cagtaaacct cccggagatg tggatatgtc tctttctctt ttgcaagaaa   1800
tcagtgcttt gcaagaaaag ctagaagtca cacatactga ccaccagaac gaggtgacgt   1860
ctctgaagga ccactttgga actcgggaag agatgtttca gaaggagatc aaggctctgc   1920
acgctgccac tgaaaagctc tccaaagaga acgagtcctt gaggagcaag cttgaccatg   1980
ccaacaagga gaactcagac gtcatcgctc tgtggaagtc caaactggag accgccatcg   2040
cgtcccacca gcaggcaatg gaggagctga aggtgtcctt tagcaaaggg attggaactg   2100
actcggctga gtttgctgag ttaaagacac agatagagag actcagacta gattaccagc   2160
acgaaataga aagtttacag agtaagcagg actccgaacg gtctgcccat gctaaagaga   2220
tggagtccat gaaggccaag ctgatgaaga tcatcaaaga gaaggaggac agcctggagg   2280
ccgtcaaagc acggctggac acggcggaag accagcacct ggtggagatg gaggagatgc   2340
tcagcaagct gcaggaggca gagattaaga agaaaaagtt tgccagcgct cagaggagg    2400
ccgtctctac tcagacaagt atgcaagata ctgttaataa actgcaccaa aaggaggaac   2460
agtttaatat gttgtcttct gaactggaga agctgagaga aaatttaaca gacatggagg   2520
caaaatttaa agagaaggat gaacgggaag atcagctggt aaaggcaaag gaaaagttag   2580
aaaatgacat tgcagaaata atgaagatgt caggggacaa ctcttctcag ctgacaaaga   2640
tgaatgacga attacgtctg aaggaaaggt ctgtggaaga actacaactc aaacttacaa   2700
aggctaatga aaatgcaagt cttctgcaga aaagtatcgg ggaagtaact cttaaagctg   2760
aacagagtca acaggaagca gccaaaaaac atgaagagga aaagaaagaa ctggagaaca   2820
aattgttgga actggaaaag aagatggaaa ctagccacta ccagtgtcag gacctgaaag   2880
ccaagtatga aaaagccagt tctgagacta aaataaagca cgaagaaatc ctgcaaaact   2940
tccagaagat gctggtggac acggaggata aactgaaggc tgcccaggag gccaacagag   3000
acctgatgcg ggacatggag gagctgaaat cccaggccga caaagccaaa gctgctcaga   3060
ctgcagaaga cgccatgcag atcatggaac agatgaccaa agagaaaaca gaaacactgg   3120
cctccttgga ggacaccaag caaacgaatg caaaactaca gagcgaattg gacacactta   3180
aggaaaacaa cttgaaaact gtggaagagc tgaacaagtc aaaagaactt ctgaacgaag   3240
agaaccaaaa aatggaagaa ttcaagaagg aaatagaaac cctaaagcag gcagcagctc   3300
agaagtccca gcagctttca gcactgcagg aagagaacgt caaacttgcc gaggagctgg   3360
ggaggacgcg ggacgaagtc acaagtcatc aaaagctgga agaagaacga tctgtactca   3420
ataatcagtt gttagaaatg aaaaagagct acccagtaa cacccttaaga gaatccgagt   3480
acagaaaaga cgccgatgaa gagaaagcct ccttgcagaa atccatcagc ctcaccagtg   3540
ccttactcac ggagaaggac gcagagctgg agaagctgag gaatgaggtc acagtgctca   3600
ggggggaaaa cgcctctgcc aagtccctgc actcagtcgt gcagaccctg agtcggata    3660
aggtgaagct tgagctcaag gtcaaaaacc tggaacttca actcaaggaa acaagaggc    3720
agctcagcag ctcctcaggt aacactgatg ttcagacaga agaggatgag agagcccagg   3780
agagtcagca aatgattgat ttcctcaact cggtaatagt ggaccttcaa agaaagaacc   3840
```

-continued

```
aagacctcaa gatgaaggtg gagatgatgt ctgaaggtgc gctgaacggc aacggggagg    3900
atccgaacag ttacgacagt gatgaccagg agaagcagtc caagaagaaa ccccgcctct    3960
tctgtgacat ttgtgactgc tttgatctcc acgacacaga ggactgcccc acccaggcgc    4020
agatgtcaga agaccctccg cactccactc accacggcag ccggagcgag gagcggccat    4080
actgtgagat ctgtgagatg tttggccact gggccaccaa ctgcaacgac gatgagacct    4140
tctgaggagg ccgggcacac aggactgggc ttcccggacg ccggcccctc agcagctttc    4200
caccagcgct gcccacgtga cttcggaaga actccttatt ttttgacccc cctgtcaaca    4260
aatctgagaa agtattttga tcttcaacag atttcccttt cttttcctct cgtaagttaa    4320
aataataaac atttggtagg tgggcttgca cttccgtcct tgttttctgg atttttaaag    4380
tttaagacat tgtacgaggt gctacagtaa cttttttgttc ccggagaaac accctgggac    4440
aagctggacc ctggcagtgt cttatttaag aaactttaaa ttatgacgtt aagcctcata    4500
tttgcactaa aatgtttcct ggcttcatct gtatatttcg gttgttgttt ttgttacgct    4560
ttgacactgg aatgagttgc aaaaaaaaaa aaaaaaa                              4597
```

<210> SEQ ID NO 44
<211> LENGTH: 1320
<212> TYPE: PRT
<213> ORGANISM: Rattus norvegicus

<400> SEQUENCE: 44

```
Met Ser Met Leu Lys Pro Ser Gly Leu Lys Ala Pro Thr Lys Ile Leu
1               5                   10                  15

Lys Pro Gly Ser Thr Ala Leu Lys Thr Pro Ala Ala Ala Ala Ala Pro
            20                  25                  30

Leu Glu Lys Thr Val Pro Ser Glu Lys Ala Ser Gly Pro Pro Ser Ser
        35                  40                  45

Glu Thr Gln Glu Glu Phe Val Asp Asp Phe Arg Val Gly Glu Arg Val
    50                  55                  60

Trp Val Asn Gly Asn Lys Pro Gly Phe Ile Gln Phe Leu Gly Glu Thr
65                  70                  75                  80

Gln Phe Ala Pro Gly Gln Trp Ala Gly Ile Val Leu Asp Glu Pro Ile
                85                  90                  95

Gly Lys Asn Asp Gly Ser Val Ala Gly Val Arg Tyr Phe Gln Cys Glu
            100                 105                 110

Pro Leu Lys Gly Ile Phe Thr Arg Pro Ser Lys Leu Thr Arg Lys Val
        115                 120                 125

Gln Ala Glu Asp Glu Ala Asn Gly Leu Gln Thr Ala His Ala Arg Ala
    130                 135                 140

Ala Ser Pro Leu Ser Thr Ala Ala Ala Thr Met Val Ser Ser Ser Pro
145                 150                 155                 160

Ala Thr Pro Ser Asn Ile Pro Gln Lys Pro Ser Gln Pro Val Ala Lys
                165                 170                 175

Glu Thr Ser Ala Thr Pro Gln Ile Ser Asn Leu Thr Lys Thr Ala Ser
            180                 185                 190

Glu Ser Ile Ser Asn Leu Ser Glu Ala Gly Ser Val Lys Lys Gly Glu
        195                 200                 205

Arg Glu Leu Lys Ile Gly Asp Arg Val Leu Val Gly Gly Thr Lys Ala
    210                 215                 220

Gly Val Val Arg Phe Leu Gly Glu Thr Asp Phe Ala Lys Gly Glu Trp
225                 230                 235                 240
```

-continued

```
Cys Gly Val Glu Leu Asp Glu Pro Leu Gly Lys Asn Asp Gly Ala Val
            245                 250                 255
Ala Gly Thr Arg Tyr Phe Gln Cys Gln Pro Lys Tyr Gly Leu Phe Ala
        260                 265                 270
Pro Val His Lys Val Thr Lys Ile Gly Phe Pro Ser Thr Thr Pro Ala
    275                 280                 285
Lys Ala Lys Ala Ala Val Arg Arg Val Met Ala Thr Thr Pro Ala
290                 295                 300
Ser Leu Lys Arg Ser Pro Ser Ala Ser Ser Leu Ser Ser Met Ser Ser
305                 310                 315                 320
Val Ala Ser Ser Val Ser Ser Lys Pro Ser Arg Thr Gly Leu Leu Thr
                325                 330                 335
Glu Thr Ser Ser Arg Tyr Ala Arg Lys Ile Ser Gly Thr Thr Ala Leu
            340                 345                 350
Gln Glu Ala Leu Lys Glu Lys Gln Gln His Ile Glu Gln Leu Leu Ala
        355                 360                 365
Glu Arg Asp Leu Glu Arg Ala Glu Val Ala Lys Ala Thr Ser His Val
    370                 375                 380
Gly Glu Ile Glu Gln Leu Ala Leu Ala Arg Asp Gly His Asp Gln
385                 390                 395                 400
His Val Leu Glu Leu Glu Ala Lys Met Asp Gln Leu Arg Thr Met Val
                405                 410                 415
Glu Ala Ala Asp Arg Glu Lys Val Glu Leu Leu Asn Gln Leu Glu Glu
            420                 425                 430
Glu Lys Arg Lys Val Glu Asp Leu Gln Phe Arg Val Glu Glu Ser
        435                 440                 445
Ile Thr Lys Gly Asp Leu Glu Thr Gln Thr Lys Leu Glu His Ala Arg
    450                 455                 460
Ile Lys Glu Leu Glu Gln Ser Leu Leu Phe Glu Lys Thr Lys Ala Asp
465                 470                 475                 480
Lys Leu Gln Arg Glu Leu Glu Asp Thr Arg Val Ala Thr Val Ser Glu
                485                 490                 495
Lys Ser Arg Ile Met Glu Leu Glu Lys Asp Leu Ala Leu Arg Val Gln
            500                 505                 510
Glu Val Ala Glu Leu Arg Arg Arg Leu Glu Ser Ser Lys Pro Pro Gly
        515                 520                 525
Asp Val Asp Met Ser Leu Ser Leu Leu Gln Glu Ile Ser Ala Leu Gln
    530                 535                 540
Glu Lys Leu Glu Val Thr His Thr Asp His Gln Asn Glu Val Thr Ser
545                 550                 555                 560
Leu Lys Asp His Phe Gly Thr Arg Glu Glu Met Phe Gln Lys Glu Ile
                565                 570                 575
Lys Ala Leu His Ala Ala Thr Glu Lys Leu Ser Lys Glu Asn Glu Ser
            580                 585                 590
Leu Arg Ser Lys Leu Asp His Ala Asn Lys Glu Asn Ser Asp Val Ile
        595                 600                 605
Ala Leu Trp Lys Ser Lys Leu Glu Thr Ala Ile Ala Ser His Gln Gln
    610                 615                 620
Ala Met Glu Glu Leu Lys Val Ser Phe Ser Lys Gly Ile Gly Thr Asp
625                 630                 635                 640
Ser Ala Glu Phe Ala Glu Leu Lys Thr Gln Ile Glu Arg Leu Arg Leu
                645                 650                 655
Asp Tyr Gln His Glu Ile Glu Ser Leu Gln Ser Lys Gln Asp Ser Glu
```

-continued

```
                660                 665                 670
Arg Ser Ala His Ala Lys Glu Met Glu Ser Met Lys Ala Lys Leu Met
            675                 680                 685
Lys Ile Ile Lys Glu Lys Glu Asp Ser Leu Glu Ala Val Lys Ala Arg
            690                 695                 700
Leu Asp Thr Ala Glu Asp Gln His Leu Val Glu Met Glu Glu Met Leu
705                 710                 715                 720
Ser Lys Leu Gln Glu Ala Glu Ile Lys Lys Glu Lys Phe Ala Ser Ala
            725                 730                 735
Ser Glu Glu Ala Val Ser Thr Gln Thr Ser Met Gln Asp Thr Val Asn
            740                 745                 750
Lys Leu His Gln Lys Glu Glu Gln Phe Asn Met Leu Ser Ser Glu Leu
            755                 760                 765
Glu Lys Leu Arg Glu Asn Leu Thr Asp Met Glu Ala Lys Phe Lys Glu
            770                 775                 780
Lys Asp Glu Arg Glu Asp Gln Leu Val Lys Ala Lys Glu Lys Leu Glu
785                 790                 795                 800
Asn Asp Ile Ala Glu Ile Met Lys Met Ser Gly Asp Asn Ser Ser Gln
            805                 810                 815
Leu Thr Lys Met Asn Asp Glu Leu Arg Leu Lys Glu Arg Ser Val Glu
            820                 825                 830
Glu Leu Gln Leu Lys Leu Thr Lys Ala Asn Glu Asn Ala Ser Leu Leu
            835                 840                 845
Gln Lys Ser Ile Gly Glu Val Thr Leu Lys Ala Glu Gln Ser Gln Gln
            850                 855                 860
Glu Ala Ala Lys Lys His Glu Glu Lys Lys Glu Leu Glu Asn Lys
865                 870                 875                 880
Leu Leu Glu Leu Glu Lys Lys Met Glu Thr Ser His Tyr Gln Cys Gln
            885                 890                 895
Asp Leu Lys Ala Lys Tyr Glu Lys Ala Ser Ser Glu Thr Lys Ile Lys
            900                 905                 910
His Glu Glu Ile Leu Gln Asn Phe Gln Lys Met Leu Val Asp Thr Glu
            915                 920                 925
Asp Lys Leu Lys Ala Ala Gln Glu Ala Asn Arg Asp Leu Met Gln Asp
            930                 935                 940
Met Glu Glu Leu Lys Ser Gln Ala Asp Lys Ala Lys Ala Ala Gln Thr
945                 950                 955                 960
Ala Glu Asp Ala Met Gln Ile Met Glu Gln Met Thr Lys Glu Lys Thr
            965                 970                 975
Glu Thr Leu Ala Ser Leu Glu Asp Thr Lys Gln Thr Asn Ala Lys Leu
            980                 985                 990
Gln Ser Glu Leu Asp Thr Leu Lys  Glu Asn Asn Leu Lys  Thr Val Glu
            995                 1000                1005
Glu Leu  Asn Lys Ser Lys Glu  Leu Leu Asn Glu Glu  Asn Gln Lys
            1010                1015                1020
Met Glu  Glu Phe Lys Lys Glu  Ile Glu Thr Leu Lys  Gln Ala Ala
            1025                1030                1035
Ala Gln  Lys Ser Gln Gln Leu  Ser Ala Leu Gln Glu  Glu Asn Val
            1040                1045                1050
Lys Leu  Ala Glu Glu Leu Gly  Arg Thr Arg Asp Glu  Val Thr Ser
            1055                1060                1065
His Gln  Lys Leu Glu Glu Glu  Arg Ser Val Leu Asn  Asn Gln Leu
            1070                1075                1080
```

```
Leu Glu Met Lys Lys Ser Leu Pro Ser Asn Thr Leu Arg Glu Ser
    1085                1090                1095

Glu Tyr Arg Lys Asp Ala Asp Glu Glu Lys Ala Ser Leu Gln Lys
    1100                1105                1110

Ser Ile Ser Leu Thr Ser Ala Leu Leu Thr Glu Lys Asp Ala Glu
    1115                1120                1125

Leu Glu Lys Leu Arg Asn Glu Val Thr Val Leu Arg Gly Glu Asn
    1130                1135                1140

Ala Ser Ala Lys Ser Leu His Ser Val Val Gln Thr Leu Glu Ser
    1145                1150                1155

Asp Lys Val Lys Leu Glu Leu Lys Val Lys Asn Leu Glu Leu Gln
    1160                1165                1170

Leu Lys Glu Asn Lys Arg Gln Leu Ser Ser Ser Gly Asn Thr
    1175                1180                1185

Asp Val Gln Thr Glu Glu Asp Glu Arg Ala Gln Glu Ser Gln Gln
    1190                1195                1200

Met Ile Asp Phe Leu Asn Ser Val Ile Val Asp Leu Gln Arg Lys
    1205                1210                1215

Asn Gln Asp Leu Lys Met Lys Val Glu Met Met Ser Glu Gly Ala
    1220                1225                1230

Leu Asn Gly Asn Gly Glu Asp Pro Asn Ser Tyr Asp Ser Asp Asp
    1235                1240                1245

Gln Glu Lys Gln Ser Lys Lys Pro Arg Leu Phe Cys Asp Ile
    1250                1255                1260

Cys Asp Cys Phe Asp Leu His Asp Thr Glu Asp Cys Pro Thr Gln
    1265                1270                1275

Ala Gln Met Ser Glu Asp Pro Pro His Ser Thr His His Gly Ser
    1280                1285                1290

Arg Ser Glu Glu Arg Pro Tyr Cys Glu Ile Cys Glu Met Phe Gly
    1295                1300                1305

His Trp Ala Thr Asn Cys Asn Asp Asp Glu Thr Phe
    1310                1315                1320

<210> SEQ ID NO 45
<211> LENGTH: 3846
<212> TYPE: DNA
<213> ORGANISM: Mus musculus

<400> SEQUENCE: 45
atggcccaga gcaggaggca catgtccagt cggacgccga gtggcagcag gatgagtacg    60
gaggcaagcg cccggcccct gcgggttggc tcccgcgtgg aggtgattgg aagggccac   120 cgaggcactg tggcctatgt tggagccaca ctctttgcca ctggcaaatg ggtgggcgtg   180
attctggatg aagcaaaagg caaaaatgat ggcactgtcc agggaaggaa gtatttcaca   240
tgtgatgaag ccacggcat ctttgtacgc cagtcccaga tccaagtatt tgaagatgga   300
gcagatacta cttccccaga gactcctgat tcttctgctt caaaggtcct caagagagag   360
ggagccgatg cagctgcaaa gaccagcaaa ctgcggggac tgaagcctaa gaaggcaccg   420
acagcccgaa agaccacaac tcgacggccc aagcctactc gcccagccag cactggggtg   480
gctgggccca gtagctccct tggcccctct ggctcagcgt cagccgggga actaagcagc   540
agtgagccca gcaccccagc tcagactccg ctggcagcac ccatcatccc cacaccggcc   600
ctcacctctc ctggagcagc acccccactt ccatctccct ctaaggaaga ggaagggctg   660
```

```
agggctcagg tacgggacct ggaggagaag ctggagaccc tgcgcctaaa acgctcagaa    720
gacaaagcaa agctgaaaga gctggagaag cacaagatcc agctggagca ggtgcaggaa    780
tggaagagca aaatgcagga gcagcaggca gacctgcagc ggcgcctcaa ggaggctcgg    840
aaggaagcca aggaggcgct agaggcaaag gaacgctaca tggaggagat ggccgacaca    900
gccgacgcta tcgagatggc cactctggac aaggagatgg ctgaagagcg cgctgagtct    960
ctgcagcaag aggtggaggc actgaaggaa cgggtagacg agctcaccac agacctggag   1020
attctcaagg ctgaaatcga agagaaaggc tctgatgggg ccgcatcaag ctaccagctc   1080
aagcagctgg aggagcagaa tgcccgcctg aaggatgccc tggtgaggat gcgagacctc   1140
tcttcctcag agaagcagga gcacgtgaag ctgcagaaac tcatggaaaa gaaaaaccag   1200
gagctggagg tcgtgcggca gcagcgcgag cgtcttcagg aggagctgag ccaggctgag   1260
agcaccatcg atgagctcaa agagcaggtg gacgccgctt gggagccga ggagatggtg    1320 gagatgctga ccgaccggaa cctgaatcta gaggagaaag tgcgggagtt acgggagact   1380
gtgggggact tggaagccat gaacgagatg aacgatgagc tgcaggagaa cgcacgggag   1440
acggagctga aactccgaga gcagctggac atggcgggcg cccgagtgag ggaagcgcag   1500
aagcgagtgg aagccgccca ggagacagtc gccgactacc agcagaccat caagaagtac   1560
cgccagttga ctgcccacct acaggatgtc aatcgggagc tgacaaacca gcaggaagcg   1620
tctgtagaga ggcagcagca gccgccgcca gagacttttg atttcaaaat caagtttgct   1680
gagaccaagg ctcatgccaa ggccattgag atggagttga acagatgga agttgcccag    1740 gccaaccggc acatgtccct gctgacagcc tttatgcctg acagcttcct tcggccaggt   1800
ggagaccacg actgtgtcct ggtgctgctg ctcatgcccc gactcatttg caaggcagag   1860
ctcatccgga agcaggccca ggagaagttt gacctgagcg agaactgttc ggagcggccc   1920
gggctgcggg gagctgccgg ggagcagctg agctttgctg ctggactggt gtactcgctg   1980
agtctgctgc aggccacgct gcaccgctat gagcatgccc tctctcagtg cagtgtggac   2040
gtgtataaga aggtcggcag cctgtacccc gagatgagcg cccacgagcg ctccttagat   2100
ttcctcattg agctgctgca aaggatcag ctggatgaga ctgtcaacgt ggagcccctc    2160
accaaggcca tcaagtatta ccagcatctg tacagcatcc acctcgctga acaacccgag   2220
gactccacca tgcagctggc tgaccacatc aagttcaccc agagtgccct ggactgcatg   2280
ggcgtgaggt ggggcggct gcgtgccttc ttgcagggtg gcaggaggc aacagatatt    2340 gcccttcttc tccgagacct ggaaacatca tgtagtgaca cccgtcagtt ctgcaagaag   2400
atccgaaggc ggatgccggg gacggatgct cctgggatcc cagcagcgct ggcctttggc   2460
tcacaggtat ccgacacact cctggactgc aggaagcact tgacgtgggt ggtagctgtt   2520
ctgcaggagg tggcagctgc agccgcccag cttattgccc ccttggcaga aacgagggg    2580 ctgcctgtgg ctgcactgga ggagctggcc ttcaaagcaa gcgagcagat ctacgggagc   2640
ccctccagca gcccctatga gtgtctacgc cagtcatgca ccatcctcat cagcacgatg   2700
aacaagctgg ccacagccat gcaagaaggc gagtatgacg cagagcgacc cccgagcaag   2760
cctcctccgg ttgaacttcg ggctgcagcc ctgcgtgcag agatcacaga tgctgaaggt   2820
ctgggtttga agcttgagga tcagagaca gttatcaagg agttaaagaa gtcactcaag    2880
attaagggag aggagctgag tgaggccaac gtgcggctca gcctcctgga agaagttg     2940 gacagcgctg ccaaggatgc agacgagcga atcgagaaag ttcagacacg gctgacgag    3000 actcagaccc tgctgcggaa gaaggagaaa gactttgagg agacaatgga cgcactccag   3060
```

```
gctgacatcg accagctgga ggcagagaag gcagagctca agcagcgcct gaacagccag    3120
tccaagcgca caatcgaggg gctccggggc cccctccgt caggcatcgc taccctggtc     3180
tctggcatcg ctggtgagga accacagcga ggggcgctc ctgggcaggc tccgggcgcc     3240
ttgccaggcc cggggctggt gaaggactcc ccactgctgc ttcagcagat ctctgctatg    3300
aggctacaca tctctcagct ccagcatgag aacagcatcc tcagaggagc ccagatgaag    3360
gcgtccttgg cagctctgcc ccctctgcat gttgcaaagc tttccctccc accccatgag    3420
ggccccggtg gtaacctagt ggctggggca ctgtaccgca agaccagcca gctcctggag    3480
aaactaaacc agctgagtac ccacacccac gtggtggata tcactcggag cagcccagct    3540
gccaagagcc cgtcagctca gcttatggaa caagtggctc agctcaagtc cctgagtgac    3600
accattgaga agctcaagga tgaggtcctc aaggagacag tgactcagcg ccctggagcc    3660
actgtgccca ccgactttgc cactttccct tcatctgcct tcctcagggc caaggaagag    3720
cagcaagatg acacagtcta catgggcaaa gtgaccttt catgcgcggc aggcctagga   3780
cagcgacacc gcctggtgct gacccaggag cagctgcacc agcttcacag tcgcctcatc    3840
tcctaa                                                              3846
```

<210> SEQ ID NO 46
<211> LENGTH: 1281
<212> TYPE: PRT
<213> ORGANISM: Mus musculus

<400> SEQUENCE: 46

```
Met Ala Gln Ser Arg Arg His Met Ser Ser Arg Thr Pro Ser Gly Ser
1               5                   10                  15

Arg Met Ser Thr Glu Ala Ser Ala Arg Pro Leu Arg Val Gly Ser Arg
            20                  25                  30

Val Glu Val Ile Gly Lys Gly His Arg Gly Thr Val Ala Tyr Val Gly
        35                  40                  45

Ala Thr Leu Phe Ala Thr Gly Lys Trp Val Gly Val Ile Leu Asp Glu
    50                  55                  60

Ala Lys Gly Lys Asn Asp Gly Thr Val Gln Gly Arg Lys Tyr Phe Thr
65                  70                  75                  80

Cys Asp Glu Gly His Gly Ile Phe Val Arg Gln Ser Gln Ile Gln Val
                85                  90                  95

Phe Glu Asp Gly Ala Asp Thr Thr Ser Pro Glu Thr Pro Asp Ser Ser
            100                 105                 110

Ala Ser Lys Val Leu Lys Arg Glu Gly Ala Asp Ala Ala Lys Thr
        115                 120                 125

Ser Lys Leu Arg Gly Leu Lys Pro Lys Lys Ala Pro Thr Ala Arg Lys
    130                 135                 140

Thr Thr Thr Arg Arg Pro Lys Pro Thr Arg Pro Ala Ser Thr Gly Val
145                 150                 155                 160

Ala Gly Pro Ser Ser Leu Gly Pro Ser Gly Ser Ala Ser Ala Gly
                165                 170                 175

Glu Leu Ser Ser Ser Glu Pro Ser Thr Pro Ala Gln Thr Pro Leu Ala
            180                 185                 190

Ala Pro Ile Ile Pro Thr Pro Ala Leu Thr Ser Pro Gly Ala Ala Pro
        195                 200                 205

Pro Leu Pro Ser Pro Ser Lys Glu Glu Glu Gly Leu Arg Ala Gln Val
    210                 215                 220
```

```
Arg Asp Leu Glu Glu Lys Leu Glu Thr Leu Arg Leu Lys Arg Ser Glu
225                 230                 235                 240

Asp Lys Ala Lys Leu Lys Glu Leu Glu Lys His Lys Ile Gln Leu Glu
            245                 250                 255

Gln Val Gln Glu Trp Lys Ser Lys Met Gln Glu Gln Ala Asp Leu
        260                 265                 270

Gln Arg Arg Leu Lys Glu Ala Arg Lys Glu Ala Lys Glu Ala Leu Glu
        275                 280                 285

Ala Lys Glu Arg Tyr Met Glu Met Ala Asp Thr Ala Asp Ala Ile
290                 295                 300

Glu Met Ala Thr Leu Asp Lys Glu Met Ala Glu Glu Arg Ala Glu Ser
305                 310                 315                 320

Leu Gln Gln Glu Val Glu Ala Leu Lys Glu Arg Val Asp Glu Leu Thr
                325                 330                 335

Thr Asp Leu Glu Ile Leu Lys Ala Glu Ile Glu Glu Lys Gly Ser Asp
                340                 345                 350

Gly Ala Ala Ser Ser Tyr Gln Leu Lys Gln Leu Glu Glu Gln Asn Ala
            355                 360                 365

Arg Leu Lys Asp Ala Leu Val Arg Met Arg Asp Leu Ser Ser Ser Glu
370                 375                 380

Lys Gln Glu His Val Lys Leu Gln Lys Leu Met Glu Lys Lys Asn Gln
385                 390                 395                 400

Glu Leu Glu Val Val Arg Gln Arg Glu Arg Leu Gln Glu Glu Leu
                405                 410                 415

Ser Gln Ala Glu Ser Thr Ile Asp Glu Leu Lys Glu Gln Val Asp Ala
            420                 425                 430

Ala Leu Gly Ala Glu Glu Met Val Glu Met Leu Thr Asp Arg Asn Leu
            435                 440                 445

Asn Leu Glu Glu Lys Val Arg Glu Leu Arg Glu Thr Val Gly Asp Leu
450                 455                 460

Glu Ala Met Asn Glu Met Asn Asp Glu Leu Gln Glu Asn Ala Arg Glu
465                 470                 475                 480

Thr Glu Leu Glu Leu Arg Glu Gln Leu Asp Met Ala Gly Ala Arg Val
                485                 490                 495

Arg Glu Ala Gln Lys Arg Val Glu Ala Ala Gln Glu Thr Val Ala Asp
            500                 505                 510

Tyr Gln Gln Thr Ile Lys Lys Tyr Arg Gln Leu Thr Ala His Leu Gln
            515                 520                 525

Asp Val Asn Arg Glu Leu Thr Asn Gln Gln Glu Ala Ser Val Glu Arg
            530                 535                 540

Gln Gln Gln Pro Pro Glu Thr Phe Asp Phe Lys Ile Lys Phe Ala
545                 550                 555                 560

Glu Thr Lys Ala His Ala Lys Ala Ile Glu Met Glu Leu Arg Gln Met
                565                 570                 575

Glu Val Ala Gln Ala Asn Arg His Met Ser Leu Leu Thr Ala Phe Met
            580                 585                 590

Pro Asp Ser Phe Leu Arg Pro Gly Gly Asp His Asp Cys Val Leu Val
            595                 600                 605

Leu Leu Leu Met Pro Arg Leu Ile Cys Lys Ala Glu Leu Ile Arg Lys
            610                 615                 620

Gln Ala Gln Glu Lys Phe Asp Leu Ser Glu Asn Cys Ser Glu Arg Pro
625                 630                 635                 640

Gly Leu Arg Gly Ala Ala Gly Glu Gln Leu Ser Phe Ala Ala Gly Leu
```

-continued

```
            645                 650                 655
Val Tyr Ser Leu Ser Leu Leu Gln Ala Thr Leu His Arg Tyr Glu His
            660                 665                 670

Ala Leu Ser Gln Cys Ser Val Asp Val Tyr Lys Lys Val Gly Ser Leu
            675                 680                 685

Tyr Pro Glu Met Ser Ala His Glu Arg Ser Leu Asp Phe Leu Ile Glu
            690                 695                 700

Leu Leu His Lys Asp Gln Leu Asp Glu Thr Val Asn Val Glu Pro Leu
705                 710                 715                 720

Thr Lys Ala Ile Lys Tyr Tyr Gln His Leu Tyr Ser Ile His Leu Ala
                    725                 730                 735

Glu Gln Pro Glu Asp Ser Thr Met Gln Leu Ala Asp His Ile Lys Phe
                740                 745                 750

Thr Gln Ser Ala Leu Asp Cys Met Gly Val Glu Val Gly Arg Leu Arg
            755                 760                 765

Ala Phe Leu Gln Gly Gly Gln Glu Ala Thr Asp Ile Ala Leu Leu Leu
            770                 775                 780

Arg Asp Leu Glu Thr Ser Cys Ser Asp Thr Arg Gln Phe Cys Lys Lys
785                 790                 795                 800

Ile Arg Arg Arg Met Pro Gly Thr Asp Ala Pro Gly Ile Pro Ala Ala
                    805                 810                 815

Leu Ala Phe Gly Ser Gln Val Ser Asp Thr Leu Leu Asp Cys Arg Lys
                820                 825                 830

His Leu Thr Trp Val Val Ala Val Leu Gln Glu Val Ala Ala Ala Ala
            835                 840                 845

Ala Gln Leu Ile Ala Pro Leu Ala Glu Asn Glu Gly Leu Pro Val Ala
850                 855                 860

Ala Leu Glu Glu Leu Ala Phe Lys Ala Ser Glu Gln Ile Tyr Gly Ser
865                 870                 875                 880

Pro Ser Ser Ser Pro Tyr Glu Cys Leu Arg Gln Ser Cys Thr Ile Leu
                    885                 890                 895

Ile Ser Thr Met Asn Lys Leu Ala Thr Ala Met Gln Glu Gly Glu Tyr
                900                 905                 910

Asp Ala Glu Arg Pro Pro Ser Lys Pro Pro Val Glu Leu Arg Ala
            915                 920                 925

Ala Ala Leu Arg Ala Glu Ile Thr Asp Ala Glu Gly Leu Gly Leu Lys
930                 935                 940

Leu Glu Asp Arg Glu Thr Val Ile Lys Glu Leu Lys Lys Ser Leu Lys
945                 950                 955                 960

Ile Lys Gly Glu Glu Leu Ser Glu Ala Asn Val Arg Leu Ser Leu Leu
                    965                 970                 975

Glu Lys Lys Leu Asp Ser Ala Ala Lys Asp Ala Asp Glu Arg Ile Glu
                980                 985                 990

Lys Val Gln Thr Arg Leu Asp Glu  Thr Gln Thr Leu Leu  Arg Lys Lys
                995                 1000                1005

Glu Lys  Asp Phe Glu Glu Thr  Met Asp Ala Leu Gln  Ala Asp Ile
        1010                1015                1020

Asp Gln  Leu Glu Ala Glu Lys  Ala Glu Leu Lys Gln  Arg Leu Asn
        1025                1030                1035

Ser Gln  Ser Lys Arg Thr Ile  Glu Gly Leu Arg Gly  Pro Pro Pro
        1040                1045                1050

Ser Gly  Ile Ala Thr Leu Val  Ser Gly Ile Ala Gly  Glu Glu Pro
        1055                1060                1065
```

```
Gln Arg Gly Gly Ala Pro Gly Gln Ala Pro Gly Ala Leu Pro Gly
        1070                1075                1080
Pro Gly Leu Val Lys Asp Ser Pro Leu Leu Gln Gln Ile Ser
    1085                1090                1095
Ala Met Arg Leu His Ile Ser Gln Leu Gln His Glu Asn Ser Ile
        1100                1105                1110
Leu Arg Gly Ala Gln Met Lys Ala Ser Leu Ala Ala Leu Pro Pro
        1115                1120                1125
Leu His Val Ala Lys Leu Ser Leu Pro Pro His Glu Gly Pro Gly
        1130                1135                1140
Gly Asn Leu Val Ala Gly Ala Leu Tyr Arg Lys Thr Ser Gln Leu
        1145                1150                1155
Leu Glu Lys Leu Asn Gln Leu Ser Thr His Thr His Val Val Asp
        1160                1165                1170
Ile Thr Arg Ser Ser Pro Ala Ala Lys Ser Pro Ser Ala Gln Leu
        1175                1180                1185
Met Glu Gln Val Ala Gln Leu Lys Ser Leu Ser Asp Thr Ile Glu
        1190                1195                1200
Lys Leu Lys Asp Glu Val Leu Lys Glu Thr Val Thr Gln Arg Pro
        1205                1210                1215
Gly Ala Thr Val Pro Thr Asp Phe Ala Thr Phe Pro Ser Ser Ala
        1220                1225                1230
Phe Leu Arg Ala Lys Glu Glu Gln Gln Asp Asp Thr Val Tyr Met
        1235                1240                1245
Gly Lys Val Thr Phe Ser Cys Ala Ala Gly Leu Gly Gln Arg His
        1250                1255                1260
Arg Leu Val Leu Thr Gln Glu Gln Leu His Gln Leu His Ser Arg
        1265                1270                1275
Leu Ile Ser
    1280

<210> SEQ ID NO 47
<211> LENGTH: 5073
<212> TYPE: DNA
<213> ORGANISM: Drosophila melanogaster

<400> SEQUENCE: 47
atgagtgatg atacgagcgc ttcgggcggg acaagtgccc cttttccatc gccagttact      60
gcggacccgg aaccaggagc cactgcctcc aaattaccgg gtcccatcag atccaatatt     120
cccacgcccg ctacttctgg taccggaatc ccgcagccca gcaaaatgaa ggcaccatct     180
agttttggat cgacgggttc tgtttccaaa atcggaagac cgtgctgcaa tcacacaact     240
cccaaatccg gtccaccacc aagagaagcc accagcatga gtcgtgaaag cgatgacaat     300
ttaagttcga tcaattcggc ttatacagat aacagcagcg ccgtgctgac agcaaacaca     360
gagcagttca tcattggaca gcgggtttgg ctgggtggca ctcgtcccgg acagattgcc     420
ttcattggag acacacactt tgctgctggc gaatgggcgg tgttgtcct tgacgagcct     480
aatggtaaaa acgatggctg tgtgtcgggc aaaaggtact ccagtgcga gccgaaacga     540
ggcatttct cacgcctcac acgtcttacc acatatccct tggccggagc ccagactccg     600
acctctccat tggccaaaag ctcccccagac agatcgcgca cagtttctcc aactgcgagt     660
attcgcagct ctatgcttcg cagtcccggc attgaggca agaatggaat ggctgtgggc     720
gatcgtgtga ttgtctcttc tggatttggt agtcgtcctg gtatcttacg ctatttggga     780
```

```
gagacacagt tgctcccgg caactggtgc ggtgtggaat tggatgagcc tagcggcaaa    840
aacgatggaa ctgtcgatga tatcagatac tttgagtgca agcccaagta cggggtgttt    900
gtacctattg cgaaggtttc actgtcgccg tcgtccaaga aaacgcgtct ttccaggacc    960
ggatcaaggg agtcgctcac ctcgattggc accatgaaca gcatcgccac cacggccacg   1020
tcgcgcatgc gcatgaatgc tcagcagcgc aagtcgagca cgcccgttaa gccaatttta   1080
gcgacgccga aaagccaatt ttccatgcag gatctgctgc gcgagaagca caacatgtg    1140
gagaagctga tggtggagcg cgacctggac cgcgaggatg cccagaacca ggcgctgcag   1200
ctgcagaaga acatcaacga gctaaaagca agaatcgttg aattggagtc ggcattggac   1260
aatgaacgaa agaaaactga agaattgcag tgctccatag acgaagccca gttttgtggc   1320
gatgaattga atgctcagtc acaggtttac aaggaaaaaa tccatgatct ggagtcaaaa   1380
atcacaaaac tggtgtccgc cacgccaagc ctacaaagta tactaccgcc cgatctacct   1440
tcagacgatg gtgctttgca ggaggaaatc gccaagctgc aggaaaagat gaccattcag   1500
cagaaggagg ttgaatctcg gattgcggaa cagctggagg aggagcagcg gttgagggaa   1560
aatgtaaagt accttaatga gcaaatcgcc actctacagt ccgagttggt gtccaaagat   1620
gaggccctgg agaaattctc cctctcggaa tgtggcatcg agaatctccg aagggaactc   1680
gaacttctca aggaggagaa cgaaaagcaa gctcaggagg ctcaggctga gttcacccga   1740
aaactagccg aaaaatccgt agaggtgtta agattaagct ctgaattgca aaacttgaag   1800
gcaacatccg attccctgga aagcgaaagg gttaacaaaa ccgacgaatg tgaaattctt   1860
caaaccgaag tacgaatgcg ggatgagcaa atcagagagc taaaccaaca actcgatgag   1920
gttaccacac aactaaatgt acaaaaagcg gatagttctg ctctggatga tatgcttcga   1980
ttgcaaaagg agggtactga agaaaaatct actctttag agaaaccga aaaggagcta   2040
gttcaaagca agaacaagc tgcgaaaact ctaaatgata aggaacaact tgaaaaacag   2100
atatcagatt taaagcaatt ggcggaacaa gaaaaactag tcagggaaat gactgaaaat   2160
gcaatcaatc aaatacaact agaaaaagaa tccatagaac agcaattggc tttaaaacaa   2220
aacgaacttg aggacttcca aaagaaacag tcagaatcgg aagttcatct tcaggaaatc   2280
aaagctcaga acacgcagaa ggattttgaa ttagttgaat ctggtgagtc ccttaaaaaa   2340
ctgcaacagc aattggagca gaaaactttg ggtcatgaaa aactgcaagc tgctttggaa   2400
gaactaaaga aagaaaagga aacgatcata aaggaaaagg agcaggagct ccagcagctc   2460
caaagcaagt cagctgaatc cgaaagtgct ttaaaagtcg tacaagtaca actagagcaa   2520
ctccagcaac aggctgccgc atctggagaa gagggatcca aaactgtggc caaattgcac   2580
gatgagatta gtcagcttaa gtcccaagct gaagaaactc agtccgagtt aaaatccacc   2640
caatccaact tggaagccaa aagcaaacaa ttggaggcag caaatggcag cctgaagag    2700
gaagccaaga agtcaggcca tctgctggaa cagattacca aacttaaatc tgaagtaggg   2760
gagacgcagg cagctctcag ttcatgtcat acggatgtgg aatccaaaac taagcaactt   2820
gaagccgcaa atgcagctct ggagaaggtc aacaaggaat acgcggaatc ccgagcggag   2880
gcttctgatc tgcaagataa ggtgaaggag atcaccgata cgctacatgc tgagcttcaa   2940
gctgaacgat cgtcctccag tgctctccat actaagctgt ccaagttctc ggatgaaata   3000
gctaccggcc acaaggaact gaccagcaaa gccgatgcct ggagccagga gatgctgcaa   3060
aaagagaagg aactacagga gctgcgacag caacttcaag atagtcaaga ctctcaaaca   3120
```

```
aagctgaaag cagagggaga gcggaaagaa aagtctttcg aggaatctat aaagaatctt   3180
caggaagaag tcactaaggc caagacggag aatctagagc taagcactgg cacacagacg   3240
accataaagg acctgcagga gcgactggaa atcaccaatg ctgagctcca gcacaaggaa   3300
aaaatggcaa gcgaagatgc gcagaagatt gccgacctta agacccttgt ggaagccatc   3360
caggtggcta atgccaatat atcagctaca aatgcggagc tctccactgt attggaagtt   3420
cttcaggcgg agaagagtga aacaaatcac atattcgagc tctttgaaat ggaagccgat   3480
atgaactcag agcggttgat cgaaaaagtt actgggatta ggaggaact aaaggaaacc   3540 catctgcaac tggatgagcg acagaaaaag ttcgaggagt tggaggagaa attgaagcaa   3600
gctcagcaaa gtgaacaaaa gttgcaacag gagtctcaga cttccaagga gaaacttacg   3660
gaaatacaac aatccttgca agaactccaa gattctgtaa agcaaaagga agaacttgtc   3720
cagaacttgg aagaaaaggt tagggaaagc agttccatca tagaagcgca gaacacgaaa   3780
ctaaatgaaa gcaatgttca gttggaaaac aaaacttctt gtttaaagga aacccaagat   3840
caattgctag agtcacagaa gaaggagaaa caattgcagg aagaggctgc caaactttcc   3900
ggtgagctgc agcaagtgca agaggccaat ggagacataa aggattccct agtaaaagta   3960
gaggaactag taaaggtgtt ggaggaaaaa ctccaagcag ccacctccca gttggatgcc   4020
caacaagcca caataagga actccaggag ttgctggtta atctcaaga aaacgaggga   4080 aatctgcaag gagaatcttt ggcagtcact gagaaactac aacaactgga gcaagcaaat   4140
ggggagctta aggaggctct gtgtcaaaaa gagaatggcc ttaaagaact tcagggcaaa   4200
cttgatgaaa gtaatactgt attagaaagt caaaagaaga gccacaacga aattcaggat   4260
aagttagaac aggcccagca aaaggagagg actcttcaag aggaaacatc caagttggcg   4320
gagcaactga gccaattaaa gcaggctaat gaagagctcc agaaatccct tcagcaaaag   4380
cagttacttt tggaaaaggg taatgaattc gacacccagc tggcagaata tcagaaagtc   4440
attgatgaga tggatgatgc ggcttccgtt aaatccgcgc tgctggaaca gctacaaaat   4500
agagttgcgg aactggagac cgcactccgt caagccaacg atgcccaaaa gactgcttat   4560
ctggagacta aggaactgag gcgccagctg gaatcgctgg aactggagaa gtcgagggag   4620
gttctgagcc taaaggctca gatgaatggt gcgagcagta ggtccggaaa gggtgatgaa   4680
gtggagtcac tggacatcga aaccagtctt gccaagatta acttcctgaa ctcaattatt   4740
gctgacatgc agcagaagaa tgatgcactc aaggcaaagg tgcagaccct tgaaaccttg   4800
ccaatggatt tcaccaaacc tcatgccttc gatgccctga caaagcggaa accggctccc   4860
agacttttct gcgacatctg cgatgagttt gatcagcacg atacggagga ttgtccaatc   4920
cagggaagcg aagatcaaga ctactccaca ccgtcatccg agtccaacaa caacgagaag   4980
gagcggaagc tgccggcacc caggaaatac tgtgattcct gcgaggtttt tggccacgat   5040
acgagcgaat gtgccgatga tgaaacctat tag                                5073
```

<210> SEQ ID NO 48
<211> LENGTH: 1690
<212> TYPE: PRT
<213> ORGANISM: Drosophila melanogaster

<400> SEQUENCE: 48

```
Met Ser Asp Asp Thr Ser Ala Ser Gly Gly Thr Ser Ala Pro Phe Pro
1               5                   10                  15

Ser Pro Val Thr Ala Asp Pro Glu Pro Gly Ala Thr Ala Ser Lys Leu
            20                  25                  30
```

-continued

```
Pro Gly Pro Ile Arg Ser Asn Ile Pro Thr Pro Ala Thr Ser Gly Thr
         35                  40                  45
Gly Ile Pro Gln Pro Ser Lys Met Lys Ala Pro Ser Ser Phe Gly Ser
 50                  55                  60
Thr Gly Ser Val Ser Lys Ile Gly Arg Pro Cys Cys Asn His Thr Thr
 65                  70                  75                  80
Pro Lys Ser Gly Pro Pro Arg Glu Ala Thr Ser Met Ser Arg Glu
                 85                  90                  95
Ser Asp Asp Asn Leu Ser Ser Ile Asn Ser Ala Tyr Thr Asp Asn Ser
             100                 105                 110
Ser Ala Val Leu Thr Ala Asn Thr Glu Gln Phe Ile Ile Gly Gln Arg
         115                 120                 125
Val Trp Leu Gly Gly Thr Arg Pro Gly Gln Ile Ala Phe Ile Gly Asp
         130                 135                 140
Thr His Phe Ala Ala Gly Glu Trp Ala Gly Val Val Leu Asp Glu Pro
145                 150                 155                 160
Asn Gly Lys Asn Asp Gly Cys Val Ser Gly Lys Arg Tyr Phe Gln Cys
                165                 170                 175
Glu Pro Lys Arg Gly Ile Phe Ser Arg Leu Thr Arg Leu Thr Thr Tyr
            180                 185                 190
Pro Leu Ala Gly Ala Gln Thr Pro Thr Ser Pro Leu Ala Lys Ser Ser
        195                 200                 205
Pro Asp Arg Ser Arg Thr Val Ser Pro Thr Ala Ser Ile Arg Ser Ser
210                 215                 220
Met Leu Arg Ser Pro Gly Ile Gly Lys Asn Gly Met Ala Val Gly
225                 230                 235                 240
Asp Arg Val Ile Val Ser Ser Gly Phe Gly Ser Arg Pro Gly Ile Leu
                245                 250                 255
Arg Tyr Leu Gly Glu Thr Gln Phe Ala Pro Gly Asn Trp Cys Gly Val
            260                 265                 270
Glu Leu Asp Glu Pro Ser Gly Lys Asn Asp Gly Thr Val Asp Asp Ile
        275                 280                 285
Arg Tyr Phe Glu Cys Lys Pro Lys Tyr Gly Val Phe Val Pro Ile Ala
290                 295                 300
Lys Val Ser Leu Ser Pro Ser Ser Lys Lys Thr Arg Leu Ser Arg Thr
305                 310                 315                 320
Gly Ser Arg Glu Ser Leu Thr Ser Ile Gly Thr Met Asn Ser Ile Ala
                325                 330                 335
Thr Thr Ala Thr Ser Arg Met Arg Met Asn Ala Gln Arg Lys Ser
            340                 345                 350
Ser Thr Pro Val Lys Pro Ile Leu Ala Thr Pro Lys Ser Gln Phe Ser
        355                 360                 365
Met Gln Asp Leu Leu Arg Glu Lys Gln His Val Glu Lys Leu Met
            370                 375                 380
Val Glu Arg Asp Leu Asp Arg Glu Asp Ala Gln Asn Gln Ala Leu Gln
385                 390                 395                 400
Leu Gln Lys Asn Ile Asn Glu Leu Lys Ala Arg Ile Val Glu Leu Glu
                405                 410                 415
Ser Ala Leu Asp Asn Glu Arg Lys Lys Thr Glu Glu Leu Gln Cys Ser
            420                 425                 430
Ile Asp Glu Ala Gln Phe Cys Gly Asp Glu Leu Asn Ala Gln Ser Gln
        435                 440                 445
```

-continued

```
Val Tyr Lys Glu Lys Ile His Asp Leu Glu Ser Lys Ile Thr Lys Leu
    450                 455                 460

Val Ser Ala Thr Pro Ser Leu Gln Ser Ile Leu Pro Pro Asp Leu Pro
465                 470                 475                 480

Ser Asp Asp Gly Ala Leu Gln Glu Glu Ile Ala Lys Leu Gln Glu Lys
                485                 490                 495

Met Thr Ile Gln Gln Lys Glu Val Glu Ser Arg Ile Ala Glu Gln Leu
            500                 505                 510

Glu Glu Glu Gln Arg Leu Arg Glu Asn Val Lys Tyr Leu Asn Glu Gln
        515                 520                 525

Ile Ala Thr Leu Gln Ser Glu Leu Val Ser Lys Asp Glu Ala Leu Glu
    530                 535                 540

Lys Phe Ser Leu Ser Glu Cys Gly Ile Glu Asn Leu Arg Arg Glu Leu
545                 550                 555                 560

Glu Leu Leu Lys Glu Glu Asn Glu Lys Gln Ala Gln Glu Ala Gln Ala
                565                 570                 575

Glu Phe Thr Arg Lys Leu Ala Glu Lys Ser Val Glu Val Leu Arg Leu
            580                 585                 590

Ser Ser Glu Leu Gln Asn Leu Lys Ala Thr Ser Asp Ser Leu Glu Ser
        595                 600                 605

Glu Arg Val Asn Lys Thr Asp Glu Cys Glu Ile Leu Gln Thr Glu Val
    610                 615                 620

Arg Met Arg Asp Glu Gln Ile Arg Glu Leu Asn Gln Gln Leu Asp Glu
625                 630                 635                 640

Val Thr Thr Gln Leu Asn Val Gln Lys Ala Asp Ser Ser Ala Leu Asp
                645                 650                 655

Asp Met Leu Arg Leu Gln Lys Glu Gly Thr Glu Glu Lys Ser Thr Leu
            660                 665                 670

Leu Glu Lys Thr Glu Lys Glu Leu Val Gln Ser Lys Glu Gln Ala Ala
        675                 680                 685

Lys Thr Leu Asn Asp Lys Glu Gln Leu Glu Lys Gln Ile Ser Asp Leu
    690                 695                 700

Lys Gln Leu Ala Glu Gln Lys Leu Val Arg Glu Met Thr Glu Asn
705                 710                 715                 720

Ala Ile Asn Gln Ile Gln Leu Glu Lys Glu Ser Ile Glu Gln Gln Leu
                725                 730                 735

Ala Leu Lys Gln Asn Glu Leu Glu Asp Phe Gln Lys Lys Gln Ser Glu
            740                 745                 750

Ser Glu Val His Leu Gln Glu Ile Lys Ala Gln Asn Thr Gln Lys Asp
        755                 760                 765

Phe Glu Leu Val Glu Ser Gly Glu Ser Leu Lys Lys Leu Gln Gln Gln
    770                 775                 780

Leu Glu Gln Lys Thr Leu Gly His Glu Lys Leu Gln Ala Ala Leu Glu
785                 790                 795                 800

Glu Leu Lys Lys Glu Lys Glu Thr Ile Ile Lys Glu Lys Glu Gln Glu
                805                 810                 815

Leu Gln Gln Leu Gln Ser Lys Ser Glu Ser Glu Ser Ala Leu Lys
            820                 825                 830

Val Val Gln Val Gln Leu Glu Gln Leu Gln Gln Ala Ala Ala Ser
        835                 840                 845

Gly Glu Glu Gly Ser Lys Thr Val Ala Lys Leu His Asp Glu Ile Ser
    850                 855                 860

Gln Leu Lys Ser Gln Ala Glu Glu Thr Gln Ser Glu Leu Lys Ser Thr
```

-continued

```
            865                 870                 875                 880
Gln Ser Asn Leu Glu Ala Lys Ser Lys Gln Leu Glu Ala Ala Asn Gly
                885                 890                 895

Ser Leu Glu Glu Glu Ala Lys Lys Ser Gly His Leu Leu Glu Gln Ile
                900                 905                 910

Thr Lys Leu Lys Ser Glu Val Gly Glu Thr Gln Ala Ala Leu Ser Ser
                915                 920                 925

Cys His Thr Asp Val Glu Ser Lys Thr Lys Gln Leu Glu Ala Ala Asn
        930                 935                 940

Ala Ala Leu Glu Lys Val Asn Lys Glu Tyr Ala Glu Ser Arg Ala Glu
945                 950                 955                 960

Ala Ser Asp Leu Gln Asp Lys Val Lys Glu Ile Thr Asp Thr Leu His
                965                 970                 975

Ala Glu Leu Gln Ala Glu Arg Ser Ser Ser Ala Leu His Thr Lys
                980                 985                 990

Leu Ser Lys Phe Ser Asp Glu Ile Ala Thr Gly His Lys Glu Leu Thr
                995                 1000                1005

Ser Lys Ala Asp Ala Trp Ser Gln Glu Met Leu Gln Lys Glu Lys
    1010                1015                1020

Glu Leu Gln Glu Leu Arg Gln Gln Leu Gln Asp Ser Gln Asp Ser
    1025                1030                1035

Gln Thr Lys Leu Lys Ala Glu Gly Glu Arg Lys Glu Lys Ser Phe
    1040                1045                1050

Glu Glu Ser Ile Lys Asn Leu Gln Glu Glu Val Thr Lys Ala Lys
    1055                1060                1065

Thr Glu Asn Leu Glu Leu Ser Thr Gly Thr Gln Thr Thr Ile Lys
    1070                1075                1080

Asp Leu Gln Glu Arg Leu Glu Ile Thr Asn Ala Glu Leu Gln His
    1085                1090                1095

Lys Glu Lys Met Ala Ser Glu Asp Ala Gln Lys Ile Ala Asp Leu
    1100                1105                1110

Lys Thr Leu Val Glu Ala Ile Gln Val Ala Asn Ala Asn Ile Ser
    1115                1120                1125

Ala Thr Asn Ala Glu Leu Ser Thr Val Leu Glu Val Leu Gln Ala
    1130                1135                1140

Glu Lys Ser Glu Thr Asn His Ile Phe Glu Leu Phe Glu Met Glu
    1145                1150                1155

Ala Asp Met Asn Ser Glu Arg Leu Ile Glu Lys Val Thr Gly Ile
    1160                1165                1170

Lys Glu Glu Leu Lys Glu Thr His Leu Gln Leu Asp Glu Arg Gln
    1175                1180                1185

Lys Lys Phe Glu Glu Leu Glu Glu Lys Leu Lys Gln Ala Gln Gln
    1190                1195                1200

Ser Glu Gln Lys Leu Gln Gln Glu Ser Gln Thr Ser Lys Glu Lys
    1205                1210                1215

Leu Thr Glu Ile Gln Gln Ser Leu Gln Glu Leu Gln Asp Ser Val
    1220                1225                1230

Lys Gln Lys Glu Glu Leu Val Gln Asn Leu Glu Glu Lys Val Arg
    1235                1240                1245

Glu Ser Ser Ser Ile Ile Glu Ala Gln Asn Thr Lys Leu Asn Glu
    1250                1255                1260

Ser Asn Val Gln Leu Glu Asn Lys Thr Ser Cys Leu Lys Glu Thr
    1265                1270                1275
```

```
Gln Asp Gln Leu Leu Glu Ser Gln Lys Lys Glu Lys Gln Leu Gln
    1280                1285               1290

Glu Glu Ala Ala Lys Leu Ser Gly Glu Leu Gln Gln Val Gln Glu
    1295                1300               1305

Ala Asn Gly Asp Ile Lys Asp Ser Leu Val Lys Val Glu Glu Leu
    1310                1315               1320

Val Lys Val Leu Glu Glu Lys Leu Gln Ala Ala Thr Ser Gln Leu
    1325                1330               1335

Asp Ala Gln Gln Ala Thr Asn Lys Glu Leu Gln Glu Leu Leu Val
    1340                1345               1350

Lys Ser Gln Glu Asn Glu Gly Asn Leu Gln Gly Glu Ser Leu Ala
    1355                1360               1365

Val Thr Glu Lys Leu Gln Gln Leu Glu Gln Ala Asn Gly Glu Leu
    1370                1375               1380

Lys Glu Ala Leu Cys Gln Lys Glu Asn Gly Leu Lys Glu Leu Gln
    1385                1390               1395

Gly Lys Leu Asp Glu Ser Asn Thr Val Leu Glu Ser Gln Lys Lys
    1400                1405               1410

Ser His Asn Glu Ile Gln Asp Lys Leu Glu Gln Ala Gln Gln Lys
    1415                1420               1425

Glu Arg Thr Leu Gln Glu Glu Thr Ser Lys Leu Ala Glu Gln Leu
    1430                1435               1440

Ser Gln Leu Lys Gln Ala Asn Glu Glu Leu Gln Lys Ser Leu Gln
    1445                1450               1455

Gln Lys Gln Leu Leu Leu Glu Lys Gly Asn Glu Phe Asp Thr Gln
    1460                1465               1470

Leu Ala Glu Tyr Gln Lys Val Ile Asp Glu Met Asp Asp Ala Ala
    1475                1480               1485

Ser Val Lys Ser Ala Leu Leu Glu Gln Leu Gln Asn Arg Val Ala
    1490                1495               1500

Glu Leu Glu Thr Ala Leu Arg Gln Ala Asn Asp Ala Gln Lys Thr
    1505                1510               1515

Ala Tyr Leu Glu Thr Lys Glu Leu Arg Arg Gln Leu Glu Ser Leu
    1520                1525               1530

Glu Leu Glu Lys Ser Arg Glu Val Leu Ser Leu Lys Ala Gln Met
    1535                1540               1545

Asn Gly Ala Ser Ser Arg Ser Gly Lys Gly Asp Glu Val Glu Ser
    1550                1555               1560

Leu Asp Ile Glu Thr Ser Leu Ala Lys Ile Asn Phe Leu Asn Ser
    1565                1570               1575

Ile Ile Ala Asp Met Gln Gln Lys Asn Asp Ala Leu Lys Ala Lys
    1580                1585               1590

Val Gln Thr Leu Glu Thr Leu Pro Met Asp Phe Thr Lys Pro His
    1595                1600               1605

Ala Phe Asp Ala Leu Thr Lys Arg Lys Pro Ala Pro Arg Leu Phe
    1610                1615               1620

Cys Asp Ile Cys Asp Glu Phe Asp Gln His Asp Thr Glu Asp Cys
    1625                1630               1635

Pro Ile Gln Gly Ser Glu Asp Gln Asp Tyr Ser Thr Pro Ser Ser
    1640                1645               1650

Glu Ser Asn Asn Asn Glu Lys Glu Arg Lys Leu Pro Ala Pro Arg
    1655                1660               1665
```

-continued

```
Lys Tyr  Cys Asp Ser Cys Glu  Val Phe Gly His Asp  Thr Ser Glu
    1670             1675              1680

Cys Ala  Asp Asp Glu Thr Tyr
    1685             1690
```

<210> SEQ ID NO 49
<211> LENGTH: 3155
<212> TYPE: DNA
<213> ORGANISM: Saccharomyces cerevisiae

<400> SEQUENCE: 49

| | | | | | |
|---|---|---|---|---|---|
| atggacatca | ttcaaggact | gatacagcaa | ccaaaaattc | aatctgtgga | tgaaaccatt | 60 |
| ccgacgttgt | gcgatcgagt | tgagaactcc | actttgatta | gcgataggag | atccgctgtg | 120 |
| ctgggattaa | aggcatttag | ccggcagtat | agagaatcag | tgattgcatc | cgggctaaaa | 180 |
| ccgttgctca | atactttgaa | acgtgattat | atggatgaag | attcggtaaa | ggctatatta | 240 |
| gaaacaattt | tgattctttt | catcagaggc | gatggccatg | acgacttaac | tagaggttgg | 300 |
| atttctcaac | aatcgcggtt | gcagaatggc | aagtatccct | caccattggt | gatgaagcaa | 360 |
| gaaaaggaac | aagtagatca | gttctcgtta | tggattgctg | atgctttgac | gcagtctgaa | 420 |
| gatttaattc | acctacttgt | tgaattttgg | gaaatcgata | atttccatat | tagattgtac | 480 |
| acaattcaat | tactagaggc | agtgatggcc | acgaggccgt | tgaaggcgag | aagtgctttg | 540 |
| atttcacttc | caacgagcat | atccacaatg | gtctcactcc | tagatgacat | gcatgagccc | 600 |
| atcagggatt | aagctatttt | attattaatg | gcagtagtga | acgattcacc | tcacgttcaa | 660 |
| aaattggttg | cttttgaaaa | catttttgaa | aggctctttt | ccatcatcga | agaagaaggt | 720 |
| gggttaagag | gctctctcgt | cgtcaatgat | tgtttatcgt | tgatcaataa | catcctgaag | 780 |
| tataacactt | ctaatcaaac | tttattcctt | gagacaggaa | acttgccaaa | actggcacac | 840 |
| cttttgagtg | aaccaatatc | tcaagatgaa | gttttttttt | ggaatgatca | aaggatagtt | 900 |
| aatatcaata | cagctttaga | tatcgtcagc | ctaacagtag | agccaggaaa | tactgtcacc | 960 |
| actaagcatc | aaaatgcgtt | gcttgactca | agcgtattaa | tggttgtgtt | gcgacttgca | 1020 |
| ttctttcata | atatcccaaa | aaaagttaga | ccggttgctc | ttttgactgc | cgcaaacatg | 1080 |
| gttagaagta | atgaacatgc | acagctagag | tttagtaaga | tcgatgttcc | atatttcgat | 1140 |
| ccttcattac | ctgtaaactc | tactgcaaac | ggtggtccaa | ttaaattaat | tcctgtagtc | 1200 |
| agcatcttga | taaattggat | gctctatgcc | aactccgttc | acacgtttga | tacaagagtt | 1260 |
| gcgtgttcta | gactattaaa | ggcttatttc | atggataatt | ttgatcttca | aagagatttt | 1320 |
| ttactaaaac | aagtccaatt | gtgtaataat | tcaacaaata | atgtcggcga | caatgctaaa | 1380 |
| gaaaatggtg | ttctaacaa | atctgataaa | gaaagtgatt | cagataaaga | taccgacggg | 1440 |
| aaggatggca | ctgaatatga | aggttctttc | aaggcaaatc | tattcgaagt | cctgttaaat | 1500 |
| tatgacgcag | aattgaatct | gaacccttttt | aaattattct | tcacaactga | tattttatg | 1560 |
| ttttttttcc | aacaggatca | caaatatagc | gaagaactac | gtgaaataac | aagaaatgtt | 1620 |
| accaccggta | acgatctcga | agacgaagaa | cccttaaagg | caattcaaac | aataagtgaa | 1680 |
| ttgctaacta | cttcccttac | tgctgctgac | ataagaattc | ctatttccta | cttaacgttc | 1740 |
| ctaatatatt | ggctctttgg | cgactttaag | gccacgaacg | attttctttc | ggataaatcc | 1800 |
| gtgattaaat | ccttgctttc | cttctcttac | caaattcaag | atgaagacgt | tactatcaaa | 1860 |
| tgccttgtaa | caatgttact | aggtgtggca | tacgagtttt | cctcgaaaga | atctccattc | 1920 |
| ccaagaaagg | aatacttcga | attcatcact | aaaactttgg | gaaaagacaa | ttatgcttct | 1980 |

-continued

```
cgaatcaaac aatttaaaaa agattcatat ttctcaaaag ttgatatgaa tgaagacagt     2040
atactaactc cggagcttga tgaaactggt ttaccaaaag tttatttcag cacttacttc     2100
atacagttat ttaatgaaaa catatacagg atcagaactg cattgtctca cgaccctgac     2160
gaagagccaa tcaataaaat atctttcgaa gaagtcgaaa aattacagag gcaatgtaca     2220
aaattgaagg gtgagataac ttctttgcaa acagaaacgg aaagcaccca tgagaacctc     2280
accgaaaaat tgattgcgtt gactaatgaa cacaaagagt tggatgagaa ataccaaatt     2340
ttgaattcct cacattcttc gttgaaagaa aactttttcca ttttggaaac tgaattgaag     2400
aacgtcagag attccttgga tgaaatgacg caactgagag atgtactgga aactaaggac     2460
aaagaaaatc aaactgcttt actggagtac aaaagcacaa tccacaaaca agaagactct     2520
atcaaaactt tagaaaaagg acttgaaact attttgtctc aaaagaaaaa ggcagaagat     2580
ggtataaaca aaatgggtaa agatttattc gctctgagta gagagatgca agcagttgag     2640
gagaattgta aaaatttaca gaaggaaaaa gataaaagca atgtcaacca tcagaaagag     2700
actaaatcac taaagaagaa tattgcggca aaaattactg aaataaaagc tatcaatgaa     2760
aatctggaag aaatgaaaat tcaatgtaat aatttatcaa agaaaagga acatatttcg     2820 aaggaacttg ttgagtacaa atcccgcttt cagagtcatg acaatctagt agcgaaacta     2880
acagaaaaat tgaaatcctt agcaaataac tataaggata tgcaagctga aaatgagtct     2940
ctaataaaag ctgtagaaga gtcaaaaaac gaaagcagca tacaattgtc taatttgcaa     3000
aataaaattg attctatgtc acaggaaaaa gaaaattttc aaatagaaag aggcagtata     3060
gaaaaaaata tcgaacaact aaaaaaaacc atctctgact tagaacaaac gaaggaggaa     3120
attatctcaa aatccgattc ttcaaaagat gaata                                3155
```

<210> SEQ ID NO 50
<211> LENGTH: 1790
<212> TYPE: PRT
<213> ORGANISM: Saccharomyces cerevisiae

<400> SEQUENCE: 50

```
Met Asp Ile Ile Gln Gly Leu Ile Gln Gln Pro Lys Ile Gln Ser Val
1               5                   10                  15

Asp Glu Thr Ile Pro Thr Leu Cys Asp Arg Val Glu Asn Ser Thr Leu
            20                  25                  30

Ile Ser Asp Arg Arg Ser Ala Val Leu Gly Leu Lys Ala Phe Ser Arg
        35                  40                  45

Gln Tyr Arg Glu Ser Val Ile Ala Ser Gly Leu Lys Pro Leu Leu Asn
    50                  55                  60

Thr Leu Lys Arg Asp Tyr Met Asp Glu Asp Ser Val Lys Ala Ile Leu
65                  70                  75                  80

Glu Thr Ile Leu Ile Leu Phe Ile Arg Gly Asp Gly His Asp Asp Leu
                85                  90                  95

Thr Arg Gly Trp Ile Ser Gln Gln Ser Arg Leu Gln Asn Gly Lys Tyr
            100                 105                 110

Pro Ser Pro Leu Val Met Lys Gln Glu Lys Glu Gln Val Asp Gln Phe
        115                 120                 125

Ser Leu Trp Ile Ala Asp Ala Leu Thr Gln Ser Glu Asp Leu Ile His
    130                 135                 140

Leu Leu Val Glu Phe Trp Glu Ile Asp Asn Phe His Ile Arg Leu Tyr
145                 150                 155                 160
```

```
Thr Ile Gln Leu Leu Glu Ala Val Met Ala Thr Arg Pro Leu Lys Ala
                165                 170                 175

Arg Ser Ala Leu Ile Ser Leu Pro Thr Ser Ile Ser Thr Met Val Ser
            180                 185                 190

Leu Leu Asp Asp Met His Glu Pro Ile Arg Asp Glu Ala Ile Leu Leu
            195                 200                 205

Leu Met Ala Val Val Asn Asp Ser Pro His Val Gln Lys Leu Val Ala
            210                 215                 220

Phe Glu Asn Ile Phe Glu Arg Leu Phe Ser Ile Ile Glu Glu Glu Gly
225                 230                 235                 240

Gly Leu Arg Gly Ser Leu Val Val Asn Asp Cys Leu Ser Leu Ile Asn
                245                 250                 255

Asn Ile Leu Lys Tyr Asn Thr Ser Asn Gln Thr Leu Phe Leu Glu Thr
            260                 265                 270

Gly Asn Leu Pro Lys Leu Ala His Leu Leu Ser Glu Pro Ile Ser Gln
            275                 280                 285

Asp Glu Val Phe Phe Trp Asn Asp Gln Arg Ile Val Asn Ile Asn Thr
290                 295                 300

Ala Leu Asp Ile Val Ser Leu Thr Val Glu Pro Gly Asn Thr Val Thr
305                 310                 315                 320

Thr Lys His Gln Asn Ala Leu Leu Asp Ser Ser Val Leu Met Val Val
            325                 330                 335

Leu Arg Leu Ala Phe Phe His Asn Ile Pro Lys Lys Val Arg Pro Val
            340                 345                 350

Ala Leu Leu Thr Ala Ala Asn Met Val Arg Ser Asn Glu His Ala Gln
            355                 360                 365

Leu Glu Phe Ser Lys Ile Asp Val Pro Tyr Phe Asp Pro Ser Leu Pro
            370                 375                 380

Val Asn Ser Thr Ala Asn Gly Gly Pro Ile Lys Leu Ile Pro Val Val
385                 390                 395                 400

Ser Ile Leu Ile Asn Trp Met Leu Tyr Ala Asn Ser Val His Thr Phe
            405                 410                 415

Asp Thr Arg Val Ala Cys Ser Arg Leu Leu Lys Ala Tyr Phe Met Asp
            420                 425                 430

Asn Phe Asp Leu Gln Arg Asp Phe Leu Leu Lys Gln Val Gln Leu Cys
            435                 440                 445

Asn Asn Ser Thr Asn Asn Val Gly Asp Asn Ala Lys Glu Asn Gly Gly
450                 455                 460

Ser Asn Lys Ser Asp Lys Glu Ser Asp Ser Asp Lys Asp Thr Asp Gly
465                 470                 475                 480

Lys Asp Gly Thr Glu Tyr Glu Gly Ser Phe Lys Ala Asn Leu Phe Glu
            485                 490                 495

Val Leu Leu Asn Tyr Asp Ala Glu Leu Asn Leu Asn Pro Phe Lys Leu
            500                 505                 510

Phe Phe Thr Thr Asp Ile Phe Met Phe Phe Gln Gln Asp His Lys
            515                 520                 525

Tyr Ser Glu Glu Leu Arg Glu Ile Thr Arg Asn Val Thr Thr Gly Asn
            530                 535                 540

Asp Leu Glu Asp Glu Glu Pro Leu Lys Ala Ile Gln Thr Ile Ser Glu
545                 550                 555                 560

Leu Leu Thr Thr Ser Leu Thr Ala Ala Asp Ile Arg Ile Pro Ile Ser
                565                 570                 575

Tyr Leu Thr Phe Leu Ile Tyr Trp Leu Phe Gly Asp Phe Lys Ala Thr
```

-continued

```
                580                 585                 590
Asn Asp Phe Leu Ser Asp Lys Ser Val Ile Lys Ser Leu Leu Ser Phe
            595                 600                 605

Ser Tyr Gln Ile Gln Asp Glu Asp Val Thr Ile Lys Cys Leu Val Thr
            610                 615                 620

Met Leu Leu Gly Val Ala Tyr Glu Phe Ser Ser Lys Glu Ser Pro Phe
625                 630                 635                 640

Pro Arg Lys Glu Tyr Phe Glu Phe Ile Thr Lys Thr Leu Gly Lys Asp
            645                 650                 655

Asn Tyr Ala Ser Arg Ile Lys Gln Phe Lys Lys Asp Ser Tyr Phe Ser
            660                 665                 670

Lys Val Asp Met Asn Glu Asp Ser Ile Leu Thr Pro Glu Leu Asp Glu
            675                 680                 685

Thr Gly Leu Pro Lys Val Tyr Phe Ser Thr Tyr Phe Ile Gln Leu Phe
            690                 695                 700

Asn Glu Asn Ile Tyr Arg Ile Arg Thr Ala Leu Ser His Asp Pro Asp
705                 710                 715                 720

Glu Glu Pro Ile Asn Lys Ile Ser Phe Glu Glu Val Glu Lys Leu Gln
            725                 730                 735

Arg Gln Cys Thr Lys Leu Lys Gly Glu Ile Thr Ser Leu Gln Thr Glu
            740                 745                 750

Thr Glu Ser Thr His Glu Asn Leu Thr Glu Lys Leu Ile Ala Leu Thr
            755                 760                 765

Asn Glu His Lys Glu Leu Asp Glu Lys Tyr Gln Ile Leu Asn Ser Ser
            770                 775                 780

His Ser Ser Leu Lys Glu Asn Phe Ser Ile Leu Glu Thr Glu Leu Lys
785                 790                 795                 800

Asn Val Arg Asp Ser Leu Asp Glu Met Thr Gln Leu Arg Asp Val Leu
            805                 810                 815

Glu Thr Lys Asp Lys Glu Asn Gln Thr Ala Leu Leu Glu Tyr Lys Ser
            820                 825                 830

Thr Ile His Lys Gln Glu Asp Ser Ile Lys Thr Leu Glu Lys Gly Leu
            835                 840                 845

Glu Thr Ile Leu Ser Gln Lys Lys Ala Glu Asp Gly Ile Asn Lys
850                 855                 860

Met Gly Lys Asp Leu Phe Ala Leu Ser Arg Glu Met Gln Ala Val Glu
865                 870                 875                 880

Glu Asn Cys Lys Asn Leu Gln Lys Glu Lys Asp Lys Ser Asn Val Asn
            885                 890                 895

His Gln Lys Glu Thr Lys Ser Leu Lys Glu Asp Ile Ala Ala Lys Ile
            900                 905                 910

Thr Glu Ile Lys Ala Ile Asn Glu Asn Leu Glu Glu Met Lys Ile Gln
            915                 920                 925

Cys Asn Asn Leu Ser Lys Glu Lys His Ile Ser Lys Glu Leu Val
            930                 935                 940

Glu Tyr Lys Ser Arg Phe Gln Ser His Asp Asn Leu Val Ala Lys Leu
945                 950                 955                 960

Thr Glu Lys Leu Lys Ser Leu Ala Asn Asn Tyr Lys Asp Met Gln Ala
                965                 970                 975

Glu Asn Glu Ser Leu Ile Lys Ala Val Glu Glu Ser Lys Asn Glu Ser
            980                 985                 990

Ser Ile Gln Leu Ser Asn Leu Gln  Asn Lys Ile Asp Ser  Met Ser Gln
            995                 1000                 1005
```

-continued

Glu Lys Glu Asn Phe Gln Ile Glu Arg Gly Ser Ile Glu Lys Asn
1010              1015                1020

Ile Glu Gln Leu Lys Lys Thr Ile Ser Asp Leu Glu Gln Thr Lys
1025              1030                1035

Glu Glu Ile Ile Ser Lys Ser Asp Ser Ser Lys Asp Glu Tyr Glu
1040              1045                1050

Ser Gln Ile Ser Leu Leu Lys Glu Lys Leu Glu Thr Ala Thr Thr
1055              1060                1065

Ala Asn Asp Glu Asn Val Asn Lys Ile Ser Glu Leu Thr Lys Thr
1070              1075                1080

Arg Glu Glu Leu Glu Ala Glu Leu Ala Ala Tyr Lys Asn Leu Lys
1085              1090                1095

Asn Glu Leu Glu Thr Lys Leu Glu Thr Ser Glu Lys Ala Leu Lys
1100              1105                1110

Glu Val Lys Glu Asn Glu Glu His Leu Lys Glu Lys Ile Gln
1115              1120                1125

Leu Glu Lys Glu Ala Thr Glu Thr Lys Gln Gln Leu Asn Ser Leu
1130              1135                1140

Arg Ala Asn Leu Glu Ser Leu Glu Lys Glu His Glu Asp Leu Ala
1145              1150                1155

Ala Gln Leu Lys Lys Tyr Glu Gln Ile Ala Asn Lys Glu Arg
1160              1165                1170

Gln Tyr Asn Glu Glu Ile Ser Gln Leu Asn Asp Glu Ile Thr Ser
1175              1180                1185

Thr Gln Gln Glu Asn Glu Ser Ile Lys Lys Lys Asn Asp Glu Leu
1190              1195                1200

Glu Gly Glu Val Lys Ala Met Lys Ser Thr Ser Glu Glu Gln Ser
1205              1210                1215

Asn Leu Lys Lys Ser Glu Ile Asp Ala Leu Asn Leu Gln Ile Lys
1220              1225                1230

Glu Leu Lys Lys Lys Asn Glu Thr Asn Glu Ala Ser Leu Leu Glu
1235              1240                1245

Ser Ile Lys Ser Val Glu Ser Glu Thr Val Lys Ile Lys Glu Leu
1250              1255                1260

Gln Asp Glu Cys Asn Phe Lys Glu Lys Glu Val Ser Glu Leu Glu
1265              1270                1275

Asp Lys Leu Lys Ala Ser Glu Asp Lys Asn Ser Lys Tyr Leu Glu
1280              1285                1290

Leu Gln Lys Glu Ser Glu Lys Ile Lys Glu Glu Leu Asp Ala Lys
1295              1300                1305

Thr Thr Glu Leu Lys Ile Gln Leu Glu Lys Ile Thr Asn Leu Ser
1310              1315                1320

Lys Ala Lys Glu Lys Ser Glu Ser Glu Leu Ser Arg Leu Lys Lys
1325              1330                1335

Thr Ser Ser Glu Glu Arg Lys Asn Ala Glu Glu Gln Leu Glu Lys
1340              1345                1350

Leu Lys Asn Glu Ile Gln Ile Lys Asn Gln Ala Phe Glu Lys Glu
1355              1360                1365

Arg Lys Leu Leu Asn Glu Gly Ser Ser Thr Ile Thr Gln Glu Tyr
1370              1375                1380

Ser Glu Lys Ile Asn Thr Leu Glu Asp Glu Leu Ile Arg Leu Gln
1385              1390                1395

```
Asn Glu Asn Glu Leu Lys Ala Lys Glu Ile Asp Asn Thr Arg Ser
    1400            1405            1410

Glu Leu Glu Lys Val Ser Leu Ser Asn Asp Glu Leu Leu Glu Glu
    1415            1420            1425

Lys Gln Asn Thr Ile Lys Ser Leu Gln Asp Glu Ile Leu Ser Tyr
    1430            1435            1440

Lys Asp Lys Ile Thr Arg Asn Asp Glu Lys Leu Leu Ser Ile Glu
    1445            1450            1455

Arg Asp Asn Lys Arg Asp Leu Glu Ser Leu Lys Glu Gln Leu Arg
    1460            1465            1470

Ala Ala Gln Glu Ser Lys Ala Lys Val Glu Glu Gly Leu Lys Lys
    1475            1480            1485

Leu Glu Glu Glu Ser Ser Lys Glu Lys Ala Glu Leu Glu Lys Ser
    1490            1495            1500

Lys Glu Met Met Lys Lys Leu Glu Ser Thr Ile Glu Ser Asn Glu
    1505            1510            1515

Thr Glu Leu Lys Ser Ser Met Glu Thr Ile Arg Lys Ser Asp Glu
    1520            1525            1530

Lys Leu Glu Gln Ser Lys Lys Ser Ala Glu Glu Asp Ile Lys Asn
    1535            1540            1545

Leu Gln His Glu Lys Ser Asp Leu Ile Ser Arg Ile Asn Glu Ser
    1550            1555            1560

Glu Lys Asp Ile Glu Glu Leu Lys Ser Lys Leu Arg Ile Glu Ala
    1565            1570            1575

Lys Ser Gly Ser Glu Leu Glu Thr Val Lys Gln Glu Leu Asn Asn
    1580            1585            1590

Ala Gln Glu Lys Ile Arg Ile Asn Ala Glu Glu Asn Thr Val Leu
    1595            1600            1605

Lys Ser Lys Leu Glu Asp Ile Glu Arg Glu Leu Lys Asp Lys Gln
    1610            1615            1620

Ala Glu Ile Lys Ser Asn Gln Glu Glu Lys Glu Leu Leu Thr Ser
    1625            1630            1635

Arg Leu Lys Glu Leu Glu Gln Glu Leu Asp Ser Thr Gln Gln Lys
    1640            1645            1650

Ala Gln Lys Ser Glu Glu Glu Arg Arg Ala Glu Val Arg Lys Phe
    1655            1660            1665

Gln Val Glu Lys Ser Gln Leu Asp Glu Lys Ala Met Leu Leu Glu
    1670            1675            1680

Thr Lys Tyr Asn Asp Leu Val Asn Lys Glu Gln Ala Trp Lys Arg
    1685            1690            1695

Asp Glu Asp Thr Val Lys Lys Thr Thr Asp Ser Gln Arg Gln Glu
    1700            1705            1710

Ile Glu Lys Leu Ala Lys Glu Leu Asp Asn Leu Lys Ala Glu Asn
    1715            1720            1725

Ser Lys Leu Lys Glu Ala Asn Glu Asp Arg Ser Glu Ile Asp Asp
    1730            1735            1740

Leu Met Leu Leu Val Thr Asp Leu Asp Glu Lys Asn Ala Lys Tyr
    1745            1750            1755

Arg Ser Lys Leu Lys Asp Leu Gly Val Glu Ile Ser Ser Asp Glu
    1760            1765            1770

Glu Asp Asp Glu Glu Asp Glu Glu Asp Glu Glu Glu Gly Gln
    1775            1780            1785

Val Ala
```

-continued

1790

<210> SEQ ID NO 51
<211> LENGTH: 666
<212> TYPE: DNA
<213> ORGANISM: Caenorhabditis elegans

<400> SEQUENCE: 51

```
atgagcctgt tcggcaaaat tttcggaggc aggaagcaag aagctccgtc tactccacaa      60
gaatctattc aaaaacttcg ggaaacagag gagatgcttg agaagaaaca gaattcttg      120
gagaaaaaag ttatcgacga aaagcaaaat gccgtgaagt atggaacgaa aaacaagcga     180
atggctctcc agtgtttgaa tagaaagaga aatttcgaga gcagttggc ccatattgac      240
ggagttttgt ctactatcgg atatcagaga gaagccctcg aaaatgcttc aacgaatgct     300
gaagttctca atgttatggg aactgctagc aaggcgttga agcggctca taacaacatg      360
gatatcgacc aagttcatga tttgatggaa gacatagctg agcaacaaga agtggcaaac     420
gaaatcgctg aagctatttc aaaccctgtc ggcttcagca ccgcagttga cgatgacgat     480
ttgatgcgcg agttggaggc tcttgaacag gaagaacttg acaagaatt gcttgatgcg      540
agagctccac cagtcacgct tccggatact ccaaatattg cacttccagc agttccggct     600
tccagaccga gagcgaaaga agctgacaag gatctcgaag acctcgaaag ctgggcaaac     660
gcgtga                                                                666
```

<210> SEQ ID NO 52
<211> LENGTH: 221
<212> TYPE: PRT
<213> ORGANISM: Caenorhabditis elegans

<400> SEQUENCE: 52

Met Ser Leu Phe Gly Lys Ile Phe Gly Gly Arg Lys Gln Glu Ala Pro
1               5                   10                  15

Ser Thr Pro Gln Glu Ser Ile Gln Lys Leu Arg Glu Thr Glu Glu Met
            20                  25                  30

Leu Glu Lys Lys Gln Glu Phe Leu Glu Lys Lys Val Ile Asp Glu Lys
        35                  40                  45

Gln Asn Ala Val Lys Tyr Gly Thr Lys Asn Lys Arg Met Ala Leu Gln
    50                  55                  60

Cys Leu Asn Arg Lys Arg Asn Phe Glu Lys Gln Leu Ala His Ile Asp
65                  70                  75                  80

Gly Val Leu Ser Thr Ile Gly Tyr Gln Arg Glu Ala Leu Glu Asn Ala
                85                  90                  95

Ser Thr Asn Ala Glu Val Leu Asn Val Met Gly Thr Ala Ser Lys Ala
            100                 105                 110

Leu Lys Ala Ala His Asn Asn Met Asp Ile Asp Gln Val His Asp Leu
        115                 120                 125

Met Glu Asp Ile Ala Glu Gln Gln Glu Val Ala Asn Glu Ile Ala Glu
    130                 135                 140

Ala Ile Ser Asn Pro Val Gly Phe Ser Thr Ala Val Asp Asp Asp
145                 150                 155                 160

Leu Met Arg Glu Leu Glu Ala Leu Glu Gln Glu Leu Asp Lys Glu
                165                 170                 175

Leu Leu Asp Ala Arg Ala Pro Pro Val Thr Leu Pro Asp Thr Pro Asn
            180                 185                 190

Ile Ala Leu Pro Ala Val Pro Ala Ser Arg Pro Arg Ala Lys Glu Ala

```
                    195                 200                 205
Asp Lys Asp Leu Glu Asp Leu Glu Ser Trp Ala Asn Ala
    210                 215                 220

<210> SEQ ID NO 53
<211> LENGTH: 675
<212> TYPE: DNA
<213> ORGANISM: Homo sapiens

<400> SEQUENCE: 53
atgtcggtgt tcgggaagct gttcggggct ggaggggta aggccggcaa gggcggcccg      60
accccccagg aggccatcca gcggctgcgg gacacggaag agatgttaag caagaaacag     120
gagttcctgg agaagaaaat cgagcaggag ctgacggccg ccaagaagca cggcaccaaa     180
aacaagcgcg cggccctcca ggcactgaag cgtaagaaga ggtatgagaa gcagctggcg     240
cagatcgacg gcacattatc aaccatcgag ttccagcggg aggccctgga gaatgccaac     300
accaacaccg aggtgctcaa gaacatgggc tatgccgcca aggccatgaa ggcggcccat     360
gacaacatgg acatcgataa agttgatgag ttaatgcagg acattgctga ccagcaagaa     420
cttgcagagg agatttcaac agcaatttcg aaacctgtag ggtttggaga agagtttgac     480
gaggatgagc tcatggcgga attagaagaa ctagaacagg aggaactaga caagaatttg     540
ctggaaatca gtggacccga aacagtccct ctaccaaatg ttccctctat agccctacca     600
tcaaaacccg ccaagaagaa agaagaggag gacgacgaca tgaaggaatt ggagaactgg     660
gctggatcca tgtaa                                                     675

<210> SEQ ID NO 54
<211> LENGTH: 224
<212> TYPE: PRT
<213> ORGANISM: Homo sapiens

<400> SEQUENCE: 54

Met Ser Val Phe Gly Lys Leu Phe Gly Ala Gly Gly Lys Ala Gly
1               5                   10                  15

Lys Gly Gly Pro Thr Pro Gln Glu Ala Ile Gln Arg Leu Arg Asp Thr
            20                  25                  30

Glu Glu Met Leu Ser Lys Lys Gln Glu Phe Leu Glu Lys Lys Ile Glu
        35                  40                  45

Gln Glu Leu Thr Ala Ala Lys Lys His Gly Thr Lys Asn Lys Arg Ala
    50                  55                  60

Ala Leu Gln Ala Leu Lys Arg Lys Lys Arg Tyr Glu Lys Gln Leu Ala
65                  70                  75                  80

Gln Ile Asp Gly Thr Leu Ser Thr Ile Glu Phe Gln Arg Glu Ala Leu
                85                  90                  95

Glu Asn Ala Asn Thr Asn Thr Glu Val Leu Lys Asn Met Gly Tyr Ala
            100                 105                 110

Ala Lys Ala Met Lys Ala Ala His Asp Asn Met Asp Ile Asp Lys Val
        115                 120                 125

Asp Glu Leu Met Gln Asp Ile Ala Asp Gln Gln Leu Ala Glu Glu
    130                 135                 140

Ile Ser Thr Ala Ile Ser Lys Pro Val Gly Phe Gly Glu Glu Phe Asp
145                 150                 155                 160

Glu Asp Glu Leu Met Ala Glu Leu Glu Glu Leu Glu Gln Glu Glu Leu
                165                 170                 175

Asp Lys Asn Leu Leu Glu Ile Ser Gly Pro Glu Thr Val Pro Leu Pro
```

-continued

```
                      180                 185                 190
Asn Val Pro Ser Ile Ala Leu Pro Ser Lys Pro Ala Lys Lys Lys Glu
        195                 200                 205

Glu Glu Asp Asp Asp Met Lys Glu Leu Glu Asn Trp Ala Gly Ser Met
    210                 215                 220

<210> SEQ ID NO 55
<211> LENGTH: 675
<212> TYPE: DNA
<213> ORGANISM: Mus musculus

<400> SEQUENCE: 55
atgtcggtgt tcgggaagct gttcggggct ggaggggta aggcgggcaa gggcggcccg      60 acccccagg aggccatcca gcggcttcgg gacacggagg agatgttaag caagaagcag     120
gagttcctgg agaagaaaat cgaacaggag ctgacggctg ccaagaagca cggcaccaaa     180
aataagcgcg ccgccctgca ggctctgaag cgcaagaaga ggtatgagaa gcagctggca     240
caaattgatg gcaccctgtc aaccatcgag ttccagcggg aggccctaga gaacgccaac     300
accaacacgg aggtgctcaa gaacatgggc tatgccgcca aggccatgaa ggctgcccac     360
gacaacatgg acattgataa ggtggatgag ttaatgcagg acattgctga ccagcaagaa     420
cttgcagagg agatttccac agctatctcc aaacctgtgg gctttggaga gagttcgac     480 gaggatgagc tcatggcaga gttggaggaa cttgaacaag aggagttgga caagaatttg     540
ttggagatca gtgggcccga acagtccct ctaccaaatg tccctccgt agccctacca      600 tccaaacccg ccaagaagaa ggaagaggaa gatgacgaca tgaaggaatt ggagaactgg     660
gccggatcca tgtaa                                                      675

<210> SEQ ID NO 56
<211> LENGTH: 224
<212> TYPE: PRT
<213> ORGANISM: Mus musculus

<400> SEQUENCE: 56

Met Ser Val Phe Gly Lys Leu Phe Gly Ala Gly Gly Gly Lys Ala Gly
1               5                  10                  15

Lys Gly Gly Pro Thr Pro Gln Glu Ala Ile Gln Arg Leu Arg Asp Thr
            20                  25                  30

Glu Glu Met Leu Ser Lys Lys Gln Glu Phe Leu Glu Lys Lys Ile Glu
        35                  40                  45

Gln Glu Leu Thr Ala Ala Lys Lys His Gly Thr Lys Asn Lys Arg Ala
    50                  55                  60

Ala Leu Gln Ala Leu Lys Arg Lys Lys Arg Tyr Glu Lys Gln Leu Ala
65                  70                  75                  80

Gln Ile Asp Gly Thr Leu Ser Thr Ile Glu Phe Gln Arg Glu Ala Leu
                85                  90                  95

Glu Asn Ala Asn Thr Asn Thr Glu Val Leu Lys Asn Met Gly Tyr Ala
            100                 105                 110

Ala Lys Ala Met Lys Ala Ala His Asp Asn Met Asp Ile Asp Lys Val
        115                 120                 125

Asp Glu Leu Met Gln Asp Ile Ala Asp Gln Gln Glu Leu Ala Glu Glu
    130                 135                 140

Ile Ser Thr Ala Ile Ser Lys Pro Val Gly Phe Gly Glu Glu Phe Asp
145                 150                 155                 160

Glu Asp Glu Leu Met Ala Glu Leu Glu Glu Leu Glu Gln Glu Glu Leu
```

```
                     165                 170                 175
Asp Lys Asn Leu Leu Glu Ile Ser Gly Pro Glu Thr Val Pro Leu Pro
            180                 185                 190

Asn Val Pro Ser Val Ala Leu Pro Ser Lys Pro Ala Lys Lys Lys Glu
        195                 200                 205

Glu Glu Asp Asp Asp Met Lys Glu Leu Glu Asn Trp Ala Gly Ser Met
    210                 215                 220

<210> SEQ ID NO 57
<211> LENGTH: 1524
<212> TYPE: DNA
<213> ORGANISM: Drosophila melanogaster

<400> SEQUENCE: 57
atgcctcgct ctgatacgga ggctttggtg gccgatgtgg agactggcga agattcggca    60
ccacgcatac tggacgcatc atctgcggcc agcagtgagc aggtggaccc gcctccggta   120
ccgccgcctc atgactacag cagctatcgc tggttcatcc tggagcccgc agttttttta   180
atcttcttcg ccagaaattt aattggggcg gtttatcaga accaaattct ctaccaaacc   240
tgcatcacca tcgagaaatt caatgccacg caatgtgaac cgctgctggg cattgatcgc   300
ggatcggacg cggataaaga agtcgaggtg atagtacaga cgtattctgc aaatattatg   360
atgacaacct ctctgctaga gagcattatt cctgccttcg cgagtctgtt cctgggtccc   420
tggtccgaca agttcggaag gcggccaatc ctgctgacaa cttttacggg ctacctcact   480
ggcgcactca tactgatagt aatcacttac ataacgaggt ccacgaatat aagtccatgg   540
tggttcctcc tttcctcggt ccttccgtc gtaagcggcg aacttgcgc cttgattact    600 ggaatctatt gctacatatc cgatgtggcc aaggagcgaa agaaggctct gagaatggtc   660
ctcaatgaag cctccctctg tgctggcata atggtgggca atgtggccag cggttatatc   720
tatgctgcca caaatgctct ggtgttgttt tccattgctg gtagcctgat gatgtttgcc   780
ttgatgtacg tgcttctgtt tgtacctgaa agcctaaatc aggtgacat tcacaccgga    840 tcgcgagtcc gtgagttctt ccgtttcgat tggtcacgg acctgattcg cacctgcttt    900
aagaggcgcc caactttga tcgcacaatc atctggctta caatgattgc ccttacgata    960
gccattttcg acatggaggg agagagcact gtaaattaca tgttcgtgca ggataaattc   1020
aactggacca ttaaggactt cagtctattc aacgcatccc gcatcgtgat ccagattgtg   1080
ggcagcatcg ttggcatgtt ggtattgcgc cgcgttctaa agatgtctat cgtaaccatg   1140
gcaatgctct ccctggcttg ctgtgttctg gagagcacgg ttcgagccac agcagtctac   1200
tggcaagagc tgtatctggg catgacgctg ggtatgatgc gtggcgtcat gggacctatg   1260
tgccgcgcga ttctctcgca cgttgcaccc gcgactgaag ttggcaagat ctttgctctg   1320
accacctcca tggaatcggt ttcgccactg gcgctgcac ctctgtacac aaccgtctac    1380
aaggcaactt tggaaaatta cccggagct ttcaacttta ttagcgccgc tctctacttt    1440
gtgtgttaca ttctgatagc cgtgatcttc ggcatccaga agtcgatggg tagtagcagt   1500
gtctaccagg ccattggcag ctaa                                          1524

<210> SEQ ID NO 58
<211> LENGTH: 220
<212> TYPE: PRT
<213> ORGANISM: Drosophila melanogaster

<400> SEQUENCE: 58
```

```
Met Phe Gly Gly Lys Lys Glu Val Ala Pro Thr Thr Gly Glu Ala Ile
1               5                   10                  15

Gln Lys Leu Arg Glu Thr Glu Asn Met Leu Ile Lys Lys Gln Glu Phe
            20                  25                  30

Leu Glu Ala Lys Ile Glu Asp Glu Leu Asn Ile Ala Arg Lys Asn Ala
        35                  40                  45

Ser Lys Asn Lys Arg Val Ala Leu Gln Ala Leu Lys Lys Lys Arg
50                  55                  60

Leu Glu Lys Gln Leu Gln Gln Ile Asp Gly Thr Leu Ser Thr Ile Glu
65                  70                  75                  80

Met Gln Arg Glu Ala Leu Glu Ser Ala Asn Thr Asn Thr Ala Val Leu
                85                  90                  95

Thr Thr Met Lys Asn Ala Ala Asp Ala Leu Lys Arg Ala His Gln Asn
            100                 105                 110

Met Asp Val Asp Lys Val His Asp Met Met Asp Ile Ala Glu Gln
            115                 120                 125

Gln Asp Val Ala Arg Glu Ile Ser Asp Ala Ile Ser Asn Pro Val Ala
    130                 135                 140

Phe Gly Ala Asp Leu Asp Asp Glu Asp Leu Glu Arg Glu Leu Asp Glu
145                 150                 155                 160

Leu Glu Gln Glu Asn Phe Asp Lys Glu Ile Ile Gly Ile Pro Glu Pro
                165                 170                 175

Thr Pro Thr Leu Pro Glu Ala Pro Thr Glu Asp Leu Pro Glu Lys Ala
            180                 185                 190

Lys Glu Lys Lys Lys Ala Thr Thr Thr Ala Val Glu Asp Asp
        195                 200                 205

Asp Pro Asp Met Lys Gln Leu Leu Ser Trp Ser Asn
    210                 215                 220

<210> SEQ ID NO 59
<211> LENGTH: 723
<212> TYPE: DNA
<213> ORGANISM: Saccharomyces cerevisiae

<400> SEQUENCE: 59
atgtggtcat cacttttggg ttggacatca agtaatgcca agaataaaga gtcaccaaca     60
aaggccatag tgcggttgag ggagcatatc aaccttctat ccaaaaagca atcgcattta    120
cgtactcaaa ttacaaatca agagaatgaa gctagaatct ttttgacgaa gggcaataaa    180
gtaatggcga agaatgcact taaaaagaag aagacaatcg aacaactttt aagtaaggta    240
gaaggcacaa tggagtctat ggaacagcag ctattctcta gaaaagtgc aaacttaaat     300 ctagagacaa tgagggctat gcaggaaggt gctaaggcaa tgaaaactat tcacagtggc    360
cttgacatag ataaagtgga tgaaactatg gacgagataa gggagcaagt cgaattagga    420
gatgaaataa gcgacgctat atccaggcct ttaattactg ggcaaacga ggtggatgaa     480 gatgagctgg acgaggaatt ggacatgctg gctcaagaaa atgctaacca agaaacgtcc    540
aagatcgtta ataataatgt taatgcggcg cctatctcag agaacaaagt ctcactacct    600
agtgttccaa gtaataaaat taaacaaagt gagaactctg tgaaggacgg ggaagaggaa    660
gaggatgaag aagatgaaga tgaaaaagca ttaagagaac tacaagcaga aatggggctt    720
tga                                                                  723

<210> SEQ ID NO 60
<211> LENGTH: 240
```

```
<212> TYPE: PRT
<213> ORGANISM: Saccharomyces cerevisiae

<400> SEQUENCE: 60

Met Trp Ser Ser Leu Phe Gly Trp Thr Ser Asn Ala Lys Asn Lys
1               5                   10                  15

Glu Ser Pro Thr Lys Ala Ile Val Arg Leu Arg Glu His Ile Asn Leu
            20                  25                  30

Leu Ser Lys Lys Gln Ser His Leu Arg Thr Gln Ile Thr Asn Gln Glu
        35                  40                  45

Asn Glu Ala Arg Ile Phe Leu Thr Lys Gly Asn Lys Val Met Ala Lys
50                  55                  60

Asn Ala Leu Lys Lys Lys Lys Thr Ile Glu Gln Leu Leu Ser Lys Val
65                  70                  75                  80

Glu Gly Thr Met Glu Ser Met Glu Gln Gln Leu Phe Ser Ile Glu Ser
                85                  90                  95

Ala Asn Leu Asn Leu Glu Thr Met Arg Ala Met Gln Glu Gly Ala Lys
            100                 105                 110

Ala Met Lys Thr Ile His Ser Gly Leu Asp Ile Asp Lys Val Asp Glu
        115                 120                 125

Thr Met Asp Glu Ile Arg Glu Gln Val Glu Leu Gly Asp Glu Ile Ser
130                 135                 140

Asp Ala Ile Ser Arg Pro Leu Ile Thr Gly Ala Asn Glu Val Asp Glu
145                 150                 155                 160

Asp Glu Leu Asp Glu Glu Leu Asp Met Leu Ala Gln Glu Asn Ala Asn
                165                 170                 175

Gln Glu Thr Ser Lys Ile Val Asn Asn Val Asn Ala Ala Pro Ile
            180                 185                 190

Ser Glu Asn Lys Val Ser Leu Pro Ser Val Pro Ser Asn Lys Ile Lys
        195                 200                 205

Gln Ser Glu Asn Ser Val Lys Asp Gly Glu Glu Glu Asp Glu Glu
            210                 215                 220

Asp Glu Asp Glu Lys Ala Leu Arg Glu Leu Gln Ala Glu Met Gly Leu
225                 230                 235                 240

<210> SEQ ID NO 61
<211> LENGTH: 19
<212> TYPE: DNA
<213> ORGANISM: Unknown
<220> FEATURE:
<223> OTHER INFORMATION: T7 polymerase promoter sequence

<400> SEQUENCE: 61
taatacgact cactatagg                                                19

<210> SEQ ID NO 62
<211> LENGTH: 19
<212> TYPE: DNA
<213> ORGANISM: Unknown
<220> FEATURE:
<223> OTHER INFORMATION: T3 polymerase promoter sequence

<400> SEQUENCE: 62
aattaaccct cactaaagg                                                19

<210> SEQ ID NO 63
<211> LENGTH: 39
<212> TYPE: DNA
<213> ORGANISM: Unknown
```

<220> FEATURE:
<223> OTHER INFORMATION: Forward PCR primer for in vitro dsRNA synthesis

<400> SEQUENCE: 63
taatacgact cactataggg cggctctttt cttccattt                                39

<210> SEQ ID NO 64
<211> LENGTH: 39
<212> TYPE: DNA
<213> ORGANISM: Unknown
<220> FEATURE:
<223> OTHER INFORMATION: Reverse PCR primer for in vitro dsRNA synthesis

<400> SEQUENCE: 64
aattaaccct cactaaaggt ttcattcgtc ttcctcgct                                39

<210> SEQ ID NO 65
<211> LENGTH: 39
<212> TYPE: DNA
<213> ORGANISM: Unknown
<220> FEATURE:
<223> OTHER INFORMATION: Forward PCR primer for in vitro dsRNA synthesis

<400> SEQUENCE: 65
taatacgact cactataggc acttaatgcg cccattttc                                39

<210> SEQ ID NO 66
<211> LENGTH: 39
<212> TYPE: DNA
<213> ORGANISM: Unknown
<220> FEATURE:
<223> OTHER INFORMATION: Reverse PCR primer for in vitro dsRNA synthesis

<400> SEQUENCE: 66
aattaaccct cactaaaggt tagcgggact gctattgct                                39

<210> SEQ ID NO 67
<211> LENGTH: 39
<212> TYPE: DNA
<213> ORGANISM: Unknown
<220> FEATURE:
<223> OTHER INFORMATION: Forward PCR primer for in vitro dsRNA synthesis

<400> SEQUENCE: 67
taatacgact cactatagga gaggtcgaga acgagacca                                39

<210> SEQ ID NO 68
<211> LENGTH: 39
<212> TYPE: DNA
<213> ORGANISM: Unknown
<220> FEATURE:
<223> OTHER INFORMATION: Reverse PCR primer for in vitro dsRNA synthesis

<400> SEQUENCE: 68
aattaaccct cactaaagga tcgaactgct ctggctgat                                39

<210> SEQ ID NO 69
<211> LENGTH: 39
<212> TYPE: DNA
<213> ORGANISM: Unknown
<220> FEATURE:
<223> OTHER INFORMATION: Forward PCR primer for in vitro dsRNA synthesis

<400> SEQUENCE: 69
taatacgact cactataggc ttcaccgaaa gccaagaag                                39

```
<210> SEQ ID NO 70
<211> LENGTH: 39
<212> TYPE: DNA
<213> ORGANISM: Unknown
<220> FEATURE:
<223> OTHER INFORMATION: Reverse PCR primer for in vitro dsRNA synthesis

<400> SEQUENCE: 70
aattaaccct cactaaaggg aggtttgaaa gcgatggtg                              39

<210> SEQ ID NO 71
<211> LENGTH: 39
<212> TYPE: DNA
<213> ORGANISM: Unknown
<220> FEATURE:
<223> OTHER INFORMATION: Forward PCR primer for in vitro dsRNA synthesis

<400> SEQUENCE: 71
taatacgact cactatagga actttcagg tccgctcaa                              39

<210> SEQ ID NO 72
<211> LENGTH: 39
<212> TYPE: DNA
<213> ORGANISM: Unknown
<220> FEATURE:
<223> OTHER INFORMATION: Reverse PCR primer for in vitro dsRNA synthesis

<400> SEQUENCE: 72
aattaaccct cactaaaggc ctgaatagcc agatccgaa                             39

<210> SEQ ID NO 73
<211> LENGTH: 39
<212> TYPE: DNA
<213> ORGANISM: Unknown
<220> FEATURE:
<223> OTHER INFORMATION: Forward PCR primer for in vitro dsRNA synthesis

<400> SEQUENCE: 73
taatacgact cactataggg ctgatatggc agtttgggt                             39

<210> SEQ ID NO 74
<211> LENGTH: 39
<212> TYPE: DNA
<213> ORGANISM: Unknown
<220> FEATURE:
<223> OTHER INFORMATION: Reverse PCR primer for in vitro dsRNA synthesis

<400> SEQUENCE: 74
aattaaccct cactaaaggg caactgagca atcccattt                             39

<210> SEQ ID NO 75
<211> LENGTH: 39
<212> TYPE: DNA
<213> ORGANISM: Unknown
<220> FEATURE:
<223> OTHER INFORMATION: Forward PCR primer for in vitro dsRNA synthesis

<400> SEQUENCE: 75
taatacgact cactataggt tcgggaaaca gaggagatg                             39

<210> SEQ ID NO 76
<211> LENGTH: 39
<212> TYPE: DNA
<213> ORGANISM: Unknown
<220> FEATURE:
<223> OTHER INFORMATION: Reverse PCR primer for in vitro dsRNA synthesis
```

```
<400> SEQUENCE: 76
aattaaccct cactaaaggc cttgtcagct tctttcgct                              39

<210> SEQ ID NO 77
<211> LENGTH: 21
<212> TYPE: DNA
<213> ORGANISM: Unknown
<220> FEATURE:
<223> OTHER INFORMATION: siRNA sequence for scrambled negative control
      (first strand)

<400> SEQUENCE: 77
aguacugcuu acgauacggt t                                                21

<210> SEQ ID NO 78
<211> LENGTH: 21
<212> TYPE: DNA
<213> ORGANISM: Unknown
<220> FEATURE:
<223> OTHER INFORMATION: siRNA sequence for scrambled negative control
      (second strand)

<400> SEQUENCE: 78
ccguaucgua agcaguacut t                                                21

<210> SEQ ID NO 79
<211> LENGTH: 21
<212> TYPE: DNA
<213> ORGANISM: Unknown
<220> FEATURE:
<223> OTHER INFORMATION: siRNA sequence for positive control (PCNA,
      proliferating cell nuclear antigen) (first strand)

<400> SEQUENCE: 79
ggagaaaguu ucagacuaut t                                                21

<210> SEQ ID NO 80
<211> LENGTH: 21
<212> TYPE: DNA
<213> ORGANISM: Unknown
<220> FEATURE:
<223> OTHER INFORMATION: siRNA sequence for positive control (PCNA,
      proliferating cell nuclear antigen) (second strand)

<400> SEQUENCE: 80
auagucugaa acuuucucct g                                                21

<210> SEQ ID NO 81
<211> LENGTH: 21
<212> TYPE: DNA
<213> ORGANISM: Unknown
<220> FEATURE:
<223> OTHER INFORMATION: siRNA sequence for NP_056972.1 (first strand)

<400> SEQUENCE: 81
gguugcucca gcuuauuuut t                                                21

<210> SEQ ID NO 82
<211> LENGTH: 21
<212> TYPE: DNA
<213> ORGANISM: Unknown
<220> FEATURE:
<223> OTHER INFORMATION: siRNA sequence for NP_056972.1 (second strand)

<400> SEQUENCE: 82
```
aaaauaagcu ggagcaacct c                                              21

<210> SEQ ID NO 83
<211> LENGTH: 21
<212> TYPE: DNA
<213> ORGANISM: Unknown
<220> FEATURE:
<223> OTHER INFORMATION: siRNA sequence for CAD38936 (first strand)

<400> SEQUENCE: 83
gguucucuuu gaagccuaut t                                              21

<210> SEQ ID NO 84
<211> LENGTH: 21
<212> TYPE: DNA
<213> ORGANISM: Unknown
<220> FEATURE:
<223> OTHER INFORMATION: siRNA sequence for CAD38936 (second strand)

<400> SEQUENCE: 84
auaggcuuca aagagaacct g                                              21

<210> SEQ ID NO 85
<211> LENGTH: 21
<212> TYPE: DNA
<213> ORGANISM: Unknown
<220> FEATURE:
<223> OTHER INFORMATION: siRNA sequence for NP_060387.1 (first strand)

<400> SEQUENCE: 85
ggcuucaggg aaaauacugt t                                              21

<210> SEQ ID NO 86
<211> LENGTH: 21
<212> TYPE: DNA
<213> ORGANISM: Unknown
<220> FEATURE:
<223> OTHER INFORMATION: siRNA sequence for NP_060387.1 (second strand)

<400> SEQUENCE: 86
caguauuuuc ccugaagcct t                                              21

<210> SEQ ID NO 87
<211> LENGTH: 21
<212> TYPE: DNA
<213> ORGANISM: Unknown
<220> FEATURE:
<223> OTHER INFORMATION: siRNA sequence for NP_076974.1 (first strand)

<400> SEQUENCE: 87
ggacccuagu agagaugaat t                                              21

<210> SEQ ID NO 88
<211> LENGTH: 21
<212> TYPE: DNA
<213> ORGANISM: Unknown
<220> FEATURE:
<223> OTHER INFORMATION: siRNA sequence for NP_076974.1 (second strand)

<400> SEQUENCE: 88
uucaucucua cuagguccct c                                              21

<210> SEQ ID NO 89
<211> LENGTH: 21
<212> TYPE: DNA
<213> ORGANISM: Unknown

```
<220> FEATURE:
<223> OTHER INFORMATION: siRNA sequence for NP_060658.1 (first strand)

<400> SEQUENCE: 89
gucccacagg ugccucauut t                                              21

<210> SEQ ID NO 90
<211> LENGTH: 21
<212> TYPE: DNA
<213> ORGANISM: Unknown
<220> FEATURE:
<223> OTHER INFORMATION: siRNA sequence for NP_060658.1 (second strand)

<400> SEQUENCE: 90
aaugaggcac cugugggact t                                              21

<210> SEQ ID NO 91
<211> LENGTH: 1961
<212> TYPE: PRT
<213> ORGANISM: Rattus norvegicus

<400> SEQUENCE: 91
```

| | | | | | | | | | | | | | | |
|---|---|---|---|---|---|---|---|---|---|---|---|---|---|---|
| Met | Ala | Gln | Gln | Ala | Ala | Asp | Lys | Tyr | Leu | Tyr | Val | Asp | Lys | Asn | Phe |
| 1 | | | | 5 | | | | | 10 | | | | | 15 | |

| Ile | Asn | Asn | Pro | Leu | Ala | Gln | Ala | Asp | Cys | Gly | Ala | Lys | Lys | Leu | Val |
|---|---|---|---|---|---|---|---|---|---|---|---|---|---|---|---|
| | | | 20 | | | | | 25 | | | | | 30 | | |

| Trp | Val | Pro | Ser | Thr | Lys | Asn | Gly | Phe | Glu | Pro | Ala | Ser | Leu | Lys | Glu |
|---|---|---|---|---|---|---|---|---|---|---|---|---|---|---|---|
| | | | 35 | | | | | 40 | | | | | 45 | | |

Glu Val Gly Glu Glu Ala Ile Val Glu Leu Val Glu Asn Gly Lys Lys
             50                   55                  60

Val Lys Val Asn Lys Asp Asp Ile Gln Lys Met Asn Pro Pro Lys Phe
65                  70                  75                  80

Ser Lys Val Glu Asp Met Ala Glu Leu Thr Cys Leu Asn Glu Ala Ser
                85                  90                  95

Val Leu His Asn Leu Lys Glu Arg Tyr Tyr Ser Gly Leu Ile Tyr Thr
            100                 105                 110

Tyr Ser Gly Leu Phe Cys Val Val Ile Asn Pro Tyr Lys Asn Leu Pro
        115                 120                 125

Ile Tyr Ser Glu Glu Ile Val Asp Met Tyr Lys Gly Lys Lys Arg His
    130                 135                 140

Glu Met Pro Pro His Ile Tyr Ala Ile Thr Asp Thr Ala Tyr Arg Ser
145                 150                 155                 160

Met Met Gln Asp Arg Glu Asp Gln Ser Ile Leu Cys Thr Gly Glu Ser
                165                 170                 175

Gly Ala Gly Lys Thr Glu Asn Thr Lys Lys Val Ile Gln Tyr Leu Ala
            180                 185                 190

His Val Ala Ser Ser His Lys Ser Lys Lys Asp Gln Gly Glu Leu Glu
        195                 200                 205

Arg Gln Leu Leu Gln Ala Asn Pro Ile Leu Glu Ala Phe Gly Asn Ala
    210                 215                 220

Lys Thr Val Lys Asn Asp Asn Ser Ser Arg Phe Gly Lys Phe Ile Arg
225                 230                 235                 240

Ile Asn Phe Asp Val Asn Gly Tyr Ile Val Gly Ala Asn Ile Glu Thr
                245                 250                 255

Tyr Leu Leu Glu Lys Ser Arg Ala Ile Arg Gln Ala Lys Glu Glu Arg
            260                 265                 270

Thr Phe His Ile Phe Tyr Tyr Leu Leu Ser Gly Ala Gly Glu His Leu

```
                275                 280                 285
Lys Thr Asp Leu Leu Glu Pro Tyr Asn Lys Tyr Arg Phe Leu Ser
290                 295                 300
Asn Gly His Val Thr Ile Pro Gly Gln Gln Asp Lys Asp Met Phe Gln
305                 310                 315                 320
Glu Thr Met Glu Ala Met Arg Ile Met Gly Ile Pro Glu Asp Glu Gln
                325                 330                 335
Met Gly Leu Leu Arg Val Ile Ser Gly Val Leu Gln Leu Gly Asn Ile
                340                 345                 350
Val Phe Lys Lys Glu Arg Asn Thr Asp Gln Ala Ser Met Pro Asp Asn
                355                 360                 365
Thr Ala Ala Gln Lys Val Ser His Leu Leu Gly Ile Asn Val Thr Asp
370                 375                 380
Phe Thr Arg Gly Ile Leu Thr Pro Arg Ile Lys Val Gly Arg Asp Tyr
385                 390                 395                 400
Val Gln Lys Ala Gln Thr Lys Glu Gln Ala Asp Phe Ala Ile Glu Ala
                405                 410                 415
Leu Ala Lys Ala Thr Tyr Glu Arg Met Phe Arg Trp Leu Val Leu Arg
                420                 425                 430
Ile Asn Lys Ala Leu Asp Lys Thr Lys Arg Gln Gly Ala Ser Phe Ile
                435                 440                 445
Gly Ile Leu Asp Ile Ala Gly Phe Glu Ile Phe Asp Leu Asn Ser Phe
                450                 455                 460
Glu Gln Leu Cys Ile Asn Tyr Thr Asn Glu Lys Leu Gln Gln Leu Phe
465                 470                 475                 480
Asn His Thr Met Phe Ile Leu Glu Gln Glu Glu Tyr Gln Arg Glu Gly
                485                 490                 495
Ile Glu Trp Asn Phe Ile Asp Phe Gly Leu Asp Leu Gln Pro Cys Ile
                500                 505                 510
Asp Leu Ile Glu Lys Pro Ala Gly Pro Pro Gly Ile Leu Ala Leu Leu
                515                 520                 525
Asp Glu Glu Cys Trp Phe Pro Lys Ala Thr Asp Lys Ser Phe Val Glu
                530                 535                 540
Lys Val Val Gln Glu Gln Gly Thr His Pro Lys Phe Gln Lys Pro Lys
545                 550                 555                 560
Gln Leu Lys Asp Lys Ala Asp Phe Cys Ile Ile His Tyr Ala Gly Lys
                565                 570                 575
Val Asp Tyr Lys Ala Asp Glu Trp Leu Met Lys Asn Met Asp Pro Leu
                580                 585                 590
Asn Asp Asn Ile Ala Thr Leu Leu His Gln Ser Ser Asp Lys Phe Val
                595                 600                 605
Ser Glu Leu Trp Lys Asp Val Asp Arg Ile Ile Gly Leu Asp Gln Val
                610                 615                 620
Ala Gly Met Ser Glu Thr Ala Leu Pro Gly Ala Phe Lys Thr Arg Lys
625                 630                 635                 640
Gly Met Phe Arg Thr Val Gly Gln Leu Tyr Lys Glu Gln Leu Ala Lys
                645                 650                 655
Leu Met Ala Thr Leu Arg Asn Thr Asn Pro Asn Phe Val Cys Cys Ile
                660                 665                 670
Ile Pro Asn His Glu Lys Lys Ala Gly Lys Leu Asp Pro His Leu Val
                675                 680                 685
Leu Asp Gln Leu Arg Cys Asn Gly Val Leu Glu Gly Ile Arg Ile Cys
                690                 695                 700
```

-continued

```
Arg Gln Gly Phe Pro Asn Arg Val Val Phe Gln Glu Phe Arg Gln Arg
705                 710                 715                 720

Tyr Glu Ile Leu Thr Pro Asn Ser Ile Pro Lys Gly Phe Met Asp Gly
            725                 730                 735

Lys Gln Ala Cys Val Leu Met Ile Lys Ala Leu Glu Leu Asp Ser Asn
            740                 745                 750

Leu Tyr Arg Ile Gly Gln Ser Lys Val Phe Phe Arg Ser Gly Val Leu
            755                 760                 765

Ala His Leu Glu Glu Glu Arg Asp Leu Lys Ile Thr Asp Val Ile Ile
770                 775                 780

Gly Phe Gln Ala Cys Cys Arg Gly Tyr Leu Ala Arg Lys Ala Phe Ala
785                 790                 795                 800

Lys Arg Gln Gln Gln Leu Thr Ala Met Lys Val Leu Gln Arg Asn Cys
                805                 810                 815

Ala Ala Tyr Leu Arg Leu Arg Asn Trp Gln Trp Trp Arg Leu Phe Thr
            820                 825                 830

Lys Val Lys Pro Leu Leu Asn Ser Ile Arg His Glu Asp Glu Leu Leu
            835                 840                 845

Ala Lys Glu Ala Glu Leu Thr Lys Val Arg Glu Lys His Leu Ala Ala
850                 855                 860

Glu Asn Arg Leu Thr Glu Met Glu Thr Met Gln Ser Gln Leu Met Ala
865                 870                 875                 880

Glu Lys Leu Gln Leu Gln Glu Gln Leu Gln Ala Lys Thr Glu Leu Cys
            885                 890                 895

Ala Glu Ala Glu Glu Leu Arg Ala Arg Leu Thr Ala Lys Lys Gln Glu
            900                 905                 910

Leu Glu Glu Ile Cys His Asp Leu Glu Ala Arg Val Glu Glu Glu Glu
            915                 920                 925

Glu Arg Cys Gln Tyr Leu Gln Ala Glu Lys Lys Met Gln Gln Asn
            930                 935                 940

Ile Gln Glu Leu Glu Glu Gln Leu Glu Glu Glu Ser Ala Arg Gln
945                 950                 955                 960

Lys Leu Gln Leu Glu Lys Val Thr Thr Glu Ala Lys Leu Lys Lys Leu
            965                 970                 975

Glu Glu Asp Gln Ile Ile Met Glu Asp Gln Asn Cys Lys Leu Ala Lys
            980                 985                 990

Glu Lys Lys Leu Leu Glu Asp Arg  Val Ala Glu Phe Thr  Thr Asp Leu
            995                 1000                1005

Met Glu  Glu Glu Lys Ser  Lys Ser Leu Ala Lys  Leu Lys Asn
    1010                1015                1020

Lys His  Glu Ala Met Ile Thr  Asp Leu Glu Glu Arg  Leu Arg Arg
    1025                1030                1035

Glu Glu  Lys Gln Arg Gln Glu  Leu Glu Lys Thr Arg  Arg Lys Leu
    1040                1045                1050

Glu Gly  Asp Ser Thr Asp Leu  Ser Asp Gln Ile Ala  Glu Leu Gln
    1055                1060                1065

Ala Gln  Ile Ala Glu Leu Lys  Met Gln Leu Ala Lys  Lys Glu Glu
    1070                1075                1080

Glu Leu  Gln Ala Ala Leu Ala  Arg Val Glu Glu  Ala Ala Gln
    1085                1090                1095

Lys Asn  Met Ala Leu Lys Lys  Ile Arg Glu Leu  Thr Gln Ile
    1100                1105                1110
```

-continued

```
Ser Glu Leu Gln Glu Asp Leu Glu Ser Glu Arg Ala Cys Arg Asn
1115                1120                1125

Lys Ala Glu Lys Gln Lys Arg Asp Leu Gly Glu Glu Leu Glu Ala
1130                1135                1140

Leu Lys Thr Glu Leu Glu Asp Thr Leu Asp Ser Thr Ala Ala Gln
1145                1150                1155

Gln Glu Leu Arg Ser Lys Arg Glu Gln Glu Val Ser Ile Leu Lys
1160                1165                1170

Lys Thr Leu Glu Asp Glu Ala Lys Thr His Glu Ala Gln Ile Gln
1175                1180                1185

Glu Met Arg Gln Lys His Ser Gln Ala Val Glu Glu Leu Ala Glu
1190                1195                1200

Gln Leu Glu Gln Thr Lys Arg Val Lys Ala Thr Leu Glu Lys Ala
1205                1210                1215

Lys Gln Thr Leu Glu Asn Glu Arg Gly Glu Leu Ala Asn Glu Val
1220                1225                1230

Lys Ala Leu Leu Gln Gly Lys Gly Asp Ser Glu His Lys Arg Lys
1235                1240                1245

Lys Val Glu Ala Gln Leu Gln Glu Leu Gln Val Lys Phe Ser Glu
1250                1255                1260

Gly Glu Arg Val Arg Thr Glu Leu Ala Asp Lys Val Ser Lys Leu
1265                1270                1275

Gln Val Glu Leu Asp Ser Val Thr Gly Leu Leu Asn Gln Ser Asp
1280                1285                1290

Ser Lys Ser Ser Lys Leu Thr Lys Asp Phe Ser Ala Leu Glu Ser
1295                1300                1305

Gln Leu Gln Asp Thr Gln Glu Leu Leu Gln Glu Glu Asn Arg Gln
1310                1315                1320

Lys Leu Ser Leu Ser Thr Lys Leu Lys Gln Met Glu Asp Glu Lys
1325                1330                1335

Asn Ser Phe Arg Glu Gln Leu Glu Glu Glu Glu Glu Ala Lys
1340                1345                1350

Arg Asn Leu Glu Lys Gln Ile Ala Thr Leu His Ala Gln Val Thr
1355                1360                1365

Asp Met Lys Lys Lys Met Glu Asp Gly Val Gly Cys Leu Glu Thr
1370                1375                1380

Ala Glu Glu Ala Lys Arg Arg Leu Gln Lys Asp Leu Glu Gly Leu
1385                1390                1395

Ser Gln Arg Leu Glu Glu Lys Val Ala Ala Tyr Asp Lys Leu Glu
1400                1405                1410

Lys Thr Lys Thr Arg Leu Gln Gln Glu Leu Asp Asp Leu Leu Val
1415                1420                1425

Asp Leu Asp His Gln Arg Gln Ser Val Ser Asn Leu Glu Lys Lys
1430                1435                1440

Gln Lys Lys Phe Asp Gln Leu Leu Ala Glu Glu Lys Thr Ile Ser
1445                1450                1455

Ala Lys Tyr Ala Glu Glu Arg Asp Arg Ala Glu Ala Glu Ala Arg
1460                1465                1470

Glu Lys Glu Thr Lys Ala Leu Ser Leu Ala Arg Ala Leu Glu Glu
1475                1480                1485

Ala Met Glu Gln Lys Ala Glu Leu Glu Arg Leu Asn Lys Gln Phe
1490                1495                1500

Arg Thr Glu Met Glu Asp Leu Met Ser Ser Lys Asp Asp Val Gly
```

-continued

```
            1505                1510                1515

Lys Ser Val His Glu Leu Glu Lys Ser Asn Arg Ala Leu Glu Gln
        1520                1525                1530

Gln Val Glu Glu Met Lys Thr Gln Leu Glu Glu Leu Glu Asp Glu
        1535                1540                1545

Leu Gln Ala Thr Glu Asp Ala Lys Leu Arg Leu Glu Val Asn Leu
        1550                1555                1560

Gln Ala Met Lys Ala Gln Phe Glu Arg Asp Leu Gln Gly Arg Asp
        1565                1570                1575

Glu Gln Ser Glu Glu Lys Lys Lys Gln Leu Val Arg Gln Val Arg
        1580                1585                1590

Glu Met Glu Ala Glu Leu Glu Asp Glu Arg Lys Gln Arg Ser Ile
        1595                1600                1605

Ala Met Ala Ala Arg Lys Lys Leu Glu Met Asp Leu Lys Asp Leu
        1610                1615                1620

Glu Ala His Ile Asp Thr Ala Asn Lys Asn Arg Glu Glu Ala Ile
        1625                1630                1635

Lys Gln Leu Arg Lys Leu Gln Ala Gln Met Lys Asp Cys Met Arg
        1640                1645                1650

Asp Val Asp Asp Thr Arg Ala Ser Arg Glu Glu Ile Leu Ala Gln
        1655                1660                1665

Ala Lys Glu Asn Glu Lys Lys Leu Lys Ser Met Glu Ala Glu Met
        1670                1675                1680

Ile Gln Leu Gln Glu Glu Leu Ala Ala Ala Glu Arg Ala Lys Arg
        1685                1690                1695

Gln Ala Gln Gln Glu Arg Asp Glu Leu Ala Asp Glu Ile Ala Asn
        1700                1705                1710

Ser Ser Gly Lys Gly Ala Leu Ala Leu Glu Glu Lys Arg Arg Leu
        1715                1720                1725

Glu Ala Leu Ile Ala Leu Leu Glu Glu Glu Leu Glu Glu Glu Gln
        1730                1735                1740

Gly Asn Thr Glu Leu Ile Asn Asp Arg Leu Lys Lys Ala Asn Leu
        1745                1750                1755

Gln Ile Asp Gln Ile Asn Thr Asp Leu Asn Leu Glu Arg Ser His
        1760                1765                1770

Ala Gln Lys Asn Glu Asn Ala Arg Gln Gln Leu Glu Arg Gln Asn
        1775                1780                1785

Lys Glu Leu Lys Ala Lys Leu Gln Glu Met Glu Ser Ala Val Lys
        1790                1795                1800

Ser Lys Tyr Lys Ala Ser Ile Ala Ala Leu Glu Ala Lys Ile Ala
        1805                1810                1815

Gln Leu Glu Glu Gln Leu Asp Asn Glu Thr Lys Glu Arg Gln Ala
        1820                1825                1830

Ala Ser Lys Gln Val Arg Arg Ala Glu Lys Lys Leu Lys Asp Val
        1835                1840                1845

Leu Leu Gln Val Glu Asp Glu Arg Arg Asn Ala Glu Gln Phe Lys
        1850                1855                1860
```

-continued

```
Asp Gln Ala Asp Lys Ala Ser Thr Arg Leu Lys Gln Leu Lys Arg
    1865            1870                1875

Gln Leu Glu Glu Ala Glu Glu Glu Ala Gln Arg Ala Asn Ala Ser
    1880            1885                1890

Arg Arg Lys Leu Gln Arg Glu Leu Glu Asp Ala Thr Glu Thr Ala
    1895            1900                1905

Asp Ala Met Asn Arg Glu Val Ser Ser Leu Lys Asn Lys Leu Arg
    1910            1915                1920

Arg Gly Asp Met Pro Phe Val Val Thr Arg Arg Ile Val Arg Lys
    1925            1930                1935

Gly Thr Gly Asp Cys Ser Asp Glu Glu Val Asp Gly Lys Ala Asp
    1940            1945                1950

Gly Ala Asp Ala Lys Ala Thr Glu
    1955            1960
```

USE OF EUKARYOTIC GENES AFFECTING SPINDLE FORMATION OR MICROTUBULE FUNCTION DURING CELL DIVISION FOR DIAGNOSIS AND TREATMENT OF PROLIFERATIVE DISEASES

RELATED APPLICATIONS

This application is a national stage application (under 35 U.S.C. 371) of PCT/EP2004/010307 filed Sep. 15, 2004 which claims benefit to U.S. provisional application 60/502,633 filed Sep. 15, 2003.

SUBMISSION ON COMPACT DISC

The contents of the following submission on compact discs are incorporated herein by reference in its entirety: two copies of the Sequence Listing (COPY 1 and COPY 2) and a computer readable form copy of the Sequence Listing (CRF COPY), all on compact disc, each containing: file name: Sequence Listing (13907-00004-US), date recorded: Mar. 13, 2006, size: 220KB.

The present invention relates to the use of agents interfering with mitotic spindle ("spindle") formation or microtubule function during cell division for the treatment of diseases, especially proliferative diseases.

Metazoan cell division (mitosis) consists of an extremely complex, highly regulated set of cellular processes which must be tightly co-ordinated, perfectly timed, and closely monitored in order to ensure the correct delivery of cellular materials to daughter cells. Defects in these processes are known to cause a wide range of so-called proliferative diseases, including all forms of cancer. Since cell division represents one of the few, if not the only cellular process that is common to the aetiology of all forms of cancer, its specific inhibition has long been recognised as a preferred site of therapeutic intervention.

Although mitotic inhibitor drugs are recognised as one of the most promising classes of chemotherapeutic agents, screening attempts to find new drug candidates in this class have been undermined by the strong inherent tendency of such screens to identify agents that target a single protein, tubulin. Tubulin polymerises to form microtubules, the primary cytoskeletal elements needed for mitotic spindle function and chromosome segregation. Microtubules as such, however, are ubiquitously needed in almost all cell types, whether dividing or not, a fact which therefore explains many of the unwanted side effects caused by anti-tubulin drugs.

Perhaps the best known example of a highly successful anti-neoplastic drug that targets tubulin is paclitaxel, and its marketed derivative, Taxol. Its applicability has indeed been seriously limited by difficulties in determining an adequate dosing regimen due to a range of problematic side effects. Taxol treatment has resulted in anaphylaxis and severe hypersensitivity reactions characterised by dyspnea and hypotension requiring treatment, angioedema, and generalised urticaria in 2-4% of patients in clinical trials. Although Taxol is administered after pretreatment with corticosteroids, fatal reactions have occurred. Severe conductance abnormalities resulting in life-threatening cardiac arrhythmia occur in less than 1 percent of patients and must be treated by insertion of a pacemaker. Taxol can cause fetal harm or fetal death in pregnant women. Furthermore, administration is commonly accompanied by tachycardia, hypotension, flushing, skin reactions and shortness-of-breath (mild dyspnea). Reasons for these strong side-effects may be that since tubulin does not only play an essential role in spindle formation, but also plays significant roles in other cellular processes like for instance cytoskeleton generation and intracellular protein transport.

Consequently, although Taxol has been hailed by many as the most successful new anti-cancer therapeutic of the last three decades, there is still a need for anti-cancer drugs that do not show the disadvantages of Taxol.

Therefore, the problem underlying the present invention resides in providing improved potent anti-cancer drugs, particularly with less severe side effects.

The problem is solved by the use of an isolated nucleic acid molecule comprising a sequence selected from the group of sequences consisting of:
  a) the nucleic acid sequences presented in SEQ ID NO. 1, 3, 5, 7, 9, 11, 13, 15, 17, 19, 21, 23, 25, 27, 29, 31, 33, 35, 37, 39, 41, 43, 45, 47, 49, 51, 53, 55, 57, 59;
  b) nucleic acid sequences encoding polypeptides that exhibit a sequence identity with the protein encoded by a nucleic acid according to a) of at least 25% over 100 residues and/or which are detectable in a computer aided search using the BLAST sequence analysis programs with an e-value of at most
  c) sequences of nucleic acid molecules which are capable of hybridizing with the nucleic acid molecules with sequences corresponding to (a) or (b) under conditions of medium or high stringency,
  d) the antisense-sequence of any of the sequences as defined in (a), (b) or (c),
  e) fragments of (a), (b), (c) or (d),
  f) double-stranded RNA or single-stranded RNA in the antisense or sense direction corresponding to any of the sequences as defined in (a), (b), (c), (d), or (e)

for the manufacture of a medicament for the inhibition of spindle formation or microtubule function during cell division.

The present invention is based on the concept to provide agents interfering with spindle formation or microtubule function during cell division. Spindle formation or microtubule function during cell division are essential parts of cell division.

As a consequence of the present invention, target genes important for spindle formation or microtubule function during cell division were identified, leaving the general cellular appearance and therefore general cellular microtubule functions intact.

Thus, as the target proteins are involved in a cell division-specific process, the inhibition of these target proteins results in an efficient impairment of mitosis as well as in a reduced number of side effects caused by the inhibition of other significant cellular processes.

The present invention discloses for the first time for a variety of proteins and genes that they are involved in spindle formation or microtubule function during cell division. Although cell division and microtubules have already been thoroughly studied, the present invention provides several classes of target genes, corresponding gene products and other agents that had previously not been implicated in cell division, particularly not in spindle formation or microtubule function during cell division.

The newly identified function of these target genes and their corresponding gene products, any homologs, orthologs and derivatives thereof enables their use in the development of a wide range of medicaments against proliferative diseases including cancer. These medicaments could be used in treatment of proliferative diseases, particularly in those cases where the disorder relates to cell division, regulation of cell division, or is dependent on spindle formation or microtubule function during cell division. Furthermore, the newly identified function enables the use in diagnosis and the development of diagnostic agents.

For the identification of target genes being involved in spindle formation or microtubule function during cell division, a large-scale RNAi technique-based screen was performed for 19514 (that means 99.7%) of the predicted open reading frames in the *C. elegans* genome. For the performance of this large-scale screen double-stranded RNA corresponding to the individual open reading frames was produced and micro-injected into adult *C. elegans* hermaphrodites, and the resulting embryos were analysed 24 hours later using time-lapse DIC microscopy.

The nematode *C. elegans* exhibits an almost entirely translucent body throughout its development, thereby offering unparalleled microscopic access for exquisitely detailed cytological documentation, even for the earliest steps of embryogenesis. This important feature, along with its short life cycle (3-5 days), its ease of cultivation, and its low maintenance costs, has helped make *C. elegans* arguably the best studied of all metazoans. Also, sequence data are now available for over 97% of the *C. elegans* genome (*C. elegans* Sequencing Consortium. Genome sequence of the nematode *C. elegans*: a platform for investigating biology. Science 282, 2012-2018 (1998)). Thus, *C. elegans* is an ideal organism for applying the new technique of RNA-mediated interference (RNAi). This technique consists in the targeted, sequence-specific inhibition of gene expression, as mediated by the introduction into an adult worm of double-stranded RNA (dsRNA) molecules corresponding to portions of the coding sequences of interest (Fire et al., Potent and specific genetic interference by double-stranded RNA in *Caenorhabditis elegans*. Nature 391, 806-811 (1998)). For the vast majority of *C. elegans* genes tested to date, this has been shown to yield a sequence-specific inhibition of the targeted gene's expression, accompanied by clearly detectable loss of function phenotypes in the treated worm's F1 progeny (and even in some cases, in the treated worm itself).

In the context of the present invention, a screening assay in *C. elegans* based on 'genomic RNA mediated interference (RNAi)' combined with a highly probative microscopic assay for documenting the first rounds of embryonic cell division was used (Sulston et al., The embryonic cell lineage of the nematode *Caenorhabditis elegans*. Dev. Biol. 100, 64-119 (1983); Gönczy et al., Dissection of cell division processes in the one cell stage *Caenorhabditis elegans* embryo by mutational analysis. J Cell Biol 144, 927-946 (1999)).

With this combination of techniques a selected gene and also a variety of selected genes can be functionally characterized with unprecedented speed and efficiency.

The DIC microscopy generated movies were analyzed to identify those samples whereby cell division was altered or disrupted. In order to perform the analysis in a robust, consistent and reproducible fashion, each movie was analyzed with regard to 47 different parameters. In other words, 47 features of normal cell division (i.e. cell division in wild type worms) were scored for every RNAi phenotype generated by the genome-wide application of RNAi across the entire *C. elegans* genome.

A powerful confirmation and validation of the DIC assay, and the depth of information that the assays yield, was that equivalent phenotypes were found to represent closely related proteins, proteins within the same family or functionally equivalent proteins. In other words, if the RNAi-induced phenotypes of two separately analyzed genes are the same, it is very likely that the two proteins are either within the same protein class or share a similar function or at the very least, are both involved in the same biological mechanism or process. Therefore, the screen can be used to class or group proteins according to their function. Consequently, any genes that give rise to similar RNAi phenotypes are related and are justified to be considered within single functional classes.

"Nucleic acids" according to the present invention comprises all known nucleic acids such as DNA, RNA, peptide nucleic acids, morpholinos, and nucleic acids with backbone structures other than phosphodiesters, such as phosphothiates or phosphoramidates.

"Microtubule function during cell division" according to the present invention relates to any function of microtubules during cell division, including microtubular structure, disassembly and reassembly, and motor-based defects. Motor-based defects according to the present invention comprise any defects of transport along microtubules related to defects of microtubule-associated transport molecules. Preferably, "microtubule function during cell division" relates to microtubule function specific for cell division, i.e. not to microtubule functions essential for non-dividing cells.

"Inhibition of spindle formation or microtubule function during cell division" according to the present invention includes halting or arresting as well as retarding or slowing down of spindle formation or microtubule function during cell division.

In a preferred embodiment of the invention, the nucleic acid molecule comprises a nucleic acid molecule with a sequence selected from the group of sequences as presented in SEQ ID NO. 1, 3, 5, 7, 9, 11, 13, 15, 17, 19, 21, 23, 25, 27, 29, 31, 33,35, 37, 39, 41, 43, 45, 47, 49, 51, 53, 55, 57, 59. Preferably, the nucleic acid molecule consists of a nucleic acid molecule with a sequence selected from said group of sequences.

The term "comprise" preferably refers to nucleic acids in which the nucleic acids with the described sequences are functionally relevant, e.g. for diagnostic use or therapeutic use, such as vectors for therapeutical use or expression of corresponding RNAs or proteins. Preferably, any additional nucleic acids upstream or downstream of the sequence are not longer than 20 kb. More preferred, the term "comprise" does not relate to large constructs accidentally including the sequence, such as genomic BAC or YAC clones.

In detail, the individual SEQ ID No. denotes the following sequences:

| | |
|---|---|
| SEQ ID NO. 1 | the nucleotide sequence of the *C. elegans* gene C13F10.2 (Wormbase accession No. CE08144) |
| SEQ ID NO. 2 | the deduced amino acid sequence of the *C. elegans* gene C13F10.2 (Wormbase accession No. CE08144) |
| SEQ ID NO. 3 | the nucleotide sequence of the human ortholog of C13F10.2 (GenBank accession No. NM_024069) |
| SEQ ID NO. 4 | the deduced amino acid sequence of the human ortholog of C13F10.2 (GenBank accession No. NP_076974) |

-continued

| | |
|---|---|
| SEQ ID NO. 5 | the nucleotide sequence of the *Drosophila* homolog of C13F10.2 (GenBank accession No. AE003541) |
| SEQ ID NO. 6 | the deduced amino acid sequence of the *Drosophila* homolog of C13F10.2 (GenBank accession No. AAF49911) |
| SEQ ID NO. 7 | the nucleotide sequence of the *C. elegans* gene C25A1.9 (Wormbase accession No. CE18532) |
| SEQ ID NO. 8 | the deduced amino acid sequence of the *C. elegans* gene C25A1.9 (Wormbase accession No. CE18532) |
| SEQ ID NO. 9 | the nucleotide sequence of the human ortholog of C25A1.9 (GenBank accession No. NM_017917) |
| SEQ ID NO. 10 | the deduced amino acid sequence of the human ortholog of C25A1.9 (GenBank accession No. NP_060387) |
| SEQ ID NO. 11 | the nucleotide sequence of the *C. elegans* gene F54B3.3 (Wormbase accession No. CE03405) |
| SEQ ID NO. 12 | the deduced amino acid sequence of the *C. elegans* gene F54B3.3 (Wormbase accession No. CE03405) |
| SEQ ID NO. 13 | the nucleotide sequence of the human ortholog of F54B3.3 (GenBank accession No. NM_018188) |
| SEQ ID NO. 14 | the deduced amino acid sequence of the human ortholog of F54B3.3 (GenBank accession No. NP_060658) |
| SEQ ID NO. 15 | the nucleotide sequence of the mouse homolog of F54B3.3 (GenBank accession No. XM_109399) |
| SEQ ID NO. 16 | the deduced amino acid sequence of the mouse homolog of F54B3.3 (GenBank accession No. XP_109399) |
| SEQ ID NO. 17 | the nucleotide sequence (corresponding to the mRNA) of the rat homolog of F54B3.3 (GenBank accession No. NM_053864) |
| SEQ ID NO. 18 | the deduced amino acid sequence of the rat homolog of F54B3.3 (GenBank accession No. NP_446316 or P46462) |
| SEQ ID NO. 19 | the nucleotide sequence of the *Drosophila* ortholog of F54B3.3 (GenBank accession No. AE003712) |
| SEQ ID NO. 20 | the deduced amino acid sequence of the *Drosophila* ortholog of F54B3.3 (GenBank accession No. AAF55289) |
| SEQ ID NO. 21 | the nucleotide sequence of the yeast homolog of F54B3.3 (GenBank accession No. NC_001148.1, base pairs 610476 to 612719) |
| SEQ ID NO. 22 | the deduced amino acid sequence of the yeast homolog of F54B3.3 (GenBank accession No. NP_015349) |
| SEQ ID NO. 23 | the nucleotide sequence of the *C. elegans* gene F08B6.2 (Wormbase accession No. CE20656) |
| SEQ ID NO. 24 | the deduced amino acid sequence of the *C. elegans* gene F08B6.2 (Wormbase accession No. CE20656) |
| SEQ ID NO. 25 | the nucleotide sequence of the human ortholog of F08B6.2 (GenBank accession No. NM_016541) |
| SEQ ID NO. 26 | the deduced amino acid sequence of the human ortholog of F08B6.2 (GenBank accession No. NP_057625) |
| SEQ ID NO. 27 | the nucleotide sequence (corresponding to the mRNA) of the rat homolog of F08B6.2 (GenBank accession No. NM_139185) |
| SEQ ID NO. 28 | the deduced amino acid sequence of the rat homolog of F08B6.2 (GenBank accession No. NP_631924 or AAA73553) |
| SEQ ID NO. 29 | the nucleotide sequence of the *Drosophila* homolog of F08B6.2 (GenBank accession No. AE003624) |
| SEQ ID NO. 30 | the deduced amino acid sequence of the *Drosophila* homolog of F08B6.2 (GenBank accession No. AAF52761) |
| SEQ ID NO. 31 | the nucleotide sequence of the *C. elegans* gene CD4.4 (Wormbase accession No. CE16952) |
| SEQ ID NO. 32 | the deduced amino acid sequence of the *C. elegans* gene CD4.4 (Wormbase accession No. CE16952) |
| SEQ ID NO. 33 | the nucleotide sequence of a human ortholog of CD4.4 (GenBank accession No. NM_024667) |
| SEQ ID NO. 34 | the deduced amino acid sequence of a human ortholog of CD4.4 (GenBank accession No. NP_078943) |
| SEQ ID NO. 35 | the nucleotide sequence (corresponding to the mRNA) of a human ortholog of CD4.4 (GenBank accession No. AL834261) |
| SEQ ID NO. 36 | the deduced amino acid sequence of a human ortholog of CD4.4 (GenBank accession No. CAD38936) |
| SEQ ID NO. 37 | the nucleotide sequence of the *Drosophila* homolog of CD4.4 (GenBank accession No. AE003603) |
| SEQ ID NO. 38 | the deduced amino acid sequence of the *Drosophila* homolog of CD4.4 (GenBank accession No. AF52060) |
| SEQ ID NO. 39 | the nucleotide sequence of the *C. elegans* gene ZK546.1 (Wormbase accession No. CE28524) |
| SEQ ID NO. 40 | the deduced amino acid sequence of the *C. elegans* gene ZK546.1 (Wormbase accession No. CE28524) |
| SEQ ID NO. 41 | the nucleotide sequence of the human ortholog of ZK546.1 (GenBank accession No. NM_015888) |
| SEQ ID NO. 42 | the deduced amino acid sequence of the human ortholog of ZK546.1 (GenBank accession No. NP_056972) |
| SEQ ID NO. 43 | the nucleotide sequence of the rat homolog of ZK546.1 (GenBank accession No. NM_031745) |

-continued

| | |
|---|---|
| SEQ ID NO. 44 | the deduced amino acid sequence of the rat homolog of ZK546.1 (GenBank accession No. XP_113933) |
| SEQ ID NO. 45 | the nucleotide sequence of the mouse homolog of ZK546.1 (GenBank accession No. XM_109474) |
| SEQ ID NO. 46 | the deduced amino acid sequence of the mouse homolog of ZK546.1 (GenBank accession No. XP_109474) |
| SEQ ID NO. 47 | the nucleotide sequence of the *Drosophila* homolog of ZK546.1 (GenBank accession No. AE003655) |
| SEQ ID NO. 48 | the deduced amino acid sequence of the *Drosophila* homolog of ZK546.1 (GenBank accession No. AAF53605) |
| SEQ ID NO. 49 | the nucleotide sequence of the yeast homolog of ZK546.1 (GenBank accession No. NC_001136, base pairs 345664 to 351036) |
| SEQ ID NO. 50 | the deduced amino acid sequence of the yeast homolog of ZK546.1 (GenBank accession No. NP_010225) |
| SEQ ID NO. 51 | the nucleotide sequence of the *C. elegans* gene C56C10.3 (Wormbase accession No. CE0256) |
| SEQ ID NO. 52 | the deduced amino acid sequence of the *C. elegans* gene C56C10.3 (Wormbase accession No. CE0256) |
| SEQ ID NO. 53 | the nucleotide sequence of the human ortholog of C56C10.3 (GenBank accession No. XM_059282) |
| SEQ ID NO. 54 | the deduced amino acid sequence of the human ortholog of C56C10.3 (GenBank accession No. XP_059282) |
| SEQ ID NO. 55 | the nucleotide sequence of the mouse ortholog of C56C10.3 (GenBank accession No. NM_029362) |
| SEQ ID NO. 56 | the deduced amino acid sequence of the mouse ortholog of C56C10.3 (GenBank accession No. NP_083638) |
| SEQ ID NO. 57 | the nucleotide sequence of the *Drosophila* ortholog of C56C10.3 (GenBank accession No. AE003834) |
| SEQ ID NO. 58 | the deduced amino acid sequence of the *Drosophila* ortholog of C56C10.3 (GenBank accession No. AAF58977) |
| SEQ ID NO. 59 | the nucleotide sequence of a yeast homolog of C56C10.3 (GenBank accession No. NC_001144, base pairs 194453 to 195175) |
| SEQ ID NO. 60 | the deduced amino acid sequence of a yeast homolog of C56C10.3 (GenBank accession No. NP_013125) |

Unless otherwise specified, the manipulations of nucleic acids and polypeptides-proteins can be performed using standard methods of molecular biology and immunology (see, e.g. Maniatis et al. (1989), Molecular cloning: A laboratory manual, Cold Spring Harbor Lab., Cold Spring Harbor, N.Y.; Ausubel, F. M. et al. (eds.) "Current protocols in Molecular Biology". John Wiley and Sons, 1995; Tijssen, P., Practice and Theory of Enzyme Immunoassays, Elsevier Press, Amsterdam, Oxford, N.Y., 1985).

The present invention describes genes identified as having essential functions in cell division in the model organism *C. elegans*. The basis for performing research in model organisms is that the newly discovered functions for the genes in *C. elegans* will be conserved in other species including humans. Cell division as well as spindle formation or microtubule function during cell division are highly conserved during evolution and therefore the approach of discovering a gene function in *C. elegans* and using the information to characterise or assign functions for human homologs or orthologs is well justified.

One theme of conservation is that the gene function can be conserved with substantial divergence of sequence. In the present invention this theme of conservation is not defined. However, if other genes are discovered to have functions that result in the gene product being identified as the same gene product as those claimed in the present invention then the present claims also apply to such genes.

However, the most frequent theme of conservation of genes during evolution is that the gene sequence is conserved. This theme of conservation is particularly frequent for genes involved in highly conserved processes such as cell division. This means that the DNA nucleotide sequence or the protein coding sequence of the gene are very similar in different species, which in turn suggests that the function of the gene is the same in the different species.

Therefore, in a further preferred embodiment, the nucleic acid molecule has a sequence that encodes a polypeptide exhibiting a sequence identity with a protein encoded by SEQ ID NO. 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 of at least 25% over 100 residues, preferably of at least 30% over 100 residues, more preferably of at least 50% over 100 residues, particularly of at least 70% over 100 residues on amino acid level.

These very high sequence similarities are usually shown by polypeptides which are orthologs or homologs of the above sequences. A homolog is a protein with similar sequence from the same or another species (an homolog's sequence similarity originates from a speciation event or from a gene duplication, i.e. a homolog is a related protein in any species or the same protein in another species). A subgroup of homologs are defined as orthologs. An ortholog is essentially the same protein as the one it is compared to, but it is derived from another species (an ortholog's sequence similarity originates from a speciation event rather than a gene duplication). It is known to a person skilled in the art, that in a conserved process such as cell division, homologous and orthologous proteins, particularly orthologous proteins, are very likely to serve the same biological function. In the present case, the most relevant biological function is the involvement in, particularly the requirement for, spindle formation or microtubule function during cell division.

Advantageously, it could be shown that human orthologs of the *C. elegans* genes identified in the context of this invention are required for proliferation, cell survival and mitosis (see Example 11). This finding indicates that the human orthologs are required for spindle formation and microtubule function during cell division and can be used in the context of diagnosis and treatment of proliferative diseases.

The person skilled in the art is familiar with different methods and criteria to identify homologs and orthologs. In the context of the present invention, homologs and orthologs were identified based on sequence similarity according to the procedure described in Example 1.

The nucleic acid molecule may also comprise a sequence that is detectable in a computer aided database search/alignment with an e-value of at most $10^{-5}$, preferably with an e-value of at most $10^{-12}$, particularly with an e-value of at most $10^{-20}$ or fragments thereof, whereby the database sequences are compared to the sequences as defined under a). The nucleic acid molecule may also comprise a sequence that is considered an ortholog according to the criteria of the present invention (see Example 1). Generally, the grade of sequence identity can be calculated by any software program that is capable to perform protein sequence alignments known in the art. Hereby it is also included that identical amino acid regions are interrupted by gaps that can be variable in their length.

For this kind of analysis or alignments the "BLAST sequence analysis programs" are particularly preferred. The "BLAST sequence analysis programs" which may be used for sequence analysis are publically available and known to anyone skilled in the art. Known analysis programs for sequence alignments, particularly the "BLAST sequence analysis programs", calculate so called "e-values" to characterize the grade of homology between the compared sequences. Generally, a small e-value characterizes a high sequence similarity, whereas larger e-values characterize lower sequence similarity.

The degree of similarity required for the sequence variant will depend upon the intended use of the sequence. It is well within the capability of a person skilled in the art to effect mutational, insertional and deletional mutations which are designed to improve the function of the sequence or otherwise provide a methodological advantage.

The aforementioned grades of sequence identities with proteins encoded by the above SEQ IDs are characteristic for such polypeptides that are strongly homologous to the above sequences, in particular for polypeptides that are "orthologous" or "homologous" to the polypeptides of a).

Table 1 shows the e-values that have been calculated for the alignments on amino acid level with homologs and orthologs of the corresponding *C. elegans* gene. Hereby, e-values lower than $10^{-5}$ on amino acid level characterize homologs of the corresponding *C. elegans* genes. If the *C. elegans* gene is itself a reciprocal hit of the identified homolog with an e-value of less than $10^{-5}$, then the homolog is identified as an ortholog (see also Example 1).

TABLE 1

Sequence similarities between the *C. elegans* genes C13F10.2, C25A1.9, F54B3.3, F08B6.2, CD4.4, ZK546.1, C56C10.3 and their human, mouse, rat, *Drosophila*, and yeast homologs and orthologs.

| *C. elegans* gene | e-value for the alignment with the *C. elegans* gene on amino acid level |
|---|---|
| C13F10.2 | Human orthol. 6 * $10^{-13}$ |
|  | *Drosoph.* orthol. 1 * $10^{-19}$ |
| C25A1.9 | Human orthol. 8 * $10^{-6}$ |
| F54B3.3 | Human orthol. 1 * $10^{-170}$ |
|  | Mouse homol. 3 * $10^{-15}$ |
|  | Rat homol. 8 * $10^{-15}$ |
|  | *Drosoph.* orthol. 1 * $10^{-163}$ |
|  | Yeast homol. 8 * $10^{-15}$ |

TABLE 1-continued

Sequence similarities between the *C. elegans* genes C13F10.2, C25A1.9, F54B3.3, F08B6.2, CD4.4, ZK546.1, C56C10.3 and their human, mouse, rat, *Drosophila*, and yeast homologs and orthologs.

| *C. elegans* gene | e-value for the alignment with the *C. elegans* gene on amino acid level |
|---|---|
| F08B6.2 | Human orthol. 4 * $10^{-6}$ |
|  | Rat homol. 2 * $10^{-6}$ |
|  | *Drosoph.* orthol. 2 * $10^{-11}$ |
| CD4.4 | Human orthol. 1 * $10^{-9}$ (GenBank Acc.No. NP_078943) |
|  | Human orthol. 2 * $10^{-8}$ (GenBank Acc.No. CAD38936) |
|  | *Drosoph.* orthol. 2 * $10^{-9}$ |
| ZK546.1 | Human orthol. 1 * $10^{-12}$ |
|  | Mouse homol. 4 * $10^{-6}$ |
|  | Rat homol. 7 * $10^{-11}$ |
|  | *Drosoph.* homol. 2 * $10^{-9}$ |
|  | Yeast homol. 3 * $10^{-14}$ |
| C56C10.3 | Human orthol. 2 * $10^{-60}$ |
|  | Mouse orthol. 3 * $10^{-60}$ |
|  | *Drosoph.*orthol. 4 * $10^{-51}$ |
|  | Yeast homol. 3 * $10^{-28}$ |

According to a further preferred embodiment, the nucleic acid molecule comprises a nucleotide sequence which is capable of hybridizing with the nucleic acid sequences of (a) or (b) under conditions of medium/high stringency.

In such hybrids, duplex formation and stability depend on substantial complementarity between the two strands of the hybrid and a certain degree of mismatch can be tolerated. Therefore, the nucleic acid molecules and probes of the present invention may include mutations (both single and multiple), deletions, insertions of the above identified sequences, and combinations thereof, as long as said sequence variants still have substantial sequence similarity to the original sequence which permits the formation of stable hybrids with the target nucleotide sequence of interest.

Suitable experimental conditions for determining whether a given DNA or RNA sequence "hybridizes" to a specified polynucleotide or oligonucleotide probe involve presoaking of the filter containing the DNA or RNA to examine for hybridization in 5×SSC (sodium chloride/sodium citrate) buffer for 10 minutes, and prehybridization of the filter in a solution of 5×SSC, 5× Denhardt's solution, 0.5% SDS and 100 mg/ml of denaturated sonicated salmon sperm DNA (Maniatis et al.,1989), followed by hybridization in the same solution containing a concentration of 10 ng/ml of a random primed (Feinberg, A. P. and Vogelstein, B. (1983), Anal. Biochem. 132:6-13), $^{32}$P-dCTP-labeled (specific activity>1×$10^9$ cpm/µg) probe for 12 hours at approximately 45° C. The filter is then washed twice for 30 minutes in 2×SSC, 0.5% SDS at at least 55° C. (low stringency), at least 60° C. (medium stringency), preferably at least 65° C. (medium/high stringency), more preferably at least 70° C. (high stringency) or most preferably at least 75° C. (very high stringency). Molecules to which the probe hybridizes under the chosen conditions are detected using an x-ray film or a "phosphor imager".

According to a further preferred embodiment, the nucleic acid molecules may also have the antisense-sequence of any of the sequences as defined in (a), (b) or (c).

According to a further preferred embodiment, fragments of the nucleic acid molecules as described above may be used.

The term "fragment" as used according to the present invention can have different meanings depending on the molecule and purpose referred to. A person skilled in the art knows how to choose appropriate fragments for the relevant purpose. Preferably, a fragment should be specific for the sequence it is derived from. The meaning of the term "specific" is known in the art. Preferably, specific in this context means that in a BLAST search performed with the sequence fragment, the original sequence (from which the fragment is derived) would be identified with a lower e-value than all other sequences relevant in the context of the current use (e.g. all other sequences of nucleic acids present in the investigated sample). More preferably, the original sequence should be identified with the lowest e-value compared to all other sequences identified. Alternatively, "specific" means that, under the applied conditions, the fragment binds only to the nucleic acid molecule it is derived from. The criterion of specificity is usually achieved by fragments larger than 15 nucleotides, preferably larger than 19 nucleotides. Preferably, the fragments are chosen from sequence regions of high complexity. Low complexity regions can be identified by database searches or low complexity filters available in standard sequence analysis programs.

"Biologically active" fragments or derivatives can be generated by a person skilled in the art. Hereby, the fragments or derivatives should have a similar "biological function" as the nucleic acid they are derived from. According to the present invention the most relevant biological function is the involvement in, inhibition of, activation of, or requirement for spindle formation or microtubule function during cell division.

The isolated nucleic acid molecules defined as under (a) to (e) may be used for influencing cell division and/or cell proliferation, particularly by inhibiting spindle formation or microtubule function during cell division, either in vitro or in vivo.

Inhibition of spindle formation or microtubule function during cell division using said nucleic acid molecules can be achieved by different ways familiar to the person skilled in the art. For example, the isolated nucleic acid molecules may be inserted downstream of a strong promotor to overexpress the corresponding protein or polypeptide. Overexpression of the protein or polypeptide may lead to suppression of the endogenous protein's biological function. By introducing deletions or other mutations into the nucleic acids, or by using suitable fragments, it is possible to generate sequences encoding dominant-negative peptides or polypeptides. Such dominant-negative peptides or polypeptides can inhibit the function of the corresponding endogenous protein.

Certain nucleic acids can be used to inhibit expression (transcription and/or translation) of the endogenous genes to inhibit spindle formation or microtubule function during cell division. E.g. peptide nucleic acids comprising sequences as identified above can suppress expression of the corresponding endogenous gene by forming DNA triplex structures with the gene. Other nucleic acids, such as antisense morpholino oligonucleotides or ribozymes, can be used to interfere with RNA transcribed from the endogenous gene.

The application of automated gene synthesis provides an opportunity for generating sequence variants of the naturally occurring genes. It will be appreciated that polynucleotides coding for synthetic variants of the corresponding amino acid sequences can be generated which, for example, will result in one or more amino acids substitutions, deletions or additions. Also, nucleic acid molecules comprising one or more synthetic nucleotide derivatives (including morpholinos) which provide said nucleotide sequence with a desired feature, e.g. a reactive or detectable group, can be prepared. Synthetic derivatives with desirable properties may also be included in the corresponding polypeptides. All such derivatives and fragments of the above identified genes and gene products showing at least part of the biological activity or biological function of the naturally occurring sequences or which are still suitable to be used, for example, as probes for, e.g. identification of homologous genes or gene products, are included within the scope of the present invention. Also included are such derivatives and fragments whose activity or function is counteracting to the biological activity or biological function of the naturally occurring sequences, e.g. derivatives and fragments that encode dominant-negative molecules.

Having herein provided the nucleotide sequences of various genes functionally involved in spindle formation or microtubule function during cell division, it will be appreciated that automated techniques of gene synthesis and/or amplification may be used to isolate said nucleic acid molecules in vitro. Because of the length of some coding sequences, application of automated synthesis may require staged gene construction, in which regions of the gene up to about 300 nucleotides in length are synthesized individually and then ligated in correct succession for final assembly. Individually sythesized gene regions can be amplified prior to assembly, using polymerase chain reaction (PCR) technology. The technique of PCR amplification may also be used to directly generate all or part of the final genes/nucleic acid molecules. In this case, primers are synthesized which will be able to prime the PCR amplification of the final product, either in one piece or in several pieces that may be ligated together. For this purpose, either cDNA or genomic DNA may be used as the template for the PCR amplification. The cDNA template may be derived from commercially available or self-constructed cDNA libraries.

According to a further preferred embodiment, the invention relates to the use of the above identified nucleic acid molecules or fragments thereof in form of RNA, particularly antisense RNA and double-stranded RNA, for the manufacture of a medicament for the inhibition of spindle formation or microtubule function during cell division. Also ribozymes can be generated for the above identified sequences and used to degrade RNA transcribed from the corresponding endogenous genes.

As stated above, double-stranded RNA oligonucleotides effect silencing of the expression of gene(s) which are highly homologous to either of the RNA strands in the duplex. Recent discoveries had revealed that this effect, called RNA interference (RNAi), that had been originally discovered in C. elegans, can also be observed in mammalian, particularly in human cells. Thus, inhibition of a specific gene function by RNA interference can also be performed in mammalian cells, particularly also in human cells As shown in FIG. 1, the inhibition of a nucleic acid molecule as defined under (a) to (f) by RNAi in C. elegans inhibits cell division by impairing spindle formation or microtubule function during cell division.

Particularly preferred is the use of these RNA molecules in a therapeutical application of the RNAi technique, particularly in humans or in human cells.

An RNAi technique particularly suited for mammalian cells makes use of double-stranded RNA oligonucleotides known as "small interfering RNA" (siRNA).

Therefore, according to a further preferred embodiment, the invention relates to the use of nucleic molecules comprising small interfering RNA with a sequence corresponding to any of the sequences identified above.

These siRNA molecules can be used for the therapeutical silencing of the expression of the genes of the invention comprising nucleic acid sequences as defined under (a) to (f), in mammalian cells, particularly in human cells, particularly for the therapy of a proliferative disease.

The inhibition of a specific target gene in mammals is achieved by the introduction of an siRNA-molecule having a sequence that is specific (see above) for the target gene into the mammalian cell. The siRNAs comprise a first and a second RNA strand, both hybridized to each other, wherein the sequence of the first RNA strand is a fragment of one of the sequences as defined in a) to f) and wherein the sequence of the second RNA strand is the antisense-strand of the first RNA strand. The siRNA-molecules may possess a characteristic 2- or 3-nucleotide 3'-overhanging sequence. Each strand of the siRNA molecule preferably has a length of 19 to 31 nucleotides.

The siRNAs can be introduced into the mammalian cell by any suitable known method of cell transfection, particularly lipofection, electroporation or microinjection. The RNA oligonucleotides can be generated and hybridized to each other in vitro or in vivo according to any of the known RNA synthesis methods.

The possibility to inhibit gene expression of disease-associated genes also in mammalian cells and in particular in human cells, make siRNAs or vector systems capable of producing siRNAs, having the sequence of those disease-associated genes, an interesting therapeutical agent for pharmaceutical compositions. Particularly siRNAs having sequences as defined in the present invention or that are homologous or orthologous to one of those genes can be used for the manufacture of medicaments for the inhibition of spindle formation or microtubule function during cell division and for the therapy of diseases, particularly proliferative diseases (see below). Similarly, nucleic acid vectors capable of producing those siRNAs can be used for the manufacture of such medicaments.

In another embodiment, the invention relates to the use of a nucleic acid molecule as defined above, wherein the nucleic acid molecule is contained in at least one nucleic acid expression vector which is capable of producing a double-stranded RNA-molecule comprising a sense-RNA-stand and an antisense-RNA-strand under suitable conditions, wherein each RNA-strand, independently from the other, has a length of 19 to 31 nucleotides.

In this alternative method (also described in Tuschl, Nature Biotechnology, Vol. 20, pp. 446-448), vector systems capable of producing siRNAs instead of the siRNAs themselves are introduced into the mammalian cell for downregulating gene expression.

The preferred lengths of the RNA-strands produced by such vectors correspond to those preferred for siRNAs in general (see below).

"Suitable conditions" for the production of the above double-stranded RNA-molecule are all in vivo or in vitro conditions that according to the state of art allow the expression of a first and a second RNA-strand with the above sequences and lengths that—when hybridized—form a double-stranded RNA-molecule. Particularly preferred "suitable conditions" for the production of the above double-stranded RNA-molecule are the "in vivo conditions" in a living human or animal cell or the "in vitro conditions" in cultured human or animal cells.

The "nucleic acid expression vector" may be an extrachromosomal entity, the replication of which is independent of chromosomal replication, e.g. a plasmid. Alternatively, the vector may be one which, when introduced into a host cell, particularly into a mammalian host cell, is integrated into the host cell genome and replicated together with the chromosome(s) into which it has been integrated. Preferably, the "nucleic acid expression vector" may be an expression vector which is usually applied in gene therapeutic methods in humans, particularly a retroviral vector or an adenoviral vector.

The coding sequence of interest may, if necessary, be operably linked to a suitable terminator or to a polyadenylation sequence. In the case of RNA, particularly siRNA, "coding sequence" refers to the sequence encoding or corresponding to the relevant RNA strand or RNA strands.

Further, the vector may comprise a DNA sequence enabling the vector to replicate in the mammalian host cell. Examples of such a sequence—particularly when the host cell is a mammalian cell—is the SV40 origin of replication.

A number of vectors suitable for expression in mammalian cells are known in the art and several of them are commercially available. Some commercially available mammalian expression vectors which may be suitable include, but are not limited to, pMC1neo (Stratagene), pXT1 (Stratagene), pSG5 (Stratagene), pcDNAI (ivitrogen), EBO-pSV2-neo (ATCC 37593), pBPV-1(8-2) (ATCC 37110), pSV2-dhfr (ATCC 37146). Preferred are all suitable gene therapeutic vectors known in the art.

In a particularly preferred embodiment of the invention the vector is a retroviral vector. Retroviruses are RNA-viruses possessing a genome that after the infection of a cell, such as a human cell, is reversely transcribed in DNA and subsequently is integrated into the genome of the host cell. Retroviruses enter their host cell by receptor-mediated endocytosis. After the endocytosis into the cell the expression of the retroviral vector may be silenced to ensure that only a single cell is infected. The integration of the viral DNA into the genome is mediated by a virus-encoded protein called integrase, wherein the integration locus is not defined. Retroviral vectors are particularly appropriate for their use in gene therapeutic methods, since their transfer by receptor-mediated endocytosis into the host cell, also known to those skilled in the art as "retroviral transduction" is particularly efficient. A person skilled in the art also knows how to introduce such retroviral vectors into the host cell using so called "packaging cells".

In another particularly preferred embodiment of the invention, the vector is an adenoviral vector or a derivative thereof. Adenoviral vectors comprise both replication-capable and and replication-deficient vectors. The latter include vectors deficient in the E1 gene.

The recombinant vector is preferably introduced into the mammalian host cells by a suitable pharmaceutical carrier that allows transformation or transfection of the mammalian, in particular human cells. Preferred transformation/transfection techniques include, but are not limited to liposome-mediated transfection, virus-mediated transfection and calcium phosphate transfection.

In a preferred embodiment, the invention relates to the use of a vector system capable of producing siRNAs as defined above, wherein the nucleic acid corresponding to the siRNA is contained in at least one nucleic acid expression vector comprising a first expression cassette containing the nucleic acid corresponding to the sense-RNA-strand under the control of a first promoter and a second expression cassette containing the nucleic acid corresponding to the antisense-RNA-strand under the control of a second promoter.

In the above mentioned vector system, the vector comprises two individual promoters, wherein the first promoter controls the transcription of the sense-strand and the second promoter controls the transcription of the antisense strand (also described in Tuschl, Nature Biotechnology, Vol. 20, pp.

446-448). Finally the siRNA duplex is constituted by the hybridisation of the first and the second RNA-strand.

The term "expression cassette" is defined herein to include all components which are necessary or advantageous for the expression of a specific target polypeptide. An "expression cassette" may include, but is not limited to, the nucleic acid sequence of interest itself (e.g. encoding or corresponding to the siRNA or polypeptide of interest) and "control sequences". These "control sequences" may include, but are not limited to, a promoter that is operatively linked to the nucleic acid sequence of interest, a ribosome binding site, translation initiation and termination signals and, optionally, a repressor gene or various activator genes. Control sequences are referred to as "homologous", if they are naturally linked to the nucleic acid sequence of interest and referred to as "heterologous" if this is not the case. The term "operably linked" indicates that the sequences are arranged so that they function in concert for their intended purpose, i.e. expression of the desired protein, or, in case of RNA, transcription of the desired RNA.

The promoter used in the aforementioned "expression cassettes" may be any DNA sequence which shows transcriptional activity in a host cell of choice, preferably in a mammalian host cell, particularly in a human host cell. The promoter may be derived from genes encoding proteins either homologous or heterologous to the host cell.

As a promoter in general every promoter known in the prior art can be used that allows the expression of the gene of interest under appropriate conditions in a mammalian host cell, in particular in a human host cell. Particularly promoters derived from RNA polymerase III transcription units, which normally encode the small nuclear RNAs (snRNAs) U6 or the human RNAse P RNA H1, can be used as promoters to express the therapeutic siRNAs. These particularly preferred promoters U6 and H1 RNA which are members of the type III class of Polymerase III promoters are—with the exception of the first transcribed nucleotide (+1 position)—only located upstream of the transcribed region.

In a preferred embodiment, the invention relates to the use of a vector system capable of producing siRNAs for the above identified nucleic acid sequences, wherein the sequence is contained in at least one nucleic acid expression vector comprising an expression cassette containing the sequence of the sense-RNA-strand and of the antisense-RNA-strand under the control of a promoter leading to a single-stranded RNA-molecule and wherein the single-stranded RNA-molecule is capable of forming a back-folded stem-loop-structure.

In this vector system (also described in Tuschl, Nature Biotechnology, Vol. 20, pp. 446-448), only a single RNA-strand is produced under the control of a single promoter, wherein the RNA strand comprises both the sense- and of the antisense-strand of the final double-stranded siRNA molecule. This structure leads to a back-folding of the RNA-strand by hybridisation of the complementary sense- and antisense-sequences under stem-loop formation. Finally the intracellular processing of this fold-back stem-loop-structure gives rise to siRNA.

In another preferred embodiment according to the present invention, the "nucleic acid expression vector" comprises an expression cassette containing the sequence of the sense-RNA-strand and of the antisense-RNA-strand both under the control of a single promoter leading to a single-stranded RNA-molecule. This single-stranded RNA-molecule is hereby capable to form a back-folded stem-loop-structure. These expressed "hairpin RNA-molecules" subsequently give rise to siRNAs after intracellular processing.

In a preferred embodiment of the invention the nucleic acid expression vector that gives rise to the expression of siRNAs according to the present invention is first introduced into therapeutic, non-toxic virus particles or virus-derived particles that are suitable for gene therapeutic applications and that can infect mammalian, in particular human target cells, such as packaging cells etc.

In a preferred embodiment, the first and the second RNA strand of the siRNA may have, independently from the other, a length of 19 to 25 nucleotides, more preferred of 20 to 25 nucleotides, and most preferred of 20 to 22 nucleotides.

In another preferred embodiment, the first and the second RNA strand of the siRNA may have, independently from the other, a length of 26 to 30 nucleotides, more preferred of 26 to 28 nucleotides, and most preferred of 27 nucleotides.

The present invention also relates to the use of and/or methods involving proteins, polypeptides and peptides encoded by the above defined sequences.

In another aspect, the invention relates to the use of isolated proteins or polypeptides comprising a sequence of the group selected of:

(a) a sequence as disclosed in SEQ ID NO. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60;

(b) a sequence that exhibits a sequence identity with any of the sequences according to (a) of at least 25% over 100 residues, (c) or fragments of the sequences defined in (a) or (b), for the manufacture of a medicament for the inhibition of spindle formation or microtubule function during cell division.

Proteins, polypeptides and peptides can be introduced into the cells by various methods known in the art. For example, amphiphilic molecules may be membrane permeable and can enter cells directly. Membrane-bound proteins or polypeptides (usually lipophilic molecules or containing transmembrane domains) may insert directly into cell membranes and can thus exert their biological function. Other ways of introduction or intracellular uptake include microinjection, lipofection, receptor-mediated endocytosis, or the use of suitable carrier-molecules particularly carrier-peptides. Suitable carrier-peptides include or can be derived from HIV-tat, antennapedia-related peptides (penetratins), galparan (transportan), polyarginine-containing peptides or polypeptides, Pep-1, herpes simplex virus VP-22 protein. Another possible introduction method is to introduce nucleic acid vectors capable of expressing such proteins, polypeptides or peptides Suitable methods to produce isolated polypeptides are known in the art. For example, such a method may comprise transferring the expression vector with an operably linked nucleic acid molecule encoding the polypeptide into a suitable host cell, cultivating said host cells under conditions which will permit the expression of said polypeptide or fragment thereof and, optionally, secretion of the expressed polypeptide into the culture medium. Depending on the cell-type different desired modifications, e.g. glycosylation, can be achieved.

The proteins, polypeptides and peptides may also be produced synthetically, e.g. by solid phase synthesis (Merrifield synthesis).

The polypeptides used in the invention may also include fusion polypeptides. In such fusion polypeptides another polypeptide may be fused at the N-terminus or the C-terminus of the polypeptide of interest or fragment thereof A fusion polypeptide is produced by fusing a nucleic acid sequence (or a portion thereof) encoding another polypeptide to a nucleic acid sequence (or a portion thereof) of the present invention.

Techniques for producing fusion polypeptides are known in the art and include ligating the coding sequences so that they are in frame and the expression of the fusion polypeptide is under control of the same promotor(s) and terminator.

Expression of the polypeptides of interest may also be performed using in vitro produced synthetic mRNA. Synthetic mRNA can be efficiently translated in various cell-free systems, including but not limited to, wheat germ extracts and reticulocyte extracts, as well as efficiently translated in cell based systems including, but not limited to, microinjection into frog oocytes, preferably Xenopus laevis oocytes.

Inhibition of spindle formation or microtubule function during cell division using said isolated proteins or polypeptides can be achieved by different ways familiar to the person skilled in the art: Overexpression of the protein or polypeptide may lead to suppression of the endogenous protein's biological function. By introducing deletions or other mutations, or by using suitable fragments, it is possible to generate sequences encoding dominant-negative peptides or polypeptides. Such dominant-negative peptides or polypeptides can inhibit the function of the corresponding endogenous protein. For example, fragments or mutants can be generated which consist only of binding domains but are enzymatically inactive (i.e. partially lacking their biological function). Such dominant-negative molecules may interfere with the biological function of the endogenous proteins or polypeptides by binding to intracellular binding partners and thus blocking activation of the endogenous molecule.

In another aspect, the invention relates to the use of an antibody which is directed against at least one polypeptide comprising a sequence as defined above for the manufacture of a medicament for the inhibition of spindle formation or microtubule function during cell division.

The term "antibody" as used herein includes both polyclonal and monoclonal antibodies, as well as fragments thereof, such as Fv, Fab and F(ab)$_2$ fragments that are capable of binding antigen or hapten. The present invention also contemplates "humanized" hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art.

Specifically, said antibodies or suitable fragments thereof, particularly in humanized form, may be used as therapeutic agents in a method for treating cancer and other proliferative diseases.

The use of said antibodies may also include the therapeutical inhibition of the above identified nucleic acid molecules or their corresponding polypeptides. In particular, this use may be directed to a proliferative disease.

The antibodies or fragments may be introduced into the body by any method known in the art Delivery of antibodies, particularly of fragments, into live cells may be performed as described for peptides, polypeptides and proteins. If the antigen is extracellular or an extracellular domain, the antibody may exert its function by binding to this domain, without need for intracellular delivery.

Antibodies can be coupled covalently to a detectable label, such as a radiolabel, enzyme label, luminescent label, fluorescent label or the like, using linker technology established for this purpose. Labeling is particularly useful for diagnostic purposes (see below) or for monitoring the distribution of the antibody within the body or a neoplastic tumor, e.g. by computed tomography, PET (positron emission tomography), or SPECT (single photon emission computed tomography).

In another embodiment, the invention relates to the use of nucleic acid molecules, peptides, polypeptides, proteins, or antibodies, as defined above, for the manufacture of a medicament for the treatment or therapy of a proliferative disease.

In a preferred embodiment, the disease is coronary restenosis or a neoplastic disease, the latter preferably selected from the group consisting of lymphoma, lung cancer, colon cancer, ovarian cancer and breast cancer (see above).

"Proliferative diseases" according to the present invention are diseases associated with excessive cell division or proliferation as for example cancer. Preferably, the proliferative disease is restenosis, particularly coronary restenois, or a neoplastic disease, the latter preferably selected from the group consisting of lymphoma, lung cancer, colon cancer, ovarian cancer and breast cancer.

Restenosis is a re-narrowing of a blood vessel due to growth of tissue at the site of angioplasty or stent implantation. Stents are tiny metal tubes to hold the previously blocked arteries open. However, restenosis still develops in many patients with implanted stents, thus necessitating second angioplasty, stent implantation or even coronary bypass surgery.

Neoplastic diseases are diseases caused by newly forming tissue or cells. In the context of the present invention, the most relevant neoplastic diseases are neoplastic tumors, particularly selected from the group consisting of lymphoma, lung cancer, colon cancer, ovarian cancer and breast cancer.

In another aspect, the invention relates to the use of an isolated nucleic acid molecule comprising a nucleic acid with a sequence selected from the group of sequences consisting of:
  a) the nucleic acid sequences presented in SEQ ID NO. 1, 3, 5, 7, 9, 11, 13, 15, 17, 19, 21, 23, 25, 27, 29, 31, 33, 35, 37, 39, 41, 43, 45, 47, 49, 51, 53, 55, 57, 59;
  b) nucleic acid sequences encoding polypeptides that exhibit a sequence identity with the protein encoded by a nucleic acid according to a) of at least 25% over 100 residues and/or which are detectable in a computer aided search using the BLAST sequence analysis programs with an e-value of at most $10^{-5}$,
  c) sequences of nucleic acid molecules which are capable of hybridizing with the nucleic acid molecules with sequences corresponding to (a) or (b) under conditions of medium or high stringency,
  d) the antisense-sequence of any of the sequences as defined in (a), (b) or (c),
  e) fragments of (a), (b), (c) or (d),
  f) RNA sequences corresponding to any of the sequences as defined in (a), (b), (c), (d), or (e), for the manufacture of a medicament for the activation of spindle formation or microtubule function during cell division.

In another aspect, the invention relates to the use of a an isolated peptide or polypeptide comprising a peptide or polypeptide with a sequence selected from the group consisting of:
  (a) a sequence as disclosed in SEQ ID NO. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60;
  (b) a sequence that exhibits a sequence identity with any of the sequences according to (a) of at least 25% over 100 residues,
  (c) fragments of the sequences defined in (a) or (b), for the manufacture of a medicament for the activation of spindle formation or microtubule function during cell division.

In another aspect, the invention relates to the use of an antibody which is directed against at least one peptide or polypeptide with a sequence as defined above for the manufacture of a medicament for the activation of spindle formation or microtubule function during cell division.

Thus, another use or method involving the above identified nucleic acid sequences, peptides, polypeptides, proteins, and antibodies is directed towards the treatment of a disease in which spindle formation or microtubule function during cell division, is abnormal, deficient or negatively affected.

Diseases with abnormal, deficient or negatively affected spindle formation or microtubule function during cell division may be characterized by increased apoptosis and developmental disorders, in particular growth retardation, or slowed wound healing.

Therefore, a preferred embodiment of the present invention relates to a use or method of the treatment of a disease, wherein the disease is characterized by increased apoptosis, growth retardation, or slowed wound healing.

"Activation of spindle formation or microtubule function during cell division" includes both initiation and stimulation of spindle formation or microtubule function during cell division.

The use may include, but is not limited to, the use of said nucleic acid molecules and their corresponding polypeptides for direct or indirect activation of the expression of said target genes and/or for activation of the function of said target genes. In particular, the use may include the replacement for or the complementation of a lack of function or activity of an endogenous gene involved in spindle formation or microtubule function during cell division.

Expression of RNA or polypeptides may be achieved by introduction of genomic DNA or cDNA containing suitable promoters, preferably constitutive or homologous promoters. Alternatively, any suitable nucleic acid expression vector can be used (see also above). The encoded protein or polypeptide may be fill-length or a fragment or peptide with a similar biological function in spindle formation or microtubule function during cell division, particularly with the capability to activate spindle formation or microtubule function during cell division.

All gene therapy techniques known in the art can be used to introduce the sequences into cells or tissues of a subject suffering from a disease negatively affecting spindle formation or microtubule function during cell division. Particularly useful for introduction of the above identified sequences are viral vectors, e.g. retroviral or adenoviral vectors, lipofection and electroporation.

The proteins, polypeptides or peptides may also be generated by any known in vivo or in vitro method and introduced directly into the cells (see above).

It is known that suitable antibodies can be used to activate the biological function of target proteins they bind to. Activation may occur by inducing conformational changes upon binding to the target protein. Another possibility is that the antibody binds two or more target proteins and brings them into sufficiently close physical proximity to induce interaction of the target proteins. The latter mode of activation is particularly known for membrane-bound dimeric receptors.

With respect to the specific embodiments relating to the used nucleic acids, peptides, polypeptides, proteins, and antibodies the same applies as defined above for the other uses of the invention.

In another embodiment, the invention relates to a medicament containing an isolated nucleic acid molecule, peptide, polypeptide, or antibody selected from the group consisting of
 a) nucleic acid molecules or nucleic acid expression vectors as defined above,
 b) a peptide or polypeptide comprising a sequence as defined above,
 c) an antibody directed against at least one peptide or polypeptide according to (b).

Preferably this isolated nucleic acid molecule is an RNA molecule and preferably is double-stranded. Particularly the isolated nucleic acid molecule is an siRNA molecule according to the present invention.

The medicaments may be used or applied in methods for the therapy of any kind of proliferative disease, such as cancer, preferably for the therapy of diseases in which spindle formation or microtubule function during cell division play a role, particularly for the therapy of a lymphoma, lung cancer, colon cancer, ovarian cancer or breast cancer.

The medicaments may also be used or applied in methods for the therapy of any kind of disease associated with abnormal or deficient spindle formation or microtubule function during cell division, particularly diseases characterized by increased apoptosis, developmental disorders or abnormalities particularly growth retardation) and slowed wound healing.

The following considerations for medicaments and their administration apply also to the medicaments of the invention as to the above disclosed uses.

The medicament preferably comprises additionally a suitable pharmaceutically acceptable carrier, preferably virus-particles or virus-derived particles that may harbour the viral vectors, transfection solutions comprising liposomes, particularly cationic liposomes, calcium phosphate etc. Preferably a carrier is used, which is capable of increasing the efficacy of the expression vector or virus particles containing the expression vector to enter the mammalian target cells. The medicament may additionally comprise other carrier substances, preferably starch, lactose, fats, stearin acid, alcohol, physiological NaCl-solutions or further additives, in particular stabilizers, preservatives, dyes and flavourings.

The medicaments may also comprise other suitable substances. For example, RNA or siRNA containing medicaments may contain substances which stabilize double-stranded RNA molecule and/or which enable the double-stranded RNA molecule or DNA expression vector to be transfected or to be injected into the human or animal cell.

Administration can be carried out by known methods, wherein a nucleic acid is introduced into a desired cell in vitro or in vivo. For therapeutic applications, the medicament may be in form of a solution, in particular an injectable solution, a cream, ointment, tablet, suspension, granulate or the like. The medicament may be administered in any suitable way, in particular by injection, by oral, nasal, rectal application. The medicament may particularly be administered parenteral, that means without entering the digestion apparatus, for example by subcutaneous injection. The medicament may also be injected intravenously in the form of solutions for infusions or injections. Other suitable administration forms may be direct administrations on the skin in the form of creams, ointments, sprays and other transdermal therapeutic substances or in the form of inhalative substances, such as nose sprays, aerosoles or in the form of microcapsules or implantates.

The optimal administration form and/or administration dosis for a medicament either comprising double-stranded RNA molecules with the above sequences or comprising nucleic acid vectors capable to express such double-stranded RNA molecules depend on the type and the progression of the disease to be treated.

Preferably, the activator or inhibitor is administered in pharmaceutically effective amount. As used herein, a "pharmaceutically effective amount" of an activator or inhibitor is an amount effective to achieve the desired physiological result, either in cells treated in vitro or in a subject treated in vivo. Specifically, a pharmaceutically effective amount is an amount sufficient to positively influence, for some period of time, one or more clinically defined pathological effects associated with proliferative diseases or diseases associated with abnormal, deficient or negatively affected spindle formation or microtubule function during cell division. The pharmaceutically effective amount may vary depending on the specific activator or inhibitor selected, and is also dependent on a variety of factors and conditions related to the subject to be treated and the severity of the disease. For example, if the activator or inhibitor is to be administered in vivo, factors such as age, weight, sex, and general health of the patient as well as dose response curves and toxicity data obtained in pre-clinical animal tests would be among the factors to be considered. If the activator or inhibitor is to be contacted with cells in vitro, one would also design a variety of pre-clinical in vitro studies to assess parameters like uptake, half-life, dose, toxicity etc. The determination of a pharmaceutically effective amount for a given agent (activator or inhibitor) is well within the ability of those skilled in the art. Preferably, the activator or inhibitor is present in a concentration of 0.1 to 50% per weight of the pharmaceutical composition, more preferably 10 to 30%.

An inhibitor, activator, or drug according to the present invention may also be a "small molecule". Small molecules are molecules which are not proteins, peptides antibodies or nucleic acids, and which exhibit a molecular weight of less than 5000 Da, preferably less than 2000 Da, more preferably less than 2000 Da, most preferably less than 500 Da Such small molecules may be identified in high throughput procedures/screening assays starting from libraries. Such methods are known in the art Suitable small molecules can also be designed or further modified by methods known as combinatorial chemistry.

The genes/proteins that are provided by the current application and that possess one of the sequences as defined in (a) to (f), can be used in a high-throughput or other screen for new agents that inhibit or activate spindle formation or microtubule function during cell division. Particularly inhibitors of spindle formation or microtubule function during cell division identified by such a screen may be used as medicaments for the therapy of proliferative diseases, particularly for the therapy of a disease in which spindle formation or microtubule function during cell division play a role.

In another aspect, the present invention relates to the use of an isolated nucleic acid molecule comprising a sequence as defined above or the use of a ligand binding specifically at least one polypeptide comprising a sequence as defined above for the in vitro diagnosis of a proliferative disease or a disease associated with abnormal spindle formation or microtubule function during cell division.

In a preferred embodiment, diagnosis relates to proliferative diseases as defined above.

In another preferred embodiment, diagnosis relates to diseases associated with abnormal, deficient or negatively affected spindle formation or microtubule function during cell division, as they are described above. Diseases with "abnormal" spindle formation or microtubule function during cell division include diseases in which spindle formation or microtubule function during cell division is deficient or negatively affected.

In a proliferative disease, expression of endogenous genes corresponding to the above identified sequences may be increased.

In a disease in which spindle formation or microtubule function during cell division are abnormal, deficient or negatively affected, expression of the corresponding endogenous genes may be lowered. Furthermore, the corresponding endogenous gene may be mutated, rendering the corresponding protein less active or non-functional.

The diagnostic use of the above identified nucleic acid molecules and probes may include, but is not limited to the quantitative detection of expression of said target genes in biological probes (preferably, but not limited to tissue samples, cell extracts, body fluids, etc.), particularly by quantitative hybridization to the endogenous nucleic acid molecules comprising the above-characterized nucleic acid sequences particularly cDNA, RNA)

Expression of the endogenous genes or their corresponding proteins can be analyzed in vitro in tissue samples, body fluids, and tissue and cell extracts. Expression analyis can be performed by any method known in the art, such as RNA in situ hybridization, PCR (including quantitative RT-PCR), and various serological or immunological assays which include, but are not limited to, precipitation, passive agglutination, enzyme-linked immunosorbent antibody (ELISA) technique and radioimmunoassay techniques.

The diagnostic use may also include the detection of mutations in endogenous genes corresponding to the above identified nucleic acid sequences.

Suitable nucleic acid probes may be synthesized by use of DNA synthesizers according to standard procedures or, preferably for long sequences, by use of PCR technology with a selected template sequence and selected primers. The probes may be labeled with any suitable label known to those skilled in the art, including radioactive and non-radioactive labels. Typical radioactive labels include $^{32}$P, $^{125}$I, $^{35}$S, or the like. A probe labeled with a radioactive isotope can be constructed from a DNA template by a conventional nick lo translation reaction using a DNase and DNA polymerase. Non-radioactive labels include, for example, ligands such as biotin or thyroxin, or various luminescent or fluorescent compounds. The probe may also be labeled at both ends with different types of labels, for example with an isotopic label at one end and a biotin label at the other end. The labeled probe and sample can then be combined in a hybridization buffer solution and held at an appropriate temperature until annealing occurs. Such nucleic acid probes may also be used for other than diagnostic purposes, e.g. for the identification of further homologs or orthologs.

"Ligands" binding specifically to said polypeptides are known in the art. Such ligands include proteins or polypeptides, for example intracellular binding partners, antibodies, molecular affinity bodies, and small molecules. Specifically binding ligands can be identified by standard screening assays known in the art (see also below), for example by yeast two-hybrid screens and affinity chromatography. A specifically binding ligand does not need to exert another function such as inhibiting or activating the molecule with which it interacts.

In a preferred embodiment, the ligand is an antibody binding specifically at least one polypeptide comprising a sequence as defined above.

"Specific binding" according to the present invention means that the polypeptide to be identified (the target polypeptide) is bound with higher affinity than any other polypeptides present in the sample. Preferred is at least 3 times higher affinity, more preferred at least 10 times higher affinity, and most preferred at least 50 times higher affinity. Non-specific binding ("cross-reactivity") may be tolerable if the target polypeptide can be identified unequivocally, e.g. by its size on a Western blot.

Preferably the specifically binding ligands can be labeled, e.g. with fluorescent labels, enzymes, molecular tags (e.g. GST, myc-tag or the like), radioactive isotopes, or with labeled substances, e.g. labeled secondary antibodies. For MRI (magnetic resonance imaging), the ligands may be chelated with gadolinium, superparamagnetic iron oxide or lanthanides. For PET (positron emission tomography) or SPECT (single photon emission computed tomography) commonly used isotopes include $^{11}C$, $^{18}F$, $^{15}O$, $^{13}N$, $^{86}Y$, $^{90}Y$, and $^{16}Co$.

In another aspect, the present invention relates to a diagnostic kit containing an isolated nucleic acid molecule as defined above and/or a ligand which is directed against at least one polypeptide as defined above for the in vitro diagnosis of a proliferative disease or a disease associated with abnormal spindle formation or microtubule function during cell division.

Diagnostic kits may comprise suitable isolated nucleic acid or amino acid sequences of the above identified genes or gene products, labelled or unlabelled, and/or specifically binding ligands (e.g. antibodies) thereto and auxiliary reagents as appropriate and known in the art. The assays may be liquid phase assays as well as solid phase assays (i.e. with one or more reagents immobilized on a support). The diagnostic kits may also include ligands directed towards other molecules indicative of the disease to be diagnosed.

In another aspect, the invention relates to the use of an isolated nucleic acid molecule or a nucleic acid expression vectors as defined above or of an antibody which is directed against at least one polypeptide comprising a sequence as defined above, in a screening assay for the identification and characterization of drugs that inhibit or activate spindle formation or microtubule function during cell division.

In another aspect, the invention relates to the use of a peptide, polypeptide or protein with a sequence as defined above in a screening assay for interacting drugs, that inhibit or activate spindle formation or microtubule function during cell division. Such interacting molecules may also be used as ligands for diagnosis as described above.

"Screening assay" according to the present invention relates to assays which allow to identify substances, particularly potential drugs, that inhibit or activate spindle formation or microtubule function during cell division, by screening libraries of substances. "Screening assay" according to the present invention also relates to assays to screen libraries for substances capable of binding to the nucleic acids, polypeptides, peptides or antibodies defined above. Suitable libraries may, for example, include small molecules, peptides, polypeptides or antibodies.

The invention relates to assays for identification as well as to assays for characterization of substances that inhibit or activate spindle formation or microtubule function during cell division or that bind to said nucleic acids, polypeptides, peptides or antibodies. Particularly, the invention relates to screening assays for drugs. Such drugs may be identified and characterized from libraries of unspecified compounds as well as libraries of drugs which are already known for treatment of other diseases. For such known drugs also potential side-effects and therapeutically applicable doses are known.

Suitable drugs include "interacting drugs", i.e. drugs that bind to the polypeptides or nucleic acids identified above. Such interacting drugs may either inhibit or activate the molecule they are bound to. Examples for interacting substances are peptide nucleic acids comprising sequences identified above, antisense RNAs, siRNAs, ribozymes, aptamers, antibodies and molecular affinity bodies (CatchMabs, Netherlands). Such drugs may be used according to any aspect of the present invention, including use for the manufacture of medicaments and methods of treatment of proliferative diseases. It is known that such interacting drugs can also be labeled and used as ligands for diagnosis of a disease associated with spindle formation or microtubule function during cell division.

Suitable screening assays are known in the art. For example, in a preferred embodiment of the invention the screening method for the identification and characterization of an inhibitor or an activator molecule that inhibits or activates spindle formation or microtubule function during cell division comprises the following steps:

a) transformation of a nucleic acid molecule or a nucleic acid expression vector as defined above into a host cell or host organism, b) cultivation of the host cell or host organism obtained in step a) under conditions that allow the overexpression of the polypeptide or RNA encoded by or corresponding to the nucleic acid of step (a) either in the presence or in the absence of at least one candidate for an inhibitor- or activator-molecule, and c) analysis of the spindle formation or microtubule function during cell division in the cultivated cell or organism and thereby identification of an inhibitor or activator of spindle formation or microtubule function during cell division.

The term "expression vector" as used herein does not only relate to RNA or siRNA expressing vectors, but also to vectors expressing peptides, polypeptides or proteins.

The transfer of the expression vector into the host cell or host organism hereby may be performed by all known transformation or transfection techniques, including, but not limited to calcium phosphate transformation, lipofection, microinjection. Host cell/host organisms may be all suitable cells or organisms that allow detection of impaired cell division, preferably of impaired spindle formation or microtubule function during cell division. A particularly preferred host organism is *C. elegans*, since its translucent body allows an easy detection of failures during cell division, including spindle formation or microtubule function during cell division. Vertebrate cells, preferably mammalian, more preferably human cells, in particular human cell lines are also preferred host cells. The expression vector may be any known vector that is suitable to allow the expression of the nucleic acid sequence as defined above. Preferred expression vectors possess expression cassettes comprising a promoter that allows an overexpression of the RNA, peptide or polypeptide as defined above.

After the transfer of the expression vector into the host cell/host organism one part of the host cells or host organisms are cultured in the presence of at least one candidate of an inhibitor- or activator-molecule and under culture conditions that allow the expression, preferably the overexpression of the RNA, peptide or polypeptide as defined above. The other part of the transfected host cells are cultured under the same culture conditions, but in the absence of the candidate of an inhibitor- or activator-molecule.

Finally, after an appropriate incubation time/culture period the proliferation state and/or cell divisions for host cells or host organisms that had been cultured in the presence or in the absence of the at least one candidate for an inhibitor or an activator molecule are detected or preferably quantified. This detection or quantification step is preferably done by time lapse fluorescence or DIC microscopy, particularly in those cases when the host organism is *C. elegans* or another mostly translucent organism that is available to be lo analysed by time lapse fluorescence or DIC microscopy. The detection/ quantification step may also be done by any other technique known to the state of the art that is suitable to analyse the proliferation state or the extent of cell division, preferably all kinds of microscopic techniques.

In another preferred embodiment, the screening method for the identification and characterization of an interacting molecule that inhibits or activates spindle formation or microtubule function during cell division from a library of test substances comprises the following steps:

a) recombinantly expressing a polypeptide encoded by a nucleic acid molecule sequence as defined above in a host cell,
 b) isolating and optionally purifying the recombinantly expressed polypeptide of step (a),
 c) optionally labelling of the test substances and/or labelling of the recombinantly expressed polypeptide,
 d) immobilizing the recombinantly expressed polypeptide to a solid phase,
 e) contacting of at least one test substance with the immobilized polypeptide,
 f) optionally one or more washing steps,
 g) detecting the binding of the at least one test substance to the immobilized polypeptid at the solid phase, and
 h) performing a functional assay for inhibition or activation of spindle formation or microtubule function during cell division.

Step a) includes the recombinant expression of the above identified polypeptide or of its derivative from a suitable expression system, in particular from cell-free translation, bacterial expression, or baculuvirus-based expression in insect cells.

Step b) comprises the isolation and optionally the subsequent purification of said recombinantly expressed polypeptides with appropriate biochemical techniques that are familiar to a person skilled in the art.

Alternatively, these screening assays may also include the expression of derivatives of the above identified polypeptides which comprises the expression of said polypeptides as a fusion protein or as a modified protein, in particular as a protein bearing a "tag"-sequence. These "tag"-sequences consist of short nucleotide sequences that are ligated 'in frame' either to the N- or to the C-terminal end of the coding region of said target gene. Commonly used tags to label recombinantly expressed genes are the poly-Histidine-tag which encodes a homopolypeptide consisting merely of histidines, particularly six or more histidines, GST (glutathion S-transferase), c-myc, FLAG®, MBP (maltose binding protein), and GFP. In this context the term "polypeptide" does not merely comprise polypeptides with the nucleic acid sequences of SEQ ID No. 1 to 59, their naturally occuring homologs, preferably orthologs, more preferably human orthologs, but also derivatives of these polypeptides, in particular fusion proteins or polypeptides comprising a tag-sequence.

These polypeptides, particularly those labelled by an appropriate tag-sequence (for instance a His-tag or GST-tag), may be purified by standard affinity chromatography protocols, in particular by using chromatography resins linked to anti-His-tag-antibodies or to anti-GST-antibodies which are both commercially available. Alternatively, His-tagged molecules may be purified by metal chelate affinity chromatography using Ni-ions. Alternatively to the use of 'label-specific' antibodies the purification may also involve the use of antibodies against said polypeptides. Screening assays that involve a purification step of the recombinantly expressed target genes as described above (step 2) are preferred embodiments of this aspect of the invention.

In an—optional—step c) the compounds tested for interaction may be labelled by incorporation of radioactive isotopes or by reaction with luminescent or fluorescent compounds. Alternatively or additionally also the recombinantly expressed polypeptide may be labelled.

In step d) the recombinantly expressed polypeptide is immobilized to a solid phase, particularly (but not limited) to a chromatography resin. The coupling to the solid phase is thereby preferably established by the generation of covalent bonds.

In step e) a candidate chemical compound that might be a potential interaction partner of the said recombinant polypeptide or a complex variety thereof particularly a drug library) is brought into contact with the immobilized polypeptide.

In an—optional—step f) one or several washing steps may be performed. As a result just compounds that strongly interact with the immobilized polypeptide remain bound to the solid (immobilized) phase.

In step g) the interaction between the polypeptide and the specific compound is detected, in particular by monitoring the amount of label remaining associated with the solid phase over background levels.

Such interacting molecules may be used without functional characterization for diagnostic purposes as described above.

In step h) the interacting molecule is further analyzed for inhibition or activation of spindle formation or microtubule function during cell division. Such analysis or functional assay can be performed according to any assay system known in the art. A suitable assay may include the cultivation of a host cell or host organism in the presence (test condition) or absence (control condition) of the interacting molecule, and comparison of spindle formation or microtubule function during cell division under test and control conditions.

In another aspect, the invention relates to a method for the preparation of a pharmaceutical composition wherein an inhibitor or activator of spindle formation or microtubule function during cell division is identified according to any of the screening methods described above, synthesized in adequate amounts and formulated into a pharmaceutical composition.

Suitable methods to synthesize said inhibitor or activator molecules are known in the art. For example, peptides or polypeptides can be synthesized by recombinant expression (see also above), antibodies can be obtained from hybridoma cell lines or immunized animals. Small molecules can be synthesized according to any known organic synthesis methods.

Adequate amounts relate to pharmaceutically effective amounts.

Similarly, the inhibitor or activator may be provided by any of the screening methods described above and formulated into a pharmaceutical composition.

BRIEF DESCRIPTION OF THE DRAWINGS

FIG. 1 shows DIC microscopy images taken from time-lapse recording of the first round of cell division in *C. elegans* F1 progeny from F0 an parent treated with dsRNA (RNAi) directed against C13F10.2.

FIG. 2 shows an amino acid sequence alignment of C13F10.2 (SEQ ID NO. 2) and the corresponding *Drosophila* and human ortholog: NP_076974 (SEQ ID NO. 4) and AAF499110 (SEQ ID NO. 6).

FIG. 3 shows DIC microscopy images taken from time-lapse recording of the first round of cell division in *C. elegans* F1 progeny from F0 a parent treated with dsRNA (RNAi) directed against C25A1.9.

FIG. 4 shows an amino acid sequence alignment of C25A1.9 (SEQ ID NO. 8) and the corresponding human ortholog NP_060387 (SEQ ID NO. 10).

FIG. 5 shows DIC microscopy images taken from time-lapse recording of the first round of cell division in *C. elegans* F1 progeny from F0 a parent treated with dsRNA (RNAi) directed against F54B3.3.

FIG. 6 shows an amino acid sequence alignment of F54B3.3 (SEQ ID NO. 12) and its corresponding *Drosophila* and human orthologs and mouse homolog: NP_060658 (SEQ ID NO. 14), AAF55289 (SEQ ID NO. 20), XP_109399 (SEQ ID NO. 16), P46462 (SEQ ID NO. 18) and NP_015349 (SEQ ID NO. 22).

Figure 7:
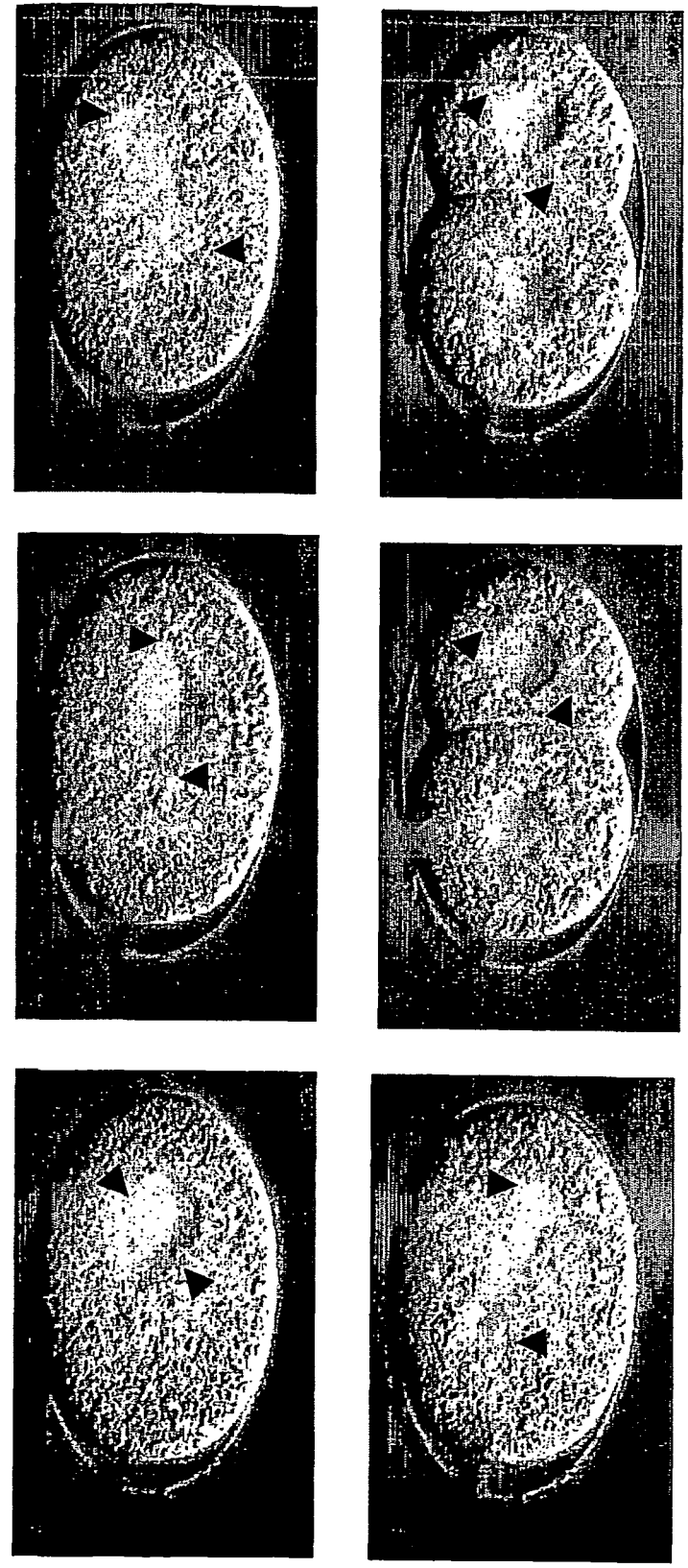

FIG. 7 shows DIC microscopy images taken from time-lapse recording of the first round of cell division in *C. elegans* F1 progeny from F0 a parent treated with dsRNA (RNAi) directed against F08B6.2.

FIG. 8 shows an amino acid sequence alignment of F08B6.2 (SEQ ID NO. 24) and its corresponding *Drosophila* and human orthologs: NP_057625 (SEQ ID NO 26), AAF52761 (SEQ ID NO. 30) and AAA73553 (SEQ ID NO. 28).

FIG. 9 shows DIC microscopy images taken from time-lapse recording of the first round of cell division in *C. elegans* F1 progeny from F0 a parent treated with dsRNA (RNAI) directed against CD4.4.

FIG. 10 shows an amino acid sequence alignment of CD4.4 (SEQ ID NO. 32) and its corresponding *Drosophila* and human orthologs: NP_078943 (SEQ ID NO. 34), CAD38936 (SEQ ID NO. 36) and AAF52060 (SEQ ID NO. 38).

FIG. 11 shows DIC microscopy images taken from time-lapse recording of the first two rounds of cell division in *C. elegans* F1 progeny from F0 a parent treated with dsRNA (RNAi) directed against ZK546.1.

FIG. 12 shows an amino acid sequence alignment of ZK546.1, (SEQ ID NO. 40), its corresponding human ortholog and its *Drosophila* and mouse homologs: NP_056972 (SEQ ID NO. 42), AAA74950 (SEQ ID NO. 91), NP_010225 (SEQ ID NO. 50), AAF53605 (SEQ ID NO. 48) and XP_109474 (SEQ ID NO. 46).

FIG. 13 shows DIC microscopy images taken from time-lapse recording of the first two rounds of cell division in *C. elegans* F1 progeny from F0 a parent treated with dsRNA (RNAi) directed against C56C10.3.

FIG. 14 shows an amino acid sequence alignment of C56C10.3 (SEQ ID NO. 52) and its corresponding human, mouse, and *Drosophila* orthologs: XP_059282 (SEQ ID NO. 54), NP_083638 (SEQ ID NO. 56) and AAF58977 (SEQ ID NO. 58).

FIG. 15 shows DIC microscopy images taken from time-lapse recording of the first two rounds of cell division in wild type untreated *C. elegans*.

Figure 16:
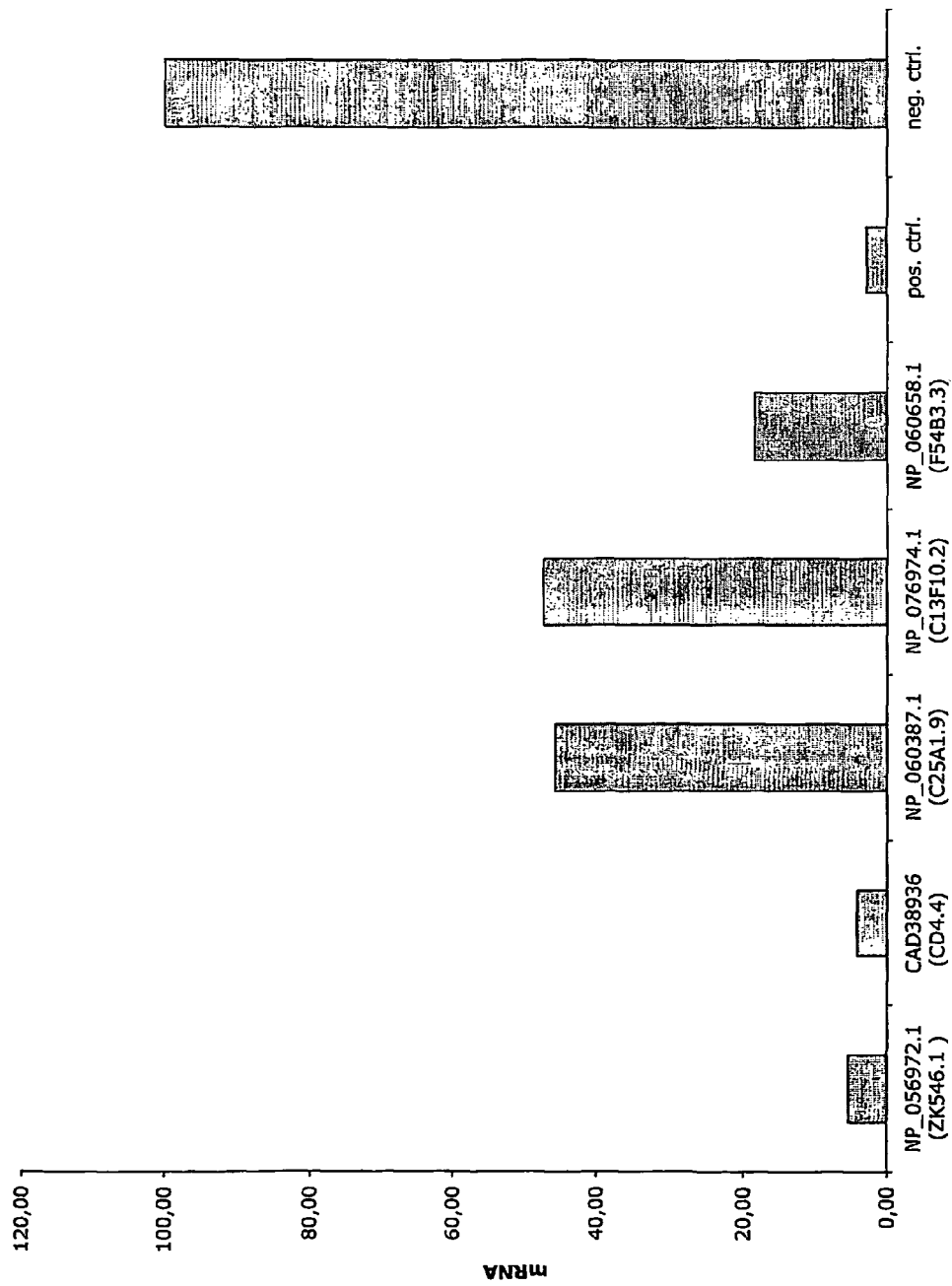

FIG. 16: shows the remaining mRNA levels after RNAi treatment of HeLa cells. RNAi treatment of HeLa cells with siRNAs directed against NP_056972.1, CAD38936, NP_060387.1, NP_076974.1 and NP_060658.1, the human orthologs of *C. elegans* genes ZK546.1, CD4.4, C25A1.9, C13F10.2 and F54B3.3 respectively, results in the specific reduction to mRNA levels below 20% compared to control treated samples for NP_056972.1, CAD38936 and NP_060658.1, and a reduction below 50% for NP_060387.1 and NP_076974.1. mRNA, remaining mRNA levels (% of negative control treated sample); pos. ctrl., positive control; neg. ctrl., negative control.

Figure 17:
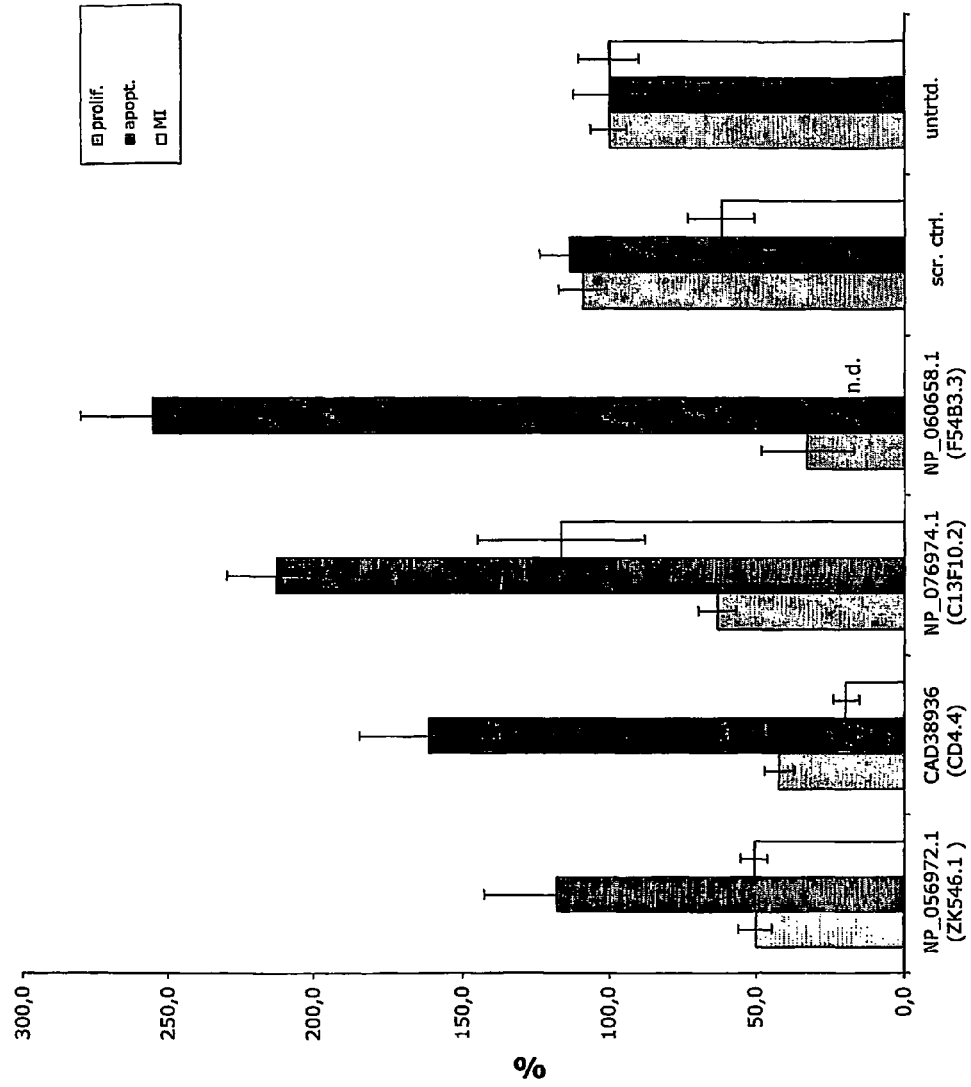

FIG. 17: shows the effect of RNAi treatment on cell proliferation, apoptosis, and mitosis in HeLa cells. For graphical presentation, the proliferation, apoptosis rate, and MI of untreated cells were set to 100. prolif., cell proliferation; apopt., apoptosis; MI, mitotic index; %, percent compared to untreated control; scr. ctrl., scrambled control; untrtd., untreated; n.d., not determined.

The following examples illustrate the present invention without, however, limiting the same thereto.

EXAMPLE 1

Protocol for Identifying Functional Orthologs in other Species

To identify orthologous genes, the following procedure was used: The identified homologous amino acid sequences themselves were used for BLAST searches. If the original *C. elegans* protein was (re-)identified by a BLAST hit with an e-value of less than $10^{-5}$, the identified homolog was defined as an ortholog. The BLAST search was performed with the default parameters and the low complexity filter on. An alternative parameter for identification of homologous genes can be the percentage of sequence identity. Over 100 residues, a sequence identity of 30% defines a homologous gene. After the BLAST search is completed, multiple sequence alignment is performed using appropriate software (for example, CLUSTAL W) and a neighbour joining phylogenetic tree is generated. Any person skilled in the art can identify the human ortholog from a phylogenetic tree. Essentially, the human sequence that is separated on the tree by a single speciation event or most closely related on the tree is likely to be an ortholog.

EXAMPLE 2

Generation of dsRNA Molecules for RNAi Experiments

First, oligonucleotide primer pair sequences were selected to amplify portions of the gene of interest's coding region using standard PCR techniques. Primer pairs were chosen to yield PCR products containing at least 500 bases of coding sequence, or a maximum of coding bases for genes smaller than 500 bases. In order to permit the subsequent use of the PCR product as a template for in vitro RNA transcription reactions from both DNA strands, the T7 polymerase promoter sequence "TAATACGACTCACTATAGG" (SEQ ID NO. 61) was added to the 5' end of forward primers, and the T3 polymerase promoter sequence "AATTAACCCTCACTAAAGG" (SEQ ID NO. 62) was added to the 5' end of reverse primers. The synthesis of oligonucleotide primers was completed by a commercial supplier (Sigma-Genosys, UK or MWG-Biotech, Germany).

PCR reactions were performed in a volume of 50 μl, with Taq polymerase using 0.8 μM primers and approximately 0.1 μg of wild-type (N2 strain) genomic DNA template. The PCR products were EtOH precipitated, washed with 70% EtOH and resuspended in 7.0 μl TE. 1.0 μl of the PCR reaction was pipetted into each of two fresh tubes for 5 μl transcription reactions using T3 and T7 RNA polymerases. The separate T3 and T7 transcription reactions were performed according to the manufacturer's instructions (Ambion, Megascript kit), each diluted to 50 µl with RNase-free water and then combined. The mixed RNA was purified using RNeasy kits according to the manufacturer's instructions (Qiagen), and eluted into a total of 130 µl of RNase-free H$_2$O. 50 µl of this was mixed with 10 µl 6× injection buffer (40 mM KPO4 pH 7.5, 6 mM potassium citrate, pH 7.5, 4% PEG 6000). The RNA was annealed by heating at 68° C. for 10 min, and at 37° C. for 30 min. Concentration of the final dsRNAs were measured to be in the range of 0.1-0.3 µl. The products of the PCR reaction, of the T3 and T7 transcription reactions, as well as the dsRNA species were run on 1% agarose gels to be examined for quality control purposes. Success of double stranding was assessed by scoring shift in gel mobility with respect to single stranded RNA, when run on non-denaturing gels.

EXAMPLE 3

Injections of dsRNA and Phenotypic Assays dsRNAs were injected bilaterally into the syncytial portion of both gonads of wild-type (N2 strain) young adult hermaphrodites, and the animals incubated at 20° C. for 24 hrs. Embryos were then dissected out from the injected animals and analyzed by time-lapse differential interference contrast videomicroscopy for potential defects in cell division processes, capturing 1 image every 5 seconds, as previously described (Gönczy et al., Dissection of cell division processes in the one cell stage *Caenorhabditis elegans* embryo by mutational analysis. *J Cell Biol* 144, 927-946 (1999)). For each experiment, embryos from at least 3 different injected worms were filmed in this manner, from shortly after fertilization until the four cell stage. Embryos from 2 additional injected worms were recorded for shorter periods, covering the 2 cell and the 4 cell stage, respectively, thus yielding documentation for at least 5 injected worms in each experiment.

In some cases, embryos exhibited acute sensitivity to osmotic changes, as evidenced by their loss of structural integrity during the dissection of the injected animals. In order to overcome this limitation, injected animals were not dissected, but rather, anaesthetized for 10 min in M9 medium containing 0.1% tricaine and 0.01% tetramisole, and mounted intact on an agarose pad to observe the F1 embryogenesis in utero (Kirby et al., Dev. Biol. 142, 203-215 (1990)). The resolution achieved by viewing through the body wall does not equal that achieved by observing dissected embryos, and only limited phenotypic analysis was conducted in these cases.

Three injected animals were also transferred to a fresh plate 24 hrs after injection of dsRNA, and left at 20° C. Two days later, the plate was checked with a stereomicroscope (20-40× total magnification) for the presence of F1 larvae (L2's-L4's), as well as their developmental stage. Two days after that, the plate was inspected again for the presence of F1 adults, as well as their overall body morphology and the presence of F2 progeny.

EXAMPLE 4

Characterization of the *C. elegans* gene C13F10.2 dsRNA was designed and used to specifically silence the expression of the *C. elegans* gene by RNAi, thereby testing its functional involvement in the first round of embryonic cell division in this metazoan species. The dsRNA was synthesized in vitro from PCR-amplified wild type genomic DNA fragments of the C13F10.2 gene. For PCR, the following primer pair was used: "TAAACGACTCACTATAGGGCG-GCTCTTTTCTTCCATTT" (SEQ ID NO. 63) with "AATTAACCCTCACTAAAGGTTTCATTCGTCTTCCTCGCT" (SEQ ID NO. 64) as forward and reverse primers, respectively. The dsRNA was purified, and injected into adult hermaphrodite worms. The phenotypic consequences of the RNAi treatment were documented 24 hours later in the F1 progeny of injected worms, using time-lapse differential interference contrast (DIC) microscopy. Embryo recordings started ~20 minutes after fertilization, while the female pronucleus is completing its meiotic divisions, until the 2 cell stage, ~15 to 20 minutes later.

Control worms were either not injected, or injected with irrelevant dsRNA. Irrelevant dsRNA was made of the same nucleotide composition as the experimental dsRNA, but the nucleotides were in random order. In the F1 progeny of such control worms the cellular events of the first two rounds of embryonic cell division were found to exhibit very limited variability, as observed by DIC microscopy. All processes that were examined and scored for the possibility of phenotypic deviations are listed and illustrated in FIG. 13. Briefly, the antero-posterior polarity of the embryo is initially determined by the position of the male pronucleus at the cortex, shortly after entry into the egg. This is accompanied by a clear, coordinated flow of yolk granules through the central portion of the cytoplasm along the embryo's longitudinal axis towards the male pronucleus, and a concomitant series of cortical waves or ruffles progressing towards the anterior of the embryo. Shortly thereafter, the male and female pronuclei undergo highly patterned migrations resulting in their meeting within the posterior half of the embryo, followed by a centration and rotation of the pronuclear pair and associated centrosomes to set up the future mitotic spindle along the embryo's longitudinal axis. After synchronous breakdown of the pronuclear envelopes, the clearly bipolar mitotic spindle is initially short, but then rockingly elongates. These movements are accompanied by a slight posterior displacement of the posterior spindle pole, while the anterior spindle pole remains approximately stationary. This then results in an asymmetric positioning of the spindle during anaphase and telophase, thereby yielding an asymmetric placement of the cytokinetic furrow, and generating unequally-sized daughter cells: a smaller posterior P1 blastomere, and larger anterior AB blastomere. While the AB nucleus then migrates directly to the center of the AB cell, the P1 nucleus typically migrates further towards the posterior of that cell, before undergoing a pronounced 90° rotation while re-migrating to the anterior P1 cortex with one of its duplicated centrosomes leading. This insures that the P1 blastomere then divides along the embryo's longitudinal lo axis, perpendicular to that of the AB blastomere. These two divisions occur asynchronously, with P1 lagging 2-3 minutes behind AB.

In the F1 embryos of worms injected with dsRNA, the following highly reproducible phenotypes are observed (FIG. 1). The mitotic spindle (indicated by arrow heads) drifts and bends during elongation, suggesting weakened microtubule-cortex interactions. The phenotype is embryonic lethal.

All observed phenotypes indicate a requirement for C13F10.2 gene function in spindle formation or microtubule function during cell division. Since this function is essential to cell division throughout metazoans, this gene and any homologs and derivatives thereof represent excellent tools for use in the development of a wide range of therapeutics including anti-proliferative agents. Analysis of the C13F10.2 gene sequence reveals clear orthologs in human (GenBank Accession No. NP_076974) and *Drosophila* (GenBank Accession No. AAF49911) which have no function ascribed to them until now. In particular, there has been no information linking the orthologs to spindle formation or microtubule function during cell division. Based on the extremely high sequence conservation at the protein level, it can be concluded that these genes most likely encode proteins with equivalent function in spindle formation or microtubule function during cell division in humans and *Drosophila*.

EXAMPLE 5

Characterization of the *C elegans* gene C25A1.9 dsRNA was designed and used to specifically silence the expression of the *C. elegans* gene by RNAi, thereby testing its functional involvement in the first round of embryonic cell division in this metazoan species. The dsRNA was synthesized in vitro from PCR-amplified wild type genomic DNA fragments of the C25A1.9 gene. For PCR, the following primer pair was used: "TAATACGACTCACTATAGGCACTTAATGCGCCCATTTTC" (SEQ ID NO. 65) with "AATTAACCTCACTAAAGGTTAGCGGGACTGCTATTGCT" (SEQ ID NO. 66) as forward and reverse primers, respectively. The dsRNA was purified, and injected into adult hermaphrodite worms. The phenotypic consequences of the RNAi treatment were documented 24 hours later in the F1 progeny of injected worms, using time-lapse differential interference contrast (DIC) microscopy. Embryo recordings started ~20 minutes after fertilization, while the female pronucleus is completing its meiotic divisions, until the 2 cell stage, ~15 to 20 minutes later.

In the F1 embryos of worms injected with dsRNA, the following highly reproducible phenotypes are observed (FIG. 3). The pronuclei remain slightly posterior, leading to incomplete pronuclear centration (FIG. 3A, B). The mitotic spindle is. hardly visible and spindle positioning lacks the rocking phase (FIG. 3C-E). In some cases, this can result in chromosome segregation defects (FIG. 3F, arrow head indicates an additional karyomere in AB blastomere). The phenotype is embryonic lethal.

All observed phenotypes indicate a requirement for C25A1.9 gene function in spindle formation or microtubule function during cell division. Since this function is essential to cell division throughout metazoans, this gene and any homologs and derivatives thereof represent excellent tools for use in the development of a wide range of therapeutics including anti-proliferative agents. Analysis of the C25A1.9 gene sequence reveals a clear homolog in human (GenBank Accession No. NP_060387) which has had no function ascribed to it until now. In particular, there has been no information linking the homolog to spindle formation or microtubule function during cell division. Based on the extremely high sequence conservation at the protein level, it can be concluded that this gene most likely encodes a protein with equivalent function in spindle formation or microtubule function during cell division in humans.

EXAMPLE 6

Characterization of the *C. elegans* Gene F54B3.3 dsRNA was designed and used to specifically silence the expression of the *C. elegans* gene by RNAi, thereby testing its functional involvement in the first round of embryonic cell division in this metazoan species. The dsRNA was synthesized in in vitro from PCR-amplified wild type genomic DNA fragments of the F54B3.3 gene. For PCR, the following primer pair was used: "TAATACGACTCACTATAGGAGAGGTCGAGAACGAGACCA" (SEQ ID NO. 67) with "AATTAACCCTCACTAAAGGATCGAACTGCTCTGGCTGAT" (SEQ ID NO. 68) as forward and reverse primers, respectively. The dsRNA was purified, and injected into adult hermaphrodite worms. The phenotypic consequences of the RNAi treatment were documented 24 hours later in the F1 progeny of injected worms, using time-lapse differential interference contrast (DIC) microscopy. Embryo recordings started ~20 minutes after fertilization, while the female pronucleus is completing its meiotic divisions, until the 2 cell stage, ~15 to 20 minutes later.

In the F1 embryos of worms injected with dsRNA, the following highly reproducible phenotypes are observed (FIG. 5). Pronuclei are not centered and a short spindle is set up along the dorso-ventral axis (FIG. 5A). This results in aberrant cleavage site specification and furrowing at three sites (FIG. 5B-D, white arrows). Cytokinesis fails, the reforming nuclei stay closely apposed to each other (FIG. 5D-H, black arrows). An additional karyomere is formed at the posterior (FIG. 5G-H, white arrow).

All observed phenotypes indicate a requirement for F54B3.3 gene function in spindle formation or microtubule function during cell division. Since this function is essential to cell division throughout metazoans, this gene and any homologs and derivatives thereof represent excellent tools for use in the development of a wide range of therapeutics including anti-proliferative agents. Analysis of the F54B3.3 gene sequence reveals clear orthologs in human (GenBank Accession No. NP_060658) and *Drosophila* (GenBank Accession No. AAF55289) which have no function ascribed to them until now. Based on sequence analysis, the *Drosophila* protein has been described as ATPase-related Additionally, homologs have been identified in mouse (GenBank Accession No.

XP_109399), rat (GenBank Accession No. P46462 or NP_446316), and *Saccharomyces cerevisiae* (GenBank Accession No. NP_015349). However, there has been no information linking the genes to spindle formation or microtubule function during cell division. Based on the extremely high sequence conservation at the protein level, it can be concluded that these genes, particularly the orthologs, most likely encode proteins with equivalent function in spindle formation or microtubule function during cell division in their respective species.

EXAMPLE 7

Characterization of the *C. elegans* Gene F08B6.2 dsRNA was designed and used to specifically silence the expression of the *C. elegans* gene by RNAi, thereby testing its finctional involvement in the first round of embryonic cell division in this metazoan species. The dsRNA was synthesized in vitro from PCR-amplified wild type genomic DNA fragments of the F08B6.2 gene. For PCR, the following primer pair was used: "TAATACGACTCACTATAGGCTTCACCGAAAGCCAAGAAG" (SEQ ID NO. 69) with "AATTAACCCTCACTAAAGGGAGGTTTGAAAGCGATGGTG" (SEQ ID NO. 70) as forward and reverse primers, respectively. The dsRNA was purified, and injected into adult hermaphrodite worms. The phenotypic consequences of the RNAi treatment were documented 24 hours later in the F1 progeny of injected worms, using time-lapse differential interference contrast (DIC) microscopy. Embryo recordings started ~20 minutes after fertilization, while the female pronucleus is completing its meiotic divisions, until the 2 cell stage, ~15 to 20 minutes later.

In the F1 embryos of worms injected with dsRNA, the following highly reproducible phenotypes are observed (FIG. 7). Pronuclear centration and rotation are inaccurate. The rocking phase of the mitotic spindle is less coordinated than normal (FIG. 7A-D, arrows). Rotation of the P1 nucleus is jerky (FIG. 7E-F, arrows). The phenotype is embryonic lethal.

All observed phenotypes indicate a requirement for F08B6.2 gene function in spindle formation or microtubule function during cell division. Since this function is essential to cell division throughout metazoans, this gene and any homologs and derivatives thereof represent excellent tools for use in the development of a wide range of therapeutics including anti-proliferative agents. Analysis of the F08B6.2 gene sequence reveals clear orthologs in human (GenBank Accession No. NP_057625) and *Drosophila* (GenBank Accession No. AAF52761) which have been described as guanine nucleotide binding proteins. A homolog of F08B6.2 has been identified in rat (GenBank Accession No. AAA73553 or NP_631924). There has been no information linking the genes to spindle formation or microtubule function during cell division. Based on the extremely high sequence conservation at the protein level, it can be concluded that these genes, particularly the orthologs, most likely encode proteins with equivalent function in spindle formation or microtubule function during cell division in their respective species.

EXAMPLE 8

Characterization of the *C. elegans* Gene CD4.4 dsRNA was designed and used to specifically silence the expression of the *C. elegans* gene by RNAi, thereby testing its finctional involvement in the first round of embryonic cell division in this metazoan species. The dsRNA was synthesized in vitro from PCR-amplified wild type genomic DNA fragments of the CD4.4 gene. For PCR, the following primer pair was used: "TAATACGACTCACTATAG-GAACTTTTCAGGTCCGCTCAA" (SEQ ID NO. 71) with "AATTAACCCTCACTAAAGGCCTGAAT-AGCCAGATCCGAA" (SEQ ID NO. 72) as forward and reverse primers, respectively. The dsRNA was purified, and injected into adult hermaphrodite worms. The phenotypic consequences of the RNAi treatment were documented 24 hours later in the Fl progeny of injected worms, using time-lapse differential interference contrast (DIC) microscopy. Embryo. recordings started ~20 minutes after ferilization, while the female pronucleus is completing its meiotic divisions, until the 2 cell stage, ~15 to 20 minutes later.

In the F1 embryos of worms injected with dsRNA, the following highly reproducible phenotypes are observed (FIG. 9). There are areas devoid of yolk granules. Small globular structures are visible in the cytoplasm (FIG. 9A-F, arrows). The structures seem to bind to microtubules and migrate to the minus end. The phenotype is embryonic lethal.

All observed phenotypes indicate a requirement for CD4.4 gene function in spindle formation or microtubule function during cell division Since this function is essential to cell division throughout metazoans, this gene and any homologs and derivatives thereof represent excellent tools for use in the development of a wide range of therapeutics including anti-proliferative agents. Analysis of the CD4.4 gene sequence reveals clear orthologs in human (two human orthologs: GenBank Accession No. NP_078943 and CAD38936) and *Drosophila* (GenBank Accession No. NP_AAF52060) which have had no function ascribed to it until now. In particular, there has been no information linking the orthologs to spindle formation or microtubule function during cell division. Based on the extremely high sequence conservation at the protein level, it can be concluded that these genes most likely encode proteins with equivalent function in spindle formation or microtubule function during cell division in humans and *Drosophila*, respectively.

EXAMPLE 9

Characterization of the *C. elegans* Gene ZK546.1 dsRNA was designed and used to specifically silence the expression of the *C. elegans* gene by RNAi, thereby testing its functional involvement in the first round of embryonic cell division in this metazoan species. The dsRNA was synthesized in vitro from PCR-amplified wild type genomic DNA fragments of the ZK546.1 gene. For PCR, the following primer pair was used: "TAATACGACTCACTATAGGGCT-GATATGGCAGTTTGGGT" (SEQ ID NO. 73) with "AAT-TAACCCTCACTAAAGGGCAACTGAG-CAATCCCATTT" (SEQ ID NO. 74) as forward and reverse primers, respectively. The dsRNA was purified, and injected into adult hermaphrodite worms. The phenotypic consequences of the RNAi treatment were documented 24 hours later in the Fl progeny of injected worms, using time-lapse differential interference contrast (DIC) microscopy. Embryo recordings started ~20 minutes after ferilization, while the female pronucleus is completing its meiotic divisions, until the 4 cell stage, ~30 minutes later.

In the F1 embryos of worms injected with dsRNA, the following highly reproducible phenotypes are observed (FIG. 11). The centrosomes detach from the male pronucleus (FIG. 11A) and migrate towards the female pronucleus (FIG. 11B-C, arrows). The spindle fails to integrate the male chromosomal material, resulting in the formation of an extra karyomere in the P1 cell. (FIG. 11D-F, arrows). The AB spindle is initially separated from the chromatin, resulting in a segregation defect (FIG. 11G-H, arrows). The phenotype is embryonic lethal.

All observed phenotypes indicate a requirement for ZK546.1 gene function in spindle formation or microtubule-function during cell division. Since this function is essential to cell division throughout metazoans, this gene and any homologs and derivatives thereof represent excellent tools for use in the development of a wide range of therapeutics including anti-proliferative agents. Analysis of the ZK546.1 gene sequence reveals a clear ortholog in human (GenBank Accession No. NP_056972) and homologs in mouse (GenBank Accession No. XP_109474), rat (Genbank Accession No. AAA74950), *Drosophila* (GenBank Accession No. AAF53605), and *Saccharomyces cerevisiae* (GenBank Accession No. NP_010225). The murine homolog (Hook1) functions in positioning of microtubular structures within the spermatid. However, there has been no information linking the genes to spindle formation or microtubule function during cell division. Based on the extremely high sequence conservation at the protein level, it can be concluded that these genes, particularly the orthologs, most likely encode proteins with equivalent function in spindle formation or microtubule function during cell division in their respective species.

EXAMPLE 10

Characterization of the *C. elegans* Gene C56C103 dsRNA was designed and used to specifically silence the expression of the *C. elegans* gene by RNAi, thereby testing its functional involvement in the first round of embryonic cell division in this metazoan species. The dsRNA was synthesized in vitro from PCR-amplified wild type genomic DNA fragments of the C56C10.3 gene. For PCR, the following primer pair was used: "TAATACGACTCACTATAGGT-TCGGGAAACAGAGGAGATG" (SEQ ID NO. 75) with "AATTAACCCTCACTAAAGGCCTTGT-CAGCTTCTTTCGCT" (SEQ ID NO. 76) as forward and reverse primers, respectively. The dsRNA was purified, and injected into adult hermaphrodite worms. The phenotypic consequences of the RNAi treatment were documented 24 hours later in the F1 progeny of injected worms, using time-lapse differential interference contrast (DIC) microscopy. Embryo recordings started ~20 minutes after ferilization, while the female pronucleus is completing its meiotic divisions, until the 4 cell stage, ~30 minutes later.

In the F1 embryos of worms injected with dsRNA, the following highly reproducible phenotypes are observed (FIG. 13). There are structures visible in the cytoplasm that seem to bind to astral microtubules or might resemble microtubule bundles. Arrows indicate aberrant structures along astral microtubules.

All observed phenotypes indicate a requirement for C56C10.3 gene function in spindle formation or microtubule function during cell division. Since this function is essential to cell division throughout metazoans, this gene and any homologs and derivatives thereof represent excellent tools for use in the development of a wide range of therapeutics including anti-proliferative agents. Analysis of the C56C10.3 gene sequence reveals clear orthologs in human (GenBank Accession No. XP_059282.3), mouse (GenBank Accession No. NP_083638.1), and *Drosophila* (GenBank Accession No. NP_610462), and a homolog in yeast (GenBank accession No. NP_013125). The function of these proteins is unknown. In particular, there has been no information linking the genes to spindle formation or microtubule function during cell division. Based on the extremely high sequence conservation at the protein level, it can be concluded that these orthologs most likely encode proteins with equivalent function in spindle formation or microtubule function during cell division in their respective species.

EXAMPLE 11

Effects of RNAi Treatment in Human Cells

Design and Synthesis of siRNAs

For all experiments in human cells short double stranded interfering RNAs (siRNAs) of 21 bases in length, comprised of a 19 bp core of complementary sequence and 2 bases overhang at the 3' end, were designed by Cenix and chemically synthesized by Ambion Inc., Austin, Tex., USA.

The following siRNA sequences were used:

Transfection

HeLa cells were treated with siRNAs at a final concentration of 100 nM using a lipofection based transfection protocol.

24 h before transfection, HeLa cells were seeded in 96 well plates at a density of 6,000 cells/well.

On the day of transfection, the transfection mix was prepared as follows: 1 μl of a 10 μg stock of siRNA was diluted with 16 μl of Opti-MEM (Invitrogen Inc.), and 0.4 μl Oligofectamine transfection reagent (Invitrogen) were diluted with 2.4 μl of Opti-MEM.

For complex formation, both solutions were gently mixed and incubated for 20 min at RT. Culture medium was removed from the cells and 80 μl of fresh medium (DMEM, Invitrogen) were added, followed by addition of 20 μl of transfection mix. Cells were incubated at 37° C. for 4 hours, 50 μl of fresh medium, supplemented with 30% fetal calf serum were added, followed by another incubation for 48-72 hours.

Determination of Silencing Level by Quantitative RT-PCR (qRT-PCR)

48 hours after transfection, total RNA was extracted from RNAi treated cells using Invisorb kits (Invitek GmbH, Berlin), and cDNA was produced with ABI TaqMan reverse transcription reagents (Applied Biosystems, USA). In both cases the manufacturer's instructions were followed. Quantitative real-time PCR was performed using the following protocol: 5.5 μl of 2× SybrGreen PCR mix (Applied Biosystems) were mixed with 3 μl of sample cDNA and 2.5 μl of a 2 μM solution of gene specific PCR primers, followed by incubation in a ABI-7900-HT real-time PCR machine at 50° C. 2 min—95° C. 10 min—45 cycles (95° C. 15 sec—60° C. 1 min)—95° C. 15 sec—60° C. 15 sec—95° C. 15 sec. In addition to the gene specific reaction, a second, reference reaction was run for each cDNA sample, using primers for 18S rRNA. Amplification signals from different gene specific samples were normalized using the reference values on 18S rRNA for these respective samples, and compared to samples from control (scrambled siRNA from Ambion Inc.) treated cells.

Proliferation Assay

In order to quantify the number of living cells after RNAi treatment, ATP levels were measured 72 h after transfection using the ATPlite assay (Perkin Elmer). Cells were extracted and treated according to the manufacturer's instructions. Luminescence read out was performed on a Victor 2 multi

```
scrambled negative control   5-AGUAGUGCUUACGAUACGGTT-3      (SEQ ID NO. 77)
                             3-TTUCAUGACGAAUGCUAUGCC-5      (SEQ ID NO. 78)

positive control (PCNA,      5-GGAGAAAGUUUCAGACUAUTT-3      (SEQ ID NO. 79)
proliferating cell nuclear   3-GTCCUCUUUCAAAGUCUGAUA-5      (SEQ ID NO. 80)
antigen)

NP_056972.1                  5-GGUUGCUCCAGCUUAUUUUTT-3      (SEQ ID NO. 81)
                             3-CTCCAACGAGGUCGAAUAAAA-5      (SEQ ID NO. 82)

CAD38936                     5-GGUUCUCUUUGAAGCCUAUTT-3      (SEQ ID NO. 83)
                             3-GTCCAAGAGAAACUUCGGAUA-5      (SEQ ID NO. 84)

NP_060387.1                  5-GGCUUCAGGGAAAAUACUGTT-3      (SEQ ID NO. 85)
                             3-TTCCGAAGUCCCUUUUAUGAG-5      (SEQ ID NO. 86)

NP_076974.1                  5-GGACCUAGUAGAGAUGAATT-3       (SEQ ID NO. 87)
                             3-CTCCUGGGAUCAUCUCUACUU-5      (SEQ ID NO. 88)

NP_060658.1                  5-GUCCCACAGGUGCCUCAUUTT-3      (SEQ ID NO. 89)
                             3-TTCAGGGUGUCCACGGAGUAA-5      (SEQ ID NO. 90)
``` label reader (Perkin Elmer). For graphical presentation purposes the proliferation of untreated cells was set to 100.

Apoptosis Assay

The levels of programmed cell death in RNAi treated cells were determined 72 hours after transfection, using the Caspase 3/7 specific fluorometric assay ApoOne by Promega, following the manufacturer's instructions. Read out was performed on a Victor 2 multi label reader (Perkin Elmer). For graphical presentation purposes the apoptosis rate of untreated cells was set to 100.

Mitotic Index (MI)

Phosphorylation at serin 10 of histone H3 is considered a hallmark of mitosis, appearing in early prophase and disappearing during telophase. Using immunofluorescence microscopy, mitotic cells can be revealed by an increased binding of a phospho-histone H3 antibody, detected by a suitable fluorescence labelled secondary antibody.

RNAi treated cells in 96 well microscopy plates were stained using the following protocol: Cells were washed with PBS and fixed with 4% para-formaldehyde for 30 min at RT, followed by three washes with PBS. Cells were then permeabilised and blocked in the presence of 0.1% Triton X-100 and 2% BSA for 30 min. The supernatant was removed and anti Phospho Histone H3 (mouse monoclonal antibody clone 6G3, Cell Signalling Technologies) was added at a dilution of 1:750 for 2 hours at RT, followed by three washes with PBS. For detection of Phosph Histone H3 labelled nuclei, goat anti mouse antibody (1:500), coupled to Alexa Fluor 568 (Molecular Probes) was added in a solution supplemented with 0.5 µg/ml Dapi (4',6-diamidino-2-phenylindole, dihydrochloride), FluoroPure™ grade, Molecular Probes) for detection of all nuclei. After incubation for 2 hours at RT, cells were washed four times and images were taken using an automated microscopy system (Discovery-1, Universal Imaging Inc.), acquiring a minimum of 6 images/well. Metamorph-HCS image processing software was used to determine the numbers of mitotic and overall nuclei. The Mitotic Index resembles the fraction of mitotic over all nuclei in a given cell population For graphical presentation purposes the MI of untreated cells was set to 100.

Effects of RNAi Treatment

As shown in FIG. 17, RNAi treatment of HeLa cells using an siRNA directed against NP_056972.1, the human ortholog of C. elegans gene ZK546.1, results in a 50% reduction of cell proliferation and a subtle decrease of Mitotic Index compared to control treated cells. RNAi treatment of HeLa cells using an siRNA directed against CAD38936, the human ortholog of C. elegans gene CD4.4, results in a 60% reduction of cell proliferation, a significant induction of apotosis and a 2.5 fold decrease in the Mitotic Index compared to control treated cells. RNAi treatment of HeLa cells using an siRNA directed against NP_076974.1, the human ortholog of C. elegans gene C13F10.2, results in a 40% reduction in cell proliferation, a 2 fold increase in the rate of apoptosis and a significant increase in the Mitotic Index compared to control treated cells. RNAi treatment of HeLa cells using an siRNA directed against NP_060658.1, the human ortholog of C. elegans gene F54B3.3, results in a 70% reduction of cell proliferation, a 2.5 fold increase in the rate of apoptosis compared to control treated cells.

The invention claimed is:

1. A method for the identification and characterization of drugs that inhibit or activate spindle formation or microtubule function during cell division, wherein the method comprises using a nucleic acid molecule in a screening assay for the identification of said drug, and performing a functional analysis for the spindle formation or microtubule function during cell division, wherein the nucleic acid molecule comprises (a) a nucleic acid sequence encoding a polypeptide that exhibits a sequence identity of at least 70% over 100 residues on the amino acid level with the protein encoded by the nucleic acid sequence of SEQ ID NO: 3,
   (b) a nucleic acid sequence that is antisense of the nucleic acid sequence as defined in (a), or
   (c) a double-stranded RNA or a single-stranded RNA in the antisense or sense direction corresponding to the nucleic acid sequence as defined in (a).

2. The method of claim 1, wherein the nucleic acid molecule comprises (a) the nucleic acid sequence of SEQ ID NO: 3,
   (b) a nucleic acid sequence encoding a polypeptide that exhibits a sequence identity with the protein encoded by the nucleic acid sequence of SEQ ID NO: 3,
   (c) a nucleic acid sequence that is antisense of the nucleic acid sequence as defined in (a) or (b), or
   (d) a double-stranded RNA or a single-stranded RNA in the antisense or sense direction corresponding to the nucleic acid sequence as defined in (a) or (b).

3. The method of claim 1, further comprising
   (a) transforming the nucleic acid molecule into a host cell or host organism,
   (b) cultivating the host cell or host organism under conditions that allow the overexpression of the polypeptide encoded by, or RNA corresponding to, the nucleic acid molecule either in the presence or in the absence of at least one candidate for an inhibitor- or activator-molecule, and
   (c) analyzing the spindle formation or microtubule function during cell division in the cultivated cell or organism.

* * * * *